US010683292B2

(12) United States Patent
Casale et al.

(10) Patent No.: US 10,683,292 B2
(45) Date of Patent: Jun. 16, 2020

(54) PURINE AND 3-DEAZAPURINE ANALOGUES AS CHOLINE KINASE INHIBITORS

(71) Applicant: NERVIANO MEDICAL SCIENCES S.R.L., Nerviano (MI) (IT)

(72) Inventors: Elena Casale, Somma Lombardo (IT); Emiliana Corti, Nerviano (IT); Paola Gnocchi, Stresa (IT); Marcella Nesi, Saronno (IT); Sten Christian Orrenius, Nerviano (IT); Francesca Quartieri, Arona (IT); Federico Riccardi Sirtori, Segrate (IT)

(73) Assignee: NERVIANO MEDICAL SCIENCES S.R.L., Nerviano (MI) (IT)

( * ) Notice: Subject to any disclaimer, the term of this patent is extended or adjusted under 35 U.S.C. 154(b) by 0 days.

(21) Appl. No.: 16/319,951

(22) PCT Filed: Jul. 19, 2017

(86) PCT No.: PCT/EP2017/068255
§ 371 (c)(1),
(2) Date: Jan. 23, 2019

(87) PCT Pub. No.: WO2018/019681
PCT Pub. Date: Feb. 1, 2018

(65) Prior Publication Data
US 2019/0225615 A1      Jul. 25, 2019

(30) Foreign Application Priority Data

Jul. 25, 2016   (EP) .................................... 16181105

(51) Int. Cl.
| | | |
|---|---|---|
| *C07D 473/34* | (2006.01) | |
| *A61P 35/00* | (2006.01) | |
| *C07D 471/04* | (2006.01) | |
| *C07D 473/40* | (2006.01) | |
| *C07D 513/04* | (2006.01) | |
| *C07D 513/14* | (2006.01) | |
| *C07D 513/18* | (2006.01) | |

(52) U.S. Cl.
CPC ............ *C07D 473/40* (2013.01); *A61P 35/00* (2018.01); *C07D 471/04* (2013.01); *C07D 473/34* (2013.01); *C07D 513/04* (2013.01); *C07D 513/14* (2013.01); *C07D 513/18* (2013.01)

(58) Field of Classification Search
CPC ... C07D 473/34; C07D 473/40; C07D 471/04
See application file for complete search history.

(56) References Cited

U.S. PATENT DOCUMENTS

2015/0166512 A1 * 6/2015 Brasca ................. C07D 401/04
514/243

FOREIGN PATENT DOCUMENTS

| | | | |
|---|---|---|---|
| EP | 0 639 582 A2 | 2/1995 | |
| WO | 2005/068429 A1 | 7/2005 | |
| WO | 2007/077203 A2 | 7/2007 | |
| WO | 2013/043960 A1 | 3/2013 | |
| WO | 2013/043961 A1 | 3/2013 | |
| WO | 2014/151761 A1 | 9/2014 | |
| WO | 2014/165216 A1 | 10/2014 | |
| WO | 2015/185780 A1 | 12/2015 | |
| WO | WO-2016196840 A1 * | 12/2016 | ........... C07D 471/04 |
| WO | WO-2017191297 A1 * | 11/2017 | ........... C07D 473/34 |

OTHER PUBLICATIONS

University of Maryland Medical Center. (2016).Web: http://umm.edu/health/medical/altmed/condition/myeloproliferative-disorders.*
MedicineNet.com (2004) Web: http://www.medterms.com.*
Auto-immune Diseases: MedlinePlus. (2014). Web: https://www.nlm.nih.gov/medlineplus/autoimmunediseases.html.*
UCSF Medical Center. Neurological Disorders. (2016) Web: https://www.ucsfhealth.org/conditions/neurological_disorders/.*
Infections: MedlinePlus. (2016) Web: https://www.nlm.nih.gov/medlineplus/infections.html.*
EP16305530.4 filed May 4, 2016 (foreign priority document of WO 2017191297A1).*
Zadra G. et al., "The Fat Side of Prostate Cancer", *Biochimica et Biophysica Acta* 1831:1518-1532 (2013).
Zhang J-H et al., "A Simple Statistical Parameter for Use in Evaluation and Validation of High Throughput Screening Assays", *Journal of Biomolecular Screening* 4(2):67-73 (1999).
International Search Report dated Nov. 9, 2017 received in International Application No. PCT/EP2017/068255.
Aoyama C. et al., "Structure and Function of Choline Kinase Isoforms in Mammalian Cells", Progress in Lipid Research 43:266-281 (2004).
Arlauckas S.P. et al., "Choline Kinase Alpha-Putting the ChoK-Hold on Tumor Metabolism", Progress in Lipid Research 63:28-40 (2016).
Asim M. et al., "Choline Kinase Alpha as an Androgen Receptor Chaperone and Prostate Cancer Therapeutic Target", JNCI J Natl. Cancer Inst 108(5):371-384 (2016).

(Continued)

*Primary Examiner* — Emily A Bernhardt
*Assistant Examiner* — Laura M Daniel
(74) *Attorney, Agent, or Firm* — Scully, Scott, Murphy & Presser, P.C.

(57) ABSTRACT

There are provided substituted purine and 3-deazapurine analogues, which modulate the activity of Choline Kinase (ChoK). The compounds of this invention are therefore useful in treating diseases caused by an altered choline metabolism, such as cancer, cell proliferative disorders, infectious diseases of different origin, immune-related disorders and neurodegenerative disorders. The present invention also provides methods for preparing these compounds, pharmaceutical compositions comprising these compounds, and methods of treating diseases utilizing pharmaceutical compositions comprising these compounds.

10 Claims, No Drawings

(56) References Cited

OTHER PUBLICATIONS

Bagnoli M. et al., "Choline Metabolism Alteration: A Focus on Ovarian Cancer", Frontiers in Oncology 6(153):1-7 (Jun. 2016).
Bañez-Coronel M. et al., "Choline Kinase Alpha Depletion Selectively Kills Tumoral Cells", Current Cancer Drug Targets 8(8):709-719 (2008).
Beloueche-Babari M. et al., "Acquired Resistance to EGFR Tyrosine Kinase Inhibitors Alters the Metabolism of Human Head and Neck Squamous Carcinoma Cells and Xenograft Tumours", British Journal of Cancer 112:1206-1214 (2015).
Bhushan R.G. et al., "Synthesis of Conformationally Restricted 2',3'-exo-Methylene Carbocyclic Nucleosides Built on a Bicyclo[3.1.0]Hexane Template", Bioorganic & Medicinal Chemistry 10:2325-2333 (Jan. 1, 2002).
Canese R. et al., "Characterisation of In Vivo Ovarian Cancer Models by Quantitative 1H Magnetic Resonance Spectroscopy and Diffusion-Weighted Imaging", NMR Biomed. 25:632-642 (2012).
Chen J-H et al., "Clinical Characteristics and Biomarkers of Breast Cancer Associated With Choline Concentration Measured by 1H MR Spectroscopy", NMR Biomed. 24(3):316-324 (Apr. 2011).
Choppin S. et al., "Unusual C-6 Lithiation of 2-Chloropyridine-Mediated by BuLi-Me2N(CH2)2OLi. New Access to 6-Functional-2-Chloropyridines and Chloro-bis-Heterocycles", Organic Letters 2(6):803-805 (2000).
Chung T. et al., "ATP-Dependent Choline Phosphage-Induced Metogenesis in Fibroblasts Involves Activation of pp70 S6 Kinase and Phosphatidylinositol 3'-Kinase Through an Extracellular Site", The Journal of Biological Chemistry 272(5):3064-3072 (Jan. 31, 1997).
Colombo M. et al., "A Fully Automated Method for Accurate Mass Determination Using High-Performance Liquid Chromatography With a Quadrupole/Orthogonal Acceleration Time-of-Flight Mass Spectrometer", Rapid Communications in Mass Spectrometry 18:511-517 (2004).
Dejmek M. et al., "Norbomane-Based Nucleoside and Nucleotide Analogues Locked in North Conformation", Bioorganic & Medicinal Chemistry 23:184-191 (Nov. 15, 2014).
De La Cueva A. et al., "Combined 5-FU and ChoKα Inhibitors as a New Alternative Therapy of Colorectal Cancer: Evidence in Human Tumor-Derived Cell Lines and Mouse Xenografts", PLOS One 8(6):e64961 (Jun. 2013).
Ding S. et al., "Expanding the Diversity of Purine Libraries", Tetrahedron Letters 42:8751-8755 (2001).
Gadiya M. et al., "Phospholipase D1 and Choline Kinase-α are Interactive Targets in Breast Cancer", Cancer Biology & Therapy 15(5):593-601 (May 2014).
Gallego-Ortega D. et al., "Involvement of Human Choline Kinase Alpha and Beta in Carcinogenesis A Different Role in Lipid Metabolism and Biological Functions", Advances in Enzyme Regulations 51:183-194 (2011).
Gallego-Ortega D. et al., "Differential Role of Human Choline Kinase α and β Enzymes in Lipid Metabolism: Implications in Cancer Onset and Treatment", PLOS One 4(11):e7819 (Nov. 2009).
Gibellini F. et al., "The Kennedy Pathway-De Novo Synthesis of Phosphatidylethanolamine and Phosphatidylcholine", IUBMB Life 62(6):414-428 (Jun. 2010).
Glunde K. et al., "Choline Metabolism-Based Molecular Diagnosis of Cancer: An Update", Expert Rev Mol Diagn. 15(6):735-747 (Jun. 2015).
Glunde K. et al., "Choline Metabolism in Malignant Transformation", Nat Rev Cancer 11(12):835-848 (Feb. 23, 2015).
Glunde K. et al., "Metabolic Tumor Imaging Using Magnetic Resonance Spectroscopy", Semin Oncol. 38(1):26-41 (Feb. 2011).
Glunde K. et al., "RNA Interference-Mediated Choline Kinase Suppression in Breast Cancer Cells Induces Differentiation and Reduces Proliferation", Cancer Research 65(23):11034-11043 (Dec. 1, 2005).
González-Díaz H. et al., "Stochastic Entropy QSAR for the In Silico Discovery of Anticancer Compounds: Prediction, Synthesis, and In Vitro Assay of New Purine Carbanucleosides", Bioorganic & Medicinal Chemistry 14:1095-1107 (Feb. 15, 2006).
Granata A. et al., "Global Metabolic Profile Indentifies Choline Kinase Alpha as a Key Regulator or Glutathione-Dependent Antioxidant Cell Defense in Ovarian Carcinoma", Oncotarget 6(13):11216-11230 (2015).
Granata A. et al., "Choline Kinase-Alpha by Regulating Cell Aggressiveness and Drug Sensitivity is a Potential Druggable Target for Ovarian Cancer", British Journal of Cancer 110:330-340 (2014).
Grinde M.T. et al., Interplay of Choline Metabolites and Genes in Patient-Derived Breast Cancer Xenografts, Breast Cancer Research 16:R5 (2014).
Gruber J. et al., "Balance of Human Choline Kinase Isoforms is Critical for Cell Cycle Regulation", FEBS Journal 279:1915-1928 (2012).
Guma M. et al., "Choline Kinase Inhibition in Rheumatoid Arthritis", Ann Rheum Dis 74:1399-1407 (2015).
Haukaas T.H. et al., "Metabolic Clusters of Breast Cancer in Relation to Gene- and Protein Expression Subtypes", Cancer & Metabolism 4(12):1-14 (2016).
Hernando E. et al., "A Critical Role for Choline Kinase Alpha in the Aggressiveness of Bladder Carcinomas", Oncogene 28(26):2425-2435 (Jul. 2009).
Iorio E. et al., "Alterations of Choline Phospholipid Metabolism in Ovarian Tumor Progression", Cancer Research 65(20):9369-9376 (Oct. 15, 2005).
Jiménze B. et al., "Generation of Phosphorylcholine as an Essential Event in the Activation of Raf-1 and MAP-Kinases in Growth Factors-Induced Mitogenic Stimulation", Journal of Cellular Biochemistry 57:141-149 (1995).
Krishnamachary B. et al., "Noninvasive Detection of Lentiviral-Mediated Choline Kinase Targeting in a Human Breast Cancer Xenograft", Cancer Research 69(8):3464-3471 (Apr. 15, 2009).
Kroemer G. et al., "Tumor Cell Metabolism: Cancer's Achilles' Heel", Cancer Cell 13:472-482 (Jun. 2008).
Kumar M. et al., "Magnetic Resonance Spectroscopy for Detection of Choline Kinase Inhibition in the Treatment of Brain Tumors", Molecular Cancer Therapeutics (2015).
Li H. et al., "The Metabolic Responses to Hepatitis B Virus Infection Shed New Light on Pathogenesis and Targets for Treatment", Scientific Reports 5:8421-8429 (2014).
Li Q. et al., "Integrative Functional Genomics of Hepatitis C Virus Infection Identifies Host Dependencies in Complete Viral Replication Cycle", PLOS Pathogens 10(5):e1004163 (May 2014).
Li Z. et al., "Phosphatidylcholine and Choline Homeostasis", Journal of Lipid Research 49:1187-1194 (2008).
Local J C, "Choline Kinase as a Precision Medicine Target for Therapy in Cancer, Autoimmune Diseases and Malaria", Precision Medicine 2:e980 (2015).
Malito E. et al., "Elucidation of Human Choline Kinase Crystal Structures in Complex With the Products ADP or Phosphocholine", J. Mol. Biol. 364:136-151 (2006).
Mazarico J.M. et al., "Choline Kinase Alpha (CHKα) as a Therapeutic Target in Pancreatic Ductal Adenocarcinoma: Expression, Predictive Value, and Sensitivity to Inhibitors", Molecular Cancer Therapeutics 15 (2):1-11 (2016).
Mitsuhashi S. et al., "Megaconial Congenital Muscular Dystrophy Due to Loss-of-Function Mutations in Choline Kinase β", Current Opinion Neurol 26(5):536-543 (Oct. 2013).
Mitsuhashi S. et al., "A Congenital Muscular Dystrophy With Mitochondrial Structural Abnormalities Caused by Defective De Novo Phosphatidylcholine Biosynthesis", The American Journal of Human Genetics 88:845-851 (Jun. 10, 2011).
Peyrottes S. et al., "Choline Analogues in Malaria Chemotherapy", Current Pharmaceutical Design 18 (24):3454-3466 (2012).
Priolo C. et al., "AKT1 and MYC Induce Distinctive Metabolic Fingerprints in Human Prostate Cancer", Cancer Research 74(24):7198-7204 (Dec. 15, 2014).
Raboisson P. et al., "Design, Synthesis and Structure-Activity Relationships of a Series of 9-Substituted Adenine Derivatives as Selective Phosphodiesterase Type-4 Inhibitors", European Journal of Medicinal Chemistry 38:199-214 (2003).

(56) References Cited

OTHER PUBLICATIONS

Ramírez De Molina A. et al., "Overexpression of Choline Kinase is a Frequent Feature in Human Tumor-Derived Cell Lines and in Lung, Prostate, and Colorectal Human Cancers", *Biochemical and Biophysical Research Communications* 296:580-583 (2002).

Rocha C.M. et al., "NMR Metabolomics of Human Lung Tumours Reveals Distinct Metabolic Signatures for Adenocarcinoma and Squamous Cell Carcinoma", *Carcinogenesis* 36(1):68-75 (2015).

Sakakibara N. et al., "Synthesis and Evaluation of Novel Carbocyclic Oxetanocin A (COA-C1) Derivatives as Potential Tube Formation Agents", *Chem. Pharm. Bull.* 63:701-709 (Sep. 1, 2015).

Shah T. et al., "Choline Kinase Overexpression Increases Invasiveness and Drug Reistance of Human Breast Cancer Cells", *NMR Biomed.* 23:633-642 (2010).

Sher R.B. et al., "A Rostrocaudal Muscular Dystrophy Caused by a Defect in Choline Kinase Beta, the First Enzyme in Phosphatidylcholine Biosynthesis", *The Journal of Biological Chemistry* 281(8):4938-4948 (Feb. 24, 2006).

Taddei D. et al., "Synthesis and Full Characterisation of 6-Chloro-2-Iodopurine, a Template for the Functionalisation of Purines", *Org. Biomol. Chem.* 2:665-670 (2004).

Trousil S. et al., "Alterations of Choline Phospholipid Metabolism in Endometrial Cancer are Caused by Choline Kinase Alpha Overexpression and a Hyperactivated Deacylation Pathway", *Molecular and Cellular Pathobiology* 74(23):6867-6877 (Dec. 1, 2014).

Ward P.S. et al., "Signaling in Control of Cell Growth and Metabolism", *Cold Spring Harb Perspect Biol* 4:a006783 (2012).

Wu G. et al., "Early Embryonic Lethality Caused by Disruption of the Gene for Choline Kinase α, the First Enzyme in Phosphatidylcholine Biosynthesis", *J Biol. Chem.* 283(3):1456-1462 (Jan. 18, 2008).

Yalcin A. et al., "Selective Inhibition of Choline Kinase Simultaneously Attenuates MAPK and PI3K/AKT Signaling", *Oncogene* 29:139-149 (2010).

Yamamoto Y. et al., "Direct Introduction of Acyl and Ethoxycarbonyl Groups into Pyrimidine Ring Through the Trimethyl-Stannyl Derivatives", *Heterocycles* 41(6):1275-1290 (Feb. 1, 1995).

Yutaka Y. et al., "Direct Introduction of Acyl and Ethoxycarbonyl Groups into Pyrimidine Ring Through the Trimethyl-Stannyl Derivatives", *Heterocycles* 41(6):1275-1290 (Feb. 1, 1995).

Xiong J. et al., "Dysregulated Choline Metabolism in T-Cell Lymphoma: Role of Choline Kinase-α and Therapeutic Targeting", *Blood Cancer Journal* 5:287-296 (2015).

\* cited by examiner

PURINE AND 3-DEAZAPURINE ANALOGUES AS CHOLINE KINASE INHIBITORS The present invention relates to certain substituted purine and 3-deazapurine analogues, which modulate the activity of Choline Kinase (ChoK). The compounds of this invention are therefore useful in treating diseases caused by an altered choline metabolism. The present invention also provides methods for preparing these compounds, pharmaceutical compositions comprising these compounds, and methods of treating diseases utilizing pharmaceutical compositions comprising these compounds.

BACKGROUND OF THE INVENTION

Metabolic reprogramming in cancer cells has been recognized as one of the most significant hallmarks of cancer. Tumorigenesis is dependent on the reprogramming of cellular metabolism as both direct and indirect consequence of oncogenic mutations. The alterations in intracellular and extracellular metabolites, that can accompany cancer-associated metabolic reprogramming, have profound effects on gene expression, cellular differentiation and tumor microenvironment and support rapid growth, metastasis, drug resistance and survival (*Cancer Cell* 2008, 13, 472-482; *Cold Spring Harb Perspect Biol* 2012, 4, a006783). Among the several changes of tumor metabolic pathways, abnormal choline metabolism is emerging as one of the metabolic hallmarks associated with oncogenesis and tumour progression. Activated choline metabolism, which is characterized by an increase in total choline-containing compounds (tCho) and, in particular, in phosphocholine (PCho) level, has been identified in tumor cells both in in vitro and in vivo studies, and by magnetic resonance spectroscopy (MRS) in primary tumors samples (*Cancer & Metabolism* 2016, 4, 12-14; *Biochimica et Biophysica Acta* 2013, 1831, 1518-1532; *NMR Biomed.* 2012, 25, 632-642; *Semin. Oncol.* 2011, 38, 26-41; *Lancet Oncol.* 2007, 8, 889-97). Choline phospholipid metabolism consists of a complex network of biosynthetic and catabolic pathways controlled by several regulatory enzymes that may be potential targets for anticancer therapy (*Prog. Lipid Res.* 2016, 63, 28-40; *Nat. Rev. Cancer,* 2011, 11, 835-848). Among the enzymes involved, Choline Kinase (ChoK) is ubiquitously distributed in eukaryotes and catalyzes the first step of the Kennedy pathway for the de novo synthesis of phosphatidylcholine (PtdCho), which is the most abundant phospholipid in mammalian cellular membranes (*IUBMB Life* 2010, 62, 414-428; *J. Lipid Res.* 2008, 49, 1187-1194). In mammalian cells two separate genes encode for three isoforms: ChoKα1, ChoKα2 and ChoKβ. ChoKα1 and ChoKα2 are formed as the result of alternative splicing of the CHKA transcript. The enzyme is active as homo or hetero dimers (*Prog. Lipid Res.* 2004, 43, 266-281). In the first step of the Kennedy pathway, ChoK converts choline into phosphocholine (PCho), which then reacts with cytidine triphosphate (CTP) to form cytidine diphosphate-choline (CDP-choline). The PCho moiety is then transferred to diacylglycerol to produce PtdCho. Moreover PCho is considered a putative second messenger involved in proliferation and its level increase is correlated to activity of ChoKα in cells (*J Cell. Bioch.* 1995, 57, 141-149; *J. Biol. Chem.* 1997, 272, 3064-3072).

Different and not redundant roles for ChoKα and ChoKβ have been suggested. ChoKα knock-out mice result in embryonic lethality (*J. Biol. Chem.* 2008, 283, 1456-1462), while ChoKβ knock-out mice develop a rostrocaudal muscular dystrophy and bone deformity (*J. Biol. Chem.* 2006, 281, 4938-4948). In human, an inactivating mutation in CHKB gene has been identified in congenital muscular dystrophy (*Am. J. Hum. Genet.* 2011, 88, 845-851; *Curr. Opin. Neurol.* 2013, 26: 536-543). Moreover ChoKα, but not ChoKβ, has been associated with malignancy and its down modulation using specific siRNA is sufficient to affect PCho level, invasion and migration of cancer cells (*FEBS Journal* 2012, 279, 1915-1928; *Adv. Enzyme Regul.* 2011, 51, 183-194; *PLoS ONE* 2009, 4, e7819). According to these data, ChoKα inhibition could be sufficient to have an antitumor activity avoiding potential toxic effect linked to ChoKβ inhibition.

Several data reported in the literature support the role of ChoKα in tumors. Down modulation or overexpression of ChoKα induce a clear effect on PCho levels and, consequently, affect in vitro invasiveness, migration and growth in several cell lines (i.e. ovary, breast, prostate cancer cells) (*Mol. Cancer Ther.* 2016, 15, 1-11; *JNCI J. Natl. Cancer Inst.* 2016, 108, 371-384; *Oncogene* 2010, 29, 139-149; *Current Cancer Drug Targets* 2008, 8, 709-719; *Cancer Res.* 2005, 65, 11034-43). Depletion of ChoKα in cell lines stably transfected with ChoKα specific shRNA showed a reduced ability to grow in vivo (*Cancer Res.* 2009, 69, 3464-3471), as well as forced over-expression has been shown to cause an increased tumor formation and aggressiveness of the disease (*NMR Biomed* 2010, 23, 633-642; *Oncogene* 2009, 28, 2425-2435).

In tumor samples, high expression of ChoKα or high levels of choline metabolites are correlated to aggressiveness of tumors like ovary, breast, brain and lung (*Front. Oncol.* 2016, 6, 153; *Carcinogenesis* 2015, 36, 68-75; *Mol. Cancer Ther.* 2015, 14, 899-908; *BJC* 2015, 112, 1206-1214; *Cancer Biol. Ther.* 2014, 15, 593-601; *Cancer Res.* 2014, 74, 6867-77; *BCR* 2014, 16, R5; *NMR Biomed.* 2011, 24, 316-324; *BBRC* 2002, 296, 580-3). Metabolomic analysis of prostate samples in in vitro and in vivo models as well as in tumor samples revealed that AKT1 activation is associated with accumulation of aerobic glycolysis metabolites, whereas MYC overexpression is associated with a dysregulated lipid metabolism and induction of ChoKα (*Cancer Res.* 2014, 74, 7198-204). Recently it has been reported that also T-cell lymphoma is characterized by high levels of ChoKα and choline metabolites and that genetic ablation of ChoKα, using specific siRNA, induces inhibition of proliferation and apoptotis both in vitro and in vivo (*Blood Cancer J.* 2015, 5, 287-296). Choline metabolites (total choline, tCho) can be monitored in patients by Magnetic Resonance Spectroscopy (MRS) or by Positron Emission Tomography (PET) and it is under evaluation as potential biomarker in preclinical and clinical studies (*Expert Rev. Mol. Diagn.* 2015, 15, 735-747).

Choline metabolism is also involved in drug resistance. Over-expression of ChoKα increases invasiveness and drug resistance to 5-fluorouracil (5FU) in human breast cancer cells (*NMR Biomed.* 2010, 23, 633-642), as well as inhibition of ChoKα activity seems to be sinergistic with 5FU in colon cancer cell lines both in vitro and in vivo (*PloS ONE* 2013, 8, e64961-74).

ChoKα silencing in different epithelial ovarian cancer cells induces a reduction in the tumorigenic properties of these cells. This antitumor activity was correlated to a specific altered ROS homeostasis induced by a reduction in cysteine and glutathione (GSH) levels in ChoKα-depleted cells. This effect was observed in tumor cells, but not in non-tumorigenic cells, and it is mediated by a decrease of the trans-sulphuration pathway (*BJC* 2014, 110, 330-340).

This outcome in ovarian cancer cells is also linked to increased drug sensitivity to cisplatin, doxorubicin and paclitaxel (*Oncotarget* 2015, 6, 11216-11230).

Choline Kinase has been identified as a potential target also in other diseases. In rheumatoid arthritis (RA) it has been demonstrated that inhibition of ChoKα suppresses cell migration and resistance to apoptosis of cultured fibroblast-like synoviocytes (FLS), involved in cartilage destruction in RA. Moreover inhibition of ChoKα abrogates joint inflammation and damage in either pretreatment or established disease protocols in K/BxN arthritis mouse model (*Ann. Rheum. Dis.* 2015, 74, 1399-1407).

ChoK is the first enzyme in the Kennedy pathway (CDP-choline pathway) for the biosynthesis of PtdCho also in malaria-causing *Plasmodium* parasites. Based on pharmacological and genetic data, the de novo biosynthesis of PtdCho appears to be essential for the intraerythrocytic growth and survival of the malaria parasite. This highlights the potential use of ChoK inhibitors, active on ChoK of *Plasmodium* parasites (e.g. *Plasmodium falciparum*), in the fight against malaria (*Curr. Pharm. Des.* 2012, 18, 3454-3466; *Precision Medicine* 2015; 2: e980-992).

Functional genomics studies identified ChoKα as a new target for Hepatitis C (HCV) or B (HBV), because it seems to be involved in entry as well as in replication of the virus inside the target cells (*Scientific Reports* 2015, 5, 8421-8429; *PLOS Pathogens* 2014, 10, e1004163-77).

ChoK inhibitors have already been reported in WO2014151761 (ARIAD PHARMACEUTICALS INC.), WO200568429 (Consejo Superior de Investigacions Cientificas, Universidad de Granada), WO200777203 (Consejo Superior de Investigacions Cientificas, Universidad de la Laguna), WO2015185780 (Universidad de Granada and Università degli Studi di Padova), WO2013043961 and WO2013043960 (both by Vertex).

SUMMARY OF THE INVENTION

Considering the above arguments, there is a strong need for the development of ChoK inhibitors for the treatment of cancer as well as RA and infectious disease, which has motivated efforts to identify agents targeting ChoK. Accordingly, it is an object of the present invention to provide such inhibitor compounds.

DETAILED DESCRIPTION OF THE INVENTION

The present inventors have discovered that compounds of general formula (I), as defined below, are kinase inhibitors and in particular are inhibitors of Choline Kinase. Particularly such compounds are inhibitors of ChoKα and are thus useful to treat diseases caused by altered choline metabolism.

Accordingly, a first object of the present invention is to provide a substituted purine or 3-deazapurine derivative of general formula (I):

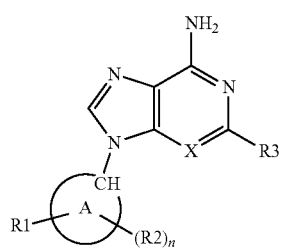

wherein
X is CH or nitrogen;
A is a 6- or 7-membered cycloalkyl or a 6- or 7-membered nitrogen-containing heterocyclyl, or A is a 7- to 9-membered carbon bicyclic system, in which one ring carbon is optionally replaced by nitrogen;
R1 is linked:
either
1) to any A ring carbon, in which case R1 is fluorine, an optionally substituted $(C_1-C_6)$alkyl or $(C_3-C_7)$cycloalkyl, —COR6, —COOR4, —CONR4R5, —NR4COOR6, —NR4COR5, —NR4R5, —NR4CONR4R5, —NR4CSNR4R5, or —NR4SO$_2$R6; or
2) to the A ring nitrogen, if present, in which case R1 is an optionally substituted $(C_1-C_6)$alkyl or $(C_3-C_7)$cycloalkyl, —COR5, —COOR6, —CONR4R5, —CSNR4R5, or —SO$_2$R6;
wherein
R4 and R5 are independently hydrogen or an optionally substituted group selected from $(C_1-C_6)$alkyl, $(C_3-C_7)$cycloalkyl, heterocyclyl, aryl, aryl$(C_1-C_6)$alkyl, heteroaryl and heteroaryl$(C_1-C_6)$alkyl; or R4 and R5, taken together with the nitrogen atom to which they are bonded, may form an optionally substituted 5- or 6-membered heterocyclyl group optionally containing one additional heteroatom selected from N, O and S;
R6 is an optionally substituted group selected from $(C_1-C_6)$alkyl, $(C_3-C_7)$cycloalkyl, heterocyclyl, aryl, aryl$(C_1-C_6)$alkyl, heteroaryl and heteroaryl$(C_1-C_6)$alkyl;
n is 0, 1 or 2;
R2 is linked to any A ring atom and is selected from the group consisting of fluorine, an optionally substituted $(C_1-C_6)$alkyl or $(C_3-C_7)$cycloalkyl, and NR4R5;
provided that
when R2 is fluorine or NR4R5, then R2 is linked to a ring carbon;
when n is 2, then the R2 groups are not necessarily the same; wherein the R1 and R2 groups can be linked to the same ring carbon;
R3 is hydrogen, halogen, cyano or an optionally substituted group selected from $(C_1-C_6)$alkyl, polyfluorinated $(C_1-C_6)$ alkyl, $(C_2-C_6)$alkenyl, $(C_2-C_6)$alkynyl, $(C_3-C_7)$cycloalkyl, heterocyclyl, aryl, heteroaryl, —OR6, —SR6, —SO$_2$R6, —NR4R5 or —CONR4R5, wherein R4, R5 and R6 are as defined above;
provided that
when X is nitrogen, then R3 is different from hydrogen or NR4R5, wherein R4 is an optionally substituted aryl and R5 hydrogen; and that
R1 and R2 may be optionally substituted by one or more groups different from hydroxy and hydroxy$(C_1-C_6)$alkyl groups;
or a pharmaceutically acceptable salt thereof.

The present invention also provides methods of preparing purine and 3-deazapurine compounds, represented by general formula (I), prepared through processes consisting of standard synthetic transformations.

The present invention also provides a method for treating diseases caused by and/or associated with altered choline metabolism, which comprises administering to a mammal in need thereof, more particularly a human, an effective amount of a purine and 3-deazapurine analogue represented by general formula (I) as defined above.

A preferred method of the present invention is to treat a disease caused by and/or associated with altered choline metabolism selected from the group consisting of cancer, cell proliferative disorders, infectious diseases of different origin (i.e. viral, parasites), immune-related disorders and neurodegenerative disorders.

Another preferred method of the present invention is to treat specific types of cancer including but not limited to: carcinomas, such as bladder, breast, colon, kidney, liver, lung, including small cell lung cancer, esophagus, gallbladder, ovary, pancreas, stomach, cervix, thyroid, prostate, and skin, including squamous cell carcinoma; hematopoietic tumors of lymphoid lineage including leukemia, acute lymphocytic leukemia, acute lymphoblastic leukemia, B-cell lymphoma, T-cell-lymphoma, Hodgkin's lymphoma, non-Hodgkin's lymphoma, hairy cell lymphoma and Burkitt's lymphoma; hematopoietic tumors of myeloid lineage, including acute and chronic myelogenous leukemias, myelodysplastic syndrome and promyelocytic leukemia; tumors of mesenchymal origin, including fibrosarcoma and rhabdomyosarcoma; tumors of the central and peripheral nervous system, including astrocytoma neuroblastoma, glioma and schwannomas; and other tumors, including melanoma, seminoma, teratocarcinoma, osteosarcoma, xeroderma pigmentosum, keratoxanthoma, thyroid cancers, such as papillary thyroid carcinoma and medullary thyroid carcinoma, and Kaposi's sarcoma.

Another preferred method of the present invention is to treat specific cellular proliferation disorders such as, for example, benign prostate hyperplasia, familial adenomatosis, polyposis, neurofibromatosis, psoriasis, vascular smooth cell proliferation associated with atherosclerosis, pulmonary fibrosis, arthritis, glomerulonephritis and post-surgical stenosis and restenosis.

Another preferred method of the present invention is to treat viral infections like HCV or HBV, comprising the prevention of AIDS development in HIV-infected individuals.

Another preferred method of the present invention is to treat parasites infections, like *Plasmodium*-caused malaria.

Another preferred method of the present invention is to treat immune-related disorders including but not limited to: transplant rejection, skin disorders like psoriasis, allergies, asthma and autoimmune-mediated diseases such as rheumatoid arthritis (RA), systemic lupus erythematosus (SLE), Crohn's disease and amyotrophic lateral sclerosis.

Another preferred method of the present invention is to treat neurodegenerative disorders including but not limited to: Alzheimer's disease, degenerative nerve diseases, encephalitis, Stroke, Parkinson's Disease, Multiple Sclerosis, Amyotrophic Lateral Sclerosis (ALS or Lou Gehrig's Disease), Huntington's Disease and Pick's Disease.

In addition, the method of the present invention also provides tumor angiogenesis and metastasis inhibition as well as the treatment of organ transplant rejection and host versus graft disease.

Moreover, the method of the present invention further comprises subjecting the mammal in need thereof to a radiation therapy or chemotherapy regimen in combination with at least one cytostatic or cytotoxic agent.

The present invention also provides a pharmaceutical composition comprising a therapeutically effective amount of a compound of formula (I) or a pharmaceutically acceptable salt thereof, as defined above, and at least one pharmaceutically acceptable excipient, carrier or diluent.

The present invention further provides a pharmaceutical composition of a compound of formula (I) further comprising one or more chemotherapeutic—e.g. cytostatic or cytotoxic—agents, antibiotic-type agents, alkylating agents, antimetabolite agents, hormonal agents, immunological agents, interferon-type agents, cyclooxygenase inhibitors (e.g. COX-2 inhibitors), matrixmetalloprotease inhibitors, telomerase inhibitors, tyrosine kinase inhibitors, anti-growth factor receptor agents, anti-HER agents, anti-EGFR agents, anti-angiogenesis agents (e.g. angiogenesis inhibitors), farnesyl transferase inhibitors, ras-raf signal transduction pathway inhibitors, cell cycle inhibitors, other cdks inhibitors, tubulin binding agents, topoisomerase I inhibitors, topoisomerase II inhibitors, and the like.

Moreover the invention provides an in vitro method for inhibiting ChoK protein activity which comprises contacting the said protein with an effective amount of a compound of formula (I) as defined above.

Additionally, the invention provides a product comprising a compound of formula (I) or a pharmaceutically acceptable salt thereof, as defined above, and one or more chemotherapeutic agents, as a combined preparation for simultaneous, separate or sequential use in anticancer therapy.

In yet another aspect the invention provides a compound of formula (I) or a pharmaceutically acceptable salt thereof, as defined above, for use as a medicament.

Moreover the invention provides a compound of formula (I) or a pharmaceutically acceptable salt thereof, as defined above, for use in a method of treating cancer.

Finally, the invention provides the use of a compound of formula (I) or a pharmaceutically acceptable salt thereof, as defined above, in the manufacture of a medicament with anticancer activity.

If a stereogenic center or another form of an asymmetric center is present in a compound of the present invention, all forms of such optical isomer or isomers, including enantiomers and diastereomers, are intended to be covered herein. Compounds containing a stereogenic center may be used as a racemic mixture, an enantiomerically enriched mixture, or the racemic mixture may be separated using well-known techniques and an individual enantiomer may be used alone. In cases in which compounds have unsaturated carbon-carbon double bonds, both the cis (Z) and trans (E) isomers are within the scope of this invention.

In cases wherein compounds may exist in tautomeric forms, such as keto-enol tautomers, each tautomeric form is contemplated as being included within this invention whether existing in equilibrium or predominantly in one form.

Pharmaceutically acceptable salts of the compounds of formula (I) include the salts with inorganic or organic acids, e.g. nitric, hydrochloric, hydrobromic, sulfuric, perchloric, phosphoric, acetic, trifluoroacetic, propionic, glycolic, lactic, oxalic, fumaric, malonic, malic, maleic, tartaric, citric, benzoic, cinnamic, mandelic, methanesulphonic, isethionic and salicylic acid.

Pharmaceutically acceptable salts of the compounds of formula (I) also include the salts with inorganic or organic bases, e.g. alkali or alkaline-earth metals, especially sodium, potassium, calcium, ammonium or magnesium hydroxides, carbonates or bicarbonates, acyclic or cyclic amines.

With the term "$(C_1$-$C_6)$alkyl", we intend an aliphatic $(C_1$-$C_6)$ hydrocarbon chain, containing carbon-carbon single bonds only, which can be straight or branched. Representative examples include, but are not limited to, methyl, ethyl, n-propyl, isopropyl, n-butyl, isobutyl, tert-butyl, sec-butyl, n-pentyl, n-hexyl, and the like.

With the term "$(C_3$-$C_7)$cycloalkyl", we intend, unless otherwise provided, a 3- to 7-membered all-carbon monocyclic ring, which may contain one or more double bonds, but does not have a completely conjugated $\tau$-electron system. Examples of $(C_3$-$C_7)$cycloalkyl groups, without limitation, are cyclopropyl, cyclobutyl, cyclopentyl, cyclopentenyl, cyclohexanyl, cyclohexenyl and cyclohexadienyl. The $(C_3-C_7)$cycloalkyl ring can be optionally further fused or linked to aromatic and non-aromatic carbocyclic and heterocyclic rings.

With the term "bicyclic system" for A, we intend a system of two carbon rings fused together, in which one ring carbon is optionally replaced by a nitrogen, in order to form a system ranging from 7 to 9 atoms, such as for instance:

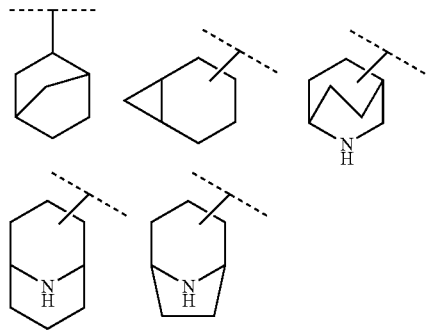

wherein the - - - - line indicates the point of attachment.

With the term "heterocyclyl", we intend a 3- to 7-membered, saturated or partially unsaturated carbocyclic ring where one or more carbon atoms are replaced by heteroatoms such as nitrogen, oxygen and sulfur. Non limiting examples of heterocyclyl groups are, for instance, pyranyl, tetrahydropyranyl, pyrrolidinyl, pyrrolinyl, imidazolinyl, imidazolidinyl, pyrazolidinyl, pyrazolinyl, thiazolinyl, thiazolidinyl, dihydrofuranyl, tetrahydrofuranyl, tetrahydropyridinyl, 1,3-dioxolanyl, piperidinyl, piperazinyl, morpholinyl and the like. The heterocyclyl ring can be optionally further fused or linked to aromatic and non-aromatic carbocyclic and heterocyclic rings.

With the term "$(C_2-C_6)$alkenyl", we intend an aliphatic $(C_2-C_6)$ hydrocarbon chain containing at least one carbon-carbon double bond and which can be straight or branched. Representative examples include, but are not limited to, ethenyl, 1-propenyl, 2-propenyl, 1- or 2-butenyl, and the like.

With the term "$(C_2-C_6)$alkynyl", we intend an aliphatic $(C_2-C_6)$ hydrocarbon chain containing at least one carbon-carbon triple bond and which can be straight or branched. Representative examples include, but are not limited to, ethynyl, 1-propynyl, 2-propynyl, 1- or 2-butynyl, and the like.

With the term "$(C_1-C_6)$alkoxy", we intend any of the above defined $(C_1-C_6)$alkyl linked to the rest of the molecule through an oxygen atom (—O—).

The term "aryl" refers to a mono-, bi- or poly-carbocyclic hydrocarbon with from 1 to 4 ring systems, optionally further fused or linked to each other by single bonds, wherein at least one of the carbocyclic rings is "aromatic", wherein the term "aromatic" refers to completely conjugated τ-electron bond system. Non limiting examples of such aryl groups are phenyl, α- or β-naphthyl, α- or β-tetrahydronaphthalenyl, biphenyl and indanyl groups.

The term "heteroaryl" refers to aromatic heterocyclic rings, typically 5- to 7-membered heterocycles with from 1 to 3 heteroatoms selected among N, O or S; the heteroaryl ring can be optionally further fused or linked to aromatic and non-aromatic carbocyclic and heterocyclic rings. Not limiting examples of such heteroaryl groups are, for instance, pyridyl, pyrazinyl, pyrimidinyl, pyridazinyl, indolyl, imidazolyl, thiazolyl, isothiazolyl, pyrrolyl, furanyl, oxazolyl, isoxazolyl, pyrazolyl, thiophenyl, thiadiazolyl, isoxazolyl, isothiazolyl, oxadiazolyl, indazolyl, cinnolinyl, benzo[1,3]dioxolyl, benzo[1,4]dioxinyl, benzothiazolyl, benzothiophenyl, benzofuranyl, isoindolinyl, benzoimidazolyl, benzoxazolyl, quinolinyl, isoquinolinyl, 1,2,3-triazolyl, 1-phenyl-1,2,3-triazolyl, 2,3-dihydroindolyl, 2,3-dihydrobenzofuranyl, 2,3-dihydrobenzothiophenyl, benzopyranyl, 2,3-dihydrobenzoxazinyl, 2,3-dihydroquinoxalinyl, 4,5,6,7-tetrahydro-1,3-benzothiazolyl, 4,5,6,7-tetrahydropyrido-[1,3]thiazolyl, 6,7-dihydro-4H-pyrano-[1,3]thiazolyl, 6,7-dihydro-4H-thiopyrano-[1,3]thiazolyl and all their possible regioisomers.

With the term "halogen", we intend fluorine, chlorine, bromine or iodine.

With the term "polyfluorinated $(C_1-C_6)$alkyl" or "polyfluorinated $(C_1-C_6)$alkoxy", we intend any of the above defined $(C_1-C_6)$alkyl or $(C_1-C_6)$alkoxy groups which are substituted by more than one fluorine atom such as, for instance, trifluoromethyl, trifluoroethyl, 1,1,1,3,3,3-hexafluoropropyl, trifluoromethoxy and the like.

With the term "hydroxy$(C_1-C_6)$alkyl" we intend any of the above defined $(C_1-C_6)$alkyl groups, bearing a hydroxyl group such as, for instance, hydroxymethyl, 2-hydroxyethyl, 3-hydroxypropyl and the like.

According to the present invention and unless otherwise provided, R1 and R2 may be optionally substituted, in any of their free positions, by one or more groups, for instance 1 to 6 groups, independently selected from: halogen, nitro, oxo group (=O), cyano, $(C_1-C_6)$alkyl, polyfluorinated $(C_1-C_6)$alkyl, polyfluorinated $(C_1-C_6)$alkoxy, $(C_2-C_6)$alkenyl, $(C_2-C_6)$alkynyl, aryl, aryl$(C_1-C_6)$alkyl, $(C_1-C_6)$alkylaryl, aryl$(C_1-C_6)$alkoxy, heteroaryl, heteroaryl$(C_1-C_6)$alkyl, $(C_1-C_6)$alkylheteroaryl, heterocyclyl, heterocyclyl$(C_1-C_6)$alkyl, $(C_1-C_6)$alkylheterocyclyl, $(C_1-C_6)$alkylheterocyclyl$(C_1-C_6)$alkyl, tri$(C_1-C_6)$alkylsilyl, $(C_3-C_7)$cycloalkyl, $(C_1-C_6)$alkoxy, aryloxy, heterocyclyloxy, methylenedioxy, $(C_1-C_6)$alkylcarbonyloxy, arylcarbonyloxy, di$(C_1-C_6)$alkylaminoheterocyclyl$(C_1-C_6)$alkyl, $(C_3-C_7)$cycloalkenyloxy, heterocyclylcarbonyloxy, $(C_1-C_6)$alkylideneaminooxy, carboxy, carboxy$(C_1-C_6)$alkyl, $(C_1-C_6)$alkoxycarbonyl, $(C_1-C_6)$alkoxycarbonyl$(C_1-C_6)$alkyl, aryloxycarbonyl, $(C_3-C_7)$cycloalkyloxycarbonyl, boronic acid, di$(C_1-C_6)$alkylboronic ester, amino, heterocyclyl$(C_1-C_6)$alkoxycarbonylamino, ureido, $(C_1-C_6)$alkylamino, amino$(C_1-C_6)$alkyl, di$(C_1-C_6)$alkylamino, arylamino, diarylamino, heterocyclylamino, formylamino, $(C_1-C_6)$alkylcarbonylamino, arylcarbonylamino, heterocyclylcarbonylamino, aminocarbonyl, aminocarbonyl$(C_1-C_6)$alkyl, $(C_1-C_6)$alkylaminocarbonyl, di$(C_1-C_6)$alkylaminocarbonyl, arylaminocarbonyl, heteroarylaminocarbonyl, arylaminocarbonyl$(C_1-C_6)$alkyl, $(C_3-C_7)$cycloalkylaminocarbonyl, heterocyclylaminocarbonyl, $(C_1-C_6)$alkoxycarbonylamino, hydroxyaminocarbonyl, $(C_1-C_6)$alkoxyimino, $(C_1-C_6)$alkylsulfonylamino, arylsulfonylamino, heterocyclylsulfonylamino, formyl, $(C_1-C_6)$alkylcarbonyl, arylcarbonyl, $(C_3-C_7)$cycloalkylcarbonyl, heterocyclylcarbonyl, heterocyclylcarbonyl$(C_1-C_6)$alkyl, $(C_1-C_6)$alkylsulfonyl, polyfluorinated $(C_1-C_6)$alkylsulfonyl, arylsulfonyl, aminosulfonyl, $(C_1-C_6)$alkylaminosulfonyl, di$(C_1-C_6)$alkylaminosulfonyl, arylaminosulfonyl, heterocyclylaminosulfonyl, arylthio, $(C_1-C_6)$alkylthio; in their turn, whenever appropriate, each of the above substituents may be further substituted by one or more of the aforementioned groups.

R3, R4, R5 and R6 may be optionally substituted, in any of their free positions, by one or more of the groups, for instance 1 to 6 groups, as defined above for R1 and R2, with the addition of hydroxy and hydroxy($C_1$-$C_6$)alkyl groups.

When R3 is aryl, examples of optional substituents are arylaminocarbonyl, further substituted by ($C_1$-$C_6$)alkylheterocyclyl($C_1$-$C_6$)alkyl or di($C_1$-$C_6$)alkylaminoheterocyclyl ($C_1$-$C_6$)alkyl, and heteroarylaminocarbonyl, further substituted by ($C_1$-$C_6$)alkyl.

Accordingly, examples of R3 are the following:

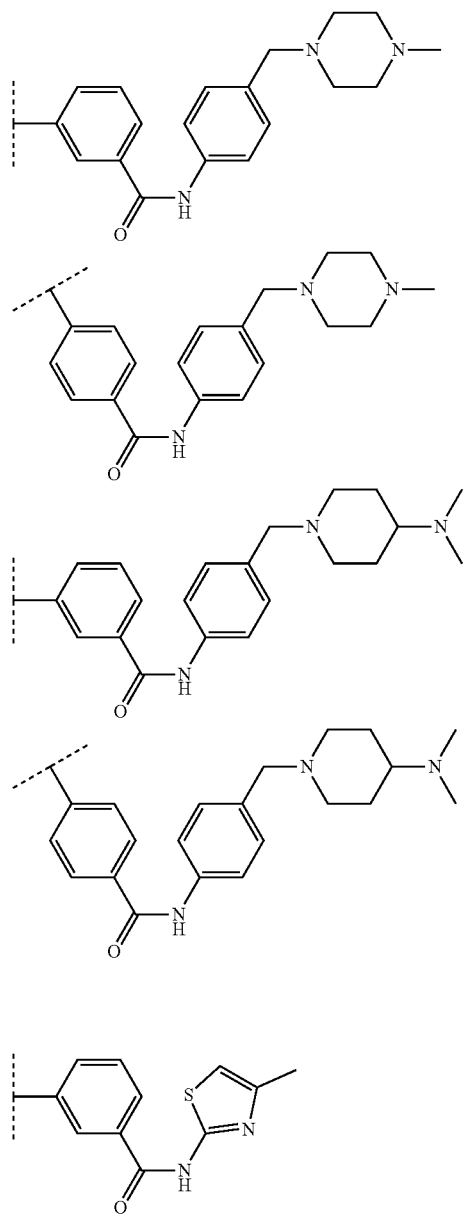

When R4 is aryl, examples of optional substituents are ($C_3$-$C_7$)cycloalkylaminocarbonyl or arylaminocarbonyl($C_1$-$C_6$)alkyl, which is further substituted by a ($C_1$-$C_6$)alkylheterocyclyl($C_1$-$C_6$)alkyl.

When R4 is heteroaryl, examples of optional substituents are heterocyclylcarbonyl($C_1$-$C_6$)alkyl, further substituted by a heterocyclyl or ($C_1$-$C_6$)alkylheterocyclyl, and aminoheterocyclyl($C_1$-$C_6$)alkyl.

Accordingly, examples of R4 are the following:

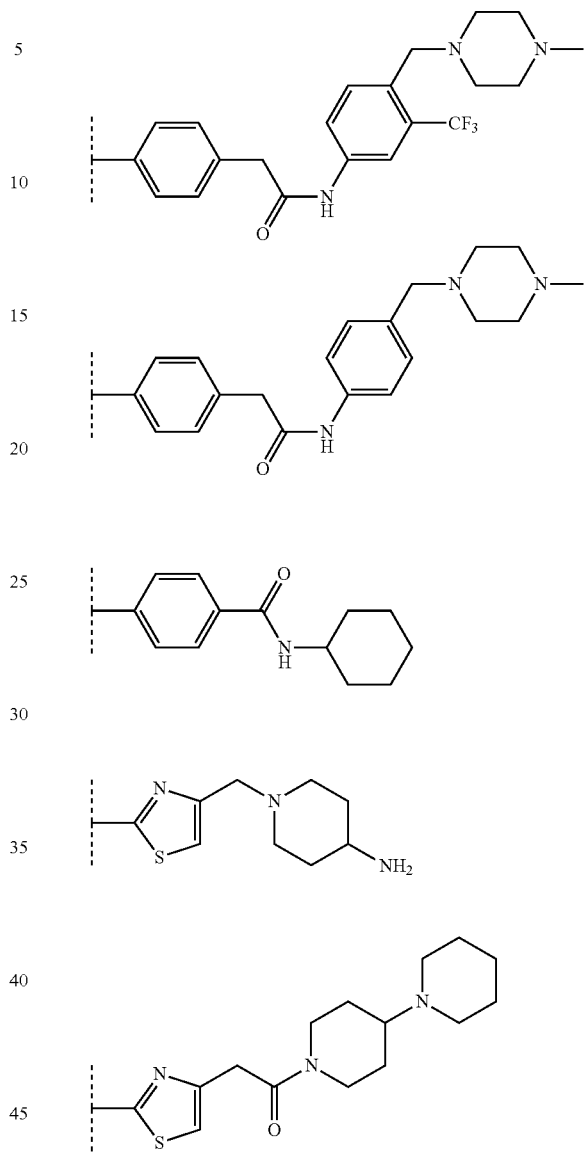

From all of the above, it is clear to the skilled person that any group which name is a composite name such as, for instance, "arylamino" has to be intended as conventionally construed by the parts from which it derives, e.g. by an amino group which is substituted by aryl, wherein aryl is as above defined.

Likewise, any of the terms such as, for instance, ($C_1$-$C_6$)alkylthio, ($C_1$-$C_6$)alkylamino, di($C_1$-$C_6$)alkylamino, ($C_1$-$C_6$)alkoxycarbonyl, ($C_1$-$C_6$)alkoxycarbonylamino, heterocyclylcarbonyl, heterocyclylcarbonylamino, ($C_3$-$C_7$)cycloalkyloxycarbonyl and the like, include groups wherein the ($C_1$-$C_6$)alkyl, ($C_1$-$C_6$)alkoxy, aryl, ($C_3$-$C_7$)cycloalkyl and heterocyclyl moieties are as above defined.

When R1 or R2 (when n is 1 or 2) are linked to a ring carbon, all the possible stereoisomers are included in general formula (I). As an example, when A is a 1,4-disubstituted 6-membered cycloalkyl, both cis and trans isomers are covered by the present invention.

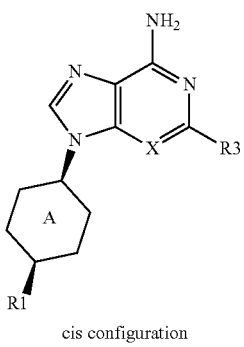

cis configuration

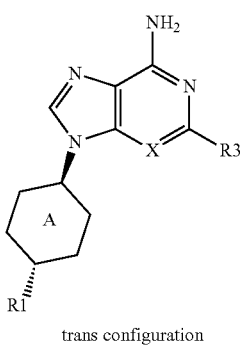

trans configuration

Preferred compounds of formula (I) are the compounds wherein:
X is CH or nitrogen;
A is a 6- or 7-membered cycloalkyl or a 6- or 7-membered nitrogen-containing heterocyclyl, or A is a 7- to 9-membered carbon bicyclic system, in which one ring carbon is optionally replaced by a nitrogen; R1 is linked:
either
1) to any A ring carbon, in which case R1 is fluorine, —COOR4, —CONR4R5, —NR4COOR6, —NR4COR5, —NR4R5, —NR4CONR4R5, —NR4CSNR4R5, or —NR4SO$_2$R6;
or
2) to the A ring nitrogen, if present, in which case R1 is —COR5, —COOR6, —CONR4R5, —CSNR4R5, or —SO$_2$R6;
wherein
R4 and R5 are independently hydrogen or an optionally substituted group selected from (C$_1$-C$_6$)alkyl, (C$_3$-C$_7$)cycloalkyl, heterocyclyl, aryl, aryl(C$_1$-C$_6$)alkyl, heteroaryl and heteroaryl(C$_1$-C$_6$)alkyl; or R4 and R5, taken together with the nitrogen atom to which they are bonded, may form an optionally substituted 5- or 6-membered heterocyclyl group optionally containing one additional heteroatom selected from N, O and S;
R6 is an optionally substituted group selected from (C$_1$-C$_6$)alkyl, (C$_3$-C$_7$)cycloalkyl, heterocyclyl, aryl, aryl(C$_1$-C$_6$)alkyl, heteroaryl and heteroaryl(C$_1$-C$_6$)alkyl;
n is 0, 1 or 2;
R2 is linked to any A ring atom and is selected from the group consisting of fluorine, an optionally substituted (C$_1$-C$_6$)alkyl and NR4R5;
provided that
when R2 is fluorine or NR4R5, then R2 is linked to a ring carbon;
when n is 2, then the R2 groups are not necessarily the same;
wherein the R1 and R2 groups can be linked to the same ring carbon;
R3 is hydrogen, halogen, cyano or an optionally substituted group selected from polyfluorinated (C$_1$-C$_6$)alkyl, (C$_3$-C$_7$)cycloalkyl, (C$_2$-C$_6$)alkynyl, heterocyclyl, aryl, heteroaryl, —OR6 or —CONR4R5, wherein R4, R5 and R6 are as defined above;
provided that when X is nitrogen, then R3 is different from hydrogen;
or a pharmaceutically acceptable salt thereof.

More preferred compounds of formula (I) are the compounds wherein:
X is CH or nitrogen;
A is a 6-membered cycloalkyl or a 6-membered nitrogen-containing heterocyclyl;
R1 is linked:
either
1) to any A ring carbon, in which case R1 is —CONR4R5, —NR4COR5, —NR4CONR4R5, —NR4CSNR4R5, or —NR4SO$_2$R6,
or
2) to the A ring nitrogen, in which case R1 is —COR5, —CONR4R5, —CSNR4R5 or —SO$_2$R6;
wherein
R4 and R5 are independently hydrogen or an optionally substituted group selected from (C$_1$-C$_6$)alkyl, aryl and heteroaryl, and;
R6 is an optionally substituted group selected from (C$_1$-C$_6$)alkyl, aryl and heteroaryl;
n is 0, 1 or 2;
R2 is an optionally substituted (C$_1$-C$_6$)alkyl;
provided that
when n is 2, then the R2 groups are not necessarily the same;
wherein the R1 and R2 groups can be linked to the same ring carbon;
R3 is halogen, cyano or an optionally substituted group selected from polyfluorinated(C$_1$-C$_6$)alkyl, (C$_2$-C$_6$)alkynyl, aryl, heteroaryl, —OR6 and —CONR4R5, wherein R4, R5 and R6 are as defined above;
or a pharmaceutically acceptable salt thereof.

Even more preferred compounds of formula (I) are the compounds of formula (I)' represented below

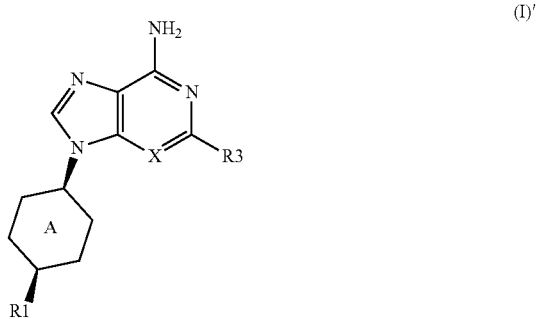

wherein:
X is nitrogen;
A is a 6-membered cycloalkyl, wherein A has a cis-1,4-disubstituted configuration;
R1 is linked:
to any A ring carbon, in which case R1 is —CONR4R5, —NR4COR5, —NR4CONR4R5;

wherein R4 and R5 are independently hydrogen or an optionally substituted group selected from aryl and heteroaryl;

n is 0;

R3 is halogen, cyano or an optionally substituted group selected from ($C_2$-$C_6$)alkynyl, aryl, heteroaryl and —OR6, wherein R6 is an optionally substituted ($C_1$-$C_6$)alkyl;

or a pharmaceutically acceptable salt thereof.

Preferred specific compounds (cpd) of formula (I), or a pharmaceutically acceptable salt thereof, are the compounds listed below:

cis-4-(6-amino-2-chloro-9H-purin-9-yl)-N-(3-methoxyphenyl)cyclohexanecarboxamide (cpd 3), cis-4-[6-amino-2-(pyridin-3-yl)-9H-purin-9-yl]-N-(3-methoxyphenyl)cyclohexanecarboxamide (cpd 4), cis-4-[6-amino-2-(pyridin-4-yl)-9H-purin-9-yl]-N-(3-methoxyphenyl)cyclohexanecarboxamide (cpd 9), cis-4-[6-amino-2-(2-fluoropyridin-4-yl)-9H-purin-9-yl]-N-(3-methoxyphenyl)cyclohexanecarboxamide (cpd 15), cis-4-[6-amino-2-(4-hydroxyphenyl)-9H-purin-9-yl]-N-(3-methoxyphenyl)cyclohexanecarboxamide (cpd 17), cis-4-[6-amino-2-(3-hydroxyphenyl)-9H-purin-9-yl]-N-(3-methoxyphenyl)cyclohexanecarboxamide (cpd 18), cis-4-[6-amino-2-(6-fluoropyridin-3-yl)-9H-purin-9-yl]-N-(3-methoxyphenyl)cyclohexanecarboxamide (cpd 19), cis-4-[6-amino-2-(2-methoxypyridin-4-yl)-9H-purin-9-yl]-N-(3-methoxyphenyl)cyclohexanecarboxamide (cpd 21), 3-(6-amino-9-{cis-4-[(3-methoxyphenyl)carbamoyl]cyclohexyl}-9H-purin-2-yl)benzamide (cpd 26), cis-4-(6-amino-2-chloro-9H-purin-9-yl)-N-{4-[(trifluoromethyl)sulfonyl]phenyl}cyclohexanecarboxamide (cpd 27), 4-(6-amino-9-{cis-4-[(3-methoxyphenyl)carbamoyl]cyclohexyl}-9H-purin-2-yl)-N-{4-[(4-methylpiperazin-1-yl)methyl]phenyl}benzamide (cpd 29), 3-(6-amino-9-{cis-4-[(3-methoxyphenyl)carbamoyl]cyclohexyl}-9H-purin-2-yl)-N-{4-[(4-methylpiperazin-1-yl)methyl]phenyl}benzamide (cpd 30), 3-(6-amino-9-{cis-4-[(3-methoxyphenyl)carbamoyl]cyclohexyl}-9H-purin-2-yl)-N-(4-{[4-(dimethyl amino)piperidin-1-yl]methyl}phenyl)benzamide (cpd 31), cis-4-(6-amino-2-chloro-9H-purin-9-yl)-N-(3,4-dimethoxyphenyl)cyclohexanecarboxamide (cpd 32), 4-(6-amino-9-{cis-4-[(3-methoxyphenyl)carbamoyl]cyclohexyl}-9H-purin-2-yl)-N-(4-{[4-(dimethylamino)piperidin-1-yl]methyl}phenyl)benzamide (cpd 33), cis-4-(6-amino-2-chloro-9H-purin-9-yl)-N-{4-[2-({4-[(4-methylpiperazin-1-yl)methyl]-3-(trifluoromethyl)phenyl}amino)-2-oxoethyl]phenyl}cyclohexanecarboxamide (cpd 35), cis-4-(6-amino-2-chloro-9H-purin-9-yl)-N-{4-[2-({4-[(4-methylpiperazin-1-yl)methyl]phenyl}amino)-2-oxoethyl]phenyl}cyclohexanecarboxamide (cpd 36), cis-4-[6-amino-2-(pyridin-4-yl)-9H-purin-9-yl]-N-(3,4-dimethoxyphenyl)cyclohexanecarboxamide (cpd 37), cis-4-(6-amino-2-iodo-9H-purin-9-yl)-N-(3-methoxyphenyl)cyclohexanecarboxamide (cpd 41), cis-4-(6-amino-2-ethynyl-9H-purin-9-yl)-N-(3-methoxyphenyl)cyclohexanecarboxamide (cpd 45), cis-4-(6-amino-2-chloro-9H-purin-9-yl)-N-(3-methylphenyl)cyclohexanecarboxamide (cpd 48), cis-4-[6-amino-2-(pyridin-4-yl)-9H-purin-9-yl]-N-(3-methylphenyl)cyclohexanecarboxamide (cpd 50), cis-4-(6-amino-2-chloro-9H-purin-9-yl)cyclohexanecarboxamide (cpd 53), cis-4-[6-amino-2-(3-hydroxyprop-1-yn-1-yl)-9H-purin-9-yl]-N-(3-methoxyphenyl)cyclohexanecarboxamide (cpd 60), cis-4-(6-amino-2-chloro-9H-purin-9-yl)-N-[5-(trifluoromethyl)-1,3,4-thiadiazol-2-yl]cyclohexanecarboxamide (cpd 64), cis-4-(6-amino-2-chloro-9H-purin-9-yl)-N-(4-methyl-1,3-thiazol-2-yl)cyclohexanecarboxamide (cpd 65), cis-4-(6-amino-2-chloro-9H-purin-9-yl)-N-(1,3-benzothiazol-6-yl)cyclohexanecarboxamide (cpd 69), cis-4-(6-amino-2-iodo-9H-purin-9-yl)-N-(4-methyl-1,3-thiazol-2-yl)cyclohexanecarboxamide (cpd 70), 4-({[cis-4-(6-amino-2-chloro-9H-purin-9-yl)cyclohexyl]carbonyl}amino)-N-cyclohexylbenzamide (cpd 71), cis-4-(6-amino-2-chloro-9H-purin-9-yl)-N-(1,3-thiazol-2-yl)cyclohexanecarboxamide (cpd 72), cis-4-(6-amino-2-chloro-9H-purin-9-yl)-N-(5-methyl-1,3-thiazol-2-yl)cyclohexanecarboxamide (cpd 73), cis-4-(6-amino-2-chloro-9H-purin-9-yl)-N-(4-phenyl-1,3-thiazol-2-yl)cyclohexanecarboxamide (cpd 74), cis-4-(6-amino-2-chloro-9H-purin-9-yl)-N-(1,3-benzothiazol-2-yl)cyclohexanecarboxamide (cpd 75), cis-4-(6-amino-2-chloro-9H-purin-9-yl)-N-(pyridin-2-yl)cyclohexanecarboxamide (cpd 76), cis-4-(6-amino-2-ethynyl-9H-purin-9-yl)-N-(4-methyl-1,3-thiazol-2-yl)cyclohexanecarboxamide (cpd 77), cis-4-(6-amino-2-chloro-9H-purin-9-yl)-N-(1H-imidazol-2-yl)cyclohexanecarboxamide (cpd 79), cis-4-[6-amino-2-(pyridin-4-yl)-9H-purin-9-yl]-N-(4-methyl-1,3-thiazol-2-yl)cyclohexanecarboxamide (cpd 81), cis-4-(6-amino-2-methoxy-9H-purin-9-yl)-N-(3-methoxyphenyl)cyclohexanecarboxamide (cpd 83), cis-4-(6-amino-2-methoxy-9H-purin-9-yl)-N-(4-methyl-1,3-thiazol-2-yl)cyclohexanecarboxamide (cpd 84), 3-(6-amino-9-{cis-4-[(4-methyl-1,3-thiazol-2-yl)carbamoyl]cyclohexyl}-9H-purin-2-yl)-N-(4-{[4-(dimethylamino)piperidin-1-yl]methyl}phenyl)benzamide bis-trifluoroacetate (cpd 85), cis-4-(6-amino-2-chloro-9H-purin-9-yl)-N-{4-[2-(1,4'-bipiperidin-1'-yl)-2-oxoethyl]-1,3-thiazol-2-yl}cyclohexanecarboxamide (cpd 86), cis-4-(6-amino-2-cyclopropyl-9H-purin-9-yl)-N-(3-methoxyphenyl)cyclohexanecarboxamide (cpd 87), methyl cis-4-(6-amino-2-chloro-9H-purin-9-yl)cyclohexanecarboxylate (cpd 88), cis-4-(6-amino-2-chloro-9H-purin-9-yl)-N-[6-(methylsulfonyl)-1,3-benzothiazol-2-yl]cyclohexanecarboxamide (cpd 89), cis-4-(6-amino-2-chloro-9H-purin-9-yl)-N-(6-chloro-1,3-benzothiazol-2-yl)cyclohexanecarboxamide (cpd 90), cis-4-(6-amino-2-chloro-9H-purin-9-yl)-N-(4-methoxy-1,3-benzothiazol-2-yl)cyclohexanecarboxamide (cpd 91), cis-4-(6-amino-2-chloro-9H-purin-9-yl)-N-(6-methoxy-1,3-benzothiazol-2-yl)cyclohexanecarboxamide (cpd 92), cis-4-(6-amino-2-chloro-9H-purin-9-yl)-N-(5,6-dimethyl-1,3-benzothiazol-2-yl)cyclohexanecarboxamide (cpd 93), cis-4-(6-amino-2-chloro-9H-purin-9-yl)-N-(5-chloro-1,3-benzoxazol-2-yl)cyclohexanecarboxamide (cpd 94), cis-4-(6-amino-2-chloro-9H-purin-9-yl)-N-(1-methyl-1H-benzimidazol-2-yl)cyclohexanecarboxamide (cpd 95), 3-(6-amino-9-{cis-4-[(4-methyl-1,3-thiazol-2-yl)carbamoyl]cyclohexyl}-9H-purin-2-yl)benzamide (cpd 96), 3-(6-amino-9-{trans-4-[(4-methyl-1,3-thiazol-2-yl)carbamoyl]cyclohexyl}-9H-purin-2-yl)benzamide (cpd 97), cis-4-{6-amino-2-[(trimethylsilyl)ethynyl]-9H-purin-9-yl}-N-(4-methyl-1,3-thiazol-2-yl)cyclohexanecarboxamide (cpd 98), cis-4-{6-amino-2-[3-(benzyloxy)phenyl]-9H-purin-9-yl}-N-(4-methyl-1,3-thiazol-2-yl)cyclohexanecarboxamide (cpd 100), cis-4-(6-amino-2-cyano-9H-purin-9-yl)-N-(4-methyl-1,3-thiazol-2-yl)cyclohexanecarboxamide (cpd 102), cis-4-[6-amino-2-(3-hydroxyphenyl)-9H-purin-9-yl]-N-(4-methyl-1,3-thiazol-2-yl)cyclohexanecarboxamide (cpd 103), cis-4-[6-amino-2-(1H-pyrazol-3-yl)-9H-purin-9-yl]-N-(3-methoxyphenyl)cyclohexanecarboxamide (cpd 107), cis-4-(6-amino-2-chloro-9H-purin-9-yl)-N-(5-methyl-1,3,4-thiadiazol-2-yl)cyclohexanecarboxamide (cpd 108), cis-4-(6-amino-2-chloro-9H-purin-9-yl)-N-(1,5-dimethyl-1H-pyrazol-3-yl)cyclohexanecarboxamide (cpd 109), cis-4-[6-amino-2-(1H-pyrazol-3-yl)-9H-purin-9-yl]-N-(4-methyl-1,3-thiazol-2-yl)cyclohexanecarboxamide (cpd 112), trans-4-[6-amino-2-(1H-pyrazol-3-yl)-9H-purin-9-yl]-N-(4-methyl-1,3-thiazol-2-yl)cyclohexanecarboxamide (cpd 113), cis-4-(6-amino-2-chloro-9H-purin-9-yl)-N-(5-chloro-1,3-thiazol-2-yl)cyclohexanecarboxamide (cpd 114), cis-4-(6-amino-2-chloro-9H-purin-9-yl)-N-[4-(trifluoromethyl)-1,3-thiazol-2-yl]cyclohexanecarboxamide (cpd 115), cis-4-(6-amino-2-iodo-9H-purin-9-yl)-N-(4-methoxy-1,3-benzothiazol-2-yl)cyclohexanecarboxamide (cpd 116), cis-4-(6-amino-2-ethynyl-9H-purin-9-yl)-N-(4-methoxy-1,3-benzothiazol-2-yl)cyclohexanecarboxamide (cpd 119), cis-4-(6-amino-2-chloro-9H-purin-9-yl)-N-{4-[(4-aminopiperidin-1-yl)methyl]-1,3-thiazol-2-yl}cyclohexanecarboxamide (cpd 120), cis-4-(6-amino-2-chloro-9H-purin-9-yl)-N-(4-hydroxy-1,3-benzothiazol-2-yl)cyclohexanecarboxamide (cpd 122), cis-4-(6-amino-2-fluoro-9H-purin-9-yl)-N-(4-methyl-1,3-thiazol-2-yl)cyclohexanecarboxamide (cpd 124), cis-4-(6-amino-2-fluoro-9H-purin-9-yl)-N-(4-methoxy-1,3-benzothiazol-2-yl)cyclohexanecarboxamide (cpd 126), cis-4-(6-amino-2-fluoro-9H-purin-9-yl)-N-(4-hydroxy-1,3-benzothiazol-2-yl)cyclohexanecarboxamide (cpd 127), cis-4-(6-amino-2-fluoro-9H-purin-9-yl)-N-(6-fluoro-1,3-benzothiazol-2-yl)cyclohexanecarboxamide (cpd 128), cis-4-[6-amino-2-(trifluoromethyl)-9H-purin-9-yl]-N-(4-methyl-1,3-thiazol-2-yl)cyclohexanecarboxamide (cpd 129), cis-4-[6-amino-2-(trifluoromethyl)-9H-purin-9-yl]-N-(6-fluoro-1,3-benzothiazol-2-yl)cyclohexanecarboxamide (cpd 132), cis-4-(6-amino-2-chloro-9H-purin-9-yl)-N-(6-fluoro-1,3-benzothiazol-2-yl)cyclohexanecarboxamide (cpd 134), cis-4-(6-amino-2-chloro-9H-purin-9-yl)-N-[4-(2-amino-2-oxoethyl)-1,3-thiazol-2-yl]cyclohexanecarboxamide (cpd 135), cis-4-(6-amino-2-chloro-9H-purin-9-yl)-N-(6-hydroxy-1,3-benzothiazol-2-yl)cyclohexanecarboxamide (cpd 137), cis-4-(6-amino-2-chloro-9H-purin-9-yl)-N-([1,3]thiazolo[5,4-c]pyridin-2-yl)cyclohexanecarboxamide (cpd 138), N-[cis-4-(6-amino-2-chloro-9H-purin-9-yl)cyclohexyl]-4-methyl-1,3-thiazole-2-carboxamide (cpd 139), N-[cis-4-(6-amino-2-chloro-9H-purin-9-yl)cyclohexyl]-1,3-benzothiazole-2-carboxamide (cpd 140), N-[cis-4-(6-amino-2-chloro-9H-purin-9-yl)cyclohexyl]-3-methoxybenzenesulfonamide (cpd 141), N-[cis-4-(6-amino-2-chloro-9H-purin-9-yl)cyclohexyl]-3-methoxybenzamide (cpd 144), 6-amino-9-{cis-4-[(4-methyl-1,3-thiazol-2-yl)carbamoyl]cyclohexyl}-9H-purine-2-carboxamide (cpd 146), 2-amino-1,3-benzothiazol-6-yl cis-4-(6-amino-2-chloro-9H-purin-9-yl)cyclohexanecarboxylate (cpd 159), 2-amino-1,3-benzothiazol-4-yl cis-4-(6-amino-2-fluoro-9H-purin-9-yl)cyclohexanecarboxylate (cpd 160), 2-({[cis-4-(6-amino-2-chloro-9H-purin-9-yl)cyclohexyl]carbonyl}amino)-1,3-benzothiazole-6-carboxamide (cpd 163), cis-4-(6-amino-2-chloro-9H-purin-9-yl)-N-[4-(2-amino-2-oxoethyl)-1,3-thiazol-2-yl]-N-methylcyclohexanecarboxamide (cpd 164), cis-4-(6-amino-2-chloro-9H-purin-9-yl)-N-[6-(dimethylamino)-1,3-benzothiazol-2-yl]cyclohexanecarboxamide (cpd 165), cis-4-(6-amino-2-chloro-9H-purin-9-yl)-N-[5-(2-amino-2-oxoethyl)-1,3-thiazol-2-yl]cyclohexanecarboxamide (cpd 166), cis-4-(6-amino-2-chloro-9H-purin-9-yl)-N-(4,6-difluoro-1,3-benzothiazol-2-yl)cyclohexanecarboxamide (cpd 167), cis-4-(6-amino-2-chloro-9H-purin-9-yl)-N-(5,6-difluoro-1,3-benzothiazol-2-yl)cyclohexanecarboxamide (cpd 168), tert-butyl 2-({[cis-4-(6-amino-2-chloro-9H-purin-9-yl)cyclohexyl]carbonyl}amino)-6,7-dihydro[1,3]thiazolo[5,4-c]pyridine-5(4H)-carboxylate (cpd 169), cis-4-(6-amino-2-methoxy-9H-purin-9-yl)-N-(6-fluoro-1,3-benzothiazol-2-yl)cyclohexanecarboxamide (cpd 170), cis-4-(6-amino-2-chloro-9H-purin-9-yl)-N-(5,6,7-trifluoro-1,3-benzothiazol-2-yl)cyclohexanecarboxamide (cpd 171), cis-4-(6-amino-2-chloro-9H-purin-9-yl)-N-(4,5,6,7-tetrahydro[1,3]thiazolo[5,4-c]pyridin-2-yl)cyclohexanecarboxamide hydrochloride (cpd 172), cis-4-(6-amino-2-chloro-9H-purin-9-yl)-N-(5-methyl-4,5,6,7-tetrahydro[1,3]thiazolo[5,4-c]pyridin-2-yl)cyclohexanecarboxamide (cpd 173), methyl [2-({[cis-4-(6-amino-2-chloro-9H-purin-9-yl)cyclohexyl]carbonyl}amino)-1,3-benzothiazol-6-yl]acetate (cpd 174), cis-4-(6-amino-2-chloro-9H-purin-9-yl)-N-(6-bromo-1,3-benzothiazol-2-yl)cyclohexanecarboxamide (cpd 175),

[2-({[cis-4-(6-amino-2-chloro-9H-purin-9-yl)cyclohexyl]carbonyl}amino)-1,3-benzothiazol-6-yl]acetic acid (cpd 176), cis-4-(6-amino-2-chloro-9H-purin-9-yl)-N-[6-(2-amino-2-oxoethyl)-1,3-benzothiazol-2-yl]cyclohexanecarboxamide (cpd 177), cis-4-(6-amino-2-chloro-9H-purin-9-yl)-N-(4,4,6,6-tetramethyl-4,5,6,7-tetrahydro[1,3]thiazolo[5,4-c]pyridin-2-yl)cyclohexanecarboxamide (cpd 178), cis-4-(6-amino-2-fluoro-9H-purin-9-yl)-N-(5-methyl-4,5,6,7-tetrahydro[1,3]thiazolo[5,4-c]pyridin-2-yl)cyclohexanecarboxamide (cpd 179), cis-4-(6-amino-2-chloro-9H-purin-9-yl)-N-[6-(difluoromethoxy)-1,3-benzothiazol-2-yl]cyclohexanecarboxamide (cpd 180), cis-4-(6-amino-2-chloro-9H-purin-9-yl)-N-[6-(trifluoromethoxy)-1,3-benzothiazol-2-yl]cyclohexanecarboxamide (cpd 181), cis-4-(6-amino-2-chloro-9H-purin-9-yl)-N-[5-(propan-2-yl)-4,5,6,7-tetrahydro[1,3]thiazolo[5,4-c]pyridin-2-yl]cyclohexanecarboxamide (cpd 182), cis-N-[6-(acetylamino)-1,3-benzothiazol-2-yl]-4-(6-amino-2-chloro-9H-purin-9-yl)cyclohexanecarboxamide (cpd 183), cis-4-(6-amino-2-chloro-9H-purin-9-yl)-N-(5-cyclopropyl-4,5,6,7-tetrahydro[1,3]thiazolo[5,4-c]pyridin-2-yl)cyclohexanecarboxamide (cpd 184), cis-4-(6-amino-2-chloro-9H-purin-9-yl)-N-(6,7-dihydro-4H-pyrano[4,3-d][1,3]thiazol-2-yl)cyclohexanecarboxamide (cpd 185), cis-4-(6-amino-2-chloro-9H-purin-9-yl)-N-([1,3]dioxolo[4,5-f][1,3]benzothiazol-6-yl)cyclohexanecarboxamide (cpd 186), tert-butyl (5S,8R)-2-({[cis-4-(6-amino-2-chloro-9H-purin-9-yl)cyclohexyl]carbonyl}amino)-5,6,7,8-tetrahydro-4H-5,8-epiminocyclohepta[d][1,3]thiazole-9-carboxylate (cpd 187), cis-4-(6-amino-2-chloro-9H-purin-9-yl)-N-(6,6-difluoro-4,5,6,7-tetrahydro-1,3-benzothiazol-2-yl)cyclohexanecarboxamide (cpd 188), cis-4-(6-amino-2-chloro-9H-purin-9-yl)-N-[(5S,8R)-5,6,7,8-tetrahydro-4H-5,8-epiminocyclohepta[d][1,3]thiazol-2-yl]cyclohexanecarboxamide hydrochloride (cpd 189), cis-4-(6-amino-2-fluoro-9H-purin-9-yl)-N-(4,4,6,6-tetramethyl-4,5,6,7-tetrahydro[1,3]thiazolo[5,4-c]pyridin-2-yl)cyclohexanecarboxamide (cpd 190), cis-4-(6-amino-2-fluoro-9H-purin-9-yl)-N-(6,6-difluoro-4,5,6,7-tetrahydro-1,3-benzothiazol-2-yl)cyclohexanecarboxamide (cpd 191), cis-4-(6-amino-2-chloro-9H-purin-9-yl)-N-(5,5-dioxido-6,7-dihydro-4H-thiopyrano[4,3-d][1,3]thiazol-2-yl)cyclohexanecarboxamide (cpd 194), cis-4-(6-amino-2-chloro-9H-purin-9-yl)-N-(6,6-dimethyl-6,7-dihydro-4H-pyrano[4,3-d][1,3]thiazol-2-yl)cyclohexanecarboxamide (cpd 195), cis-4-(6-amino-2-chloro-9H-purin-9-yl)-N-[5-(2-amino-2-oxoethyl)-4,5,6,7-tetrahydro[1,3]thiazolo[5,4-c]pyridin-2-yl]cyclohexanecarboxamide (cpd 196), 1-[cis-4-(6-amino-2-chloro-9H-purin-9-yl)cyclohexyl]-3-(3-methoxyphenyl)urea (cpd1 197), cis-4-(6-amino-2-iodo-9H-purin-9-yl)-N-(5-methyl-4,5,6,7-tetrahydro[1,3]thiazolo[5,4-c]pyridin-2-yl)cyclohexanecarboxamide (cpd 198), cis-4-{6-amino-2-[(trimethylsilyl)ethynyl]-9H-purin-9-yl}-N-(5-methyl-4,5,6,7-tetrahydro[1,3]thiazolo[5,4-c]pyridin-2-yl)cyclohexanecarboxamide (cpd 199), cis-4-(6-amino-2-fluoro-9H-purin-9-yl)-N-(6,7-dihydro-4H-pyrano[4,3-d][1,3]thiazol-2-yl)cyclohexanecarboxamide (cpd 200), cis-4-(6-amino-2-ethynyl-9H-purin-9-yl)-N-(5-methyl-4,5,6,7-tetrahydro[1,3]thiazolo[5,4-c]pyridin-2-yl)cyclohexanecarboxamide (cpd 201), cis-4-(4-amino-1H-imidazo[4,5-c]pyridin-1-yl)-N-(4-methyl-1,3-thiazol-2-yl)cyclohexanecarboxamide (cpd 204), cis-4-(6-amino-2-chloro-9H-purin-9-yl)-N-(4,5,6,7-tetrahydro-1,3-benzothiazol-2-yl)cyclohexanecarboxamide (cpd 205), cis-4-(6-amino-2-fluoro-9H-purin-9-yl)-N-(4,5,6,7-tetrahydro-1,3-benzothiazol-2-yl)cyclohexanecarboxamide (cpd 206).

The present invention also provides processes for the preparation of the compound of general formula (I) as defined above, by using the reaction routes and synthetic schemes described below, employing the techniques available in the art and starting materials readily available. The preparation of certain embodiments of the present invention is described in the examples that follow, but those of ordinary skill in the art will recognize that the preparations described may be readily adapted to prepare other embodiments of the present invention. For example, the synthesis of non-exemplified compounds according to the invention may be performed by apparent modifications to those skilled in the art, for instance by appropriately protecting interfering groups, by suitably replacing reagents with others known in the art, or by making routine modifications of reaction conditions. Alternatively, other reactions referred to herein or known in the art will be recognized as having adaptability for preparing other compounds of the invention. The compounds of this invention can be prepared from readily available starting materials using the following general methods and procedures. Unless otherwise indicated, the starting materials are known compounds or may be prepared from known compounds according to well known procedures. It will be appreciated that, where typical or preferred process conditions (i.e. reaction temperatures, times, mole ratios of reactants, solvents, pressures) are described, different process conditions can also be used unless otherwise stated. Optimum reaction conditions may vary with the particular reactants or solvent used, but such conditions can be determined by one skilled in the art by routine optimization procedures. Additionally, as it will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, several protecting groups are described in T. Greene and P.G.M. Wuts, Protecting Groups in Organic Synthesis, Second Edition, Wiley, New York, 1991, and references cited therein.

The compound of general formula (I), as defined above, can be prepared according to the general synthetic processes described in Scheme 1, starting from an intermediate compound of formula (VI):

Scheme 1

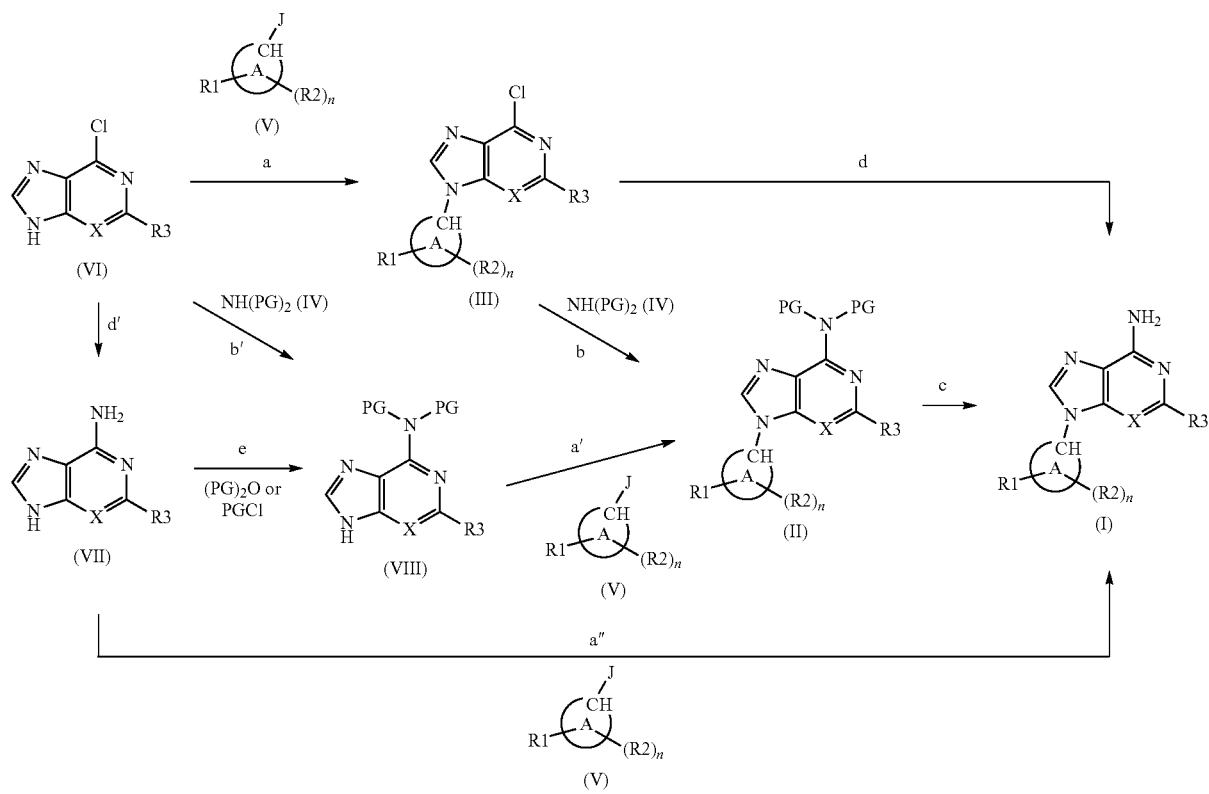

Accordingly, a process of the present invention comprises one of the following sequences of steps: either Sequence A:

Step a) alkylating an intermediate compound of formula (VI):

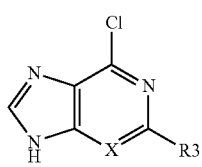
(VI)

wherein X and R3 are as defined above, with an intermediate compound of formula (V):

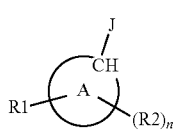
(V)

wherein A, R1, R2 and n are as defined above and J is selected from the group consisting of bromine, iodine, hydroxy, methansulfonyl (-OMs) and p-toluensulfonyl (-OTs);

Step b) substituting the chlorine of the resultant intermediate compound of formula (III)

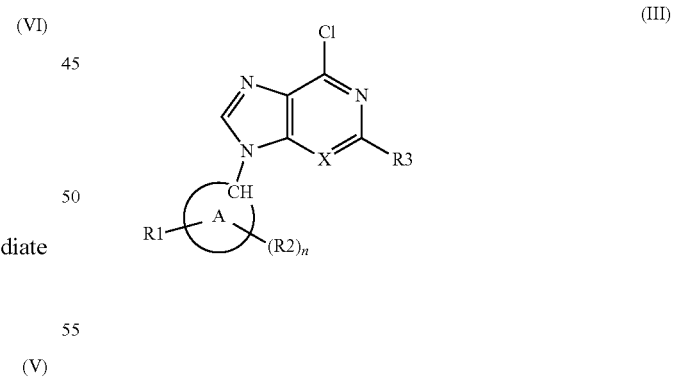
(III)

wherein X, A, R1, R2, R3 and n are as defined above, with a protected nitrogen source compound $NH(PG)_2$ (IV), wherein PG is independently hydrogen or a protecting group —COOR7, wherein R7 is a $(C_1-C_6)$alkyl, such as for instance methyl, ethyl or tert-butyl, or an aryl$(C_1-C_6)$alkyl, such as for instance benzyl, with the proviso that such PGs are not simultaneously hydrogen; and Step c) removing the protecting group(s) PG of the resultant intermediate compound of formula (II)

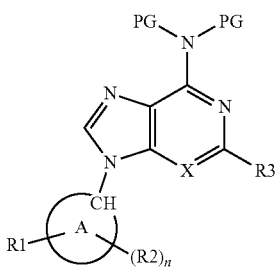

(II)

wherein X, A, R1, R2, R3, PG and n are as defined above, to yield a compound of general formula (I), as defined above;
or
Step d) substituting the chlorine of the intermediate compound of formula (III), resulting from step a), with a nitrogen source, such as an ammonia solution, to yield a compound of general formula (I), as defined above;
or
Sequence B
Step b') substituting the chlorine of an intermediate compound of formula (VI):

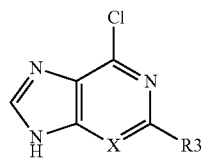

(VI)

wherein X and R3 are as defined above, with a protected nitrogen source compound $NH(PG)_2$ (IV), as described for step b), to yield an intermediate compound of formula (VIII):

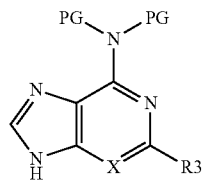

(VIII)

wherein X, R3 and PG are as defined above;
or
Step d') substituting the chlorine of an intermediate compound of formula (VI) with a nitrogen source, such as an ammonia solution, as described for step d); and
Step e), protecting the $NH_2$ group of the resultant intermediate compound of formula (VII)

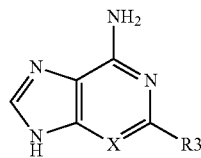

(VII)

wherein X and R3 are as defined above, with a reagent of formula $(PG)_2O$ or PGCl to yield an intermediate compound of formula (VIII), as defined in step b');
then
Step a') alkylating the protected intermediate compound of formula (VIII), resulting from either step b' or step e, with an intermediate compound of formula (V), as defined in step a and in the conditions described therein; Step c) removing the protecting group(s) PG of the resultant intermediate compound of formula (II) as defined above in Sequence A, to yield a compound of general formula (I), as defined above;
or
Sequence C
Step d') substituting the chlorine of an intermediate compound of formula (VI) according to Sequence B;
Step a") alkylating the resulting intermediate compound of formula (VII), as defined in Sequence B, with an intermediate of formula (V), according to the conditions described for step a) in Sequence A;
optionally converting a first compound of formula (I) into a second compound of formula (I), and, if desired, converting a compound of formula (I) into a pharmaceutically acceptable salt thereof or converting a salt into the free compound (I).

According to step a, the alkylation of an intermediate of formula (VI) with an intermediate of formula (V), wherein J is bromine, iodine, -OMs or -OTs, can be carried out in the presence of a suitable base, such as $Na_2CO_3$, $K_2CO_3$, $Cs_2CO_3$, NaH, KH and the like, in a suitable solvent, such as DMF, DMA, ACN, acetone, THF and the like, at a temperature ranging from 0° C. to reflux to give a compound of formula (III), as defined above. When an intermediate of formula (V), wherein J is hydroxy, is used, the reaction is preferentially carried out under Mitsunobu alkylation conditions in the presence of a suitable reagent such as, for instance, diethylazodicarboxylate (DEAD), diisopropylazodicarboxylate (DIAD), ditertbutylazodicarboxylate (DBAD), 1,1'-(azodicarbonyl)dipiperidine (ADDP), and a phosphine reagent such as, for instance, trimethylphosphine, tritertbutylphosphine, triphenylphosphine and the like, in a suitable solvent, such as THF, DMF, DCM, toluene, benzene and the like, at a temperature ranging from 0° C. to 65° C.

According to step b, the substitution of chlorine atom of an intermediate of formula (III) can be carried out in the presence of a nitrogen source of formula $NH(PG)_2$ (IV), wherein PG is as defined above, a palladium catalyst such as $Pd(OAc)_2$, $PdCl_2$ or $Pd_2(dba)_3$, a ligand such as [1,1'-binaphthalene]-2,2'-diylbis[diphenylphosphine] (BINAP) or 4,5-bis(diphenylphosphino)-9,9-dimethylxanthene (Xantphos) and the like, in a suitable solvent such as THF, dioxane, toluene, DMF or ACN and the like, and a base such $Cs_2CO_3$, $K_2CO_3$, LiHMDS or NaHMDS at a temperature ranging from rt to reflux under conventional heating or microwave irradiation, for a time ranging from 1 to about 24 h.

According to step c, the deprotection of an intermediate of formula (II), wherein PG is a protecting group —COOR7 and R7 is a $(C_1\text{-}C_6)$alkyl, such as for instance methyl, ethyl or tert-butyl, can be carried out in acidic conditions, for instance with AcOH, TFA or HCl, or in basic conditions, for instance with NaOH, LiOH or KOH, and in the presence of a suitable solvent, such as MeOH, DCM or 1,4-dioxane, at a temperature ranging from rt to reflux and for a time ranging from 1 to about 12 h. Alternatively when PG is an aryl$(C_1\text{-}C_6)$alkyl, such as for instance benzyl, the reaction can be carried out in the presence of gaseous hydrogen or a hydrogen source, such as, for instance, formic acid, ammonium formate, cyclohexene and 1,4-cyclohexadiene, and a hydrogenation catalyst, such as palladium on carbon, in a suitable solvent, such as EtOH, MeOH, AcOEt or a mixture thereof, at temperatures ranging from rt to reflux for a time varying from 30 minutes to 24 h.

According to step d, the substitution of the chlorine of an intermediate of formula (III) can be carried out in the presence of an ammonia solution in MeOH, isopropanol or water in a solvent such as MeOH, isopropanol or 1,4-dioxane, at a temperature ranging from 60 to 150° C. for a time ranging from 1 to 24 h in classical thermal conditions or in a microwave apparatus.

According to step b', chlorine substitution can be carried out on an intermediate compound of formula (VI) as described above for step b.

According to step d', the substitution of the chlorine of an intermediate compound of formula (VI) can be carried out with a nitrogen source, such as an ammonia solution, as described for step d.

According to step e, the protection of the NH$_2$ group of an intermediate of formula (VII) can be carried out with (R7OOC)$_2$O [(PG)$_2$O] or R7OOCCl (PGCl), wherein R7 is a (C$_1$-C$_6$)alkyl, such as for instance methyl, ethyl or tert-butyl, or an aryl(C$_1$-C$_6$)alkyl, such as for instance benzyl, in the presence of a base, such as TEA, DIPEA, pyridine and the like, optionally with a catalytic amount of DMAP, and in a suitable solvent, such as THF, DCM, ACN or AcOEt, at a temperature ranging from 0° C. to rt for a time ranging from 1 to 24 h. If the protection proceeds further and the protecting group —COOR7 reacts also on one of the nitrogens of the 5-membered ring, this group can be easily removed by treatment with a base such as TEA, DIPEA, a saturated solution of NaHCO$_3$ and the like, in solvents such as MeOH, EtOH at a temperature ranging from rt to reflux for a time ranging from 1 to 4 h.

According to steps a' and a", alkylation of an intermediate compound of formula (VIII) or of formula (VII) with an intermediate compound of formula (V) can be carried out as described above for step a.

A first compound of general formula (I) can be conveniently converted into a second compound of general formula (I) by operating according to well-known synthetic conditions.

The following are examples of possible conversions:

conv. 1) converting a compound of formula (Ia), wherein X, A, R1, R2 and n are as defined above and R3 is chlorine, bromine or iodine, into a compound of formula (Ib), wherein X, A, R1, R2 and n are as defined above and R3 is an optionally substituted group selected from (C$_1$-C$_6$)alkyl, (C$_2$-C$_6$)alkenyl, (C$_2$-C$_6$)alkynyl, (C$_3$-C$_7$)cycloalkyl, heterocyclyl, aryl, heteroaryl, by reaction with reagent R3Q (IX), wherein R3 is as defined above for the compound of formula (Ib) and Q is a group selected from boronic acid, boronic ester, hydrogen and —Sn[(C$_1$-C$_6$)alkyl]$_3$, under cross-coupling conditions:

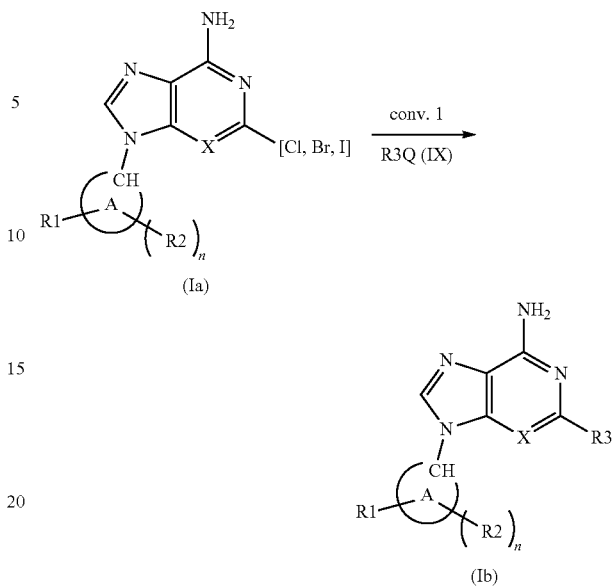

conv. 2) converting a compound of formula (Ia), as defined in conv. 1, into a compound of formula (Ic), wherein X, A, R1, R2 and n are as defined for the compound of formula (Ia) and R3 is —NR4R5, —OR6 or —SR6, wherein R4, R5 and R6 are as defined for general formula (I), by reaction with reagent HNR4R5 (X), R6OY (XI) or R6SY (XII), respectively, wherein R4, R5 and R6 are as defined above and Y is hydrogen, Na$^+$ or K$^+$, under palladium-catalized reaction conditions or nucleophilic substitution conditions:

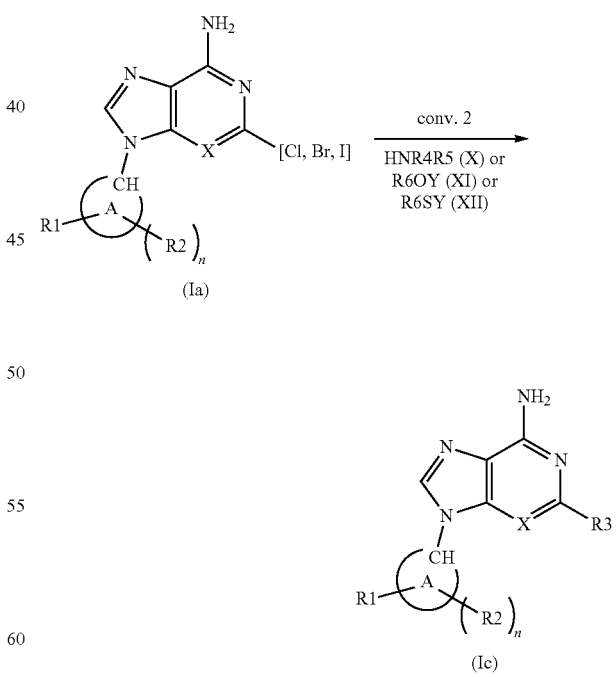

conv. 3) converting a compound of formula (Ic), as defined in conv. 2, into a compound of formula (Id), wherein X, A, R1, R2 and n are as defined above and R3 is —SO$_2$R6 under oxidative conditions;

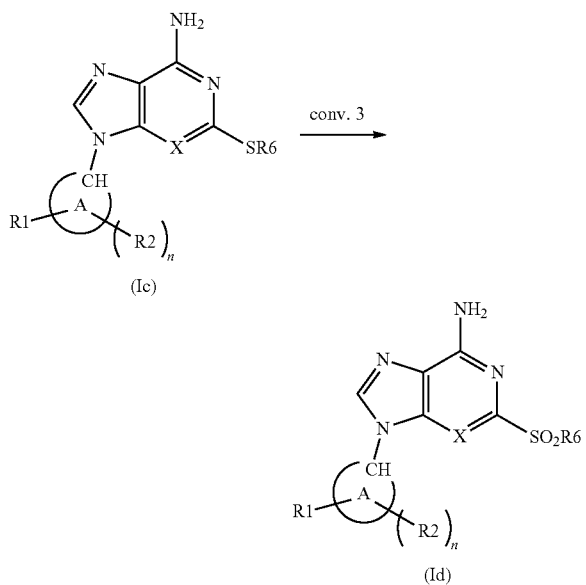

(Ic)

(Id)

conv. 4) converting a compound of formula (Ia), as defined in conv. 1, into a compound of formula (Ie), wherein X, A, R1, R2 and n are as defined above and R3 is cyano, by reaction with reagent M-CN (XIII), wherein M is zinc or copper, under palladium-catalyzed conditions.

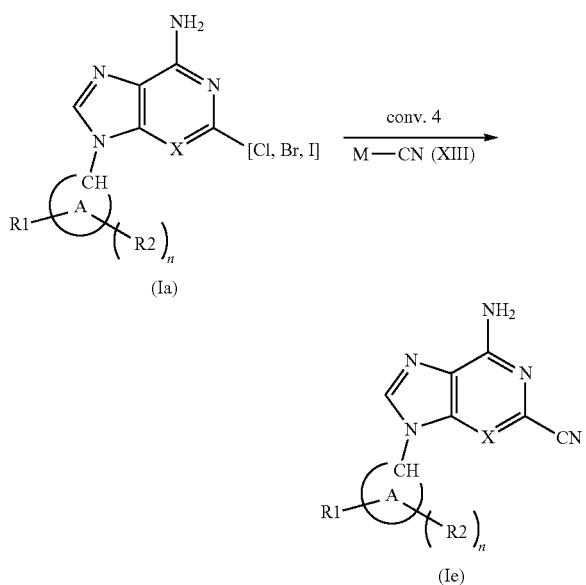

(Ia)

(Ie)

According to conv. 1, a compound of formula (Ia), as defined above, is reacted with a compound of general formula R3Q (IX), wherein R3 is an optionally substituted group selected from $(C_1-C_6)$alkyl, $(C_2-C_6)$alkenyl, $(C_3-C_7)$ cycloalkyl, heterocyclyl, aryl, heteroaryl and Q is a boronic acid or boronic ester, under standard Suzuki coupling conditions using a Pd-based catalyst, such as Pd(dppf)Cl2, PdCl$_2$(PPh$_3$)$_2$ and Pd(PPh$_3$)$_4$, with a suitable base such as Na$_2$CO$_3$, Cs$_2$CO$_3$, K$_3$PO$_4$, in a suitable solvent such as 1,4-dioxane, 1,4-dioxane/water, THF, DMF, toluene and the like, at temperatures ranging from rt to 130° C., in classical thermal conditions or in a microwave apparatus for a time period ranging from 1 hour to 48 h.

Alternatively, a compound of formula (Ia), as defined above, is reacted with a compound of general formula R3Q (IX), wherein R3 is an optionally substituted $(C_2-C_6)$alkynyl and Q is hydrogen, under standard Sonogashira coupling conditions using a Pd-based catalyst, such as Pd(dppf)Cl2, PdCl$_2$(PPh$_3$)$_2$ and Pd(PPh$_3$)$_4$, a suitable solvent, such as ACN, 1,4-dioxane, DME and DMF, in the presence of a base, such as TEA and DIPEA, with cuprous iodide or bromide, at a temperature ranging from rt to 100° C. in classical thermal conditions or in a microwave apparatus, for a time period ranging from 1 hour to 48 h.

Alternatively, a compound of formula (Ia), as defined above, is reacted with a compound of general formula R3Q (IX), wherein R3 is an optionally substituted $(C_2-C_6)$alkenyl and Q is hydrogen, under Heck coupling conditions in the presence of a Pd-based catalyst, like Pd(OAc)$_2$, Pd$_2$(dba)$_3$ or Pd(PPh$_3$)$_4$, with a phosphine ligand like triphenylphospine, in the presence of a base such as TEA, DIPEA, NaOAc or NaHCO$_3$, in a suitable solvent such as ACN, DMA, DMF and the like, at a temperature ranging from rt to 100° C. in classical thermal conditions or in a microwave apparatus for a time period ranging from 1 hour to 48 h.

Alternatively, a compound of formula (Ia), as defined above, is reacted with a compound of general formula R3Q (IX), wherein R3 is an optionally substituted $(C_2-C_6)$alkenyl and Q is $-Sn[(C_1-C_6)alkyl]_3$, under standard conditions as for Stille coupling in the presence of a Pd-based catalyst like Pd(OAc)$_2$, Pd$_2$(dba)$_3$ or Pd(PPh$_3$)$_4$, with a phosphine ligand like P(2-furanyl)$_3$, in a suitable solvent such as DMF, DMA, toluene, NMP and the like, at a temperature ranging from rt to 100° C. in classical thermal conditions or in a microwave apparatus, for a time period ranging from 1 hour to 48 h.

According to conv. 2, a compound of general formula (Ia), as defined above, is reacted with a compound of general formula HNR4R5 (X) or R6OY (XI) or R6SY (XII), wherein R4, R5 and R6 are as defined above and Y is hydrogen, in a suitable solvent such as THF, dioxane, toluene, DMF or ACN, in the presence of a Pd-based catalyst such as Pd(OAc)$_2$ or Pd$_2$(dba)$_3$, a phosphine ligand like 2-dicyclohexylphosphino-2'-(N,N-dimethylamino)-biphenyl, BINAP, 2-(dicyclohexylphosphino)-2',4',6'-triisopropyl-1,1'-biphenyl (XPhos) or 1,3-(2,4,6-trimethylphenyl) imidazolium chloride (*Tetrahedron Lett.* 2001, 42, 8751-8755) and a base such as LiHTMS, Cs$_2$CO$_3$, K$_2$CO$_3$ or KOtBu at a temperature ranging from rt to reflux and for a time ranging from 1 to about 48 h.

Alternatively, the reaction can be carried out with a compound of general formula HNR4R5 (X) or R6OY (XI) or R6SY (XII), wherein R4, R5 and R6 are as defined above and Y is a metal ion, like for instance Na$^+$ or K$^+$, in a suitable solvent such as DMF, DMA, n-butanol, NMP and THF, at a temperature ranging from rt to 150° C. and for a time ranging from 1 to about 48 h in classical thermal conditions or in a microwave apparatus.

According to conv. 3, the oxidation of a compound of general formula (Ic), as defined above, can be carried out with an oxidant agent well-known to those skilled in the art, such as for instance, oxone or m-chloroperbenzoic acid in a suitable solvent, such as THF, 1,4-dioxane, acetone, or DCM, at rt and for a time ranging from about 1 to about 4 h.

According to conv. 4, a compound of formula (Ia), as defined above, is reacted with a cyanide source, selected from a compound of formula M-CN (XIII), wherein M is zinc or copper, in the presence of Pd(OAc)$_2$ or Pd(PPh$_3$)$_4$ as catalyst, Na$_2$CO$_3$, K$_2$CO$_3$ or Cs$_2$CO$_3$ as base, in a suitable solvent such as DMF, NMP, or DMA, from 80° C. to reflux in classical thermal conditions or in a microwave apparatus, for a time ranging from 4 to about 24 h.

In addition, a first compound of general formula (I), as defined above and wherein R1 group has selected meanings and is linked to a ring carbon [compound of formula (If)], can be conveniently converted into a second compound of formula (I), precisely a compound of formula (Ig)-(Ii), by operating according to well-known synthetic conditions, as shown in Scheme 2:

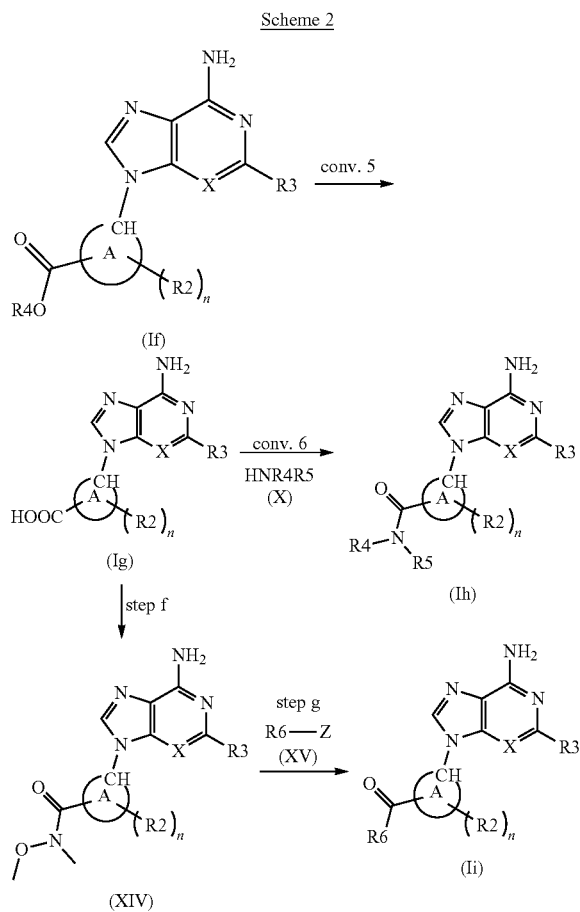

conv. 5) converting a compound of formula (If), wherein X, A, R2, R3 and n are as defined for a compound of general formula (I), and R4 is ($C_1$-$C_6$)alkyl, such as for instance methyl, ethyl or tert-butyl, into a compound of formula (Ig), wherein X, A, R2, R3 and n are as defined above and R4 is hydrogen, under acidic or basic conditions;
conv. 6) converting a compound of formula (Ig), as defined in conv. 5, into a compound of formula (Ih), wherein X, A, R2, R3 and n are as defined above and R4 and R5 are as defined for a compound of general formula (I);
step f) reacting a compound of formula (Ig), as defined in conv. 5, with NHMeOMe hydrochloride and in the presence of a suitable condensing agent, to obtain an intermediate Weinreb amide of formula (XIV), wherein X, A, R2, R3 and n are as defined above;
step g) reacting an intermediate Weinreb amide of formula (XIV), as defined above, with a reagent of formula R6-Z (XV), wherein R6 is as defined for a compound of general formula (I) and Z is Li or MgBr, to obtain a compound of formula (Ii), wherein X, A, R2, R3, R6 and n are as defined above.

According to conv. 5, a compound of general formula (If), as defined above, is converted into a compound of formula (Ig), as defined above, through basic or acidic hydrolysis conditions, widely known in the art. The reaction is carried out with aqueous alkaline solutions, such as aqueous LiOH, NaOH or KOH, or in acidic conditions, for instance with AcOH, TFA or HCl, in the presence of a suitable solvent, such as a lower alcohol, THF, DMF, DCM or 1,4-dioxane or mixtures thereof, at a temperature ranging from rt to about 80° C. for a time ranging from about 1 to about 12 h.

According to conv. 6, the amidation of a compound of formula (Ig), as defined above, is carried out in the presence of a suitable primary or secondary amine of formula NHR4R5 (X), under basic conditions, preferably with DIPEA or TEA, in a suitable solvent such as DCM, DMF, THF, 1,4-dioxane or DMA, in the presence of a suitable condensing agent, for instance dicyclohexylcarbodiimide (DCC), 1-ethyl-3-(3'-dimethylaminopropyl)carbodiimide (EDC), 3,4-dihydro-3-hydroxy-4-oxo-1,2,3-benzotriazine (DHBT), O-benzotriazolyltetramethylisouronium tetrafluoroborate (TBTU), benzotriazol-1-yloxytripyrrolidinophosphonium hexafluorophosphate (PyBOP), or 2-(1H-benzotriazole-1-yl)-1,1,3,3-tetramethyluronium hexafluorophosphate (HBTU) at a temperature ranging from about −10° C. to reflux and for a suitable time, for instance from about 30 minutes to about 96 h. Said reaction is optionally carried out in the presence of a suitable catalyst such as DMAP, or in the presence of a further coupling reagent such as N-hydroxybenzotriazole (HOBT). Alternatively, this same reaction is also carried out, for example through a mixed anhydride method, by using an alkyl chloroformate such as ethyl, isopropyl, benzyl chloroformate, in the presence of a tertiary amine, such as TEA, DIPEA or pyridine, in a suitable solvent, such as, for instance toluene, DCM, THF, DMF and the like, at rt.

Alternatively the carboxylic acid is converted into the corresponding acyl chloride in the presence of an activating agent such as thionyl chloride, oxalyl chloride, cyanuric chloride or 1-chloro-N,N,2-trimethylpropenylamine (Ghosez's reagent) neat or in a suitable solvent, such as toluene or DCM, optionally in the presence of a catalytic amount of DMF, at a temperature ranging from about −10° C. to reflux and for a suitable time, for instance from about 30 minutes to about 4 h. Said acyl chloride is then reacted with a suitable primary or secondary amine of formula NHR4R5 (X), in a suitable solvent such as DCM, chloroform, THF, diethyl ether, 1,4-dioxane, ACN, toluene, or DMF and the like at a temperature ranging from about −10° C. to reflux and for a suitable time, for instance from about 30 minutes to about 96 h. The reaction is carried out in the presence of a suitable base such as TEA, DIPEA or pyridine.

According to step f, a compound of formula (Ig), as defined above, is reacted with NHMeOMe hydrochloride under the same reaction conditions described for conv. 6.

According to step g, an intermediate Weinreb amide of formula (XIV), wherein X, A, R2, R3 and n are as defined above, is reacted with a compound of formula R6-Z (XV), wherein R6 is as described above and Z is Li or MgBr, in an ether solvent such as THF, diethylether, 1,4-dioxane and the like, at a temperature ranging from −78° C. to rt for a suitable time, for instance from 30 minutes to 24 h.

Moreover, a first compound of general formula (I) can be conveniently converted into a second compound of formula (I) by operating according to other well-known synthetic conditions.

The following are further examples of possible conversions of a first compound of formula (I), wherein R1 group has selected meanings and is linked to a ring carbon [compound of formula (Im) or (In)], into a second compound of formula (I), precisely a compound of formula (In)-(Is), by operating according to well-known synthetic conditions:

conv. 7) converting a compound of formula (Im), wherein X, A, R2, R3, R4 and n are as defined for a compound of general formula (I), and R6 is $(C_1-C_6)$alkyl, such as for instance methyl, ethyl or tert-butyl, or aryl$(C_1-C_6)$alkyl, such as for instance benzyl, into a compound of formula (In), wherein X, A, R2, R3, R4 and n are as defined above:

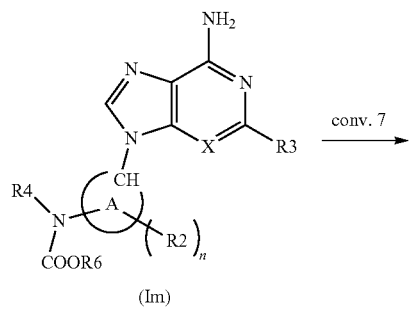

(Im)

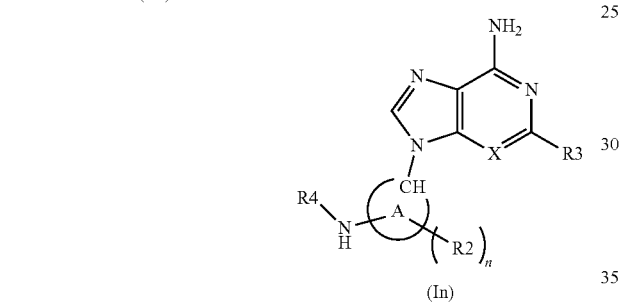

(In)

conv. 8) converting a compound of formula (In), as defined in conv. 7, into a compound of formula (Io), wherein X, A, n, R2, R3 and R4 are as defined above, and R5 is an optionally substituted group selected from $(C_1-C_6)$alkyl, $(C_3-C_7)$cycloalkyl, heterocyclyl, aryl$(C_1-C_6)$alkyl and heteroaryl$(C_1-C_6)$alkyl, by reaction with a reagent of formula R9R10CO (XVI), wherein R9 and R10 are independently hydrogen or an optionally substituted group selected from $(C_1-C_6)$alkyl, $(C_3-C_7)$cycloalkyl, heterocyclyl, aryl, aryl$(C_1-C_6)$alkyl, heteroaryl and heteroaryl$(C_1-C_6)$alkyl, or R9 and R10, taken together with the carbon atom to which they are bonded, may form an optionally substituted 5- or 6-membered cycloalkyl optionally containing one heteroatom selected from N, O and S, under reductive amination conditions:

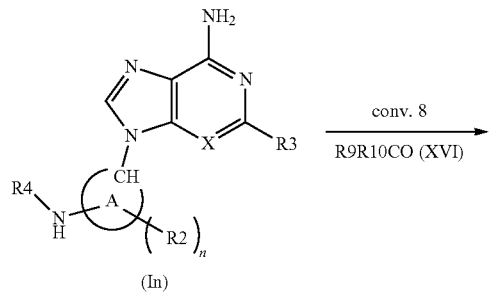

(In)

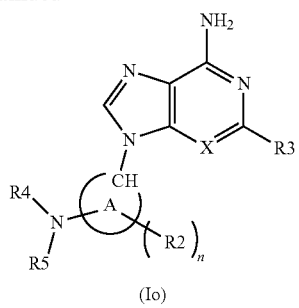

(Io)

conv. 9) converting a compound of formula (In), as defined in conv. 7, into a compound of formula (Ip), wherein X, A, R2, R3, R4, R5 and n are as defined above, by reaction with a reagent of formula R5COW (XVII), wherein R5 is as defined above and W is chlorine or hydroxy:

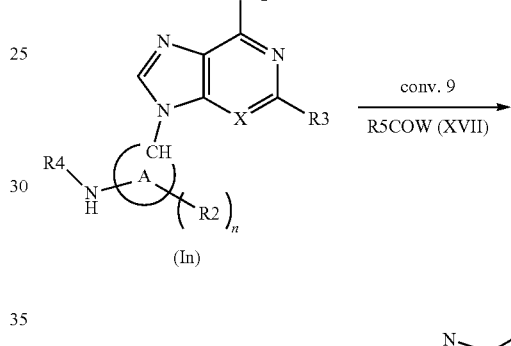

(In)

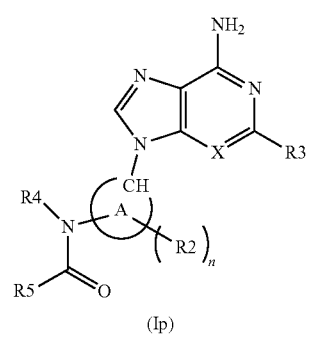

(Ip)

conv. 10) converting a compound of formula (In), as defined in conv. 7, into a compound of formula (Iq), wherein X, A, R2, R3, R4, R5 and n are as defined above, by reaction with an isocyanate of formula R5NCO (XVIII), or with an amine of general formula NHR4R5 (X), wherein R4 and R5 are as defined above, and triphosgene:

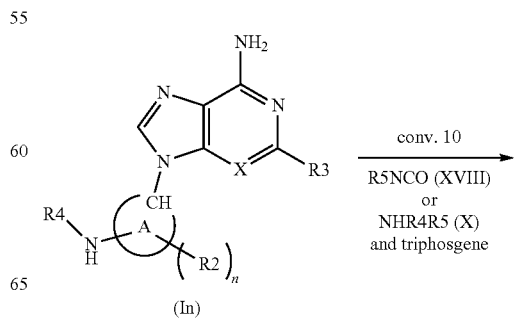

(In)

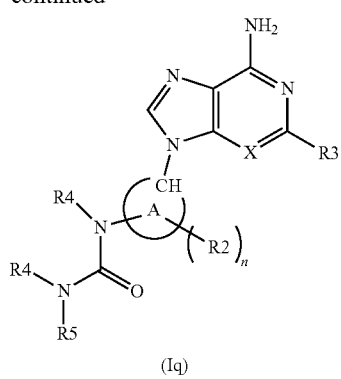

(Iq)

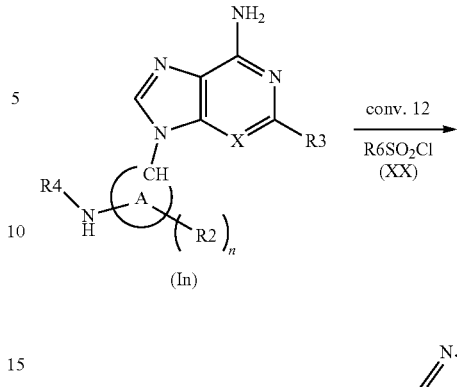

(In)

conv. 11) converting a compound of formula (In), as defined in conv. 7, into a compound of formula (Ir), wherein X, A, R2, R3, R4, R5 and n are as defined above, by reaction with an isothiocyanate of formula R5NCS (XIX), wherein R5 is as defined above:

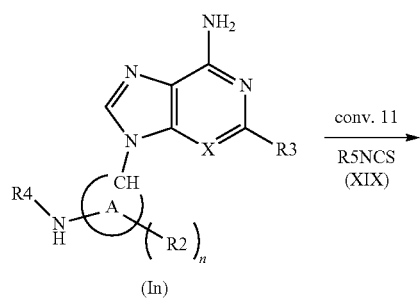

(In)

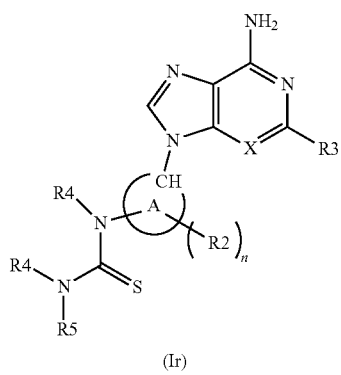

(Ir)

conv. 12) converting a compound of formula (In), as defined in conv. 7, into a compound of formula (Is), wherein X, A, R2, R3, R4, R6 and n are as defined above, by reaction with a reagent of formula R6SO$_2$Cl (XX), wherein R6 is as defined above:

(Is)

According to conv. 7, a compound of formula (Im), as defined above is converted into a compound of formula (In), as defined above, under conditions as described for step c.

According to conv. 8, a compound of formula (In), as defined above, is reacted with a carbonyl compound of formula R9R10CO (XVI), as defined above, in the presence of a reductive agent such as NaBH$_4$, NaCNBH$_3$, NaBH(OAc)$_3$ and the like, in a solvent such as MeOH, EtOH, 2,2,2-trifluoroethanol and the like, at a temperature ranging from rt to 40° C. and for a time ranging from 1 to about 12 h. Said reaction is optionally carried out in the presence of a suitable catalyst such as AcOH, TFA and the like.

According to conv. 9, a compound of general formula (In), as defined above, is reacted with a compound of formula R5COW (XVII), as defined above. When W is chlorine, the reaction is carried out in a suitable solvent, such as THF, diethyl ether, 1,4-dioxane, ACN, toluene, DCM, DMF and the like, in the presence of a base, such as TEA, DIPEA or pyridine, at a temperature ranging from about −10° C. to reflux and for a suitable time, for instance from about 30 minutes to about 96 h. When W is hydroxy, the reaction is carried out in the presence of a coupling agent, such as TBTU, DCC, 1,3-diisopropylcarbodiimide, EDCl, N-cyclohexylcarbodiimide-N'-propyloxymethyl polystyrene and N-cyclohexylcarbodiimide-N'-methyl polystyrene, in a suitable solvent, such as DCM, chloroform, THF, diethyl ether, 1,4-dioxane, ACN, toluene, or DMF, at a temperature ranging from about −10° C. to reflux and for a suitable time, for instance from about 30 minutes to about 96 h. Said reaction is optionally carried out in the presence of a suitable catalyst, for instance DMAP, or in the presence of a further coupling reagent such as HOBT. Alternatively, this same reaction is also carried out, for example, through a mixed anhydride method, by using an alkyl chloroformate, such as ethyl, iso-butyl or isopropyl chloroformate, in the presence of a tertiary base such as TEA, DIPEA or pyridine, in a suitable solvent such as, for instance, toluene, DCM, chloroform, THF, ACN, diethyl ether, 1,4-dioxane, or DMF, at a temperature ranging from about −30° C. to rt for a suitable time, for instance from about 30 minutes to about 96 h.

According to conv. 10, a compound of formula (In), as defined above, is reacted with an isocyanate of formula R5NCO (XVIII), as defined above, in a suitable solvent such as DCM or THF, normally at a temperature ranging from about −10° C. to reflux and for a time varying from about 30 minutes to about 96 h. Alternatively an amine of general formula NHR4R5 (X), as defined above, can be reacted with triphosgene (bis(trichloromethyl) carbonate, O=C(OCCl$_3$)$_2$) followed by the addition of the compound of formula (In), as defined above. This reaction can be carried out in the presence of a base such as DIPEA, TEA and Na$_2$CO$_3$, in a solvent such as DCM, chloroform, at a temperature ranging from about −10° C. to reflux and for a time varying from about 30 minutes to about 96 h.

According to conv. 11, a compound of formula (In), as defined above, is reacted with an isothiocyanate of formula R5NCS (XIX), as defined above, under conditions described for conv. 10.

According to conv. 12, a compound of formula (In), as defined above, is reacted with a compound of formula R6SO$_2$Cl (XX), as defined above, in the presence of a suitable base, such as for instance, pyridine, N-methyl morpholine, DIPEA, in a suitable solvent, such as pyridine, DCM or THF, at a temperature ranging from 0° C. to reflux and for a time varying from about 1 hour to about 96 h.

A compound of general formula (I), wherein A is 6- or 7-membered heterocyclyl or A is a 7- to 9-membered carbon bicyclic system, in which one ring carbon is replaced by a nitrogen, and R1 group has selected meanings and is linked to the ring nitrogen, can be also prepared by operating according to well-known synthetic conditions, as shown in Scheme 3:

Scheme 3

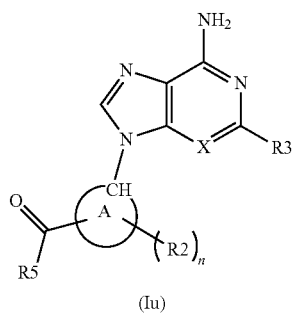

(Iu)

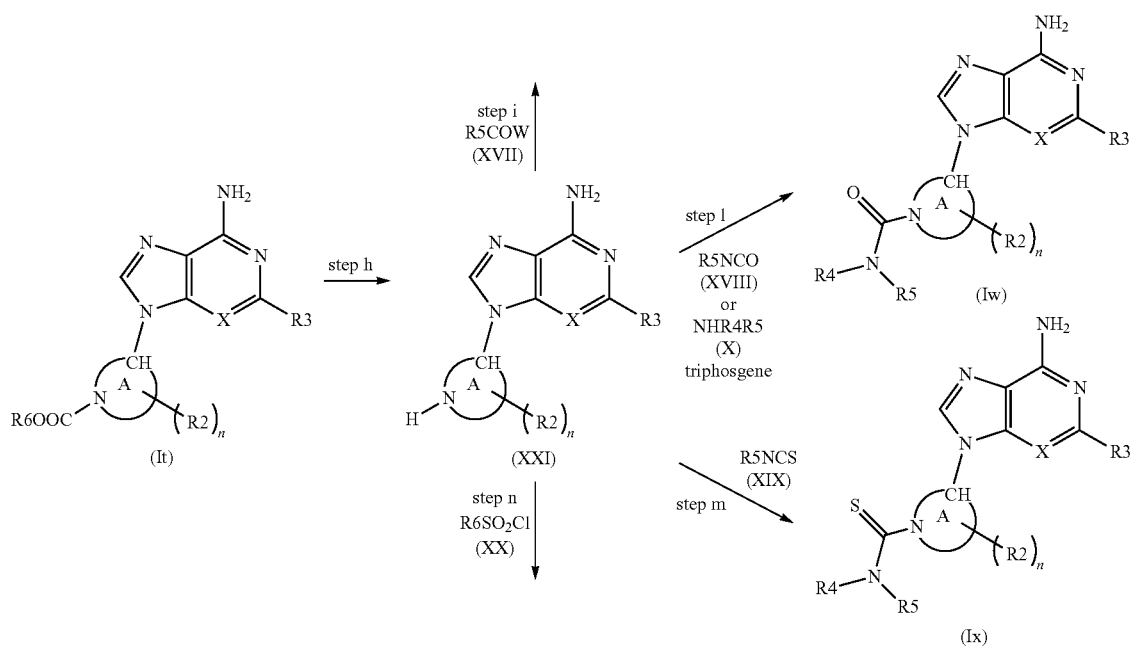

-continued

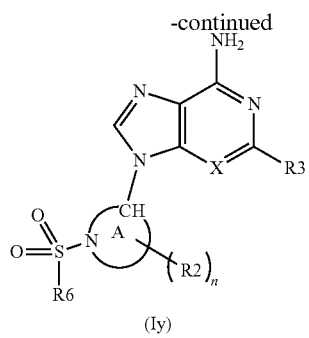

(Iy)

step h) hydrolyzing a compound of formula (It), wherein X, A, R2, R3 and n are as defined for a compound of general formula (I), and R6 is (C₁-C₆)alkyl, such as for instance methyl, ethyl or tert-butyl, or aryl(C₁-C₆)alkyl, such as for instance benzyl, to give an intermediate of formula (XXI), wherein X, A, R2, R3 and n are as defined above;

step i) reacting the intermediate of formula (XXI), as defined in step h, with a reagent of formula R5COW (XVII), as defined in conv. 9, to obtain a compound of formula (Iu), wherein X, A, R2, R3, R5 and n are as defined above;

step l) reacting the intermediate of formula (XXI), as defined in step h, with an isocyanate of formula R5NCO (XVIII) or with an amine of general formula NHR4R5 (X), as defined in conv. 10, and triphosgene, to obtain a compound of formula (Iw), wherein X, A, R2, R3, R4, R5 and n are as defined above;

step m) reacting the intermediate of formula (XXI), as defined in step h, with an isothiocyanate of formula R5NCS (XIX), as defined in conv. 11, to obtain a compound of formula (Ix), wherein X, A, R2, R3, R4, R5 and n are as defined above;

step n) reacting the intermediate of formula (XXI), as defined in step h, with a reagent of formula R6SO₂Cl (XX), as defined in conv. 12, to obtain a compound of formula (Iy), wherein X, A, R2, R3, R6 and n are as defined above.

According to step h, the carbamate hydrolysis of a compound of formula (It), as defined above, is carried out as described for conv. 7.

According to step i, the reaction of an intermediate of formula (XXI), as defined above, with a compound of formula R5COW (XVII), as defined above, is carried out as described for conv. 9.

According to step l, the reaction of an intermediate of formula (XXI), as defined above, with an isocyanate of formula R5NCO (XVIII), as defined above, or, alternatively, with an amine of general formula NHR4R5 (X), as defined above, and triphosgene, is carried out as described for conv. 10.

According to step m, the reaction of an intermediate of formula (XXI), as defined above, with an isothiocyanate of formula R5NCS (XIX), as defined above, is carried out as described for conv. 11.

According to step n, the reaction of an intermediate of formula (XXI), as defined above, with a compound of formula R6SO₂Cl (XX) as defined above is carried out as described for conv. 12.

Conversions from 1 to 12 and steps from h to n described above can also be carried out on intermediates of formula (II),

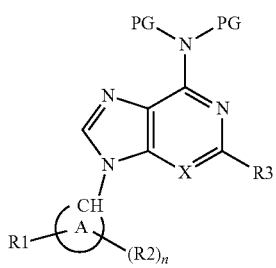

(II)

wherein PG is a suitable protecting group that is not removed during R1 manipulation. For example when R1 is —COOR4, —NR4COOR6, when linked to any ring carbon, or —COOR6, when linked to the ring nitrogen, and PG is —COOR7, then R4 or R6 is a straight (C₁-C₆)alkyl, such as for instance methyl or ethyl, and R7 is a branched (C₁-C₆) alkyl, such as tert-butyl, or an aryl(C₁-C₆)alkyl, such as for instance benzyl.

Intermediates of formula (VI), which are the starting material in Scheme 1, are commercially available or can be prepared by using synthetic methods well known in the art.

In addition, an intermediate of formula (VIa) can be converted into an intermediate of formula (VIb) as described in Scheme 4.

Scheme 4

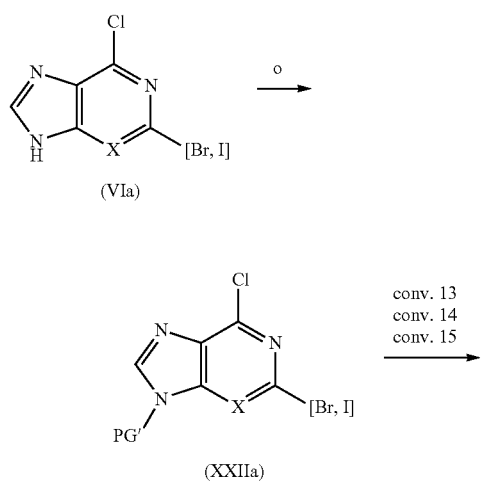

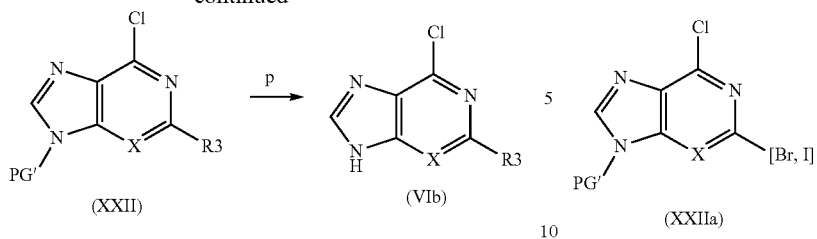

Step o) protecting an intermediate of formula (VIa), wherein X is as defined for a compound of general formula (I), with a protecting reagent to obtain an intermediate of formula (XXIIa), wherein PG' is a suitable imidazole nitrogen protecting group, such as for instance trityl, tetrahydropyranyl or 2-(trimethylsilyl)ethoxymethyl (SEM);

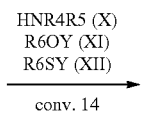

conv. 15) converting an intermediate of formula (XXIIa), as obtained in step o, into an intermediate of formula (XXIId), wherein X and PG' are as defined above and R3 is cyano, by reaction with M-CN (XIII), wherein M is Zn or Cu, under palladium-catalyzed conditions;

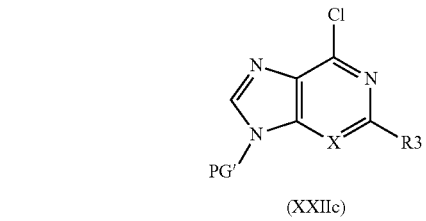

conv. 13) converting an intermediate compound of formula (XXIIa), as obtained in step o, into an intermediate of formula (XXIIb), wherein X and PG' are as defined above, and R3 is an optionally substituted group selected from $(C_1$-$C_6)$alkyl, $(C_2$-$C_6)$alkenyl, $(C_2$-$C_6)$alkynyl, $(C_3$-$C_7)$cycloalkyl, heterocyclyl, aryl and heteroaryl, by reaction with R3Q, wherein R3 is as defined above and Q is a group selected from boronic acid, boronic ester, hydrogen and —Sn[$(C_1$-$C_6)$alkyl]$_3$, under cross-coupling conditions:

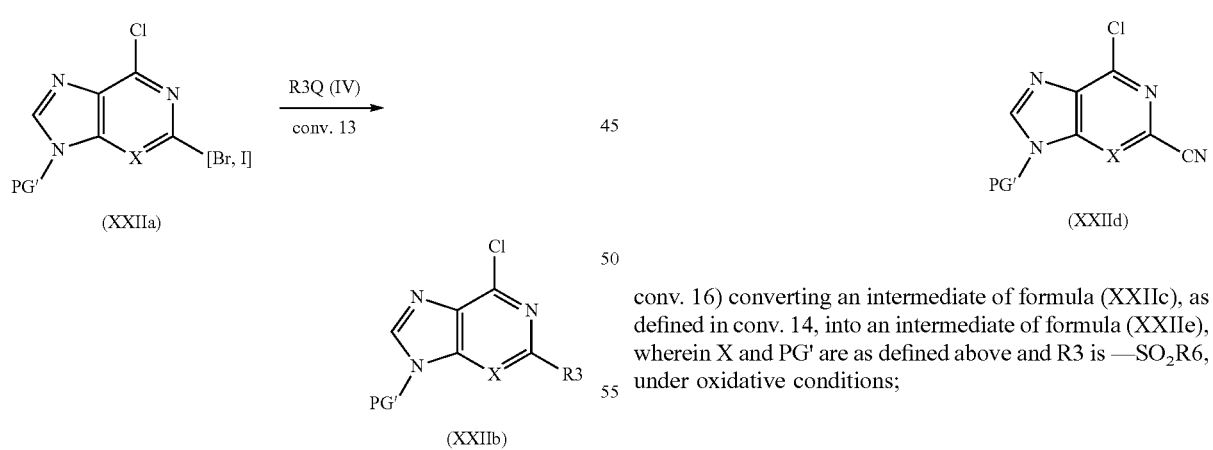

conv. 14) converting an intermediate of formula (XXIIa), as obtained in step o, into an intermediate of formula (XXIIc), wherein X and PG' are as defined above, and R3 is —NR4R5, —OR6 or —SR6, wherein R4, R5 and R6 are as defined in the compound of general formula (I), by reaction with HNR4R5 (X), R6OY (XI) or R6SY (XII), wherein R4, R5 and R6 are as defined above and Y is hydrogen, under palladium-catalyzed coupling conditions;

conv. 16) converting an intermediate of formula (XXIIc), as defined in conv. 14, into an intermediate of formula (XXIIe), wherein X and PG' are as defined above and R3 is —SO$_2$R6, under oxidative conditions;

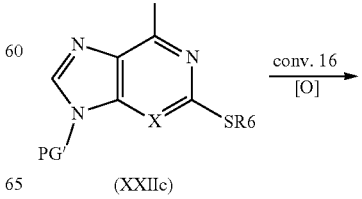

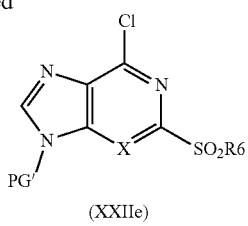

(XXIIe)

step p) deprotecting an intermediate of formula (XXIIIb)-(XXIIe), as defined above, to obtain an intermediate of formula (VIb), wherein X and R3 are as defined for the starting intermediates, respectively.

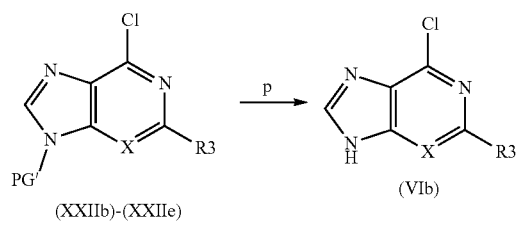

According to step o, an intermediate of formula (Via), as defined above, is treated with trityl chloride or 2-(trimethylsilyl)ethoxymethyl chloride (SEM chloride) in the presence of a base such as TEA, DIPEA or pyridine in a suitable solvent such as THF, DCM and the like, or with 3,4-dihydro-2H-pyran and a catalytic amount of p-TsOH, in a suitable solvent such as ACN, EtOAc, 1,4-dioxane, DCM and the like at a temperature ranging from rt to reflux for a time varying from 30 minutes to 24 h.

According to conv. 13, an intermediate of formula (XXIIa), as obtained in step o, is reacted with an intermediate of formula R3Q (IX), as defined above, under conditions described for conv. 1;

According to conv. 14, an intermediate of formula (XXIIa), as obtained in step o, is reacted with an intermediate of formula HNR4R5 (X), R6OY (XI) or R6SY (XII), as defined above, under palladium-catalyzed coupling conditions as described for conv. 2;

According to conv. 15, an intermediate of formula (XXIIa), as obtained in step o, is reacted with a compound of formula M-CN (XIII), as defined above, under conditions described for conv. 4.

According to conv. 16, an intermediate of formula (XXIIc), as defined in conv. 14, is oxidized as described for conv. 3.

According to step p, an intermediate of formula (XXIIb)-(XXIIe), as defined above, is deprotected under acidic conditions, such as for instance TFA, HCl and the like in a solvent such as DCM, 1,4-dioxane, or with a catalytic amount of CuCl in a suitable solvent such as MeOH, EtOH or a mixture EtOH/water at a temperature ranging from rt to reflux and for a time ranging from 1 to about 12 h.

Intermediates of formula (VII) are commercially available or, in addition to what is described for step d' of Scheme 1 starting from a compound of formula (VI), can be prepared by operating according to well-known synthetic conditions as described in Scheme 5.

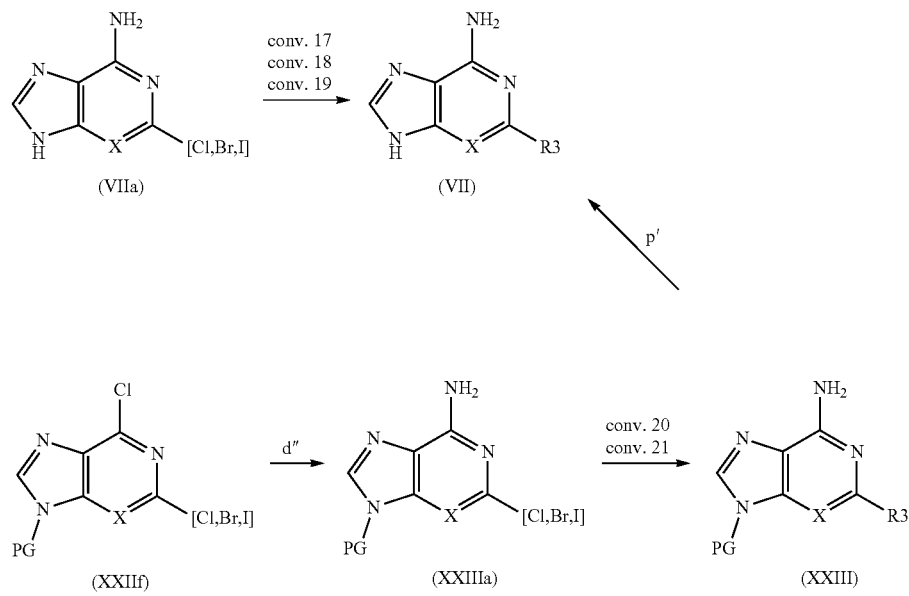

Scheme 5 conv. 17) converting an intermediate of formula (VIIa), wherein X is as defined for a compound of general formula (I), into an intermediate of formula (VIIb), wherein X is as defined above and R3 is an optionally substituted group selected from $(C_1-C_6)$alkyl, $(C_2-C_6)$alkenyl, $(C_2-C_6)$alkynyl, $(C_3-C_7)$cycloalkyl, heterocyclyl, aryl and heteroaryl, by reaction with R3Q (IX), as defined in conv. 13, under cross-coupling conditions:

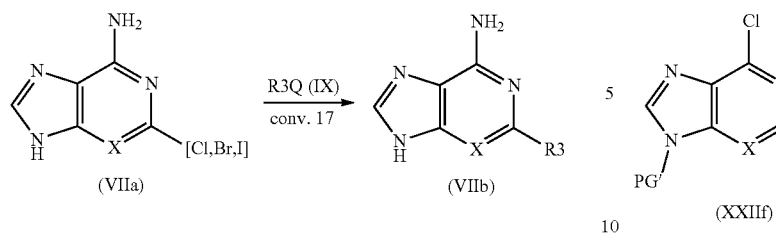

conv. 18) converting an intermediate of formula (VIIa), as defined above, into an intermediate of formula (VIIc), wherein X is as defined above and R3 is —NR4R5, —OR6 or —SR6, wherein R4, R5 and R6 are as defined for a compound of general formula (I), by reaction with HNR4R5 (X), R6OY (XI) or R6SY (XII), as defined in conv. 14, under palladium-catalyzed coupling conditions:

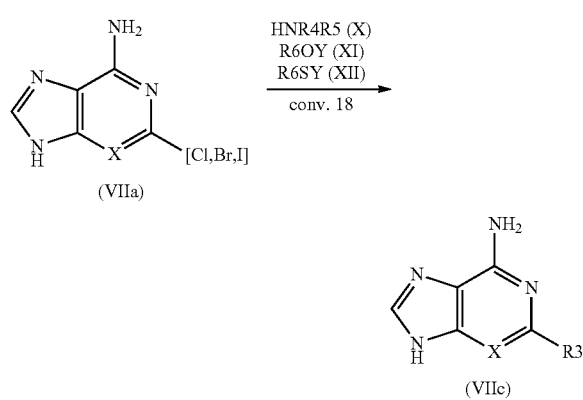

conv. 19) converting an intermediate of formula (VIIa), as defined above, into an intermediate of formula (VIId), wherein X is as defined above, by reaction with M-CN (XIII), wherein M is Zn or Cu, under palladium-catalyzed conditions.

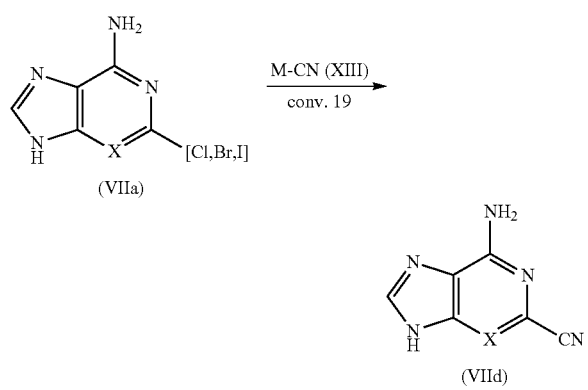

Alternatively, an intermediate of formula (VII) can be prepared according to the following steps:

step d") substituting the chlorine atom of an intermediate of formula (XXIIf), obtained as for (XXIIa) in step o, to obtain an intermediate of formula (XXIIIa), wherein X and PG' are as defined in step o, for instance with a nitrogen source, such as an ammonia solution;

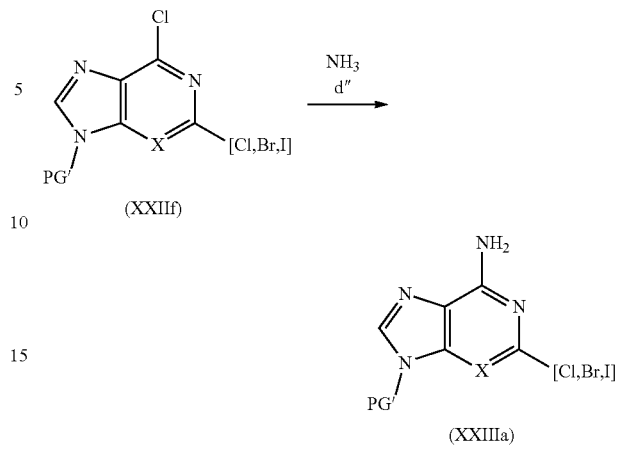

conv. 20) converting an intermediate of formula (XXIIIa), as obtained in step d", into an intermediate of formula (XXIIIb), wherein X and PG' are as defined above and R3 is —NR4R5, —OR6 or —SR6, wherein R4, R5 and R6 are as defined for a compound of general formula (I), by reaction with HNR4R5 (X), R6OY (XI) or R6SY (XII), are as defined in conv. 2, under nucleophilic substitution conditions;

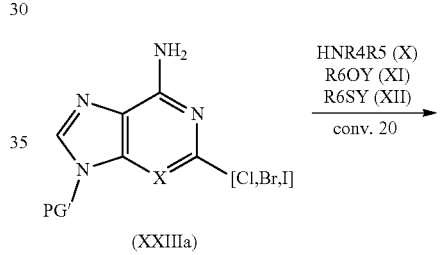

conv. 21) converting an intermediate of formula (XXIIIb), as defined in conv. 20, into an intermediate of formula (XXIIIc), wherein X, R6 and PG' are as defined above, under oxidative conditions:

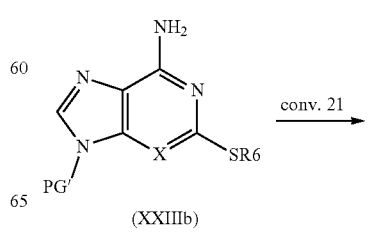

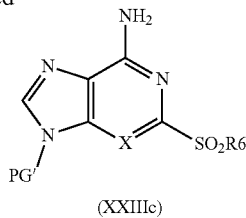

(XXIIIc)

Step p'), deprotecting an intermediate of formula (XXIII) to obtain an intermediate of formula (VII), wherein X is as defined above and R3 is —NR4R5, —OR6, —SR6, —SO₂R6, under acidic conditions.

According to conv. 17, an intermediate of formula (VIIa), as defined above, is reacted with an intermediate of formula R3Q (IX), as defined above, under conditions described for conv. 1.

According to conv. 18, an intermediate of formula (VIIa), as defined above, is reacted with an intermediate of formula HNR4R5 (X), R6OY (XI) or R6SY (XII), as defined above, under palladium-catalyzed coupling conditions described for conv. 2.

According to conv. 19, an intermediate of formula (VIIa), as defined above, is reacted with a compound of formula M-CN (XIII), wherein M is Cu or Zn, under conditions described for conv. 4.

According to step d", the substitution of the chlorine atom of an intermediate of formula (XXIIf), as defined above, can be carried out as described for step d.

According to conv. 20, an intermediate of formula (XXIIIa), as obtained form step d", is reacted with a compound of general formula HNR4R5 (X), R6OY (XI) or R6SY (XII), as defined above, under nucleophilic substitution conditions as described for conv. 2.

According to conv. 21, an intermediate of formula (XXIIIb), as defined above, is oxidized as described for conv. 3.

According to step p', an intermediate of formula (XXIII), as defined above, is deprotected under acidic conditions as described for step p.

Intermediates of formula (VIc), wherein X is as defined above, can be prepared as described in Scheme 6.

Scheme 6

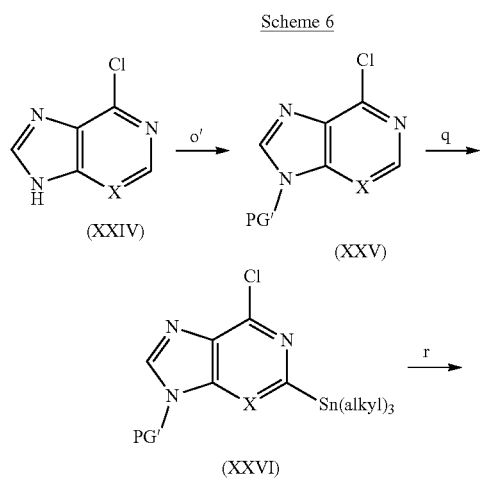

(XXIV)

(XXV)

(XXVI)

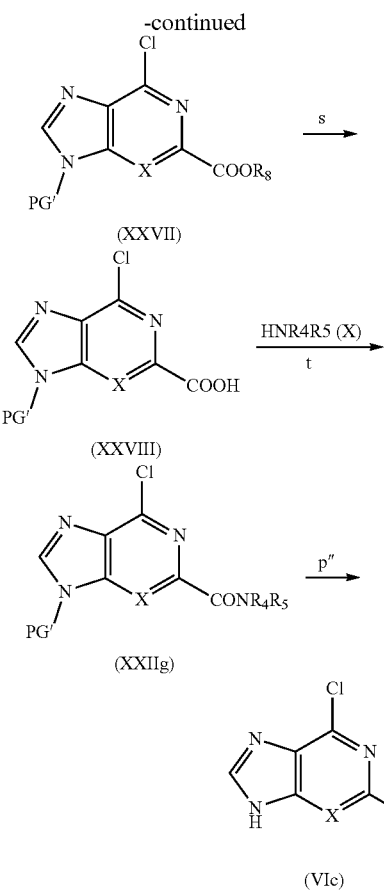

(XXVII)

(XXVIII)

(XXIIg)

(VIc)

Step o') protecting an intermediate of formula (XXIV), wherein X is as defined for a compound of general formula (I), with a protecting reagent to obtain an intermediate of formula (XXV), wherein PG' is a suitable imidazole nitrogen protecting group, such as for instance trityl, tetrahydropyranyl or 2-(trimethylsilyl)ethoxymethyl (SEM);

step q) reacting an intermediate of formula (XXV), wherein X and PG' are as defined above, with ClSn[(C₁-C₆)alkyl]₃ in the presence of a suitable base, to obtain an intermediate of formula (XXVI), wherein X and PG' are as defined above;

step r) reacting an intermediate of formula (XXVI), wherein X and PG' are as defined above, with ClCOCOOR8, wherein R8 is an optionally substituted (C₁-C₆)alkyl, such as for instance methyl or ethyl, to obtain an intermediate of formula (XXVII), wherein X, PG' and R8 are as defined above;

step s) hydrolysing an intermediate of formula (XXVII), wherein X, R8 and PG' are as defined above, to obtain an intermediate of formula (XXVIII), wherein X and PG' are as defined above;

step t) reacting an intermediate of formula (XXVIII), wherein X and PG' are as defined above, with an amine of formula HNR4R5 (X), where in R4 and R5 are as defined above, to obtain an intermediate of formula (XXIIg), wherein X, PG', R4 and R5 are as defined above;

step p") deprotecting an intermediate of formula (XXIIg), wherein PG', X, R4 and R5 are as defined above, to obtain an intermediate of formula (VIc), wherein X, R4 and R5 are as defined above.

According to step o', the reaction can be carried out as described for step o.

According to step q, the reaction can be carried out in the presence of a suitable base and ClSn[(C$_1$-C$_6$)alkyl]$_3$ as reported in *Org. Biomol. Chem.* 2004, 2, 665-670 and *Org. Lett.* 2000, 2, 803-805.

According to step r, the reaction can be carried out as reported in *Heterocycles*, 1995, 41, 1275-1290.

According to step s, the reaction can be carried out as described for conv. 5.

According to step t, the reaction can be carried out as described for conv. 6.

According to step p", the reaction can be carried out as described for step p.

Intermediates of general formula (VId), wherein R3 is an optionally substituted group selected from (C$_1$-C$_6$)alkyl, polyfluorinated (C$_1$-C$_6$)alkyl, (C$_2$-C$_6$)alkenyl, (C$_2$-C$_6$)alkynyl, (C$_3$-C$_7$)cycloalkyl, heterocyclyl, aryl or heteroaryl, can also be prepared from 5-aminoimidazole-4-carboxamide hydrochloride and a suitable acyl chloride R3COCl, as shown in Scheme 7 and described in *Eur. J. Med. Chem.* 2003, 38, 199-214, which process is herein incorporated by reference.

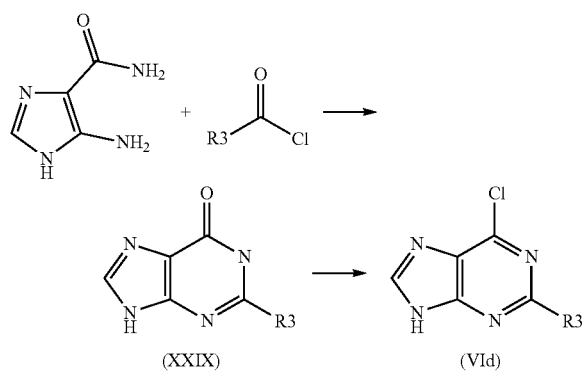

Scheme 7

When preparing the compounds of general formula (I) according to any of the above variants of the process, optional functional groups within the starting materials, the reagents or the intermediates thereof, and which could give rise to unwanted side reactions, need to be properly protected according to conventional techniques. Likewise, the conversion of these latter into the free deprotected compounds may be carried out according to known procedures.

The compounds of every general formula can be further transformed in other compounds of the same general formula according to methods well known in the literature, as reported in the experimental section.

The final compounds may be isolated and purified using conventional procedures, for example chromatography and/or crystallization and salt formation.

The compounds of general formula (I) as defined above can be converted into pharmaceutically acceptable salts.

The compounds of general formula (I) as defined above, or the pharmaceutically acceptable salts thereof, can be subsequently formulated with a pharmaceutically acceptable carrier or diluent to provide a pharmaceutical composition.

The synthesis of a compound of general formula (I), according to the synthetic processes described above, can be conducted in a stepwise manner, whereby each intermediate is isolated and purified if needed by standard purification techniques, like, for example, column chromatography, before carrying out the subsequent reaction. Alternatively, two or more steps of the synthetic sequence can be carried out in a so-called "one-pot" procedure, as known in the art, whereby only the compound resultant from the two or more steps is isolated and purified.

In cases where a compound of general formula (I) contains one or more asymmetric centers, said compound can be separated into the single stereoisomers by procedures known to those skilled in the art. Such procedures comprise standard chromatographic techniques, including chromatography using a chiral stationary phase, or crystallization. General methods for separation of compounds containing one or more asymmetric centers are reported, for instance, in Jacques, Jean; Collet, André; Wilen, Samuel H., Enantiomers, Racemates, and Resolutions, John Wiley & Sons Inc., New York (N.Y.), 1981.

From all of the above, the novel compounds of formula (I) of present invention appear to be particularly advantageous in the therapy of diseases caused by altered choline metabolism, in particular cancer.

The compounds of the present invention can be administered either as single agents or, alternatively, in combination with known anticancer treatments such as radiation therapy or chemotherapy regimen in combination with, for example, antihormonal agents such as antiestrogens, antiandrogens and aromatase inhibitors, topoisomerase I inhibitors, topoisomerase II inhibitors, agents that target microtubules, platin-based agents, alkylating agents, DNA damaging or intercalating agents, antineoplastic antimetabolites, other kinase inhibitors, other anti-angiogenic agents, inhibitors of kinesins, therapeutic monoclonal antibodies, inhibitors of mTOR, histone deacetylase inhibitors, farnesyl transferase inhibitors, and inhibitors of hypoxic response.

If formulated as a fixed dose, such combination products employ the compounds of this invention within the dosage range described below and the other pharmaceutically active agent within the approved dosage range.

Compounds of formula (I) may be used sequentially with known anticancer agents when a combination formulation is inappropriate.

The compounds of formula (I) of the present invention, suitable for administration to a mammal, e.g. to humans, can be administered by the usual routes and the dosage level depends upon the age, weight, and conditions of the patient and administration route.

For example, a suitable dosage adopted for oral administration of a compound of formula (I) may range from about 1 to about 1000 mg per dose, from 1 to 5 times daily. The compounds of the invention can be administered in a variety of dosage forms, e.g. orally, in the form of tablets, capsules, sugar or film coated tablets, liquid solutions or suspensions; rectally in the form of suppositories; parenterally, e.g. intramuscularly, or through intravenous and/or intrathecal and/or intraspinal injection or infusion.

The present invention also includes pharmaceutical compositions comprising a compound of formula (I) or a pharmaceutically acceptable salt thereof in association with a pharmaceutically acceptable excipient, which may be a carrier or a diluent.

The pharmaceutical compositions containing the compounds of the invention are usually prepared following conventional methods and are administered in a suitable pharmaceutical form.

For example, the solid oral forms may contain, together with the active compound, diluents, e.g. lactose, dextrose, saccharose, sucrose, cellulose, corn starch or potato starch; lubricants, e.g. silica, talc, stearic acid, magnesium or calcium stearate, and/or polyethylene glycols; binding agents, e.g. starches, arabic gum, gelatine methylcellulose, carboxymethylcellulose or polyvinyl pyrrolidone; disintegrating agents, e.g. starch, alginic acid, alginates or sodium starch glycolate; effervescing mixtures; dyestuffs; sweeteners; wetting agents, such as lecithin, polysorbates, laurylsulphates; and, in general, non-toxic and pharmacologically inactive substances used in pharmaceutical formulations. These pharmaceutical preparations may be manufactured in known manner, for example, by means of mixing, granulating, tabletting, sugar-coating, or film-coating processes.

The liquid dispersions for oral administration may be, e.g. syrups, emulsions and suspensions.

As an example the syrups may contain, as a carrier, saccharose or saccharose with glycerine and/or mannitol and sorbitol.

The suspensions and the emulsions may contain, as examples of carriers, natural gum, agar, sodium alginate, pectin, methylcellulose, carboxymethylcellulose or polyvinyl alcohol.

The suspension or solutions for intramuscular injections may contain, together with the active compound, a pharmaceutically acceptable carrier, e.g. sterile water, olive oil, ethyl oleate, glycols, e.g. propylene glycol and, if desired, a suitable amount of lidocaine hydrochloride.

The solutions for intravenous injections or infusions may contain, as a carrier, sterile water or preferably they may be in the form of sterile, aqueous, isotonic, saline solutions or they may contain propylene glycol as a carrier.

The suppositories may contain, together with the active compound, a pharmaceutically acceptable carrier, e.g. cocoa butter, polyethylene glycol, a polyoxyethylene sorbitan fatty acid ester surfactant or lecithin.

EXPERIMENTAL PART

Biology
Protein Production

HumanΔ49-ChoKα (Δ49N-hChoKα) cDNA fragment 362-1534, corresponding to aminoacids 50-457 (*J. Mol. Biol.* 2006, 364, 136-151), and hChoKβ full length (FL), corresponding to aminoacids 2-395 (*PLoS ONE* 2009, 4, e7819), were amplified by PCR from human library and cloned, inserting upstream a Prescission Protease recognition site, in pDonor 221 vector, using the Gateway Technology® (Invitrogen). After sequence control, LR reaction was performed in the final expression pGEX 2Tg vector. Both the proteins were expressed in *Escherichia coli* BL21pLysS (DE3) strain in auto-induction (Kessler) medium in the presence of 50 mg/mL carbenicillin at 25° C. for 16 h. Cells were harvested by centrifugation, the pellet was re-suspended in Lysis buffer (50 mM Tris-HCl pH 7.8, 150 mM NaCl, 10% glycerol, 0.2% CHAPS, 20 mM DTT, Protease Inhibitor Cocktail Tablets from Roche Biochemicals) and lysed by Gaulin homogenizer (Niro Soavi). The lysate was cleared by centrifugation. The supernatant was added to GSH resin and let flow by gravity. The GSH resin was washed with 5 column volume (CV) of cold wash buffer (50 mM Tris-HCl pH 7.8, 150 mM NaCl, 10% glycerol), then with 10 CV of the same buffer containing 2 mM of DTT. Both GST-Δ49N-hChoKα and hChoKβ were subjected to on-column cleavage of the GST tag with Prescission Protease overnight. The eluted cleaved proteins were further purified by ion exchange (ResQ 6 mL chromatography column from GE healthcare) with a gradient from 50 to 500 mM NaCl in 30 CV. The fractions containing Δ49N-hChoKα or hChoKβ were pooled, concentrated and gel filtered on a Superdex200 16/60 (GE Healthcare). The final protein concentration was estimated using the Bradford assay. All the samples purified were resolved by SDS-PAGE.

Biochemical Kinase Inhibition Assay on Δ49N-hChoKα and hChoKβ FL

The biochemical activity of compounds against Δ49N-ChoKα and ChoKβ FL were determined using the Kinase-Glo™ Luminescent Kinase Assay (Promega cat. V6711). The assay is based on incubation of the recombinant Δ49N-hChoKα and hChoKβ FL produced in house, 2.2 nM and 30 nM, respectively, with the specific substrates, choline (Sigma-Aldrich—C7017) and ATP, followed by quantification, at the end of reaction time, of the residual not reacted ATP.

Compounds were 3-fold serially diluted from 10 to 0.0005 μM, then incubated for 60 minutes at rt in the presence of ATP 5 μM, choline (5 μM for ChoKα and 20 μM for ChoKβ) and enzyme in a final volume of 19 μL of kinase buffer (50 mM Hepes pH 7.5, 10 mM $MgCl_2$, 1 mM DTT, 3 μM $Na_3VO_4$ and 0.2 mg/mL BSA). The final concentration of DMSO was 1%. The assay was run in a robotized format on 384-well plates (Perkin Elmer cat. #6005301).

At the end of the incubation, an amount of 19 μL of KinaseGlo Reagent was added to each well to stop the reaction and after 30 minutes the luminescence signal was measured using ViewLux reader (Perkin Elmer).

Each 384-well plate contained at least one curve of a standard cpd, and reference wells (total enzyme activity vs enzyme completely inhibited) for the Z' and signal to background evaluation (J. Biomol. Screening, 1999, 4, 67-73).

All information about plate dilution, distribution and raw data of inhibition are tracked via barcode reading and stored in an Oracle DB. The data per each molecule are analyzed by an internally customized version of the SW package "Assay Explorer" which provides sigmoidal fittings of the ten-dilution curves for $IC_{50}$ determination using a 4 parameter logistic equation:

$$y = \text{bottom} + (\text{top}-\text{bottom})/(1+10^{((\log IC_{50}-x)*\text{slope})})$$

where x is the logarithm of the inhibitor concentration, y is the response;
y starts at bottom and goes to top with a sigmoid shape.

The Kinase-Glo™ assay is more suitable than the NADH coupled assay reported in the literature for the screening of a library of compounds in terms of cost, automation procedure and sensitivity in the assay conditions described above.

Biochemical Activity

Biochemical potencies both on ChoKα and ChoKβ of representative compounds, which were determined according to the above described assays, are reported in Table 1 as $IC_{50}$ values (μM). (NT=Not Tested)

TABLE 1

| cpd | $IC_{50}$ ChoKα (μM) | $IC_{50}$ ChoKβ (μM) |
| --- | --- | --- |
| 3 | 0.227 | 3.767 |
| 4 | 0.479 | NT |
| 9 | 0.410 | >10 |
| 15 | 0.419 | NT |
| 17 | 0.871 | NT |
| 18 | 0.339 | NT |
| 19 | 0.795 | NT |
| 21 | 0.883 | NT |
| 26 | 0.774 | NT |
| 27 | 0.248 | NT |
| 29 | 0.257 | 1.880 |
| 30 | 0.305 | >10 |

TABLE 1-continued

| cpd | IC$_{50}$ ChoKα (µM) | IC$_{50}$ ChoKβ (µM) |
|---|---|---|
| 31 | 0.040 | >10 |
| 32 | 0.249 | 5.906 |
| 33 | 0.021 | 4.574 |
| 35 | 0.013 | 0.430 |
| 36 | 0.053 | 1.351 |
| 37 | 0.844 | >10 |
| 41 | 0.441 | >10 |
| 45 | 0.195 | 4.979 |
| 48 | 0.283 | >10 |
| 50 | 0.311 | >10 |
| 53 | 0.855 | >10 |
| 60 | 0.854 | >10 |
| 64 | 0.196 | >10 |
| 65 | 0.049 | >10 |
| 69 | 0.138 | 3.355 |
| 70 | 0.034 | >10 |
| 71 | 0.375 | 2.839 |
| 72 | 0.061 | >10 |
| 73 | 0.040 | >10 |
| 74 | 0.146 | >10 |
| 75 | 0.028 | 5.984 |
| 76 | 0.151 | >10 |
| 77 | 0.018 | 5.97 |
| 79 | 0.288 | >10 |
| 81 | 0.125 | >10 |
| 83 | 0.425 | >10 |
| 84 | 0.086 | >10 |
| 85 | 0.011 | >10 |
| 86 | 0.052 | >10 |
| 87 | 0.974 | >10 |
| 88 | 0.524 | >10 |
| 89 | 0.064 | 4.164 |
| 90 | 0.028 | >10 |
| 91 | 0.029 | 7.377 |
| 92 | 0.023 | 5.031 |
| 93 | 0.048 | 6.077 |
| 94 | 0.178 | 5.622 |
| 95 | 0.268 | 7.124 |
| 96 | 0.274 | >10 |
| 97 | 0.478 | >10 |
| 98 | 0.120 | >10 |
| 100 | 0.248 | >10 |
| 102 | 0.088 | >10 |
| 103 | 0.176 | >10 |
| 107 | 0.495 | >10 |
| 108 | 0.126 | >10 |
| 109 | 0.111 | >10 |
| 112 | 0.120 | >10 |
| 113 | 0.613 | >10 |
| 114 | 0.034 | 4.691 |
| 115 | 0.104 | >10 |
| 116 | 0.043 | >10 |
| 119 | 0.021 | 7.699 |
| 120 | 0.040 | >10 |
| 122 | 0.033 | 5.693 |
| 124 | 0.034 | >10 |
| 126 | 0.031 | >10 |
| 127 | 0.045 | >10 |
| 128 | 0.038 | >10 |
| 129 | 0.416 | >10 |
| 132 | 0.257 | >10 |
| 134 | 0.028 | >10 |
| 135 | 0.061 | >10 |
| 137 | 0.022 | 5.094 |
| 138 | 0.097 | >10 |
| 140 | 0.514 | >10 |
| 144 | 0.341 | >10 |
| 146 | 0.073 | >10 |
| 159 | 0.065 | 7.041 |
| 160 | 0.197 | >10 |
| 163 | 0.031 | >10 |
| 164 | 0.070 | >10 |
| 165 | 0.060 | >10 |
| 166 | 0.088 | 5.429 |
| 167 | 0.097 | >10 |
| 168 | 0.045 | >10 |
| 169 | 0.052 | 5.554 |
| 170 | 0.054 | >10 |
| 171 | 0.105 | 5.801 |
| 172 | 0.027 | >10 |
| 173 | 0.021 | 6.563 |
| 174 | 0.041 | >10 |
| 175 | 0.049 | >10 |
| 176 | 0.034 | 4.024 |
| 177 | 0.020 | 3.809 |
| 178 | 0.014 | >10 |
| 179 | 0.031 | >10 |
| 180 | 0.023 | 6.8 |
| 181 | 0.066 | >10 |
| 182 | 0.043 | >10 |
| 183 | 0.017 | 1.987 |
| 184 | 0.014 | 6.709 |
| 185 | 0.020 | >10 |
| 186 | 0.043 | 5.472 |
| 187 | 0.029 | 5.628 |
| 188 | 0.009 | >10 |
| 189 | 0.027 | >10 |
| 190 | 0.031 | >10 |
| 191 | 0.011 | >10 |
| 194 | 0.049 | >10 |
| 195 | 0.024 | 6.112 |
| 196 | 0.026 | >10 |
| 197 | 0.306 | 6.093 |
| 198 | 0.033 | >10 |
| 199 | 0.067 | >10 |
| 200 | 0.024 | >10 |
| 201 | 0.019 | >10 |
| 204 | 1.815 | >10 |
| 205 | 0.015 | 5.203 |
| 206 | 0.016 | >10 |

From the above data, it is clear to the person skilled in the art that compounds of formula (I) of the present invention are highly potent as ChoKα inhibitors. In addition, such compounds appear to be selective versus ChoKβ.

Phosphocholine Determination Assay (Mechanism of Action in Cells)

For the determination of phosphocholine in cells, extracts were prepared according to ref. *Cancer Res.*, 2005, 65, 9369-9376 with some modifications. MDA-MB-468 breast cancer cell line was plated at $1 \times 10^6$ cells in 10 cm petri dish culture in RPMI, 10% FCS culture medium. After 24 h, fresh medium and a compound of general formula (I) were added for further 24 h. At the end of the treatment, the cells were trypsinised, counted and the diameter was determined using a Coulter Counter (Multisizer 3, Beckman). Cells were washed twice with ice-cold physiologic saline solution and $2 \times 10^6$ cells resuspended in 0.3 mL ice-cold twice-distilled water. Then, 0.7 mL ice-cold absolut EtOH were added (final ratio EtOH/H$_2$O 70:30, v/v). After 24 h at −20° C. the samples were sonicated and centrifuged at 14,000×g for 30 minutes.

Phosphocholine concentration levels were assessed in the supernatants using an Ultra High Pressure Liquid Chromatography system (UPLC®, Waters) coupled with a triple quadrupoles mass spectrometer (TQD, Waters) operating in single reaction monitoring mode (SRM). Analyses were performed using Acquity HSS T3 column 2.1×50 mm column, 1.8 µm particle size. Mobile phase A was H$_2$O, modified with 0.15% formic acid, and mobile phase B was MeOH (100% A→97% A over 1 min, flow rate 0.5 mL/min). Waters TQD triple quad mass spectrometer was equipped with an electrospray ion source operating in the positive mode. Source parameters were set as follows: desolvation gas flow 1000 L/h, cone gas flow 50 L/h; collision gas flow 0.2 mL/min; source temperature 130° C.; desolvation temperature 450° C. Dimethyl glicine (DMG) was added to samples as internal standard at 100 μM final concentration. The monitored transitions were m/z 184.00 to 85.7 (collision energy 24 eV) for phosphocholine and m/z 103.0 to 57.5 (collision energy 13 eV) for DMG. The concentration of PCho in the sample was normalized to the total volume of cells (number cells×volume of single cell considered like a sphere).

As an example, the mechanism of action of cpd 114 and cpd 179 is reported in Table 2 (Control refers to untreated cells).

TABLE 2

| Cpd | Concentration | [Phosphocholine] in MDA-MB-468 cell extracts | |
|---|---|---|---|
| | | mM | Inhibition |
| 114 | 0 μM (Control) | 8.25 | — |
| | 2 μM | 1.98 | 76% |
| | 0.4 μM | 5.21 | 37% |
| 179 | 0 μM (Control) | 8.25 | — |
| | 2 μM | 0.69 | 92% |
| | 0.4 μM | 3.27 | 60% |
| | 0.08 μM | 6.40 | 23% |

For the determination of phosphocholine in cell medium culture, cell culture supernatants (500 μL) were denatured by adding 100 μL of trichloroacetic acid (TCA) 1M containing dimethyl glicine (DMG) (100 μM), used as internal standard. Samples were mildly vortexed for 10 minutes and centrifuged at 14,000×g for 3 min. The supernatants were subsequently analyzed for phosphocholine determination.

As an example, the mechanism of action of cpd 114 is reported in Table 3 (Control refers to untreated cells).

TABLE 3

| Cpd | Concentration | [Phosphocholine] in MDA-MB-468 cell supernatants | |
|---|---|---|---|
| | | μM | Inhibition |
| 114 | 0 μM (Control) | 7.27 | — |
| | 2 μM | 2.50 | 66% |

Preparation of Compounds of Formula (I)

For a reference to any specific compound of formula (I) of the invention, optionally in the form of a pharmaceutically acceptable salt, see the experimental section and claims. Referring to the examples that follow, compounds of the present invention were synthesized using the methods described herein, or other methods, which are well known in the art.

The short forms and abbreviations used herein have the following meaning:
g (grams) mg (milligrams)
mL (milliliters) μL (microliters)
mM (millimolar) mmol (millimoles)
μM (micromolar) MHz (Mega-Hertz)
h (hours) Hz (Hertz)
mm (millimetres) min (minutes)
μm (micron) h (hour/s)
M (molar) KOtBu (potassium tert-butoxide)
rt (room temperature) TEA (triethylamine)
DMAP (4-dimethylaminopyridine) DME (1,2-dimethoxyethane)
TFA (trifluoroacetic acid) $Na_2SO_4$ (sodium sulphate)
AcOH (acetic acid) ESI (electrospray ionization)
$Na_2CO_3$ (sodium carbonate) $K_2CO_3$ (potassium carbonate)
$Cs_2CO_3$ (caesium carbonate) $K_3PO_4$ (potassium phosphate)
LiOH (lithium hydroxide) NaOH (sodium hydroxide)
KOH (potassium hydroxide) p-TsOH (p-toluensulfonic acid)
EtOAc (ethyl acetate) LiHDMS (lithium bis(trimethylsilyl)amide)
NMP (N-methyl-2-pyrrolidone) NaH (sodium hydride)
DMA (N,N-dimethylacetamide) KH (potassium hydride)
DMF (N,N-dimethylformamide) DCM (dichloromethane)
DIPEA (N,N-diisopropyl-N-ethylamine) hex (hexane)
THF (tetrahydrofuran) DMSO (dimethylsulfoxide)
MeOH (methanol) ACN (acetonitrile)
EtOH (ethanol) Bn (benzyl)
-OMs (mesylate) -OTs (tosylate)
HOBT (N-hydroxy-benzotriazole) DCC (1,3-dicyclohexyl-carbodiimide)
EDCl (1-ethyl-3-(3-dimethylaminopropyl)carbodiimide hydrochloride)
TBTU (N, N,N',N'-tetramethyl-O-(benzotriazol-1-yl)uronium-tetrafluoroborate)
RP-HPLC (reverse phase high performance liquid chromatography)

With the aim at better illustrating the present invention, without posing any limitation to it, the following examples are given.

As used herein the symbols and conventions used in the processes, schemes and examples are consistent with those used in the contemporary scientific literature, for example, the *Journal of the American Chemical Society* or the *Journal of Biological Chemistry*.

Compound names are IUPAC names, generated by using ACD Name (by Advanced Chemistry Development, Inc.). Unless otherwise noted, all materials, including anhydrous solvent such as DMF, THF, DCM, were obtained from commercial suppliers, of the best grade and used without further purification. All reactions involving air- or moisture-sensitive compounds were performed under nitrogen or argon atmosphere.

General Purification and Analytical Methods

Flash Chromatography was performed on silica gel (Merck grade 9395, 60A).

The HPLC equipment consisted of a Waters Alliance™ HT 2795 system equipped with a Waters 996 PDA detector and Waters mod. ZQ 2000 single quadrupole mass spectrometer, equipped with an electrospray (ESI) ion source. Instrument control, data acquisition and data processing were provided by Empower 2 and MassLynx 4.1 softwares. HPLC was carried out at 25° C. at a flow rate of 1.2 mL/min using a YMC-Triart C18 (4.6×50 mm, 3 μm) column. Mobile phase B was ammonium acetate 5 mM pH=5.2 buffer with acetonitrile (95:5), and mobile phase C was $H_2O$/acetonitrile (5:95); the gradient was from 10 to 90% C in 5 minutes then ramp to 100% C in 0.1 minutes. The injection volume was 10 μL. The mass spectrometer operated in positive and in negative ion mode, the capillary voltage was set up at 3.5 kV ($ES^+$) and 2.8 kV ($ES^-$); cone voltage was 14 V ($ES^+$) and 28 V ($ES^-$); the source temperature was 120° C.; full scan, mass range from 100 to 800 amu was set up.

The preparative HPLC equipment consisted of a Shimadzu HPLC system equipped with SCL-8A System Controller, two LC-8A Pumps, SPD-6A UV Spectrophotometric Detector and manual Rheodyne injection system. Data acquisition (analogic signal) and data processing were provided by Empower 2 software. Purification was carried out at 25° C. at a flow rate of 15 mL/min using a Waters X-Terra MS RP18 (150×30 mm, 10 μm) column. Mobile phase A was 0.1% TFA in water/acetonitrile (95:5) or, alternatively, Mobile phase A was 0.05% $NH_3$ in water/acetonitrile (95:5) and mobile phase B was $H_2O$/acetonitrile (5:95); the gradient was from 10 to 90% B in 15 minutes then ramp to 100% B in 0.1 minutes. Injection volume max 500 μL.

$^1$H-NMR spectra were recorded at a constant temperature of 28° C. on a Varian INOVA 400 spectrometer operating at 400.5 MHz and equipped with a 5 mm $^1H\{^{15}N\text{-}^{31}P\}$ z-axis PFG Indirect Detection probe and on a Varian INOVA 500 spectrometer operating at 499.7 MHz and equipped with a 5 mm $1H\{^{13}C\text{-}^{15}N\}$ triple resonance Indirect Detection probe. Chemical shifts were referenced with respect to the residual solvent signals (DMSO-$d_6$: 2.50 ppm for $^1$H). Data are reported as follows: chemical shift (δ), multiplicity (s=singlet, d=doublet, t=triplet, q=quartet, br. s=broad singlet, dd=doublet of doublets, ddd=doublet of doublets of doublets, m=multiplet), coupling constants (J, Hz) and number of protons.

As formerly reported (M. Colombo, F. R. Sirtori, V. Rizzo, Rapid Commun Mass Spectrom 2004, 18(4), 511-517), ESI(+) high-resolution mass spectra (HRMS) were obtained on a Q-Tof Ultima (Waters, Manchester, UK) mass spectrometer directly connected with an Agilent 1100 micro-HPLC system (Palo Alto, US).

Example 1

Sequence A 9-(4-tert-butylcyclohexyl)-2-chloro-9H-purin-6-amine (I), cpd 80

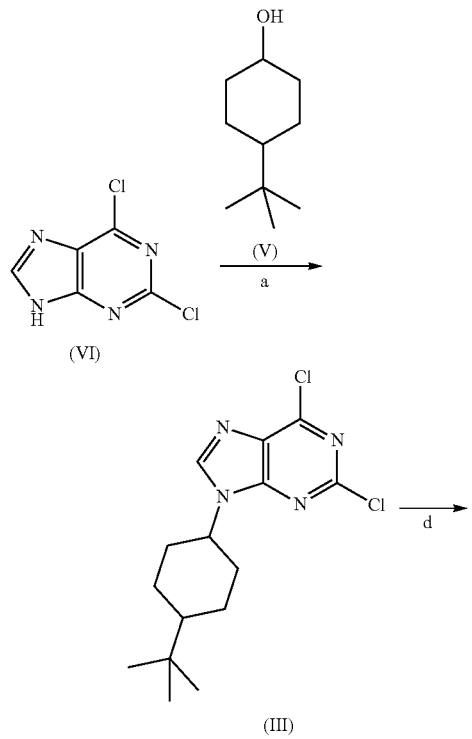

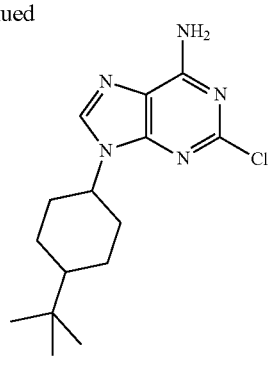

Step a 9-(4-tert-butylcyclohexyl)-2,6-dichloro-9H-purine (III)

[X=N, R1=($C_1$-$C_6$)alkyl, n=0, R3=Cl]

To a solution of 2,6-dichloro-9H-purine (VI) (100 mg, 0.53 mmol), 4-tert-butylcyclohexanol (V) (248 mg, 1.58 mmol) and triphenylphosphine (416 g, 1.58 mmol) in dry THF (7 mL), diethyl azodicarboxylate (0.25 mL, 1.58 mmol) was added dropwise at rt. The resulting mixture was heated at 50° C. for 6 h, then a second portion of diethyl azodicarboxylate (1.4 mL) was added and the mixture heated for further 6 h. The mixture was allowed to reach rt and taken to dryness under reduced pressure. The product was purified by column chromatography (eluant hex, hex:EtOAc=9:1, 8:2) and isolated as white solid (123 mg, 72%).

$^1$H NMR (401 MHz, DMSO-$d_6$) δ ppm 0.83 (s, 9H) 1.09-1.22 (m, 5H) 1.61-1.70 (m, 2H) 1.82-1.97 (m, 2H) 4.65-4.79 (m, 1H) 8.84 (s, 1H).

HRMS (ESI+): calcd. for $C_{15}H_{21}Cl_2N_4$ [M+H]$^+$ 327.1138; found 327.1138.

Operating in an analogous way, but employing suitably substituted starting materials of formula (V) and (VI), the following compounds were obtained:

methyl cis-4-(6-chloro-2-iodo-9H-purin-9-yl)cyclohexanecarboxylate (III)

[X=N, R1=COOR4, R4=($C_1$-$C_6$)alkyl, n=0, R3=I]

$^1$H NMR (500 MHz, DMSO-$d_6$) δ ppm 1.68-1.79 (m, 2H) 1.88-2.08 (m, 4H) 2.17 (d, J=12.51 Hz, 2H) 2.75-2.81 (m, 1H) 3.70 (s, 3H) 4.43-4.53 (m, 1H) 8.71 (s, 1H).

HRMS (ESI+): calcd. for $C_{13}H_{15}ClN_4O_2$ [M+H]$^+$ 420.9923; found 420.9923.

methyl cis-4-(2,6-dichloro-9H-purin-9-yl)cyclohexanecarboxylate (III)

[X=N, R1=COOR4, R4=($C_1$-$C_6$)alkyl, n=0, R3=Cl]

$^1$H NMR (500 MHz, DMSO-$d_6$) δ ppm 1.69-1.81 (m, 2H) 1.88-2.07 (m, 2H) 2.12-2.22 (m, 2H) 2.76-2.81 (m, 2H) 3.69 (s, 3H) 4.45-4.56 (m, 1H) 8.83 (s, 1H).

HRMS (ESI+): calcd. for $C_{13}H_{15}Cl_2N_4O_2$ [M+H]$^+$ 329.0567; found 329.0561.

tert-butyl [cis-4-(2,6-dichloro-9H-purin-9-yl)cyclohexyl]carbamate (III)

[X=N, R1=NR4COOR6, R4=H, R6=($C_1$-$C_6$)alkyl, n=0, R3=Cl]

HRMS (ESI+): calcd. for $C_{16}H_{22}Cl_2N_5O_2$ [M+H]$^+$ 386.1145; found 386.1140.

methyl cis-4-[6-chloro-2-(trifluoromethyl)-9H-purin-9-yl]cyclohexanecarboxylate (III)

[X=N, R1=COOR4, R4=(C$_1$-C$_6$)alkyl, n=0, R3=Polifluorinated Alkyl]

$^1$H NMR (500 MHz, DMSO-d$_6$) δ ppm 1.69-1.81 (m, 2H) 1.88-2.03 (m, 2H) 2.2-2.15 (m, 2H) 2.15-2.23 (m, 2H) 2.76-2.85 (m, 1H) 3.69 (s, 3H) 4.54-4.66 (m, 1H) 9.02 (s, 1H).

HRMS (ESI+): calcd. for $C_{14}H_{15}ClF_3N_4O_2$ [M+H]$^+$ 363.0830; found 363.0827.

methyl cis-4-(4,6-dichloro-1H-imidazo[4,5-c]pyridin-1-yl)cyclohexanecarboxylate (III)

[X=CH, R1=COOR4, R4=(C$_1$-C$_6$)alkyl, n=0, R3=Cl]

HRMS (ESI+): calcd. for $C_{14}H_{16}Cl_2N_3O_2$ [M+H]$^+$ 328.0614; found 328.0622.

Step d

9-(4-tert-butylcyclohexyl)-2-chloro-9H-purin-6-amine (I), cpd 80

[X=N, R1=(C$_1$-C$_6$)alkyl, n=0, R3=Cl]

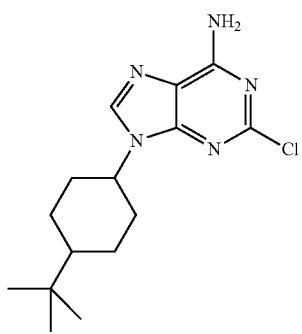 [SMILES: CC(C)(C)C1CCC(n2cnc3c(N)nc(Cl)nc32)CC1]

9-(4-tert-butylcyclohexyl)-2,6-dichloro-9H-purine (115 md, 0.35 mmol) was treated with a 7N methanolic ammonia solution (10 mL) at 100° C. overnight. After evaporation of the solvent under reduced pressure, the crude was dissolved in DCM and washed with water and brine. The organic layer was dried over Na$_2$SO$_4$, filtered and concentrated. The crude was purified by column chromatography (eluant EtOAc: hex=1:1, 6:4, EtOAc) affording the title compound (58 mg, 54%).

$^1$H NMR (499.7 MHz, DMSO-d$_6$) δ ppm 0.86 (s, 9H), 1.14-1.27 (m, 3H), 1.64-1.70 (m, 2H), 1.82-1.94 (m, 2H), 2.46-2.50 (m, 2H), 4.52-4.62 (m, 1H), 7.76 (br. s., 2H) 8.29 (m, 1H).

HRMS (ESI+): calcd. for $C_{15}H_{23}ClN_5$ [M+H]$^+$ 308.1637; found 308.1630.

Operating in an analogous way, but employing suitably substituted starting materials (III), the following compounds were obtained:

methyl cis-4-(6-amino-2-iodo-9H-purin-9-yl)cyclohexanecarboxylate (I), cpd 110

[X=N, R1=COOR4, R4=(C$_1$-C$_6$)alkyl, n=0, R3=I]

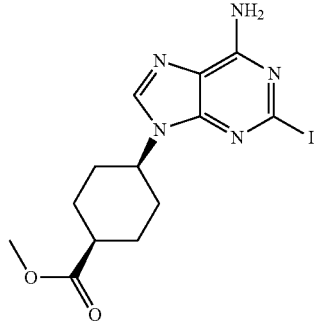 [SMILES: COC(=O)[C@H]1CC[C@@H](n2cnc3c(N)nc(I)nc32)CC1]

$^1$H NMR (499.7 MHz, DMSO-d6) δ ppm 1.67-1.76 (m, 2H), 1.86-1.97 (m, 4H), 2.11-2.18 (m, 2H), 2.74-2.78 (m, 1H), 3.69 (s, 3H), 4.27-4.34 (m, 1H), 7.61 (br. s., 2H), 8.13 (s, 1H).

HRMS (ESI+): calcd. for $C_{13}H_{17}IN_5O_2$ [M+H]$^+$ 402.0422; found 402.0424.

methyl cis-4-(6-amino-2-chloro-9H-purin-9-yl)cyclohexanecarboxylate (I), cpd 88

[X=N, R1=COOR4, R4=alkyl, n=0, R3=Cl]

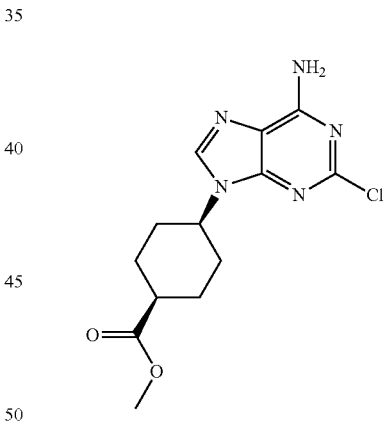

$^1$H NMR (400.5 MHz, DMSO-d$_6$) δ ppm 1.66-1.77 (m, 2H), 1.87-1.97 (m, 4H), 2.12-2.19 (m, 2H), 2.73-2.79 (m, 1H), 3.68 (s, 3H), 4.27-4.37 (m, 1H), 7.68-7.74 (m, 2H), 8.21 (s, 1H).

HRMS (ESI+): calcd. for $C_{13}H_{17}ClN_5O_2$ [M+H]$^+$ 310.1066; found 310.1066.

tert-butyl [cis-4-(6-amino-2-chloro-9H-purin-9-yl)cyclohexyl]carbamate (I), cpd 192

[X=N, R1=NR4COOR6, R4=H, R6=(C$_1$-C$_6$)alkyl, n=0, R3=Cl]

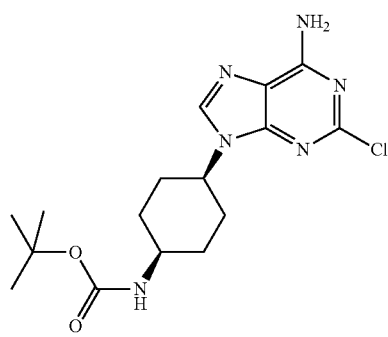 [SMILES: CC(C)(C)OC(=O)N[C@H]1CC[C@@H](n2cnc3c(N)nc(Cl)nc32)CC1]

¹H NMR (500 MHz, DMSO-d₆) δ ppm 1.42 (s, 9H) 1.64-1.73 (m, 4H) 1.75-1.84 (m, 2H) 2.03-2.22 (m, 2H) 3.72-3.81 (m, 1H) 4.24-4.36 (m, 1H) 7.01 (d, J=7.93 Hz, 1H) 7.75 (br. s., 2H) 8.31 (s, 1H).

HRMS (ESI+): calcd. for $C_{16}H_{24}ClN_6O_2$ [M+H]⁺ 367.1644; found 367.1643.

methyl cis-4-[6-amino-2-(trifluoromethyl)-9H-purin-9-yl]cyclohexanecarboxylate (I), cpd 161

[X=N, R1=COOR4, R4=alkyl, n=0, R3=polyfluorinated alkyl]

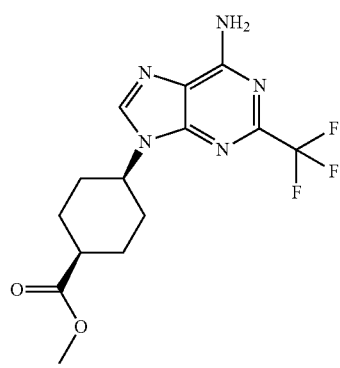 [SMILES: COC(=O)[C@H]1CC[C@@H](n2cnc3c(N)nc(C(F)(F)F)nc32)CC1]

¹H NMR (400.5 MHz, DMSO-d₆) δ ppm 1.78-1.87 (m, 2H), 1.87-2.08 (m, 4H), 2.12-2.25 (m, 2H), 2.72-2.83 (m, 1H), 3.68 (s, 3H), 4.37-4.50 (m, 1H), 7.84 (br. s., 2H), 8.40 (s, 1H).

HRMS (ESI+): calcd. for $C_{14}H_{17}F_3N_5O_2$ [M+H]⁺ 344.1329; found 344.1327.

Example 2

Sequence B cis-4-(6-amino-2-chloro-9H-purin-9-yl)-N-(3-methoxyphenyl)cyclohexanecarboxamide (I), cpd 3

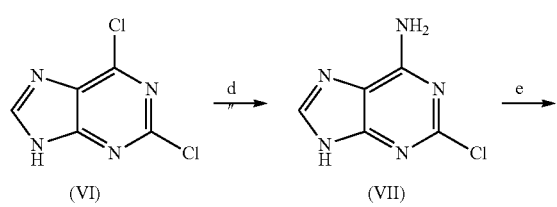

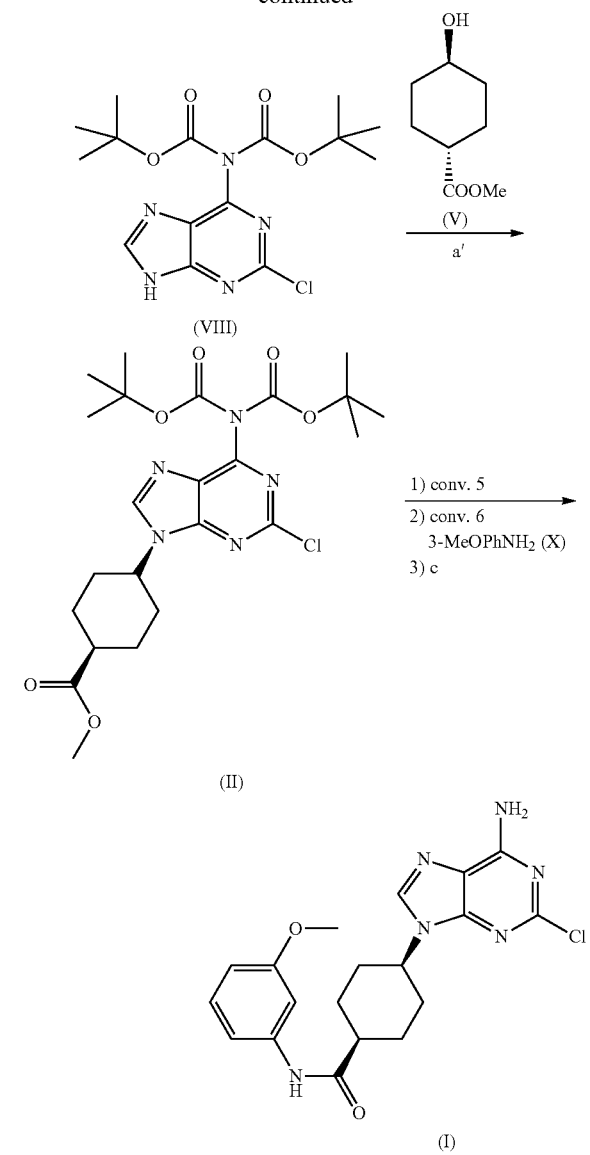

Step d'

2-Chloro-9H-purin-6-amine (VII)

[X=N, R3=Cl]

2,6-Dichloro-9H-purine (VI) (1 g, 5.29 mmol) was placed in a sealed tube and dissolved in a 7N methanolic ammonia solution (10 mL). The mixture was heated at 100° C. for 21 h. After cooling to rt, the resulting suspension was diluted with water (5 mL) and let under stirring for 30 min. The solid was filtered, washed with cold water and dried under vacuum. The title compound was isolated as pale yellow solid (830 mg, 92%).

¹H NMR (500 MHz, DMSO-d₆) δ ppm 7.62 (br. s., 2H) 8.09 (s, 1H) 13.0 (br. s., 1H).

HRMS (ESI+): calcd. for $C_5H_5ClN_5$ [M+H]⁺ 170.0228; found 170.0230.

Step e di-tert-butyl (2-chloro-9H-purin-6-yl)imidodicarbonate (VIII)

[X=N, R3=Cl, PG=COOR7, R7=(C$_1$-C$_6$)alkyl]

To a suspension of 2-chloro-9H-purin-6-amine (VII) (1 g, 5.89 mmol) and DMAP (720 mg, 5.89 mmol) in dry THF (10 mL), di-tert-butyl dicarbonate (3.86 g, 17.7 mmol) was added portionwise. The yellowish suspension turned to an orange solution while letting under stirring at rt overnight. After solvent removal under reduced pressure, the residue was dissolved in EtOAc and washed with a 1M aqueous solution of NaH$_2$PO$_4$ (1×20 mL), a saturated aqueous solution of NaHCO$_3$, water and brine. The organic layer was dried over Na$_2$SO$_4$, filtered and evaporated to dryness in vacuo. The residue was dissolved in methanol (20 mL), treated with a saturated aqueous solution of NaHCO$_3$ (9 mL) and heated at 40° C. for 1 h. After cooling at rt and removal of methanol under reduced pressure, the residue was extracted with DCM (2×20 mL). The combined organic layers were washed with water and brine, dried over Na$_2$SO$_4$, filtered and evaporated to dryness in vacuo. After column chromatography (eluant hex:EtOAc=8:2), the title compound was isolated as a white solid (1.52 g, 70%).

$^1$H NMR (401 MHz, DMSO-d$_6$) δ ppm 1.39 (s, 18H) 8.66 (br. s., 1H) 13.95 (br. s., 1H).

HRMS (ESI+): calcd. for C$_{15}$H$_{21}$ClN$_5$NaO$_4$ [M+Na]$^+$ 392.1096; found 392.1099.

Operating in an analogous way, but employing suitably substituted starting materials (VII), the following compounds were obtained:

di-tert-butyl (2-iodo-9H-purin-6-yl)imidodicarbonate (VIII)

[X=N, R3=I, PG=COOR7, R7=(C$_1$-C$_6$)alkyl]

$^1$H NMR (500 MHz, DMSO-d$_6$) δ ppm 1.38 (s, 18H) 8.58 (br. s., 1H) 13.74 (br. s., 1H)

HRMS (ESI+): calcd. for C$_{15}$H$_{21}$IN$_5$O$_4$[M+H]$^+$ 462.0633; found 462.0628.

di-tert-butyl (2-methoxy-9H-purin-6-yl)imidodicarbonate (VIII)

[X=N, R3=OR6, R6=(C$_1$-C$_6$)alkyl, PG=COOR7, R7=(C$_1$-C$_6$)alkyl]

$^1$H NMR (500 MHz, DMSO-d$_6$) δ ppm 1.38 (s, 18H) 3.92 (s, 3H) 8.37 (s, 1H) 13.39 (br. s., 1H).

HRMS (ESI+): calcd. for C$_{16}$H$_{24}$N$_5$O$_5$ [M+H]$^+$ 166.0724; found 166.0715.

Step a'

Methyl cis-4-{6-[bis(tert-butoxycarbonyl)amino]-2-chloro-9H-purin-9-yl}cyclohexanecarboxylate (II)

[X=N, R1=COOR4, R4=(C$_1$-C$_6$)alkyl, n=0, R3=Cl, PG=COOR7, R7=(C$_1$-C$_6$)alkyl]

To a solution of di-tert-butyl (2-chloro-9H-purin-6-yl) imidodicarbonate (VIII) (2.27 g, 6.14 mmol), methyl trans-4-hydroxycyclohexanecarboxylate (V) (3.2 g, 18.42 mmol) and triphenylphosphine (4.82 g, 18.42 mmol) in dry THF (20 mL), diethyl azodicarboxylate (2.86 mL, 18.42 mmol) was added dropwise at rt. The resulting mixture was let under stirring for 3 days, with a second addition of triphenylphosphine and diethyl azodicarboxylate after 48 h. The solvent was then removed under reduced pressure. The product was purified by column chromatography (eluant hex, hex:EtOAc=9:1) and isolated as colorless oil (1.5 g, 48%).

$^1$H NMR (401 MHz, DMSO-d$_6$) δ ppm 1.4 (s, 18H) 1.67-1.84 (m, 2H) 1.93-2.09 (m, 4H) 2.12-2.22 (m, 2H) 2.75-2.82 (m, 1H) 3.69 (s, 3H) 4.44-4.59 (m, 1H) 8.77 (s, 1H).

HRMS (ESI+): calcd. for C$_{23}$H$_{33}$ClN$_5$O$_6$ [M+H]$^+$ 510.2114; found 510.2115.

Operating in an analogous way, but employing suitably substituted starting materials (VIII) and (V), the following compounds were obtained:

methyl cis-4-{6-[bis(tert-butoxycarbonyl)amino]-2-iodo-9H-purin-9-yl}cyclohexanecarboxylate (II)

[X=N, R1=COOR4, R4=(C$_1$-C$_6$)alkyl, n=0, R3=I, PG=COOR7, R7=(C$_1$-C$_6$)alkyl]

$^1$H NMR (401 MHz, DMSO-d$_6$) δ ppm 1.39 (s, 18H) 1.69-1.80 (m, 2H) 1.87-2.05 (m, 4H) 2.11-2.22 (m, 2H) 2.75-2.83 (m, 1H) 3.70 (s, 3H) 4.47-4.58 (m, 1H) 8.66 (s, 1H).

HRMS (ESI+): calcd. for C$_{23}$H$_{33}$IN$_5$O$_6$[M+H]$^+$ 602.1470; found 602.1478.

methyl cis-4-{6-[bis(tert-butoxycarbonyl)amino]-2-methoxy-9H-purin-9-yl}cyclohexanecarboxylate (II)

[X=N, R1=COOR4, R4=(C$_1$-C$_6$)alkyl, n=0, R3=OR6, R6=(C$_1$-C$_6$)alkyl, PG=COOR7, R7=(C$_1$-C$_6$)alkyl]

$^1$H NMR (401 MHz, DMSO-d$_6$) δ ppm 1.39 (s, 18H) 1.62-1.76 (m, 2H) 1.85-1.96 (m, 4H) 2.10-2.19 (m, 2H) 2.72-2.80 (m, 1H) 3.65 (s, 3H) 3.91 (s, 3H) 4.34-4.45 (m, 1H) 8.41 (s, 1H)

HRMS (ESI+): calcd. for C$_{24}$H$_{36}$IN$_5$O$_7$[M+H]$^+$ 506.2610; found 506.2605.

di-tert-butyl (2-chloro-9-{cis-4-[(3-methoxyphenyl) carbamoyl]cyclohexyl}-9H-purin-6-yl)imidodicarbonate (II)

[X=N, R1=CONR4R5, R4=Substituted Aryl, R5=H, n=0, R3=Cl, PG=COOR7, R7=(C$_1$-C$_6$)alkyl]

$^1$H NMR (401 MHz, DMSO-d$_6$) δ ppm 1.40 (s, 18H) 1.76-1.88 (m, 2H) 1.96-2.12 (m, 4H) 2.24-2.41 (m, 2H) 2.68-2.75 (m, 1H) 3.73 (s, 3H) 4.52-4.62 (m, 1H) 6.61 (dt, J=7.38, 2.17 Hz, 1H) 7.15-7.22 (m, 2H) 7.33-7.37 (m, 1H) 8.78 (s, 1H) 9.80 (br. s., 1H).

HRMS (ESI+): calcd. for C$_{29}$H$_{38}$ClN$_6$O$_6$[M+H]$^+$ 601.2536; found 601.2552.

Conv. 5 cis-4-{6-[bis(tert-butoxycarbonyl)amino]-2-chloro-9H-purin-9-yl}cyclohexanecarboxylic acid (II)

[X=N, R1=COOR4, R4=H, n=0, R3=Cl, PG=COOR7, R7=(C$_1$-C$_6$)alkyl]

Methyl cis-4-{6-[bis(tert-butoxycarbonyl)amino]-2-chloro-9H-purin-9-yl}cyclohexanecarboxylate (11) (1.3 g, 2.55 mmol) was dissolved in a water/THF mixture (25:13 mL) and treated with 2N NaOH (6.5 mL) at rt for 3 h. The reaction was then quenched with a 2.5M solution of KHSO$_4$ (10.5 mL), diluted with EtOAc and washed with water and brine. The organic layer was dried over Na$_2$SO$_4$, filtered and taken to dryness under reduced pressure. The title compound was isolated as white solid in mixture with 20% of methyl cis-4-{6-[(tert-butoxycarbonyl)amino]-2-chloro-9H-purin-9-yl}cyclohexanecarboxylate and used without further purification.

¹H NMR (401 MHz, DMSO-d₆) δ ppm 1.4 (s, 18H) 1.65-1.78 (m, 2H) 1.91-2.10 (m, 4H) 2.11-2.22 (m, 2H) 2.64-2.70 (m, 1H) 4.46-4.56 (m, 1H) 8.77 (s, 1H) 10.30 (br. s., 1H).

HRMS (ESI+): calcd. for $C_{22}H_{30}ClNaN_5O_6$ [M+Na]⁺ 518.1777; found 518.1765.

Operating in an analogous way, but employing suitably substituted starting materials, the following compounds were obtained:

cis-4-{6-[bis(tert-butoxycarbonyl)amino]-2-iodo-9H-purin-9-yl}cyclohexanecarboxylic acid (II)

[X=N, R1=COOR4, R4=H, n=0, R3=I, PG=COOR7, R7=($C_1$-$C_6$)alkyl]

HRMS (ESI+): calcd. for $C_{22}H_{31}IN_5O_6$[M+H]⁺ 588.1314; found 588.1320.

cis-4-{6-[bis(tert-butoxycarbonyl)amino]-2-methoxy-9H-purin-9-yl}cyclohexanecarboxylic acid (II)

[X=N, R1=COOR4, R4=H, n=0, R3=OR6, R6=($C_1$-$C_6$) alkyl, PG=COOR7, R7=($C_1$-$C_6$)alkyl]

¹H NMR (401 MHz, DMSO-d₆) δ ppm 1.39 (s, 18H) 1.59-1.73 (m, 2H) 1.83-1.96 (m, 2H) 2.08-2.24 (m, 4H) 2.60-2.68 (m, 1H) 3.93 (s, 3H) 4.37-4.46 (m, 1H) 8.44 (s, 1H) 12.35 (br. s., 1H).

HRMS (ESI+): calcd. for $C_{23}H_{34}IN_5O_7$[M+H]⁺ 492.2453; found 492.2459.

cis-4-(6-amino-2-iodo-9H-purin-9-yl)cyclohexanecarboxylic acid (I), cpd 111

[X=N, R1=COOR4, R4=H, n=0, R3=I]

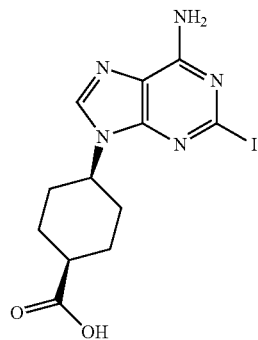 [SMILES: Nc1nc(I)nc2c1ncn2[C@H]1CC[C@@H](C(=O)O)CC1]

¹H NMR (499.7 MHz, DMSO-d₆) δ ppm 1.64-1.74 (m, 2H), 1 87-1.97 (m, 2H), 2.09-2.17 (m, 2H), 2.62-2.67 (m, 1H), 4.24-4.34 (m, 1H), 7.61 (br. s., 2H), 8.12 (s, 1H), 12.29 (br. s., 1H).

HRMS (ESI+): calcd. for $C_{12}H_{15}IN_5O_2$ [M+H]⁺ 388.0265; found 388.0269.

cis-4-(6-amino-2-chloro-9H-purin-9-yl)cyclohexanecarboxylic acid (I), cpd 117

[X=N, R1=COOR4, R4=H, n=0, R3=Cl]

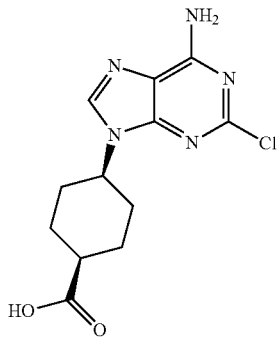 [SMILES: Nc1nc(Cl)nc2c1ncn2[C@H]1CC[C@@H](C(=O)O)CC1]

¹H NMR (499.7 MHz, DMSO-d₆) δ ppm 1.64-1.73 (m, 2H), 1.88-2.01 (m, 4H), 2.11-2.17 (m, 1H), 2.63-2.68 (m, 1H), 4.28-4.34 (m, 1H), 7.72 (br. s., 2H), 8.20 (s, 1H), 12.27 (br. s., 1H).

HRMS (ESI+): calcd. for $C_{12}H_{15}ClN_5O_2$ [M+H]⁺ 296.0909; found 296.0903.

cis-4-(6-amino-2-fluoro-9H-purin-9-yl)cyclohexanecarboxylic acid (I), cpd 125

[X=N, R1=COOR4, R4=H, n=0, R3=F]

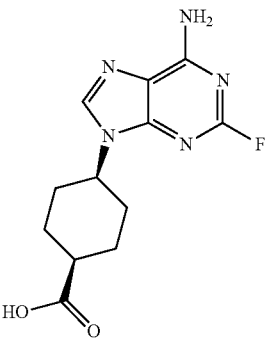 [SMILES: Nc1nc(F)nc2c1ncn2[C@H]1CC[C@@H](C(=O)O)CC1]

HRMS (ESI+): calcd. for $C_{12}H_{15}FN_5O_2$ [M+H]⁺ 280.1204; found 280.1200.

Conv. 6 di-tert-butyl (2-chloro-9-{cis-4-[(3-methoxyphenyl)carbamoyl]cyclohexyl}-9H-purin-6-yl)imidodicarbonate (II)

[X=N, R1=CONR4R5, R4=Substituted Aryl, R5=H, n=0, R3=Cl, PG=COOR7, R7=($C_1$-$C_6$)alkyl]

A mixture of cis-4-{6-[bis(tert-butoxycarbonyl)amino]-2-chloro-9H-purin-9-yl}cyclohexanecarboxylic acid (800 mg, 1.62 mmol), TBTU (624 mg, 1.94 mmol), 3-methoxyaniline (X) (0.37 mL, 3.29 mmol) and DIPEA (0.83 mL, 4.85 mmol) in DMA (30 mL) was let under stirring at rt overnight. After dilution with EtOAc (40 mL), the organic phase was washed with a saturated solution of NaHCO₃, water and brine, dried over Na₂SO₄, filtered and evaporated in vacuo. The crude product was used without any further purification in the deprotection step.

Alternatively:

cis-4-{6-[bis(tert-butoxycarbonyl)amino]-2-chloro-9H-purin-9-yl}cyclohexanecarboxylic acid (48 mg, 0.098 mmol) was suspended in dry DCM (2.5 mL) under nitrogen and treated with 1-chloro-N,N,2-trimethylprop-1-en-1-amine (Ghosez's reagent, 0.04 mL, 0.294 mmol) at rt for 1 h (the suspension turned into a pale yellow solution). A solution of 3-methoxyaniline (X) (0.0313 mL, 0.118 mmol) and DIPEA (0.034 mL, 0.245 mmol) in DCM (2 mL) was added dropwise under nitrogen and the mixture was let under stirring at rt for 2.5 h. The reaction was quenched with a saturated solution of NaHCO$_3$ and extracted with DCM (2×4 mL). The organic phase was washed with water and brine, dried over Na$_2$SO$_4$, filtered and evaporated under reduced pressure. The crude product was used without any further purification in the deprotection step.

Step c cis-4-(6-amino-2-chloro-9H-purin-9-yl)-N-(3-methoxyphenyl)cyclohexanecarboxamide (I), cpd 3

[X=N, R1=CONR4R5, R4=Substituted Aryl, R5=H, n=0, R3=Cl]

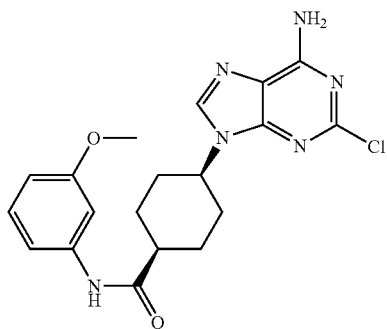 [SMILES: COc1cccc(NC(=O)[C@H]2CC[C@@H](n3cnc4c(N)nc(Cl)nc43)CC2)c1]

The crude of conv. 6 was treated with TFA (5 mL) in DCM (24 mL) at rt for 4 h. The mixture was then neutralized with a saturated solution of NaHCO$_3$ and the product was extracted with DCM (3×10 mL). The combined organic phase was washed with water and brine, dried over Na$_2$SO$_4$, filtered and evaporated under reduced pressure. The residue was treated with diethylether and the title compound was isolated by filtration as pale pink solid (380 mg). The mother liquor was purified by column chromatography (eluant EtOAc:hex=8:2, 9:1, EtOAc) yielding further 50 mg of product (430 mg, 66%).

$^1$H NMR (400.5 MHz, DMSO-d$_6$) δ ppm 1.74-1.85 (m, 2H), 1.88-1.99 (m, 2H), 2.05-2.09 (m, 2H), 2.20-2.30 (m, 2H), 2.64-2.72 (m, 1H), 3.73 (m, 3H), 4.34-4.42 (m, 1H), 6.58-6.63 (m, 1H), 7.14-7.22 (m, 2H), 7.33-7.36 (m, 1H), 7.71 (br. s., 2H), 8.21 (s, 1H), 9.79 (s, 1H).

HRMS (ESI+): calcd. for C$_{19}$H$_{22}$ClN$_6$O$_2$ [M+H]$^+$ 401.1488; found 401.1488.

Operating in an analogous way, but employing suitably substituted starting materials (II) and (X), the following compounds were obtained:

cis-4-[6-amino-2-(pyridin-3-yl)-9H-purin-9-yl]-N-{4-[(trifluoromethyl)sulfonyl]phenyl}cyclohexanecarboxamide (I), cpd 24

[X=N, R1=CONR4R5, R4=Substituted Aryl, R5=H, n=0, R3=Heteroaryl]

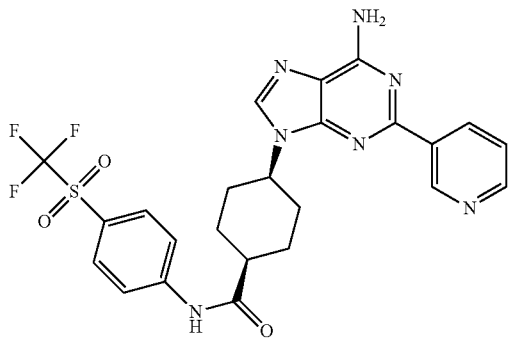 [SMILES: Nc1nc(-c2cccnc2)nc2c1ncn2[C@H]1CC[C@@H](C(=O)Nc2ccc(S(=O)(=O)C(F)(F)F)cc2)CC1]

HRMS (ESI+): calcd. for C$_{24}$H$_{23}$F$_3$N$_7$O$_3$S [M+H]$^+$ 546.1530; found 546.1531.

cis-4-(6-amino-2-chloro-9H-purin-9-yl)-N-{4-[(trifluoromethyl)sulfonyl]phenyl}cyclohexanecarboxamide (I), cpd 27

[X=N, R1=CONR4R5, R4=Substituted Aryl, R5=H, n=0, R3=Cl]

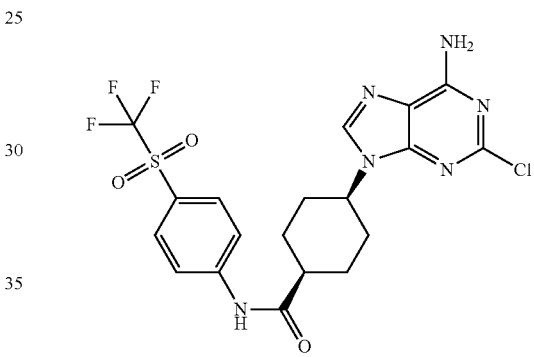

$^1$H NMR (400.5 MHz, DMSO-d$_6$) δ ppm 1.78-1.89 (m, 2H), 1.90-2.00 (m, 2H), 2.04-2.15 (m, 2H), 2.16-2.27 (m, 2H), 2.77-2.83 (m, 1H), 4.35-4.44 (m, 1H), 7.71 (br. s., 2H), 8.07 (s, 4H), 8.21 (s, 1H), 10.60 (s, 1H).

HRMS (ESI+): calcd. for C$_{19}$H$_{19}$ClF$_3$N$_6$O$_3$S [M+H]$^+$ 503.0875; found 503.0874.

cis-4-(6-amino-2-chloro-9H-purin-9-yl)-N-(3,4-dimethoxyphenyl)cyclohexanecarboxamide (I), cpd 32

[X=N, R1=CONR4R5, R4=Substituted Aryl, R5=H, n=0, R3=Cl]

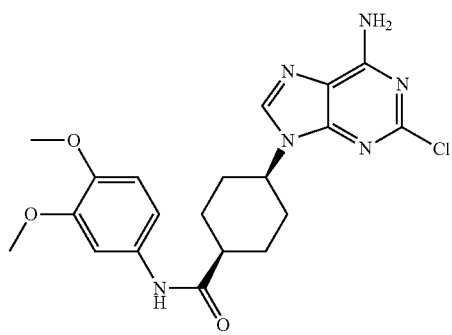 [SMILES: COc1ccc(NC(=O)[C@H]2CC[C@@H](n3cnc4c(N)nc(Cl)nc43)CC2)cc1OC]

$^1$H NMR (499.7 MHz, DMSO-d$_6$) δ ppm 1.73-1.84 (m, 2H), 1.85-1.95 (m, 2H), 2.01-2.09 (m, 2H), 2.18-2.30 (m, 2H), 2.65-2.69 (m, 1H), 3.70 (s, 3H), 3.72 (s, 3H), 4.35-4.42 (m, 1H), 6.87 (d, J=8.7 Hz, 1H), 7.12 (dd, J=8.7, 2.3 Hz, 1H), 7.35 (d, J=2.3 Hz, 1H), 7.75 (br. s., 2H), 8.22 (s, 1H), 9.69 (s, 1H).

HRMS (ESI+): calcd. for C$_{20}$H$_{24}$ClN$_6$O$_3$ [M+H]$^+$ 431.1593; found 431.1577.

cis-4-(6-amino-2-chloro-9H-purin-9-yl)-N-{4-[2-({4-[(4-methylpiperazin-1-yl)methyl]-3-(trifluoromethyl)phenyl}amino)-2-oxoethyl]phenyl}cyclohexanecarboxamide (I), cpd 35

[X=N, R1=CONR4R5, R4=Substituted Aryl, R5=H, n=0, R3=Cl]

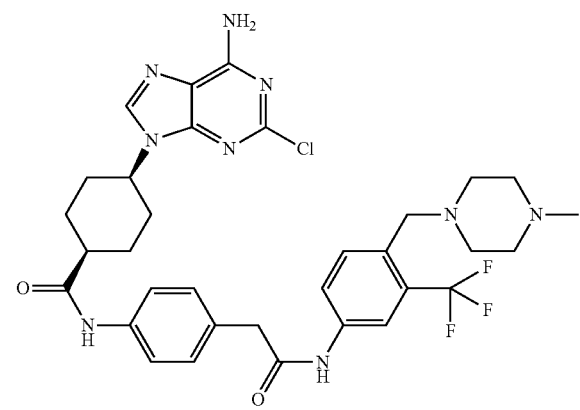 [SMILES: CN1CCN(Cc2ccc(NC(=O)Cc3ccc(NC(=O)[C@H]4CC[C@@H](n5cnc6c(N)nc(Cl)nc65)CC4)cc3)cc2C(F)(F)F)CC1]

$^1$H NMR (400.5 MHz, DMSO-d$_6$) δ ppm 1.74-1.85 (m, 2H), 1.87-1.97 (m, 2H), 2.02-2.10 (m, 2H), 2.14 (s, 3H), 2.20-2.44 (m, 10H), 2.68-2.74 (m, 1H), 3.52 (s, 2H), 3.59 (s, 2H), 4.34-4.43 (m, 1H), 7.25 (d, J=8.5 Hz, 2H), 7.57 (d, J=8.5 Hz, 2H), 7.64 (d, J=8.4 Hz, 1H), 7.71 (br. s., 2H), 7.77 (dd, J=8.4, 2.2 Hz, 1H), 8.03 (d, J=2.2 Hz, 1H), 8.19 (s, 1H), 9.80 (s, 1H), 10.39 (s, 1H).

HRMS (ESI+): calcd. for C$_{33}$H$_{38}$ClF$_3$N$_9$O$_2$ [M+H]$^+$ 684.2784; found 684.2790.

cis-4-(6-amino-2-chloro-9H-purin-9-yl)-N-{4-[2-({4-[(4-methylpiperazin-1-yl)methyl]phenyl}amino)-2-oxoethyl]phenyl}cyclohexanecarboxamide (I), cpd 36

[X=N, R1=CONR4R5, R4=Substituted Aryl, R5=H, n=0, R3=Cl]

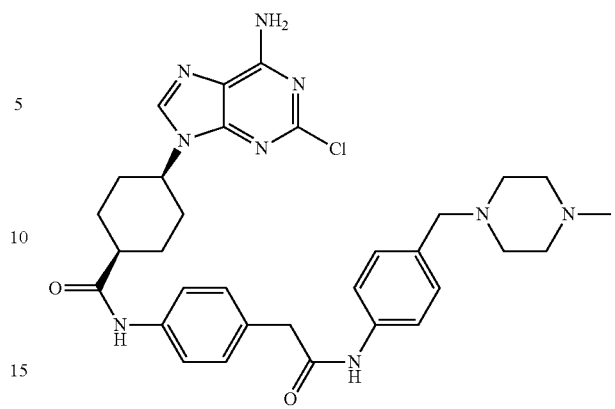

$^1$H NMR (499.7 MHz, DMSO-d$_6$) δ ppm 1.69-1.83 (m, 2H), 1.88-1.96 (m, 2H), 2.01-2.11 (m, 2H), 2.16 (s, 3H), 2.20-2.45 (m, 10H), 2.66-2.73 (m, 1H), 3.37 (s, 2H), 3.55 (s, 2H), 4.38-4.43 (m, 1H), 7.19 (d, J=8.4 Hz, 2H), 7.24 (d, J=8.4 Hz, 2H), 7.52 (d, J=8.4 Hz, 2H), 7.56 (d, J=8.4 Hz, 2H), 7.74 (br. s., 2H), 8.21 (s, 1H), 9.82 (s, 1H), 10.09 (s, 1H).

HRMS (ESI+): calcd. for C$_{32}$H$_{39}$ClN$_9$O$_2$ [M+H]$^+$ 616.2910; found 616.2921.

cis-4-(6-amino-2-iodo-9H-purin-9-yl)-N-(3-methoxyphenyl)cyclohexanecarboxamide (I), cpd 41

[X=N, R1=CONR4R5, R4=Substituted Aryl, R5=H, n=0, R3=I]

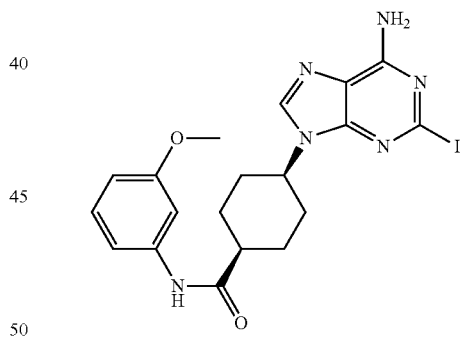

$^1$H NMR (499.7 MHz, DMSO-d$_6$) δ ppm 1.73-1.84 (m, 2H), 1.87-1.95 (m, 2H), 2.00-2.08 (m, 2H), 2.19-2.27 (m, 2H), 2.67-2.71 (m, 1H), 3.72 (s, 3H), 4.33-4.41 (m, 1H), 6.59-6.62 (m, 1H), 7.14-7.20 (m, 2H), 7.33-7.36 (m, 1H), 7.64 (br. s., 2H), 8.14 (s, 1H), 9.82 (s, 1H).

HRMS (ESI+): calcd. for C$_{19}$H$_{22}$IN$_6$O$_2$ [M+H]$^+$ 493.0844; found 493.0839.

cis-4-(6-amino-2-chloro-9H-purin-9-yl)-N-(3-methoxybenzyl)cyclohexanecarboxamide (I), cpd 47

[X=N, R1=CONR4R5, R4=substituted aryl(C$_1$-C$_6$)alkyl, R5=H, n=0, R3=Cl]

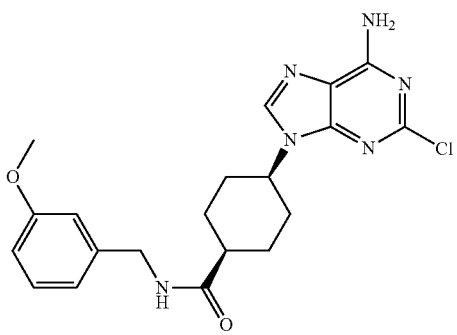 [SMILES: COc1cccc(CNC(=O)[C@H]2CC[C@@H](n3cnc4c(N)nc(Cl)nc43)CC2)c1]

¹H NMR (499.7 MHz, DMSO-d₆) δ ppm 1.67-1.76 (m, 2H), 1.86-1.92 (m, 2H), 2.00-2.06 (m, 2H), 2.12-2.21 (m, 2H), 2.53-2.56 (m, 1H), 3.72 (s, 3H), 4.28 (d, J=5.9 Hz, 2H), 4.32-4.40 (m, 1H), 6.76-6.87 (m, 3H), 7.21-7.24 (m, 1H), 7.74 (br. s., 2H), 8.14 (s, 1H), 8.33 (t, J=6.1 Hz, 1H).

HRMS (ESI+): calcd. for $C_{20}H_{24}ClN_6O_2$ [M+H]⁺ 415.1644; found 415.1654.

cis-4-(6-amino-2-chloro-9H-purin-9-yl)-N-(3-methylphenyl)cyclohexanecarboxamide (I), cpd 48

[X=N, R1=CONR4R5, R4=Substituted Aryl, R5=H, n=0, R3=Cl]

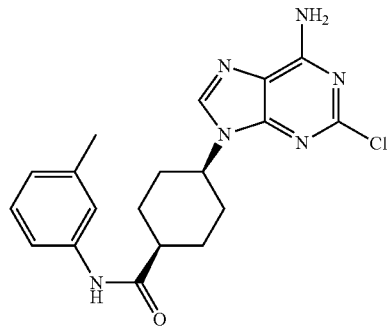 [SMILES: Cc1cccc(NC(=O)[C@H]2CC[C@@H](n3cnc4c(N)nc(Cl)nc43)CC2)c1]

¹H NMR (499.7 MHz, DMSO-d₆) δ ppm 1.73-1.83 (m, 2H), 1.88-1.95 (m, 2H), 2.02-2.09 (m, 2H), 2.19-2.29 (m, 2H), 2.27 (s, 3H), 2.66-2.73 (m, 1H), 4.34-2.43 (m, 1H), 6.85 (d, J=7.3 Hz, 1H), 7.16 (t, J=7.8 Hz, 1H), 7.38 (d, J=8.1 Hz, 1H), 7.49 (d, J=3.0 Hz, 1H), 7.75 (br. s., 2H), 8.22 (s, 1H), 9.76 (s, 1H).

HRMS (ESI+): calcd. for $C_{19}H_{22}ClN_6O$ [M+H]⁺ 385.1538; found 385.1551.

cis-4-(6-amino-2-chloro-9H-purin-9-yl)cyclohexanecarboxamide (I), cpd 53

[X=N, R1=CONR4R5, R4 and R5=H, n=0, R3=Cl]

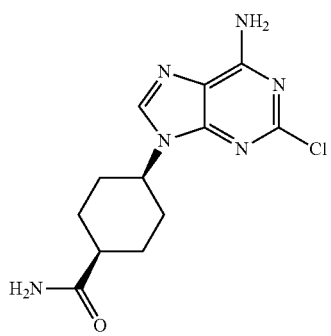 [SMILES: Nc1nc(Cl)nc2c1ncn2[C@H]1CC[C@@H](C(N)=O)CC1]

¹H NMR (400.5 MHz, DMSO-d₆) δ ppm 1.59-1.71 (m, 2H), 1.83-1.91 (m, 2H), 1.98-2.17 (m, 4H), 2.41-2.48 (m, 1H), 4.28-4.36 (m, 1H), 6.80 (br. s., 1H), 7.26 (br. s., 1H), 7.70 (br. s., 2H), 8.16 (s, 1H).

HRMS (ESI+): calcd. for $C_{12}H_{16}ClN_6O$ [M+H]⁺ 295.1069; found 295.1075.

1-{[cis-4-(6-amino-2-chloro-9H-purin-9-yl)cyclohexyl]carbonyl}piperidine-4-carboxamide (I), cpd 62

[X=N, R1=CONR4R5, R4 and R5=taken together form a substituted heterocyclyl group, n=0, R3=Cl]

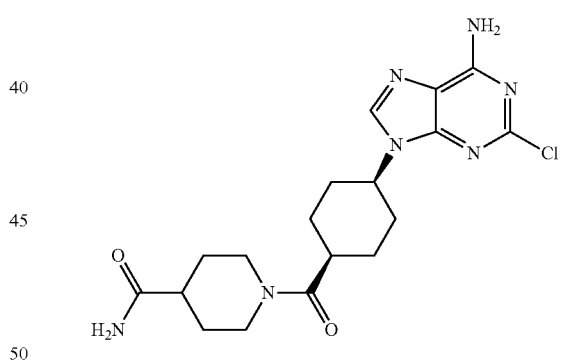

¹H NMR (400.5 MHz, DMSO-d₆) δ ppm 1.30-1.60 (m, 3H), 1.64-1.86 (m, 6H), 1.86-1.96 (m, 2H), 2.22-2.36 (m, 2H), 2.90-2.97 (m, 1H), 2.97-3.10 (m, 1H), 3.31 (m overlapped by water signal, 1H), 3.86-3.97 (m, 1H), 4.33-4.45 (m, 2H), 6.77 (br. s., 1H), 7.26 (br. s., 1H), 7.71 (br. s., 2H), 8.17 (s, 1H).

HRMS (ESI+): calcd. for $C_{18}H_{25}ClN_7O_2$ [M+H]⁺ 406.1753; found 406.1754.

cis-4-(6-amino-2-chloro-9H-purin-9-yl)-N-(tetrahydro-2H-pyran-4-yl)cyclohexanecarboxamide (I), cpd 63

[X=N, R1=CONR4R5, R4=heterocyclyl, R5=H, n=0, R3=Cl]

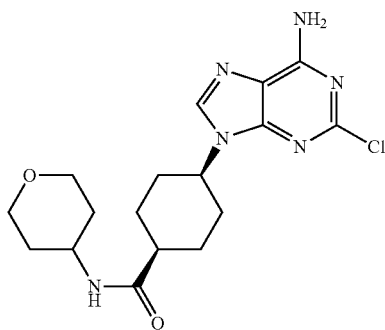 [SMILES: Nc1nc(Cl)nc2c1ncn2[C@H]1CC[C@@H](C(=O)NC2CCOCC2)CC1]

¹H NMR (400.5 MHz, DMSO-d₆) δ ppm 1.36-1.48 (m, 2H), 1.61-1.73 (m, 4H), 1.81-1.90 (m, 2H), 1.94-2.04 (m, 2H), 2.13-2.24 (m, 2H), 2.41-2.47 (m, 1H), 3.31 (m overlapped by water signal, 2H), 3.69-3.93 (m, 3H), 4.30-4.38 (m, 1H), 7.68 (d, J=8.0 Hz, 1H), 7.70 (br. s., 2H), 8.15 (s, 1H).

HRMS (ESI+): calcd. for $C_{17}H_{24}ClN_6O_2$ [M+H]⁺ 379.1644; found 379.1639.

cis-4-(6-amino-2-chloro-9H-purin-9-yl)-N-[5-(trifluoromethyl)-1,3,4-thiadiazol-2-yl]cyclohexanecarboxamide (I), cpd 64

[X=N, R1=CONR4R5, R4=Substituted Heteroaryl, R5=H, n=0, R3=Cl]

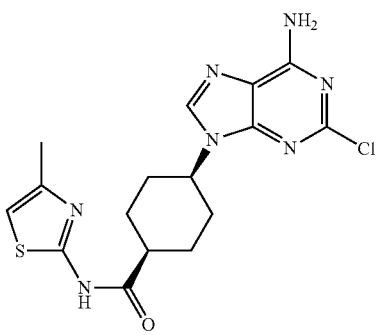

¹H NMR (400.5 MHz, DMSO-d₆) δ ppm 1.75-1.85 (m, 2H), 1.88-1.98 (m, 2H), 2.02-2.13 (m, 2H), 2.12-2.22 (m, 2H), 2.26 (d, J=0.9 Hz, 3H), 2.79-2.85 (m, 1H), 4.33-4.43 (m, 1H), 6.74 (s, 1H), 7.71 (br. s., 2H), 8.21 (s, 1H), 11.98 (s, 1H).

HRMS (ESI+): calcd. for $C_{16}H_{19}ClN_7OS$ [M+H]⁺ 392.1055; found 392.1052.

cis-4-(6-amino-2-chloro-9H-purin-9-yl)-N-cyclohexylcyclohexanecarboxamide (I), cpd 66

[X=N, R1=CONR4R5, R4=(C₃-C₇)cycloalkyl, R5=H, n=0, R3=Cl]

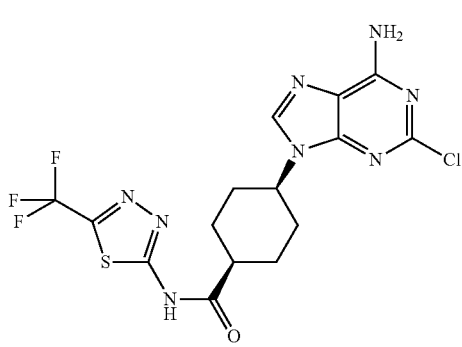 [SMILES: Nc1nc(Cl)nc2c1ncn2[C@H]1CC[C@@H](C(=O)Nc2nnc(C(F)(F)F)s2)CC1]

¹H NMR (400.5 MHz, DMSO-d₆) δ ppm 1.80-2.00 (m, 4H), 2.06-2.21 (m, 4H), 2.95-3.00 (m, 1H), 4.35-4.43 (m, 1H), 7.71 (br. s., 2H), 8.19 (s, 1H), 13.23 (br. s., 1H).

HRMS (ESI+): calcd. for $C_{15}H_{15}ClF_3N_8OS$ [M+H]⁺ 447.0725; found 447.0723.

cis-4-(6-amino-2-chloro-9H-purin-9-yl)-N-(4-methyl-1,3-thiazol-2-yl)cyclohexanecarboxamide (I), cpd 65

[X=N, R1=CONR4R5, R4=Substituted Heteroaryl, R5=H, n=0, R3=Cl]

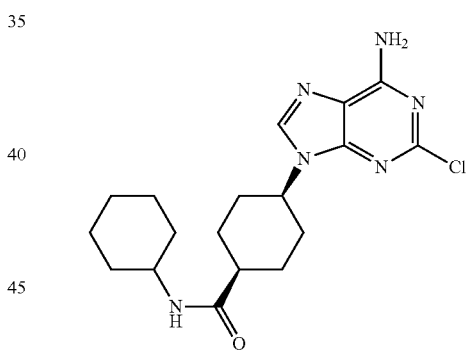

¹H NMR (400.5 MHz, DMSO-d₆) δ ppm 1.06-1.32 (m, 6H), 1.50-1.79 (m, 10H), 1.81-1.90 (m, 2H), 1.91-2.02 (m, 2H), 2.13-2.25 (m, 2H), 2.38-2.45 (m, 1H), 3.50-3.62 (m, 1H), 4.30-4.40 (m, 1H), 7.54 (d, J=7.9 Hz, 1H), 7.70 (br. s., 2H), 8.15 (s, 1H).

HRMS (ESI+): calcd. for $C_{18}H_{26}ClN_6O$ [M+H]⁺ 377.1851; found 377.1852.

cis-4-(6-amino-2-chloro-9H-purin-9-yl)-N-(2,2,6,6-tetramethylpiperidin-4-yl)cyclohexanecarboxamide (I), cpd 67

[X=N, R1=CONR4R5, R4=Substituted Heterocyclyl, R5=H, n=0, R3=Cl]

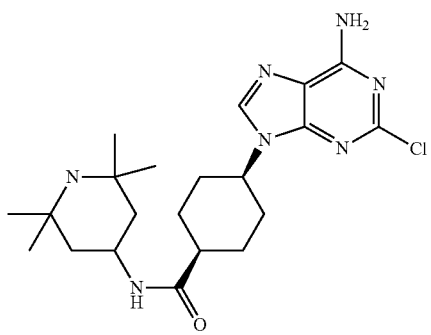 [SMILES: CC1(C)CC(NC(=O)[C@H]2CC[C@@H](n3cnc4c(N)nc(Cl)nc43)CC2)CC(C)(C)N1]

¹H NMR (400.5 MHz, DMSO-d₆) δ ppm 1.01-1.07 (m, 7H), 1.12-1.21 (m, 7H), 1.60-1.71 (m, 4H), 1.80-1.90 (m, 2H), 1.92-2.01 (m, 2H), 2.15-2.26 (m, 2H), 2.39-2.44 (m, 1H), 4.01-4.11 (m, 1H), 4.29-4.37 (m, 1H), 7.55 (d, J=6.1 Hz, 1H), 7.70 (br. s., 2H), 8.17 (s, 1H).

HRMS (ESI+): calcd. for $C_{21}H_{33}ClN_7O$ $[M+H]^+$ 434.2430; found 434.2426.

cis-4-(6-amino-2-chloro-9H-purin-9-yl)-N-(propan-2-yl)cyclohexanecarboxamide (I), cpd 68

[X=N, R1=CONR4R5, R4=(C₁-C₆)alkyl, R5=H, n=0, R3=Cl]

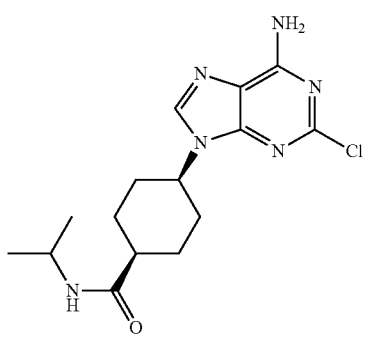 [SMILES: CC(C)NC(=O)[C@H]1CC[C@@H](n2cnc3c(N)nc(Cl)nc32)CC1]

¹H NMR (400.5 MHz, DMSO-d₆) δ ppm 1.06 (d, J=6.6 Hz, 6H), 1.60-1.70 (m, 2H), 1.79-1.90 (m, 2H), 1.93-2.00 (m, 2H), 2.13-2.24 (m, 2H), 2.88-2.43 (m, 1H), 3.85-3.93 (m, 1H), 4.29-4.37 (m, 1H), 7.55 (d, J=7.9 Hz, 1H), 7.70 (br. s., 2H), 8.15 (s, 1H).

HRMS (ESI+): calcd. for $C_{15}H_{22}ClN_6O$ $[M+H]^+$ 337.1538; found 337.1535.

cis-4-(6-amino-2-chloro-9H-purin-9-yl)-N-(1,3-benzothiazol-6-yl)cyclohexanecarboxamide (I), cpd 69

[X=N, R1=CONR4R5, R4=Heteroaryl, R5=H, n=0, R3=Cl]

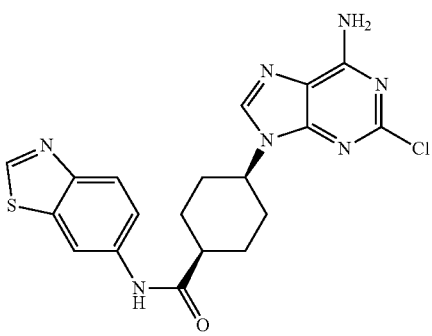 [SMILES: Nc1nc(Cl)nc2c1ncn2[C@H]1CC[C@@H](C(=O)Nc2ccc3ncsc3c2)CC1]

¹H NMR (400.5 MHz, DMSO-d₆) δ ppm 1.76-1.87 (m, 2H), 1.90-2.01 (m, 2H), 2.07-2.16 (m, 2H), 2.22-2.34 (m, 2H), 2.74-2.81 (m, 1H), 4.36-4.45 (m, 1H), 7.62 (dd, J=8.8, 2.0 Hz, 1H), 7.71 (br. s., 2H), 8.00 (d, J=8.8 Hz, 1H), 8.21 (s, 1H), 8.59 (d, J=2.0 Hz, 1H), 9.25 (s, 1H), 10.10 (s, 1H).

HRMS (ESI+): calcd. for $C_{19}H_{19}ClN_7OS$ $[M+H]^+$ 428.1055; found 428.1058.

cis-4-(6-amino-2-iodo-9H-purin-9-yl)-N-(4-methyl-1,3-thiazol-2-yl)cyclohexanecarboxamide (I), cpd 70

[X=N, R1=CONR4R5, R4=Substituted Heteroaryl, R5=H, n=0, R3=I]

¹H NMR (499.7 MHz, DMSO-d₆) δ ppm 1.76-1.85 (m, 2H), 1.89-1.96 (m, 2H), 2.04-2.11 (m, 2H), 2.11-2.19 (m, 2H), 2.26 (s, 3H), 2.79-2.83 (m, 1H), 4.32-4.39 (m, 1H), 6.74 (s, 1H), 7.63 (br. s., 2H), 8.13 (s, 1H), 12.01 (br. s., 1H).

HRMS (ESI+): calcd. for $C_{16}H_{19}IN_7OS$ $[M+H]^+$ 484.0411; found 484.0396.

4-({[cis-4-(6-amino-2-chloro-9H-purin-9-yl)cyclohexyl]carbonyl}amino)-N-cyclohexylbenzamide (I), cpd 71

[X=N, R1=CONR4R5, R4=Substituted Aryl, R5=H, n=0, R3=Cl]

73

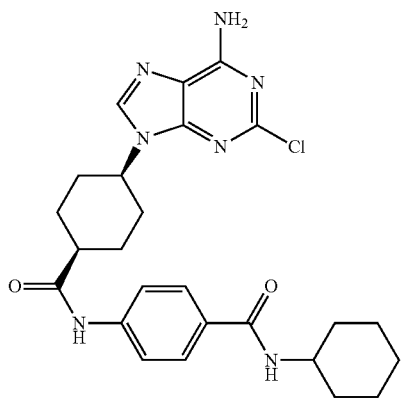 [SMILES: Nc1nc(Cl)nc2c1ncn2[C@H]1CC[C@@H](C(=O)Nc2ccc(C(=O)NC3CCCCC3)cc2)CC1]

¹H NMR (499.7 MHz, DMSO-d$_6$) δ ppm 1.74-1.85 (m, 2H), 1.89-1.96 (m, 2H), 2.04-2.09 (m, 2H), 2.10-2.18 (m, 2H), 2.26 (s, 3H), 2.78-2.84 (m, 1H), 4.32-4.40 (m, 1H), 6.74 (s, 1H), 7.63 (br. s., 2H), 8.13 (s, 1H), 12.01 (br. s., 1H).

HRMS (ESI+): calcd. for C$_{25}$H$_{31}$ClN$_7$O$_2$ [M+H]$^+$ 496.2223; found 496.2207.

cis-4-(6-amino-2-chloro-9H-purin-9-yl)-N-(1,3-thiazol-2-yl)cyclohexanecarboxamide (I), cpd 72

[X=N, R1=CONR4R5, R4=Heteroaryl, R5=H, n=0, R3=Cl]

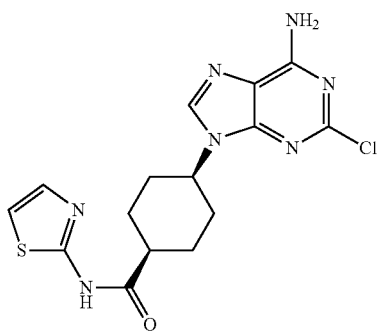

¹H NMR (499.7 MHz, DMSO-d$_6$) δ ppm 1.75-1.87 (m, 2H), 1.90-1.98 (m, 2H), 2.04-2.12 (m, 2H), 2.13-2.23 (m, 2H), 2.82-2.88 (m, 1H), 4.34-4.43 (m, 1H), 7.21 (d, J=3.5 Hz, 1H), 7.47 (d, J=3.5 Hz, 1H), 7.75 (br. s., 2H), 8.23 (s, 1H), 12.10 (br. s., 1H).

HRMS (ESI+): calcd. for C$_{15}$H$_{17}$ClN$_7$OS [M+H]$^+$ 378.0899; found 378.0895.

cis-4-(6-amino-2-chloro-9H-purin-9-yl)-N-(5-methyl-1,3-thiazol-2-yl)cyclohexanecarboxamide (I), cpd 73

[X=N, R1=CONR4R5, R4=Substituted Heteroaryl, R5=H, n=0, R3=Cl]

74

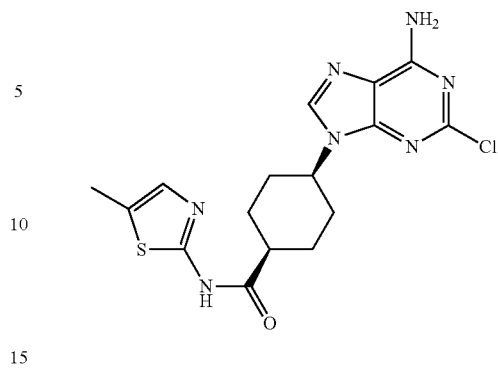

¹H NMR (499.7 MHz, DMSO-d$_6$) δ ppm 1.75-1.84 (m, 2H), 1.90-1.96 (m, 2H), 2.02-2.11 (m, 2H), 2.11-2.22 (m, 2H), 2.34 (d, J=1.0 Hz, 3H), 2.79-2.84 (m, 1H), 4.34-4.42 (m, 1H), 7.12 (q, J=1.0 Hz, 1H), 7.75 (br. s., 2H), 8.21 (s, 1H), 11.89 (br. s., 1H).

HRMS (ESI+): calcd. for C$_{15}$H$_{17}$ClN$_7$OS [M+H]$^+$ 392.1055; found 392.1048.

cis-4-(6-amino-2-chloro-9H-purin-9-yl)-N-(4-phenyl-1,3-thiazol-2-yl)cyclohexanecarboxamide (I), cpd 74

[X=N, R1=CONR4R5, R4=Substituted Heteroaryl, R5=H, n=0, R3=Cl]

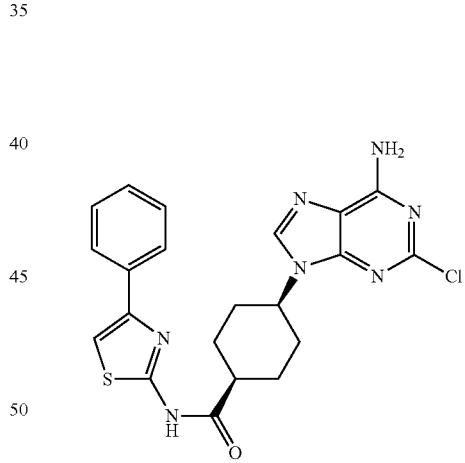

¹H NMR (499.7 MHz, DMSO-d$_6$) δ ppm 1.79-1.87 (m, 2H), 1.92-1.98 (m, 2H), 2.08-2.14 (m, 2H), 2.16-2.24 (m, 2H), 2.86-2.91 (m, 1H), 4.36-4.43 (m, 1H), 7.30-7.35 (m, 1H), 7.44-7.45 (m, 2H), 7.63 (s, 1H), 7.75 (br. s., 2H), 7.88-7.93 (m, 2H), 8.23 (s, 1H), 12.26 (br. s., 1H).

HRMS (ESI+): calcd. for C$_{21}$H$_{21}$ClN$_7$OS [M+H]$^+$ 454.1212; found 454.1196.

75 cis-4-(6-amino-2-chloro-9H-purin-9-yl)-N-(1,3-benzothiazol-2-yl)cyclohexanecarboxamide (I), cpd 75

[X=N, R1=CONR4R5, R4=Heteroaryl, R5=H, n=0, R3=Cl]

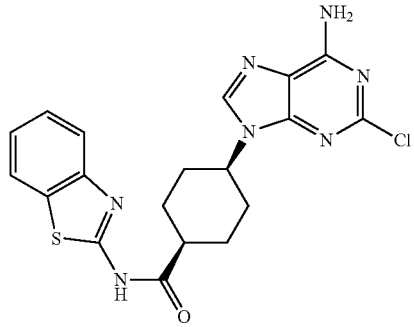

$^1$H NMR (499.7 MHz, DMSO-$d_6$) δ ppm 1.80-1.91 (m, 2H), 1.93-2.00 (m, 2H), 2.09-2.25 (m, 4H), 2.88-2.93 (m, 1H), 4.36-4.44 (m, 1H), 7.28-7.33 (m, 1H), 7.41-7.46 (m, 1H), 7.75 (br. s., 2H), 7.73-7.75 (m, 1H), 7.96-7.98 (m, 1H), 8.24 (s, 1H), 12.36 (br. s., 1H).

HRMS (ESI+): calcd. for $C_{21}H_{21}ClN_7OS$ [M+H]$^+$ 428.1055; found 428.1040.

cis-4-(6-amino-2-chloro-9H-purin-9-yl)-N-(pyridin-2-yl)cyclohexanecarboxamide (I), cpd 76

[X=N, R1=CONR4R5, R4=Heteroaryl, R5=H, n=0, R3=Cl]

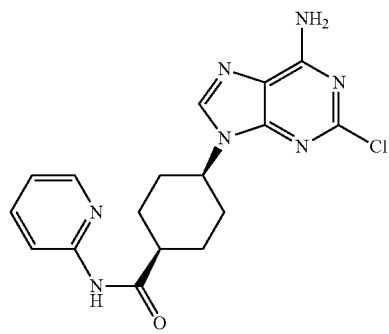 [SMILES: Nc1nc(Cl)nc2c1ncn2[C@H]1CC[C@@H](C(=O)Nc2ccccn2)CC1]

$^1$H NMR (499.7 MHz, DMSO-$d_6$) δ ppm 1.74-1.84 (m, 2H), 1.87-1.95 (m, 2H), 2.01-2.09 (m, 2H), 2.20-2.30 (m, 2H), 2.81-2.86 (m, 1H), 4.34-4.41 (m, 1H), 7.08 (ddd, J=6.7, 5.5, 0.9 Hz, 1H), 7.73 (br. s., 2H), 7.75-7.79 (m, 1H), 8.12 (d, J=8.4 Hz, 1H), 8.21 (s, 1H), 8.31 (dd, J=4.7, 1.1 Hz, 1H), 10.42 (s, 1H).

HRMS (ESI+): calcd. for $C_{17}H_{19}ClN_7O$ [M+H]$^+$ 372.1334; found 372.1322.

76 cis-4-(6-amino-2-chloro-9H-purin-9-yl)-N-(1H-imidazol-2-yl)cyclohexanecarboxamide (I), cpd 79

[X=N, R1=CONR4R5, R4=Heteroaryl, R5=H, n=0, R3=Cl]

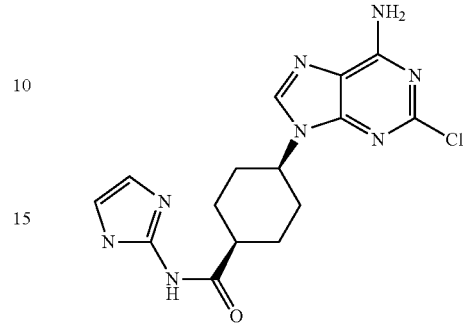

$^1$H NMR (499.7 MHz, DMSO-$d_6$) δ ppm 1.73-1.82 (m, 2H), 1.90-1.98 (m, 2H), 2.03-2.10 (m, 2H), 2.16-2.26 (m, 2H), 2.72-2.76 (m, 1H), 4.34-4.41 (m, 1H), 6.65 (br. s., 1H), 6.78 (br. s., 1H), 7.74 (br. s., 2H), 8.16 (s, 1H), 11.04 (br. s., 1H), 11.57 (br. s., 1H).

HRMS (ESI+): calcd. for $C_{15}H_{18}ClN_8O$ [M+H]$^+$ 361.1287; found 361.1278.

cis-4-(6-amino-2-methoxy-9H-purin-9-yl)-N-(3-methoxyphenyl)cyclohexanecarboxamide (I), cpd 83

[X=N, R1=CONR4R5, R4=Substituted Aryl, R H, n=0, R3 OR6, R6=(C$_1$-C$_6$)alkyl]

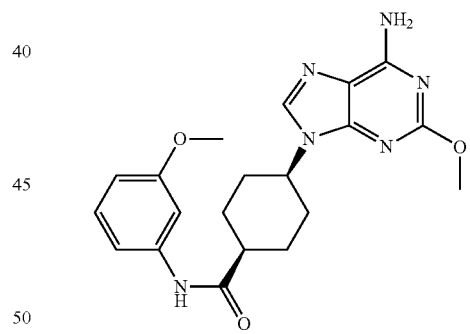

$^1$H NMR (499.7 MHz, DMSO-$d_6$) δ ppm 1.71-1.80 (m, 2H), 1.84-1.92 (m, 2H), 2.02-2.10 (m, 2H), 2.31-2.41 (m, 2H), 2.66-2.70 (m, 1H), 3.72 (s, 3H), 3.79 (s, 3H), 4.30-4.36 (m, 1H), 6.58-6.63 (m, 1H), 7.14-7.22 (m, 4H), 7.34-7.37 (m, 1H), 7.97 (s, 1H), 9.80 (s, 1H).

HRMS (ESI+): calcd. for $C_{20}H_{25}N_6O_3$ [M+H]$^+$ 397.1983; found 397.1991.

cis-4-(6-amino-2-methoxy-9H-purin-9-yl)-N-(4-methyl-1,3-thiazol-2-yl)cyclohexanecarboxamide (I), cpd 84

[X=N, R1=CONR4R5, R4=Substituted Heteroaryl, R5=H, n=0, R3=OR6, R6=(C$_1$-C$_6$)alkyl]

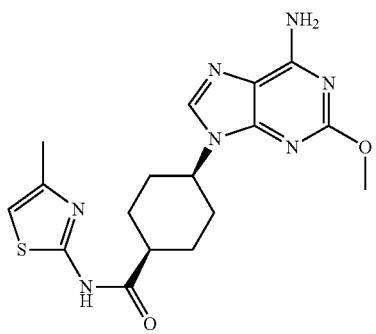 [SMILES: COc1nc(N)c2ncn([C@H]3CC[C@@H](C(=O)Nc4nc(C)cs4)CC3)c2n1]

¹H NMR (499.7 MHz, DMSO-d₆) δ ppm 1.71-1.80 (m, 2H), 1.84-1.92 (m, 2H), 2.07-2.15 (m, 2H), 2.26 (d, J=0.9 Hz, 3H), 2.27-2.36 (m, 2H), 2.78-2.83 (m, 1H), 3.78 (s, 3H), 4.27-4.34 (m, 1H), 6.74 (s, 1H), 7.18 (br. s., 2H), 7.95 (s, 1H), 11.99 (br. s., 1H).

HRMS (ESI+): calcd. for $C_{17}H_{22}N_7O_2S$ [M+H]⁺ 397.1983; found 397.1991.

cis-4-(6-amino-2-chloro-9H-purin-9-yl)-N-{4-[2-(1,4'-bipiperidin-1'-yl)-2-oxoethyl]-1,3-thiazol-2-yl}cyclohexanecarboxamide (I), cpd 86

[X=N, R1=CONR4R5, R4=Substituted Heteroaryl, R5=H, n=0, R3=Cl]

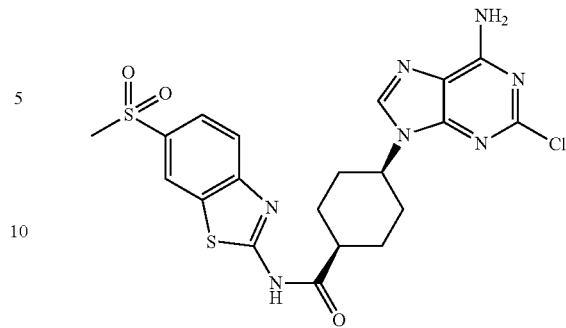

¹H NMR (499.7 MHz, DMSO-d₆) δ ppm 1.82-1.92 (m, 2H), 1.94-2.00 (m, 2H), 2.07-2.23 (m, 4H), 2.93-2.97 (m, 1H), 3.25 (s, 3H), 4.36-4.44 (m, 1H), 7.75 (br. s., 2H), 7.90-7.97 (m, 2H), 8.24 (s, 1H), 8.65 (d, J=0.9 Hz, 1H), 12.69 (s, 1H).

HRMS (ESI+): calcd. for $C_{20}H_{21}ClN_7O_3S_2$ [M+H]⁺ 506.0831; found 506.0847.

cis-4-(6-amino-2-chloro-9H-purin-9-yl)-N-(6-chloro-1,3-benzothiazol-2-yl)cyclohexanecarboxamide (I), cpd 90

[X=N, R1=CONR4R5, R4=Substituted Heteroaryl, R5=H, n=0, R3=Cl]

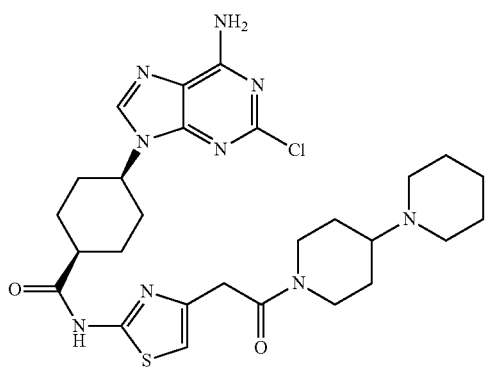 [SMILES: Nc1nc(Cl)nc2c1ncn2[C@H]1CC[C@@H](C(=O)Nc2nc(CC(=O)N3CCC(N4CCCCC4)CC3)cs2)CC1]

¹H NMR (499.7 MHz, DMSO-d₆) δ ppm 1.20-1.70 (m, 10H), 1.77-1.88 (m, 2H), 1.88-1.97 (m, 2H), 2.03-2.11 (m, 2H), 2.12-2.22 (m, 2H), 2.25-2.66 (m, 5H), 2.78-2.84 (m, 1H), 2.90-3.10 (m, 3H), 3.71 (s, 2H), 3.94-4.08 (m, 1H), 4.33-4.43 (m, 1H), 4.39-4.48 (m, 1H), 6.88 (s, 1H), 7.74 (br. s., 2H), 8.21 (s, 1H), 12.10 (br. s., 1H).

HRMS (ESI+): calcd. for $C_{27}H_{37}ClN_9O_2S$ [M+H]⁺ 586.2474; found 586.2474.

cis-4-(6-amino-2-chloro-9H-purin-9-yl)-N-[6-(methylsulfonyl)-1,3-benzothiazol-2-yl]cyclohexanecarboxamide (I), cpd 89

[X=N, R1=CONR4R5, R4=Substituted Heteroaryl, R5=H, n=0, R3=Cl]

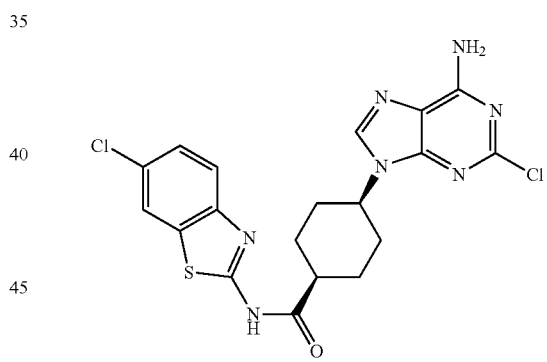

¹H NMR (499.7 MHz, DMSO-d₆) δ ppm 1.80-1.89 (m, 2H), 1.98-1.99 (m, 2H), 2.08-2.23 (m, 4H), 2.89-2.94 (m, 1H), 4.36-4.43 (m, 1H), 7.46 (dd, J=8.6, 2.2 Hz, 1H), 7.73 (d, J=8.6 Hz, 1H), 7.75 (br. s., 2H), 8.13 (d, J=2.2 Hz, 1H), 8.23 (s, 1H), 12.46 (br. s., 1H).

HRMS (ESI+): calcd. for $C_{19}H_{18}Cl_2N_7OS$ [M+H]⁺ 462.0665; found 462.0682.

cis-4-(6-amino-2-chloro-9H-purin-9-yl)-N-(4-methoxy-1,3-benzothiazol-2-yl)cyclohexanecarboxamide (I), cpd 91

[X=N, R1=CONR4R5, R4=Substituted Heteroaryl, R5=H, n=0, R3=Cl]

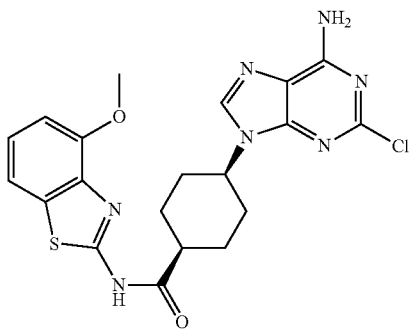 [SMILES: COc1cccc2sc(NC(=O)[C@H]3CC[C@@H](n4cnc5c(N)nc(Cl)nc54)CC3)nc12]

¹H NMR (499.7 MHz, DMSO-d$_6$) δ ppm 1.79-1.88 (m, 2H), 1.92-1.99 (m, 2H), 2.10-2.22 (m, 4H), 2.85-2.89 (m, 1H), 3.91 (s, 3H), 4.36-4.43 (m, 1H), 6.96-7.04 (dd, J=8.1, 0.8 Hz, 1H), 7.25 (t, J=8.1 Hz, 1H), 7.52 (dd, J=8.1, 0.8 Hz, 1H), 7.75 (br. s., 2H), 8.23 (s, 1H), 12.48 (s, 1H).

HRMS (ESI+): calcd. for $C_{19}H_{18}Cl_2N_7OS$ [M+H]$^+$ 462.0665; found 462.0682.

cis-4-(6-amino-2-chloro-9H-purin-9-yl)-N-(4-methoxy-1,3-benzothiazol-2-yl)cyclohexanecarboxamide (I), cpd 92

[X=N, R1=CONR4R5, R4=Substituted Heteroaryl, R5=H, n=0, R3=Cl]

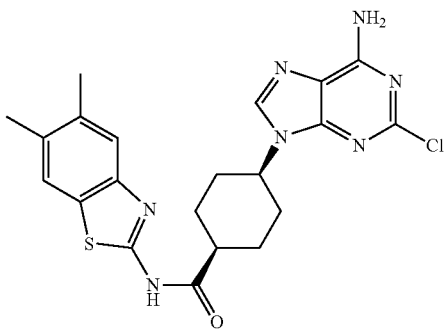

¹H NMR (499.7 MHz, DMSO-d$_6$) δ ppm 1.79-1.88 (m, 2H), 1.92-1.99 (m, 2H), 2.09-2.16 (m, 2H), 2.17-2.23 (m, 2H), 2.31 (s, 3H), 2.32 (s, 3H), 2.86-2.91 (m, 1H), 4.36-4.42 (m, 1H), 7.53 (s, 1H), 7.71 (s, 1H), 7.75 (br. s., 1H), 8.23 (s, 1H), 12.26 (s, 1H).

HRMS (ESI+): calcd. for $C_{21}H_{23}ClN_7OS$ [M+H]$^+$ 456.1368; found 456.1375.

cis-4-(6-amino-2-chloro-9H-purin-9-yl)-N-(5-chloro-1,3-benzoxazol-2-yl)cyclohexanecarboxamide (I), cpd 94

[X=N, R1=CONR4R5, R4=Substituted Heteroaryl, R5=H, n=0, R3=Cl]

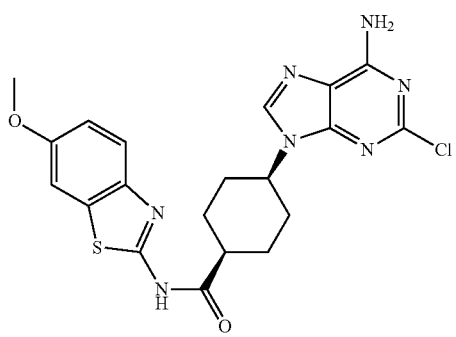 [SMILES: COc1ccc2nc(NC(=O)[C@H]3CC[C@@H](n4cnc5c(N)nc(Cl)nc54)CC3)sc2c1]

¹H NMR (499.7 MHz, DMSO-d$_6$) δ ppm 1.80-1.89 (m, 2H), 1.92-1.99 (m, 2H), 2.08-2.15 (m, 2H), 2.15-2.24 (m, 2H), 2.86-2.91 (m, 1H), 3.81 (m, 3H), 4.36-4.43 (m, 1H), 7.02 (dd, J=8.8, 2.6 Hz, 1H), 7.56 (d, J=2.6 Hz, 1H), 7.63 (d, J=8.8 Hz, 1H), 7.74 (br. s., 2H), 8.23 (s, 1H), 12.22 (s, 1H).

HRMS (ESI+): calcd. for $C_{20}H_{21}ClN_7O_2S$ [M+H]$^+$ 458.1161; found 458.1161.

cis-4-(6-amino-2-chloro-9H-purin-9-yl)-N-(5,6-dimethyl-1,3-benzothiazol-2-yl)cyclohexanecarboxamide (I), cpd 93

[X=N, R1=CONR4R5, R4=Substituted Heteroaryl, R5=H, n=0, R3=Cl]

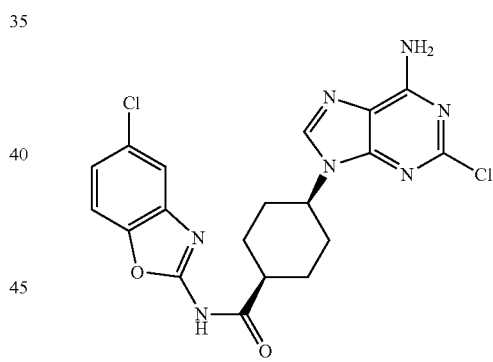

¹H NMR (499.7 MHz, DMSO-d$_6$) δ ppm 1.78-1.88 (m, 2H), 1.89-1.98 (m, 2H), 2.07-2.15 (m, 2H), 2.15-2.24 (m, 2H), 2.87-2.92 (m, 1H), 4.34-4.42 (m, 1H), 7.30 (dd, J=8.6, 2.1 Hz, 1H), 7.63-7.68 (m, 2H), 7.75 (br. s., 2H), 8.22 (s, 1H), 11.78 (br. s., 1H).

HRMS (ESI+): calcd. for $C_{19}H_{18}Cl_2N_7O_2$ [M+H]$^+$ 446.0894; found 446.0907.

cis-4-(6-amino-2-chloro-9H-purin-9-yl)-N-(1-methyl-1H-benzimidazol-2-yl)cyclohexanecarboxamide (I), cpd 95

[X=N, R1=CONR4R5, R4=Substituted Heteroaryl, R5=H, n=0, R3=Cl]

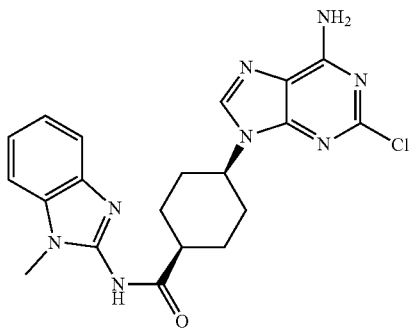 [SMILES: Cn1c(NC(=O)[C@H]2CC[C@@H](n3cnc4c(N)nc(Cl)nc43)CC2)nc2ccccc21]

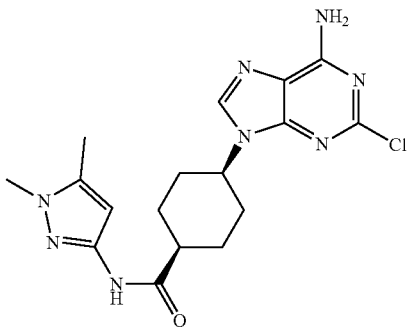

¹H NMR (499.7 MHz, DMSO-d₆; mixture of tautomers) δ ppm 1.68-2.47 (m, 8H), 2.61-2.67 and 2.84-2.92 (2×m, 1H), 3.56 and 3.65 (2×s, 3H), 4.30-4.45 (m, 1H), 7.14-7.27 (m, 2H), 7.38-7.57 (m, 2H), 7.66-7.77 (br. s., 2H), 8.15 and 8.20 (m, 1H), 10.60 and 12.54 (br. s., 1H).

HRMS (ESI+): calcd. for $C_{20}H_{22}ClN_8O$ [M+H]⁺ 425.16; found 425.1608.

cis-4-(6-amino-2-chloro-9H-purin-9-yl)-N-(5-methyl-1,3,4-thiadiazol-2-yl)cyclohexanecarboxamide (I), cpd 108

[X=N, R1=CONR4R5, R4=Substituted Heteroaryl, R5=H, n=0, R3=Cl]

¹H NMR (499.7 MHz, DMSO-d₆) δ ppm 1.67-1.78 (m, 2H), 1.85-1.93 (m, 2H), 1.96-2.03 (m, 2H), 2.20 (s, 3H), 2.16-2.24 (m, 2H), 2.64-2.68 (m, 1H), 3.59 (s, 3H), 4.33-4.39 (m, 1H), 6.30 (s, 1H), 7.73 (br. s., 2H), 8.18 (s, 1H), 10.16 (s, 1H).

HRMS (ESI+): calcd. for $C_{17}H_{22}ClN_8O$ [M+H]⁺ 389.16; found 389.1598.

cis-4-(6-amino-2-chloro-9H-purin-9-yl)-N-(5-chloro-1,3-thiazol-2-yl)cyclohexanecarboxamide (I), cpd 114

[X=N, R1=CONR4R5, R4=Substituted Heteroaryl, R5=H, n=0, R3=Cl]

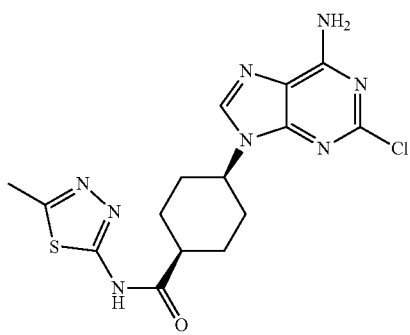 [SMILES: Cc1nnc(NC(=O)[C@H]2CC[C@@H](n3cnc4c(N)nc(Cl)nc43)CC2)s1]

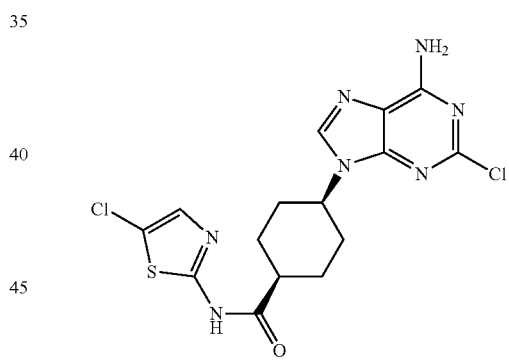

¹H NMR (499.7 MHz, DMSO-d₆) δ ppm 1.78-1.87 (m, 2H), 1.90-1.96 (m, 2H), 2.04-2.11 (m, 2H), 2.11-2.20 (m, 2H), 2.61 (s, 3H), 2.84-2.89 (m, 1H), 4.34-4.41 (m, 1H), 7.73 (br. s., 2H), 8.20 (s, 1H), 12.37 (s, 1H).

HRMS (ESI+): calcd. for $C_{15}H_{18}ClN_8OS$ [M+H]⁺ 393.1008; found 393.1008.

cis-4-(6-amino-2-chloro-9H-purin-9-yl)-N-(1,5-dimethyl-1H-pyrazol-3-yl)cyclohexanecarboxamide (I), cpd 109

[X=N, R1=CONR4R5, R4=Substituted Heteroaryl, R5=H, n=0, R3=Cl]

¹H NMR (499.7 MHz, DMSO-d₆) δ ppm 1.77-1.87 (m, 2H), 1.90-1.97 (m, 2H), 2.05-2.11 (m, 2H), 2.12-2.19 (m, 2H), 2.82-2.87 (m, 1H), 4.34-4.40 (m, 1H), 7.5 (s, 1H), 7.74 (br. s., 2H), 8.21 (s, 1H), 12.35 (br. s., 1H).

HRMS (ESI+): calcd. for $C_{15}H_{16}Cl_2N_7OS$ [M+H]⁺ 412.0509; found 412.0502.

cis-4-(6-amino-2-chloro-9H-purin-9-yl)-N-[4-(trifluoromethyl)-1,3-thiazol-2-yl]cyclohexanecarboxamide (I), cpd 115

[X=N, R1=CONR4R5, R4=Substituted Heteroaryl, R5=H, n=0, R3=Cl]

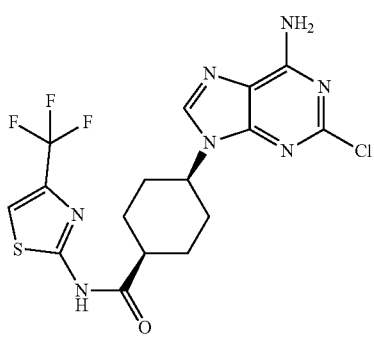 [SMILES: Nc1nc(Cl)nc2c1ncn2[C@H]1CC[C@@H](C(=O)Nc2nc(C(F)(F)F)cs2)CC1]

¹H NMR (499.7 MHz, DMSO-d₆) δ ppm 1.78-1.88 (m, 2H), 1.90-1.97 (m, 2H), 2.08-2.20 (m, 4H), 2.84-2.88 (m, 1H), 4.34-4.40 (m, 1H), 7.74 (br. s., 2H), 7.95 (q, $J_{HF}$=0.8 Hz, 1H), 8.22 (s, 1H), 12.56 (br. s., 1H).

HRMS (ESI+): calcd. for $C_{16}H_{16}ClF_3N_7OS$ [M+H]⁺ 446.0772; found 446.0767.

Example 3

Sequence C cis-4-(6-amino-2-ethynyl-9H-purin-9-yl)-N-(3-methoxyphenyl)cyclohexanecarboxamide (I), cpd 45

Conv. 17

4-(6-amino-9H-purin-2-yl)-2-methylbut-3-yn-2-ol (VIIb)

[X=N, R3=Substituted (C₂-C₆)alkynyl]

2-Iodo-9H-purin-6-amine (VIIa) (137 mg, 0.525 mmol), CuI (5 mg, 0.026 mmol) and PdCl₂dppf (21 mg, 0.026 mmol) were charged in a Schlenk tube under argon. ACN (2 mL), TEA (0.146 mL, 1.05 mmol) and 2-methylbut-3-yn-2-ol (IX) (0.066 mL, 0.682 mmol) were added and the mixture was heated at 80° C. for 5 h. After cooling at rt, the product was filtered, washed with ACN and dried under vacuo (110 mg, 97%).

¹H NMR (500 MHz, DMSO-d₆) δ ppm 1.45 (s, 6H) 5.54 (s, 1H) 7.25 (br. s., 2H) 8.12 (br. s., 1H) 12.87 (br. s., 1H).

HRMS (ESI+): calcd. for $C_{10}H_{12}N_5O$ [M+H]⁺ 218.1037; found 218.1042.

Deprotection

2-Ethynyl-9H-purin-6-amine (VIIb)

[X=N, R3=(C₂-C₆)alkynyl]

KOH in pellets (80 mg, 1.42 mmol) was dissolved in i-propanol (13 mL), then 4-(6-amino-9H-purin-2-yl)-2-methylbut-3-yn-2-ol (VIIb) (110 mg, 0.507 mmol) was added and the solution was heated at 80° C. for 1 h. After cooling to rt, the solvent was removed under reduced

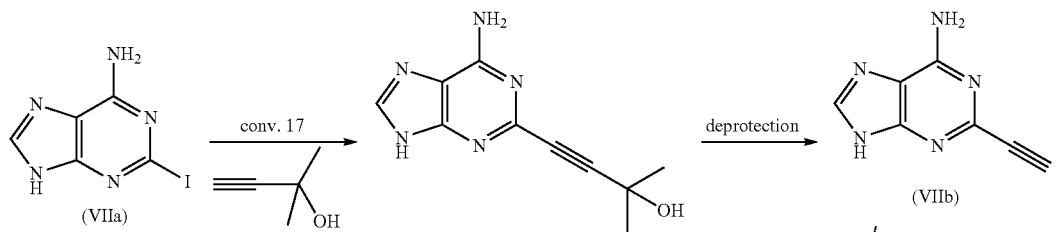

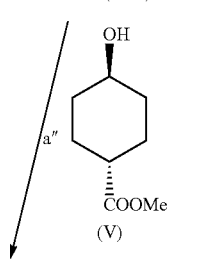

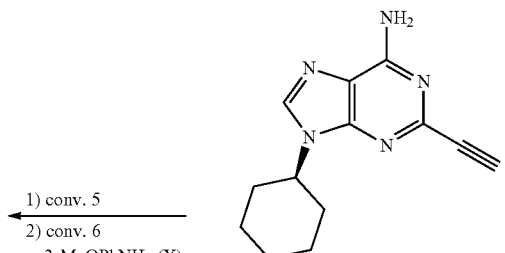

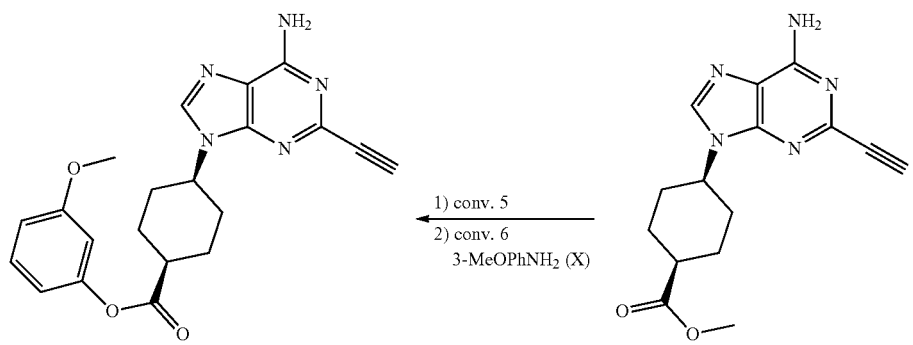

pressure and the residue was dissolved in water (10 mL). After treatment with 1M solution of $NaH_2PO_4$ (1 mL), the product was extracted with n-butanol (2×10 mL) and the organic layer was washed with water and brine. After evaporation in vacuo, the product was purified by column chromatography (eluant DCM:MeOH=9:1) and isolated as white solid (34 mg, 42%).

$^1$H NMR (500 MHz, DMSO-$d_6$) δ ppm 3.92 (s, 1H) 7.29 (br. s., 2H) 8.17 (s, 1H) 12.93 (br. s., 1H).

HRMS (ESI+): calcd. for $C_7H_6N_5$ [M+H]$^+$ 160.0618; found 160.0612.

Step a''

Methyl cis-4-(6-amino-2-ethynyl-9H-purin-9-yl) cyclohexanecarboxylate (I), cpd 44

[X=N, R1=COOR4, R4=($C_1$-$C_6$)alkyl, R3=($C_2$-$C_6$)alkynyl]

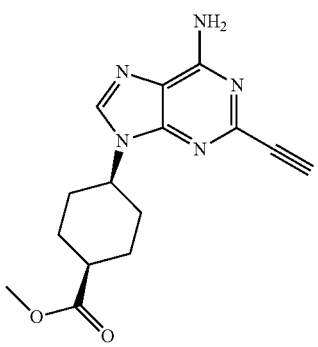 [SMILES: C#Cc1nc(N)c2ncn([C@H]3CC[C@@H](C(=O)OC)CC3)c2n1]

To a solution of 2-ethynyl-9H-purin-6-amine (VIIb) (18 mg, 0.113 mmol), methyl trans-4-hydroxycyclohexanecarboxylate (36 mg, 0.226 mmol) and triphenylphosphine (89 mg, 0.339 mmol) in dry THF (1 mL), diethyl azodicarboxylate (0.053 mL, 0.339 mmol) was added dropwise. The solution was heated at 50° C. for 2 h. The solvent was evaporated in vacuo and the title compound was isolated by column chromatography (eluant DCM, DCM:MeOH=9:1) as colorless oil (26 mg, 77%).

$^1$H NMR (400.5 MHz, DMSO-$d_6$) δ ppm 1.78-1.88 (m, 2H), 1.90-1.96 (m, 2H), 2.13-2.19 (m, 2H), 2.75-2.79 (m, 1H), 3.69 (s, 3H), 3.95 (s, 1H), 4.34-4.40 (m, 1H), 7.36 (br. s., 1H), 8.26 (s, 1H), 8.96 (br. s., 1H).

HRMS (ESI+): calcd. for $C_{15}H_{18}N_5O_2$ [M+H]$^+$ 300.1455; found 300.1460.

Operating in an analogous way, but employing a suitably substituted starting material (VII), the following compound was obtained:

methyl cis-4-(6-amino-2-fluoro-9H-purin-9-yl)cyclohexanecarboxylate (I), cpd 123

[X=N, R1=COOR4, R4=($C_1$-$C_6$)alkyl, R3=F]

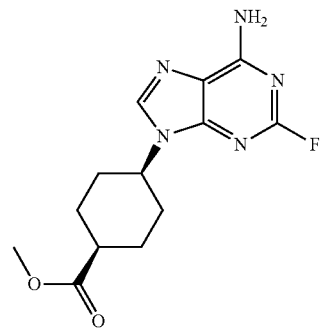 [SMILES: COC(=O)[C@H]1CC[C@@H](n2cnc3c(N)nc(F)nc32)CC1]

$^1$H NMR (499.7 MHz, DMSO-$d_6$) δ ppm 1.64-1.77 (m, 2H), 1.85-1.99 (m, 4H), 2.11-2.18 (m, 2H), 2.72-2.78 (m, 1H), 3.68 (s, 3H), 4.25-4.32 (m, 1H), 7.73 (br. s., 2H), 8.17 (s, 1H).

HRMS (ESI+): calcd. for $C_{13}H_7FN_5O$ [M+H]$^+$ 294.1361; found 294.1357.

methyl cis-4-(4-amino-1H-imidazo[4,5-c]pyridin-1-yl)cyclohexanecarboxylate (I), cpd 202

[X=CH, R1=COOR4, R4=($C_1$-$C_6$)alkyl, R3=H]

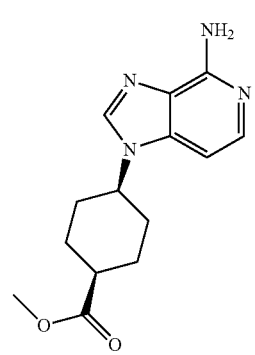 [SMILES: COC(=O)[C@H]1CC[C@@H](n2cnc3c(N)nccc32)CC1]

$^1$H NMR (500 MHz, DMSO-$d_6$) δ ppm 1.64-1.85 (m, 2H) 1.88-1.98 (m, 4H) 2.11-2.24 (m, 2H) 2.75-2.87 (m, 1H) 3.69 (s, 3H) 4.25-4.37 (m, 1H) 6.11 (br. s., 2H) 6.78 (d, J=5.80 Hz, 1H) 7.65 (d, J=5.80 Hz, 1H) 8.11 (s, 1H).

HRMS (ESI+): calcd. for $C_{14}H_{19}N_4O_2$ [M+H]$^+$ 275.1503; found 275.1505.

Conv. 5 cis-4-(6-amino-2-ethynyl-9H-purin-9-yl)cyclohexanecarboxylic acid (I), cpd 158

[X=N, R1=COOR4, R4=H, R3=(C$_2$-C$_6$)alkynyl]

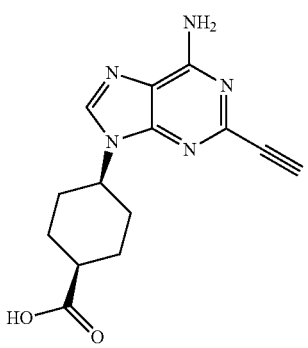 [SMILES: C#Cc1nc(N)c2ncn([C@H]3CC[C@@H](C(=O)O)CC3)c2n1]

A solution of methyl cis-4-(6-amino-2-ethynyl-9H-purin-9-yl)cyclohexanecarboxylate (26 mg, 0.087 mmol) in a (1:1:1) mixture of H$_2$O/MeOH/THF (1 mL) was treated with LiOH H$_2$O (5.5 mg, 0.13 mmol) and let under stirring at rt overnight. After solvent removal under reduced pressure, the residue was dissolved in water and treated with AcOH (0.009 mL). The solid was filtered, washed with water and dried (5 mg). The mother liquor was diluted with water and extracted with n-butanol. The organic layer was evaporated in vacuo affording further 14 mg of title compound as white solid (19 mg, 77%).

HRMS (ESI+): calcd. for C$_{14}$H$_{16}$N$_5$O$_2$ [M+H]$^+$ 286.1299; found 286.1291.

cis-4-[6-amino-2-(trifluoromethyl)-9H-purin-9-yl]cyclohexanecarboxylic acid (I), cpd 162

[X=N, R1=COOR4, R4=H, R3=polyfluorinated alkyl]

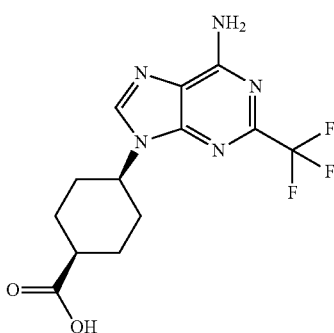 [SMILES: Nc1nc(C(F)(F)F)nc2c1ncn2[C@H]1CC[C@@H](C(=O)O)CC1]

HRMS (ESI+): calcd. for C$_{13}$H$_{15}$F$_3$N$_5$O$_2$ [M+H]$^+$ 330.1173; found 330.1172.

cis-4-(4-amino-1H-imidazo[4,5-c]pyridin-1-yl)cyclohexanecarboxylic acid (I), cpd 203

[X=CH, R1=COOR4, R4=R3=H]

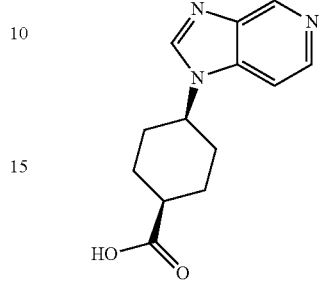

HRMS (ESI+): calcd. for C$_{13}$H$_{17}$N$_4$O$_2$ [M+H]$^+$ 261.1346; found 261.1350.

Conv. 6 cis-4-(6-amino-2-ethynyl-9H-purin-9-yl)-N-(3-methoxyphenyl)cyclohexanecarboxamide (I), cpd 45

[X=N, R1=CONR4R5, R4=Substituted Aryl, R5=H, R3=(C$_2$-C$_6$)alkynyl]

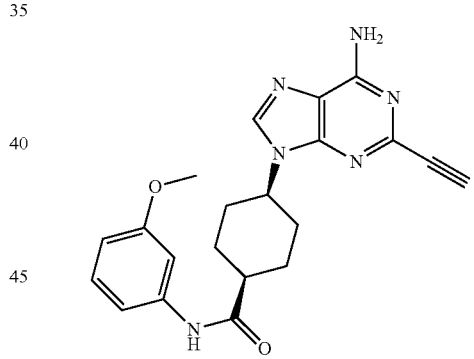

A mixture of cis-4-(6-amino-2-ethynyl-9H-purin-9-yl)cyclohexanecarboxylic acid (19 mg, 0.067 mmol), TBTU (32 mg, 0.1 mmol), 3-methoxyaniline (X) (0.011 mL, 0.1 mmol) and DIPEA (0.017 mL, 0.1 mmol) in DMF (0.15 mL) was let under stirring at rt overnight. After dilution with EtOAc (15 mL), the organic phase was washed with a saturated solution of NaHCO$_3$, water and brine, dried over Na$_2$SO$_4$, filtered and evaporated in vacuo. Purification by column chromatography afforded the title compound as brownish solid (3 mg, 11%).

$^1$H NMR (499.7 MHz, DMSO-d$_6$) δ ppm 1.75-1.83 (m, 2H), 1.90-1.96 (m, 2H), 2.02-2.10 (m, 2H), 2.21-2.30 (m, 2H), 2.67-2.72 (m, 1H), 3.72 (s, 3H), 3.97 (s, 1H), 4.39-4.47 (m, 1H), 6.59-6.61 (m, 1H), 7.15-7.22 (m, 2H), 7.34-7.36 (m, 1H), 7.41 (br. s., 2H), 8.27 (s, 1H) 9.83 (br. s., 1H).

HRMS (ESI+): calcd. for C$_{21}$H$_{23}$N$_6$O$_2$ [M+H]$^+$ 391.1877; found 391.1888.

Example 4

Conv. 1 cis-4-[6-amino-2-(pyridin-3-yl)-9H-purin-9-yl]-N-(3-methoxyphenyl)cyclohexanecarboxamide (I), cpd 4

[X=N, R1=CONR4R5, R4=Substituted Aryl, R5=H, R3=Heteroaryl]

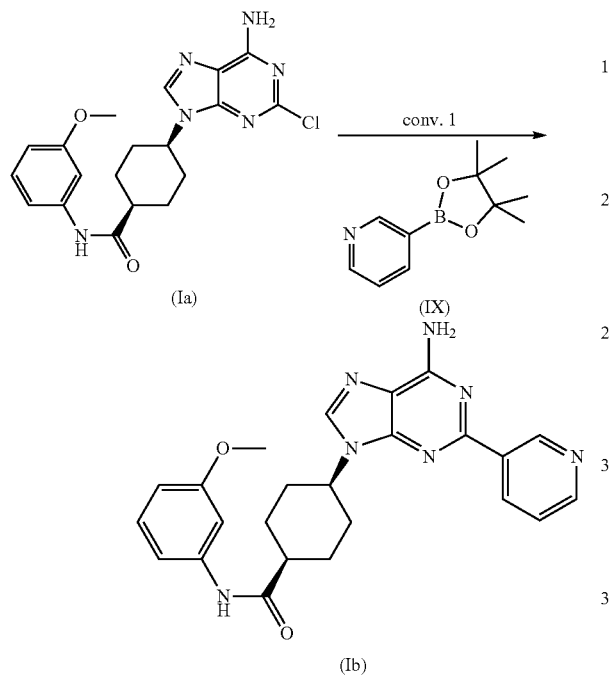

cis-4-(6-Amino-2-chloro-9H-purin-9-yl)-N-(3-methoxyphenyl)cyclohexanecarboxamide (Ia) (29 mg, 0.071 mmol), 3-(4,4,5,5-tetramethyl-1,3,2-dioxaborolan-2-yl)pyridine (IX) (45 mg, 0.123 mmol) and Cs$_2$CO$_3$ (138 mg, 0.426 mmol) were charged in a two necked round bottom flask under argon and dissolved in 1,4-dioxane (3 mL) and water (1 mL). PdCl$_2$dppf (3 mg, 0.003 mmol) was then added under argon and the mixture heated at 100° C. for 7 h. After cooling to rt, the mixture was diluted with EtOAc (10 mL) and filtered over a pad of celite. The filtrate was washed with water and brine and the organic layer dried over Na$_2$SO$_4$, filtered and evaporated under reduced pressure. The title compound was isolated by column chromatography (eluant EtOAc, EtOAc:MeOH=97:3, 95:5) as white solid (15 mg, 48%).

$^1$H NMR (400.5 MHz, DMSO-d$_6$) δ ppm 1.75-1.86 (m, 2H), 1.90-1.99 (m, 2H), 2.07-2.18 (m, 2H), 2.53-2.62 (m, 2H), 2.71-2.77 (m, 1H), 3.74 (s, 3H), 4.49-4.60 (m, 1H), 6.60-6.64 (m, 1H), 7.16-7.26 (m, 2H), 7.32 (br. s., 2H), 7.38-7.40 (m, 1H), 7.45 (ddd, J=8.0, 4.7, 0.7 Hz, 1H), 8.21 (s, 1H), 8.62 (dd, J=4.7, 1.7 Hz, 1H), 8.66 (dt, J=8.0, 1.9 Hz, 1H), 9.52 (dd, J=1.9, 0.7 Hz, 1H), 9.80 (s, 1H).

HRMS (ESI+): calcd. for C$_{24}$H$_{26}$N$_7$O$_2$ [M+H]$^+$ 444.2143; found 444.2144.

Alternatively, the same reaction can be performed under microwave irradiation at 120° C. for 1 h. When the reaction did not reach a complete conversion, a second portion of PdCl$_2$dppf and boronic acid or boronic ester were added, and the mixture was subjected to microwave irradiation at 120° C. for another hour.

When the formation of a mixture of cis and trans product isomers was detected in the crude, said isomers could be generally separated by column chromatography.

Operating in an analogous way, but employing suitably substituted starting material (Ia) and (IX), the following compounds were obtained:

methyl cis-4-[6-amino-2-(furan-3-yl)-9H-purin-9-yl]cyclohexanecarboxylate (I), cpd 1

[X=N, R1=COOR4, R4=(C$_1$-C$_6$)alkyl, R3=Heteroaryl]

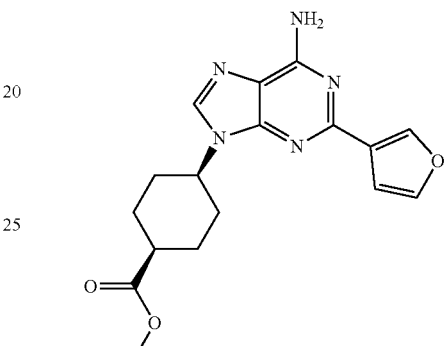

$^1$H NMR (400.5 MHz, DMSO-d$_6$) δ ppm 1.66-1.77 (m, 2H), 1.85-1.94 (m, 2H), 2.13-2.28 (m, 4H), 2.76-2.82 (m, 1H), 3.71 (s, 3H), 4.35-4.45 (m, 1H), 6.97 (dd, J=1.8, 0.7 Hz, 1H), 7.11 (br. s., 2H), 7.72 (t, J=1.7 Hz, 1H), 8.11 (s, 1H), 8.14 (dd, J=1.6, 0.7 Hz, 1H).

HRMS (ESI+): calcd. for C$_{17}$H$_{20}$N$_5$O$_3$ [M+H]$^+$ 342.1561; found 342.1559.

methyl cis-4-[6-amino-2-(pyridin-3-yl)-9H-purin-9-yl]cyclohexanecarboxylate (I), cpd 2

[X=N, R1=COOR4, R4=(C$_1$-C$_6$)alkyl, R3=Heteroaryl]

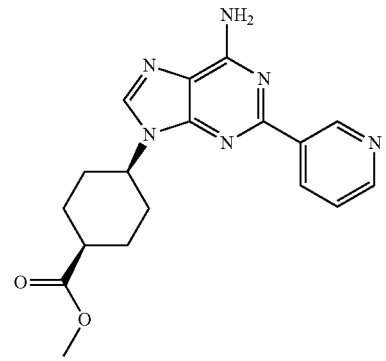 [SMILES: COC(=O)[C@H]1CC[C@@H](n2cnc3c(N)nc(-c4cccnc4)nc32)CC1]

$^1$H NMR (400.5 MHz, DMSO-d$_6$) δ ppm 1.67-1.80 (m, 2H), 1.88-1.97 (m, 2H), 2.13-2.34 (m, 4H), 2.79-2.84 (m, 1H), 3.74 (s, 3H), 4.42-4.53 (m, 1H), 7.32 (br. s., 2H), 7.46-7.52 (m, 1H), 8.19 (s, 1H), 8.58-8.64 (m, 2H), 8.57-8.64 (m, 2H), 9.49 (d, J=1.5 Hz, 1H).

HRMS (ESI+): calcd. for C$_{18}$H$_{21}$N$_6$O$_2$ [M+H]$^+$ 353.1721; found 353.1721.

cis-4-[6-amino-2-(furan-3-yl)-9H-purin-9-yl]-N-(3-methoxyphenyl)cyclohexanecarboxamide (I), cpd 5

[X=N, R1=CONR4R5, R4=Substituted Aryl, R5=H, R3=Heteroaryl]

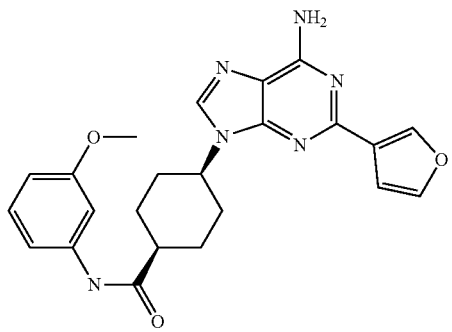 [SMILES: COc1cccc(NC(=O)[C@H]2CC[C@@H](n3cnc4c(N)nc(-c5ccoc5)nc43)CC2)c1]

¹H NMR (400.5 MHz, DMSO-d₆) δ ppm 1.72-1.83 (m, 2H), 1.84-1.94 (m, 2H), 2.08-2.17 (m, 2H), 2.47-2.57 (m, 2H), 2.68-2.75 (m, 1H), 3.74 (s, 3H), 4.42-4.50 (m, 1H), 6.58-6.66 (m, 1H), 7.00 (dd, J=1.8, 0.7 Hz, 1H), 7.11 (br. s, 2H), 7.19-7.22 (m, 2H), 7.40-7.42 (m, 1H), 7.66 (t, J=1.7 Hz, 1H), 8.12 (s, 1H), 8.15 (dd, J=1.6, 0.7 Hz, 1H), 9.79 (s, 1H).

HRMS (ESI+): calcd. for $C_{23}H_{25}N_6O_3$ [M+H]⁺ 433.1983; found 433.1989.

cis-4-(6-amino-2-phenyl-9H-purin-9-yl)-N-(3-methoxyphenyl)cyclohexanecarboxamide (I), cpd 6

[X=N, R1=CONR4R5, R4=Substituted Aryl, R5=H, R3=aryl]

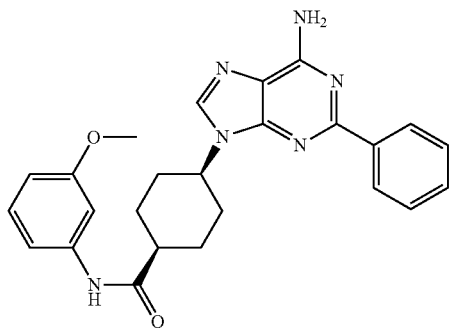 [SMILES: COc1cccc(NC(=O)[C@H]2CC[C@@H](n3cnc4c(N)nc(-c5ccccc5)nc43)CC2)c1]

¹H NMR (400.5 MHz, DMSO-d₆) δ ppm 1.74-1.87 (m, 2H), 1.87-1.98 (m, 2H), 2.09-2.19 (m, 2H), 2.57-2.63 (m, 2H), 2.71-2.78 (m, 1H), 3.74 (s, 3H), 4.46-4.58 (m, 1H), 6.59-6.67 (m, 1H), 7.18 (br. s., 2H), 7.19-7.27 (m, 2H), 7.37 (t, J=1.5 Hz, 1H), 7.38-7.44 (m, 3H), 8.17 (s, 1H), 8.36-8.43 (m, 2H), 9.79 (s, 1H).

HRMS (ESI+): calcd. for $C_{25}H_{27}N_6O_2$ [M+H]⁺ 443.2190; found 443.2195.

cis-4-{6-amino-2-[4-(dimethylamino)phenyl]-9H-purin-9-yl}-N-(3-methoxyphenyl)cyclohexanecarboxamide (I), cpd 7

[X=N, R1=CONR4R5, R4=Substituted Aryl, R5=H, R3=Substituted Aryl]

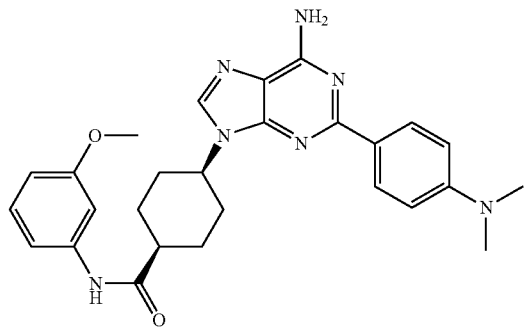 [SMILES: COc1cccc(NC(=O)[C@H]2CC[C@@H](n3cnc4c(N)nc(-c5ccc(N(C)C)cc5)nc43)CC2)c1]

¹H NMR (400.5 MHz, DMSO-d₆) δ ppm 1.70-1.83 (m, 2H), 1.85-1.94 (m, 2H), 2.13-2.21 (m, 2H), 2.54-2.64 (m, 2H), 2.70-2.76 (m, 1H), 2.97 (s, 6H), 3.73 (s, 3H), 4.41-4.51 (m, 1H), 6.60-6.65 (m, 1H), 6.68 (d, J=9.1 Hz, 2H), 6.98 (br. s., 2H) 7.18-7.24 (m, 1H), 7.24-7.29 (m, 1H), 7.44 (t, J=2.2 Hz, 1H), 8.05 (s, 1H), 8.22 (d, J=9.1 Hz, 2H), 9.77 (s, 1H).

HRMS (ESI+): calcd. for $C_{27}H_{32}N_7O_2$ [M+H]⁺ 486.2612; found 486.2622.

cis-4-[6-amino-2-(4-fluorophenyl)-9H-purin-9-yl]-N-(3-methoxyphenyl)cyclohexanecarboxamide (I), cpd 8

[X=N, R1=CONR4R5, R4=Substituted Aryl, R5=H, R3=Substituted Aryl]

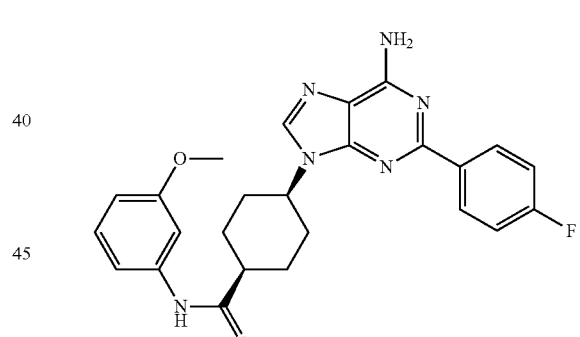

¹H NMR (400.5 MHz, DMSO-d₆) δ ppm 1.72-1.84 (m, 2H), 1.84-1.95 (m, 2H), 2.11-2.21 (m, 2H), 2.55-2.66 (m, 2H), 2.71-2.76 (m, 1H), 3.75 (s, 3H), 4.40-4.56 (m, 1H), 6.61-6.66 (m, 1H), 7.14-7.26 (m, 6H), 7.45-7.48 (m, 1H), 8.16 (s, 1H), 8.38-8.47 (m, 2H), 9.79 (s, 1H).

HRMS (ESI+): calcd. for $C_{25}H_{26}FN_6O_2$ [M+H]⁺ 461.2096; found 461.2097.

cis-4-[6-amino-2-(pyridin-4-yl)-9H-purin-9-yl]-N-(3-methoxyphenyl)cyclohexanecarboxamide (I), cpd 9

[X=N, R1=CONR4R5, R4=Substituted Aryl, R5=H, R3=Heteroaryl]

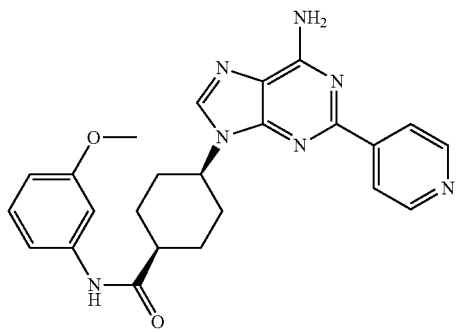 [SMILES: COc1cccc(NC(=O)[C@H]2CC[C@@H](n3cnc4c(N)nc(-c5ccncc5)nc43)CC2)c1]

¹H NMR (400.5 MHz, DMSO-d₆) δ ppm 1.72-1.84 (m, 2H), 1.87-1.97 (m, 2H), 2.11-2.21 (m, 2H), 2.55-2.65 (m, 2H), 2.71-2.78 (m, 1H), 3.74 (s, 3H), 4.48-4.56 (m, 1H), 6.61-6.66 (m, 1H), 7.19-7.24 (m, 1H), 7.23-7.28 (m, 1H), 7.36 (s, 2H), 7.42 (t, J=2.0 Hz, 1H), 8.24 (s, 1H), 8.24-8.29 (m, 2H), 8.59-8.68 (m, 2H), 9.80 (s, 1H).

HRMS (ESI+): calcd. for $C_{24}H_{26}N_7O_2$ [M+H]⁺ 444.2143; found 444.2143.

cis-4-[6-amino-2-(3-fluorophenyl)-9H-purin-9-yl]-N-(3-methoxyphenyl)cyclohexanecarboxamide (I), cpd 10

[X=N, R1=CONR4R5, R4=Substituted Aryl, R5=H, R3=Substituted Aryl]

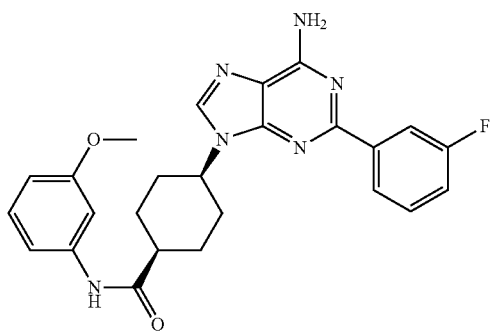 [SMILES: COc1cccc(NC(=O)[C@H]2CC[C@@H](n3cnc4c(N)nc(-c5cccc(F)c5)nc43)CC2)c1]

¹H NMR (400.5 MHz, DMSO-d₆) δ ppm 1.72-1.86 (m, 2H), 1.88-1.98 (m, 2H), 2.08-2.18 (m, 2H), 2.52-2.62 (m, 2H), 2.71-2.76 (m, 1H), 3.73 (s, 3H), 4.46-4.57 (m, 1H), 6.60-6.64 (m, 1H), 7.15-7.23 (m, 1H), 7.23-7.30 (m, 4H), 7.36 (t, J=2.2 Hz, 1H), 7.44-7.50 (m, 1H), 8.13 (ddd, J=10.9, 2.7, 1.4 Hz, 1H), 8.20 (s, 1H), 8.25 (dt, J=7.9, 1.4 Hz, 1H), 9.80 (s, 1H).

HRMS (ESI+): calcd. for $C_{25}H_{26}FN_6O_2$ [M+H]⁺ 461.2096; found 461.2095.

cis-4-{6-amino-2-[3-(trifluoromethyl)phenyl]-9H-purin-9-yl}-N-(3-methoxyphenyl)cyclohexanecarboxamide (I), cpd 11

[X=N, R1=CONR4R5, R4=Substituted Aryl, R5=H, R3=Substituted Aryl]

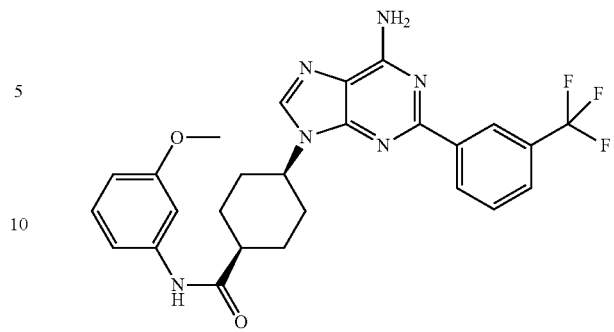

¹H NMR (400.5 MHz, DMSO-d₆) δ ppm 1.72-1.88 (m, 2H), 1.90-2.01 (m, 2H), 2.12 (m, 2H), 2.52-2.61 (m, 2H), 2.71-2.76 (m, 1H), 3.74 (s, 3H), 4.51-4.58 (m, 1H), 6.60-6.65 (m, 1H), 7.17-7.27 (m, 2H), 7.35 (br. s., 2H), 7.39 (t, J=2.1 Hz, 1H), 7.67 (dd, J=7.9, 7.7 Hz, 1H), 7.80 (d, J=7.7 Hz, 1H), 8.22 (s, 1H), 8.67 (s, 1H), 8.72 (d, J=7.9 Hz, 1H), 9.81 (s, 1H).

HRMS (ESI+): calcd. for $C_{26}H_{26}F_3N_6O_2$ [M+H]⁺ 511.2064; found 511.2064.

cis-4-{6-amino-2-[4-(trifluoromethyl)phenyl]-9H-purin-9-yl}-N-(3-methoxyphenyl)cyclohexanecarboxamide (I), cpd 13

[X=N, R1=CONR4R5, R4=Substituted Aryl, R5=H, R3=Substituted Aryl]

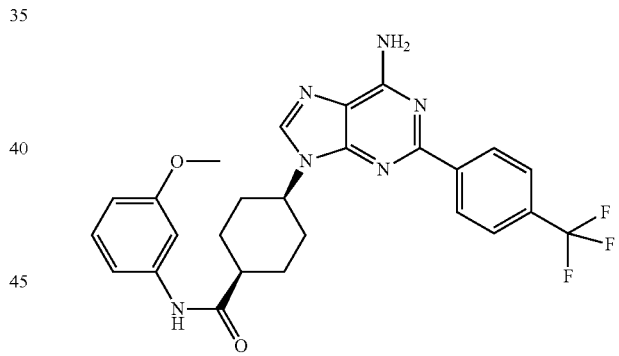

¹H NMR (400-5 MHz, DMSO-d₆) δ ppm 1.73-1.82 (m, 2H), 1.85-1.94 (m, 2H), 2.14-2.22 (m, 2H), 2.62-2.72 (m, 2H), 2.72-2.80 (m, 1H), 3.74 (s, 3H), 4.46-4.54 (m, 1H), 6.62-6.67 (m, 1H), 7.16-7.25 (m, 2H), 7.31 (br. s., 2H), 7.51-7.54 (m, 1H), 7.76 (d, J=8.2 Hz, 2H), 8.20 (s, 1H), 8.59 (d, J=8.2 Hz, 2H), 9.80 (s, 1H).

HRMS (ESI+): calcd. for $C_{26}H_{26}F_3N_6O_2$ [M+H]⁺ 511.2064; found 511.2065.

cis-4-[6-amino-2-(2-fluorophenyl)-9H-purin-9-yl]-N-(3-methoxyphenyl)cyclohexanecarboxamide (I), cpd 14

[X=N, R1=CONR4R5, R4=Substituted Aryl, R5=H, R3=Substituted Aryl]

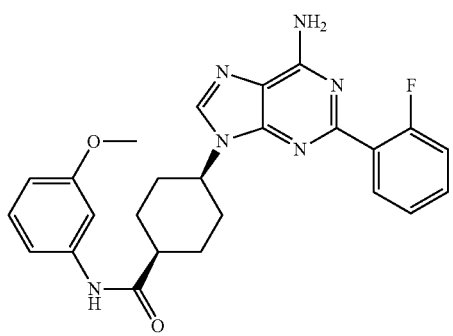 [SMILES: COc1cccc(NC(=O)[C@H]2CC[C@@H](n3cnc4c(N)nc(-c5ccccc5F)nc43)CC2)c1]

¹H NMR (400.5 MHz, DMSO-d₆) δ ppm 1.73-1.83 (m, 2H), 1.93-2.01 (m, 2H), 2.02-2.13 (m, 2H), 2.35-2.46 (m, 2H), 2.67-2.72 (m, 1H), 3.73 (s, 3H), 4.44-4.55 (m, 1H), 6.60-6.63 (m, 1H), 7.14-7.29 (m, 6H), 7.33-7.37 (m, 1H), 7.41-7.49 (m, 1H), 7.90 (td, J=7.9, 1.8 Hz, 1H), 8.23 (s, 1H), 9.78 (s, 1H).

HRMS (ESI+): calcd. for $C_{25}H_{26}FN_6O_2$ [M+H]⁺ 461.2096; found 461.2104.

cis-4-[6-amino-2-(2-fluoropyridin-4-yl)-9H-purin-9-yl]-N-(3-methoxyphenyl)cyclohexanecarboxamide (I), cpd 15

[X=N, R1=CONR4R5, R4=Substituted Aryl, R5=H, R3=Substituted Heteroaryl]

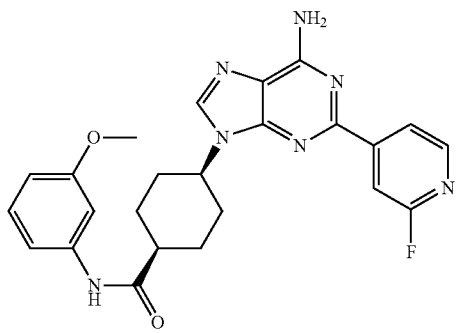 [SMILES: COc1cccc(NC(=O)[C@H]2CC[C@@H](n3cnc4c(N)nc(-c5ccnc(F)c5)nc43)CC2)c1]

¹H NMR (400.5 MHz, DMSO-d₆) δ ppm 1.74-1.86 (m, 2H), 1.87-1.96 (m, 2H), 2.08-2.19 (m, 2H), 2.56-2.66 (m, 2H), 2.72-2.79 (m, 1H), 3.73 (s, 3H), 4.48-4.59 (m, 1H), 6.63 (ddd, J=8.1, 2.4, 0.9 Hz, 1H), 7.18-7.23 (m, 1H), 7.27-7.30 (m, 1H), 7.36 (t, J=2.4 Hz, 1H), 7.44 (br. s., 2H), 7.93 (s, 1H), 8.21-8.25 (m, 1H), 8.27 (s, 1H), 8.28-8.31 (m, 1H), 9.80 (s, 1H).

HRMS (ESI+): calcd. for $C_{24}H_{25}FN_7O_2$ [M+H]⁺ 462.2049; found 462.2042.

cis-4-{6-amino-2-[4-(benzyloxy)phenyl]-9H-purin-9-yl}-N-(3-methoxyphenyl)cyclohexanecarboxamide (I), cpd 16

[X=N, R1=CONR4R5, R4=Substituted Aryl, R5=H, R3=Substituted Aryl]

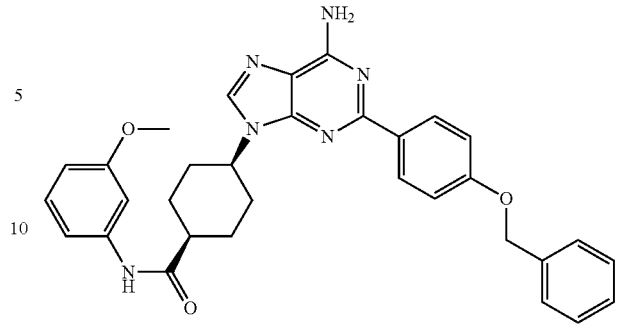

HRMS (ESI+): calcd. for $C_{32}H_{32}N_6O_3$ [M+H]⁺ 549.2609; found 549.2605.

cis-4-[6-amino-2-(6-fluoropyridin-3-yl)-9H-purin-9-yl]-N-(3-methoxyphenyl)cyclohexanecarboxamide (I), cpd 19

[X=N, R1=CONR4R5, R4=Substituted Aryl, R5=H, R3=Substituted Heteroaryl]

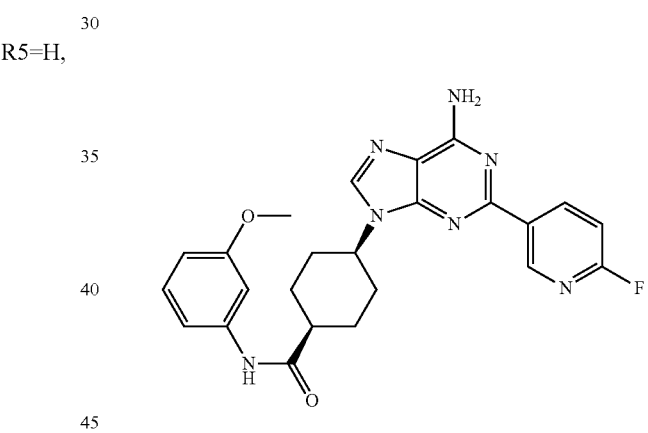

¹H NMR (400.5 MHz, DMSO-d₆) δ ppm 1.73-1.85 (m, 2H), 1.87-1.97 (m, 2H), 2.08-2.19 (m, 2H), 2.54-2.65 (m, 2H), 2.71-2.77 (m, 1H), 3.75 (s, 3H), 4.46-4.56 (m, 1H), 6.50-6.66 (m, 1H), 7.18-7.24 (m, 3H), 7.35 (br. s., 2H), 7.43 (m, 1H), 8.20 (s, 1H), 8.81-8.86 (m, 1H), 9.15 (d, J=2.4 Hz, 1H), 9.81 (s, 1H).

HRMS (ESI+): calcd. for $C_{24}H_{25}FN_7O_2$ [M+H]⁺ 462.2049; found 462.2041.

cis-4-{6-amino-2-[3-(benzyloxy)phenyl]-9H-purin-9-yl}-N-(3-methoxyphenyl)cyclohexanecarboxamide (I), cpd 20

[X=N, R1=CONR4R5, R4=Substituted Aryl, R5=H, R3=Substituted Aryl]

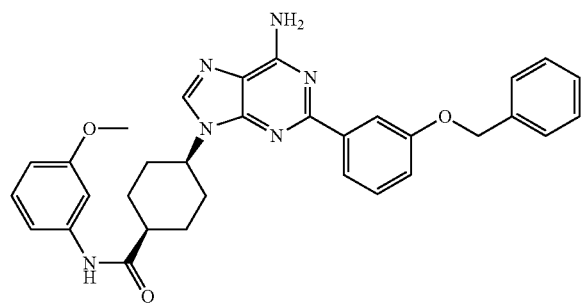 [SMILES: COc1cccc(NC(=O)[C@H]2CC[C@@H](n3cnc4c(N)nc(-c5cccc(OCc6ccccc6)c5)nc43)CC2)c1]

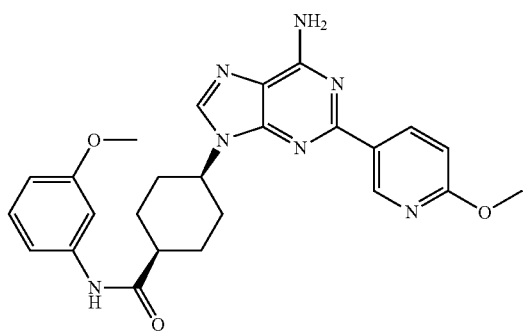

¹H NMR (400.5 MHz, DMSO-d₆) δ ppm 1.76-1.87 (m, 2H), 1.90-2.00 (m, 2H), 2.05-2.16 (m, 2H), 2.44-2.57 (m, 2H), 2.71-2.76 (m, 1H), 3.73 (s, 3H), 4.48-4.57 (m, 1H), 5.18 (s, 2H), 6.52-6.70 (m, 1H), 7.08 (ddd, J=8.2, 2.6, 0.8 Hz, 1H), 7.15-7.25 (m, 3H), 7.27-7.45 (m, 4H), 7.46-7.54 (m, 2H), 7.92-8.06 (m, 2H), 8.18 (s, 1H), 9.81 (s, 1H).

HRMS (ESI+): calcd. for $C_{32}H_{32}N_6O_3$ [M+H]⁺ 549.2609; found 549.2612.

cis-4-[6-amino-2-(2-methoxypyridin-4-yl)-9H-purin-9-yl]-N-(3-methoxyphenyl)cyclohexanecarboxamide (I), cpd 21

[X=N, R1=CONR4R5, R4=Substituted Aryl, R5=H, R3=Substituted Heteroaryl]

¹H NMR (400.5 MHz, DMSO-d₆) δ ppm 1.73-1.83 (m, 2H), 1.87-1.98 (m, 2H), 2.06-2.18 (m, 2H), 2.53-2.64 (m, 2H), 2.70-2.76 (m, 1H), 3.74 (s, 3H), 3.92 (s, 3H), 4.44-4.55 (m, 1H), 6.59-6.67 (m, 1H), 6.85 (d, J=8.7 Hz, 1H), 7.14-7.26 (m, 3H), 7.39-7.41 (s, 1H), 8.15 (s, 1H), 8.59 (dd, J=8.7, 2.3 Hz, 1H), 9.12 (d, J=2.3 Hz, 1H), 9.80 (s, 1H).

HRMS (ESI+): calcd. for $C_{25}H_{28}N_7O_3$ [M+H]⁺ 474.2248; found 474.2245.

cis-4-[6-amino-2-(3-aminophenyl)-9H-purin-9-yl]-N-(3-methoxyphenyl)cyclohexanecarboxamide (I), cpd 23

[X=N, R1=CONR4R5, R4=Substituted Aryl, R5=H, R3=Substituted Aryl]

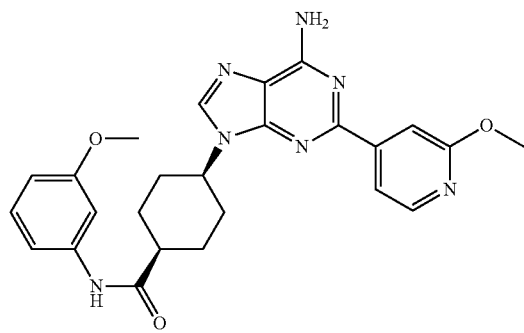 [SMILES: COc1cccc(NC(=O)[C@H]2CC[C@@H](n3cnc4c(N)nc(-c5ccnc(OC)c5)nc43)CC2)c1]

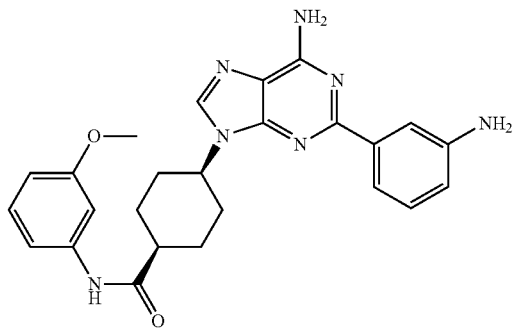 [SMILES: COc1cccc(NC(=O)[C@H]2CC[C@@H](n3cnc4c(N)nc(-c5cccc(N)c5)nc43)CC2)c1]

¹H NMR (400.5 MHz, DMSO-d₆) δ ppm 1.74-1.85 (m, 2H), 1.89-1.97 (m, 2H), 2.09-2.18 (m, 2H), 2.52-2.61 (m, 2H), 2.71-2.76 (m, 1H), 3.73 (s, 3H), 3.90 (s, 3H), 4.46-4.58 (m, 1H), 6.62 (ddd, J=8.1, 2.4, 1.0 Hz, 1H), 7.20 (dd, J=8.7, 8.1 Hz, 1H), 7.26 (d, J=8.7 Hz, 1H), 7.34 (br. s., 2H), 7.37 (t, J=2.2 Hz, 1H), 7.67 (s, 1H), 7.88 (dd, J=5.4, 1.2 Hz, 1H), 8.20 (d, J=5.4 Hz, 1H), 8.24 (s, 1H), 9.79 (s, 1H).

HRMS (ESI+): calcd. for $C_{25}H_{28}N_7O_3$ [M+H]⁺ 474.2248; found 474.2244.

cis-4-[6-amino-2-(6-methoxypyridin-3-yl)-9H-purin-9-yl]-N-(3-methoxyphenyl)cyclohexanecarboxamide (I), cpd 22

[X=N, R1=CONR4R5, R4=Substituted Aryl, R5=H, R3=Substituted Heteroaryl]

¹H NMR (400.5 MHz, DMSO-d₆) δ ppm 1.75-1.85 (m, 2H), 1.91-2.00 (m, 2H), 2.06-2.17 (m, 2H), 2.40-2.46 (m, 2H), 2.70-2.75 (m, 1H), 3.73 (s, 3H), 4.47-4.56 (m, 1H), 5.05 (br. s., 2H), 6.59-6.66 (m, 2H), 7.04-7.07 (m, 1H), 7.07 (br. s., 1H), 7.15-7.23 (m, 2H), 7.35-7.38 (m, 1H), 7.58 (d, J=7.7 Hz, 1H), 7.59-7.61 (m, 1H), 8.16 (s, 1H), 9.80 (s, 1H).

HRMS (ESI+): calcd. for $C_{25}H_{28}N_7O_2$ [M+H]⁺ 458.2299; found 458.2290.

cis-4-{6-amino-2-[3-(formylamino)phenyl]-9H-purin-9-yl}-N-(3-methoxyphenyl)cyclohexanecarboxamide (I), cpd 25

[X=N, R1=CONR4R5, R4=Substituted Aryl, R5=H, R3=Substituted Aryl]

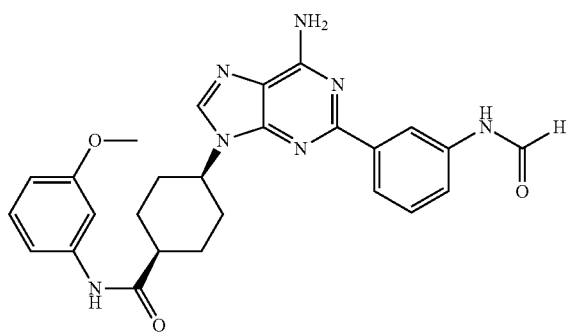 [SMILES: COc1cccc(NC(=O)[C@H]2CC[C@@H](n3cnc4c(N)nc(-c5cccc(NC=O)c5)nc43)CC2)c1]

¹H NMR (400.5 MHz, DMSO-d₆) δ ppm 1.75-1.86 (m, 2H), 1.91-2.01 (m, 2H), 2.08-2.16 (m, 2H), 2.34-2.56 (m, 2H), 2.70-2.76 (m, 1H), 3.73 (s, 3H), 4.49-4.57 (m, 1H), 6.59-6.64 (m, 1H), 7.12-7.25 (m, 4H), 7.33-7.40 (m, 2H), 7.73 (d, J=8.9 Hz, 1H), 8.12 (d, J=7.9 Hz, 1H), 8.20 (s, 1H), 8.30 (d, J=1.7 Hz, 1H), 8.45-8.47 (m, 1H), 9.80 (s, 1H), 10.25 (s, 1H).

HRMS (ESI+): calcd. for $C_{26}H_{28}N_7O_3$ [M+H]⁺ 486.2248; found 486.2243.

3-(6-amino-9-{cis-4-[(3-methoxyphenyl)carbamoyl]cyclohexyl}-9H-purin-2-yl)benzamide (I), cpd 26

[X=N, R1=CONR4R5, R4=Substituted Aryl, R5=H, R3=Substituted Aryl]

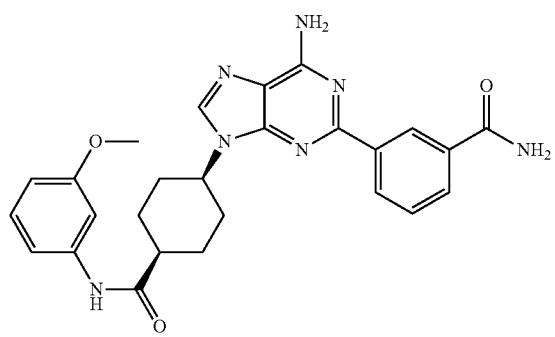 [SMILES: COc1cccc(NC(=O)[C@H]2CC[C@@H](n3cnc4c(N)nc(-c5cccc(C(N)=O)c5)nc43)CC2)c1]

¹H NMR (400.5 MHz, DMSO-d₆) δ ppm 1.74-1.88 (m, 2H), 1.91-2.01 (m, 2H), 2.08-2.16 (m, 2H), 2.45-2.55 (m, 2H), 2.72-2.76 (m, 1H), 3.74 (s, 3H), 4.51-4.62 (m, 1H), 6.59-6.65 (m, 1H), 7.16-7.23 (m, 2H), 7.26 (br. s., 2H), 7.36 (br. s., 1H), 7.38-7.40 (m, 1H), 7.46-7.51 (m, 1H), 7.90 (dt, J=7.8, 1.4 Hz, 1H), 8.02 (br. s., 1H), 8.20 (s, 1H), 8.54 (dt, J=7.8, 1.3 Hz, 1H), 8.85 (t, J=1.7 Hz, 1H), 9.81 (s, 1H).

HRMS (ESI+): calcd. for $C_{26}H_{28}N_7O_3$ [M+H]⁺ 486.2248; found 486.2244.

cis-4-[6-amino-2-(pyridin-4-yl)-9H-purin-9-yl]-N-{4-[(trifluoromethyl)sulfonyl]phenyl}cyclohexanecarboxamide (I), cpd 28

[X=N, R1=CONR4R5, R4=Substituted Aryl, R5=H, R3=Heteroaryl]

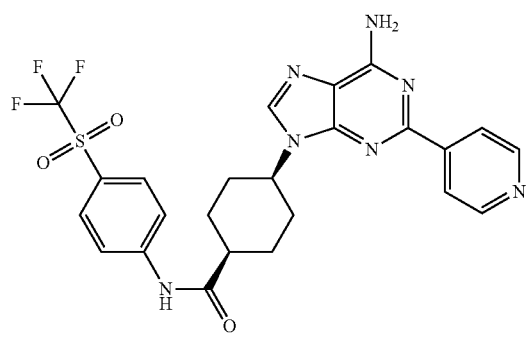 [SMILES: Nc1nc(-c2ccncc2)nc2c1ncn2[C@H]1CC[C@@H](C(=O)Nc2ccc(S(=O)(=O)C(F)(F)F)cc2)CC1]

¹H NMR (400.5 MHz, DMSO-d₆) δ ppm 1.78-1.90 (m, 2H), 1.92-2.00 (m, 2H), 2.14-2.24 (m, 2H), 2.54-2.62 (m, 2H), 2.83-2.89 (m, 1H), 4.48-4.60 (m, 1H), 7.37 (br. s., 2H), 8.06-8.17 (m, 4H), 8.23-8.26 (m, 2H), 8.63-8.67 (m, 2H), 10.62 (s, 1H).

HRMS (ESI+): calcd. for $C_{24}H_{23}F_3N_7O_3S$ [M+H]⁺ 546.1530; found 546.1534.

4-(6-amino-9-{cis-4-[(3-methoxyphenyl)carbamoyl]cyclohexyl}-9H-purin-2-yl)-N-{4-[(4-methylpiperazin-1-yl)methyl]phenyl}benzamide (I), cpd 29

[X=N, R1=CONR4R5, R4=Substituted Aryl, R5=H, R3=Substituted Aryl]

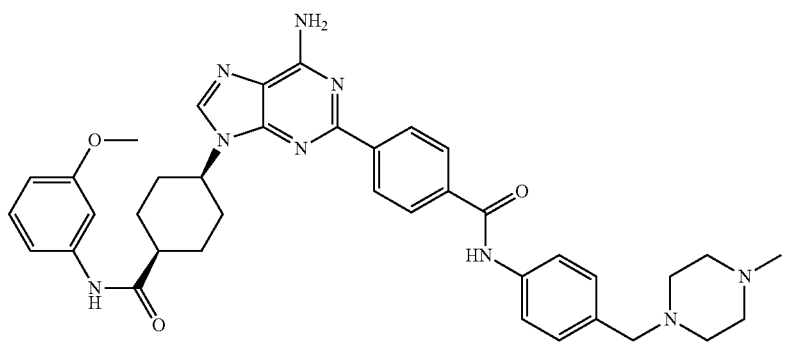 [SMILES: COc1cccc(NC(=O)[C@H]2CC[C@@H](n3cnc4c(N)nc(-c5ccc(C(=O)Nc6ccc(CN7CCN(C)CC7)cc6)cc5)nc43)CC2)c1]

¹H NMR (400.5 MHz, DMSO-d₆) δ ppm 1.76-1.87 (m, 2H), 1.89-2.00 (m, 2H), 2.11-2.19 (m, 2H), 2.22-2.44 (m, 8H), 2.55-2.65 (m, 2H), 2.72-2.78 (m, 1H), 3.43 (s, 2H), 3.71 (s, 3H), 4.49-4.58 (m, 1H), 6.60 (ddd, J=6.6, 2.4, 1.1 Hz, 1H), 7.18-7.24 (m, 1H), 7.24-7.31 (m, 5H), 7.41 (t, J=2.1 Hz, 1H), 7.73-7.75 (m, 2H), 8.00-8.02 (m, 2H), 8.21 (s, 1H), 8.52-8.54 (m, 2H), 9.81 (s, 1H), 10.28 (s, 1H).

HRMS (ESI+): calcd. for $C_{38}H_{44}N_9O_3$ $[M+H]^+$ 674.3562; found 674.3578.

3-(6-amino-9-{cis-4-[(3-methoxyphenyl)carbamoyl] cyclohexyl}-9H-purin-2-yl)-N-{4-[(4-methylpiperazin-1-yl)methyl]phenyl}benzamide (I), cpd 30

[X=N, R1=CONR4R5, R4=Substituted Aryl, R5=H, R3=Substituted Aryl]

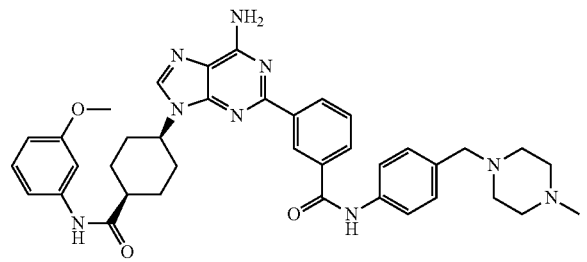 [SMILES: COc1cccc(NC(=O)[C@H]2CC[C@@H](n3cnc4c(N)nc(-c5cccc(C(=O)Nc6ccc(CN7CCN(C)CC7)cc6)c5)nc43)CC2)c1]

¹H NMR (400.5 MHz, DMSO-d₆) δ ppm 1.77-1.87 (m, 2H), 1.91-2.02 (m, 2H), 2.08-2.17 (m, 2H), 2.15 (s, 3H), 2.20-2.44 (m, 8H), 2.50-2.60 (m, 2H), 2.72-2.77 (m, 1H), 3.42 (s, 2H), 3.74 (s, 3H), 4.52-4.60 (m, 1H), 6.60-6.65 (m, 1H), 7.18-7.23 (m, 2H), 7.27 (d, J=8.5 Hz, 2H), 7.30 (br. s., 2H), 7.37-7.40 (m, 1H), 7.57 (t, J=7.8 Hz, 1H), 7.74 (d, J=8.5 Hz, 2H), 7.97 (d, J=7.8 Hz, 1H), 8.21 (s, 1H), 8.61 (d, J=7.9 Hz, 1H), 8.89 (t, J=1.7 Hz, 1H), 9.82 (s, 1H), 10.36 (s, 1H).

HRMS (ESI+): calcd. for $C_{38}H_{44}N_9O_3$ $[M+H]^+$ 674.3562; found 674.3560.

3-(6-amino-9-{cis-4-[(3-methoxyphenyl)carbamoyl] cyclohexyl}-9H-purin-2-yl)-N-(4-{[4-(dimethylamino)piperidin-1-yl]methyl}phenyl)benzamide (I), cpd 31

[X=N, R1=CONR4R5, R4=Substituted Aryl, R5=H, R3=Substituted Aryl]

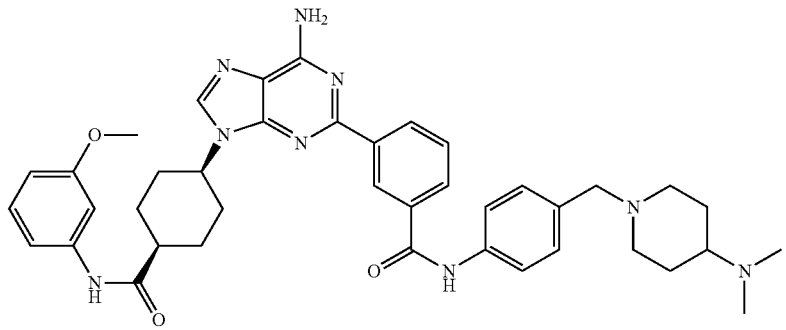 [SMILES: COc1cccc(NC(=O)[C@H]2CC[C@@H](n3cnc4c(N)nc(-c5cccc(C(=O)Nc6ccc(CN7CCC(N(C)C)CC7)cc6)c5)nc43)CC2)c1]

¹H NMR (499.7 MHz, DMSO-d₆), δ ppm 1.31-1.41 (m, 2H), 1.65-1.72 (m, 2H), 1.76-1.86 (m, 1H), 1.86-1.93 (m, 2H), 1.93-2.00 (m, 2H), 2.00-2.05 (m, 1H), 2.09-2.14 (m, 2H), 2.14 (s, 6H), 2.45-2.58 (m, 2H), 2.72-2.76 (m, 1H), 2.79-2.85 (m, 2H), 3.40 (s, 2H), 3.74 (s, 3H), 4.50-4.59 (m, 1H), 6.61-6.64 (m, 1H), 7.17-7.22 (m, 2H), 7.26 (d, J=8.4 Hz, 2H), 7.33 (br. s., 2H), 7.39-7.41 (m, 1H), 7.57 (t, J=7.7 Hz, 1H), 7.73 (d, J=8.4 Hz, 2H), 7.97 (d, J=7.7 Hz, 1H), 8.22 (s, 1H), 8.61 (d, J=7.7 Hz, 1H), 8.88 (t, J=1.5 Hz, 1H), 9.85 (s, 1H), 10.38 (s, 1H).

HRMS (ESI+): calcd. for $C_{40}H_{48}N_9O_3$ $[M+H]^+$ 702.3875; found 702.3874.

4-(6-amino-9-{cis-4-[(3-methoxyphenyl)carbamoyl] cyclohexyl}-9H-purin-2-yl)-N-(4-{[4-(dimethylamino)piperidin-1-yl]methyl}phenyl)benzamide (I), cpd 33

[X=N, R1=CONR4R5, R4=Substituted Aryl, R5=H, R3=Substituted Aryl]

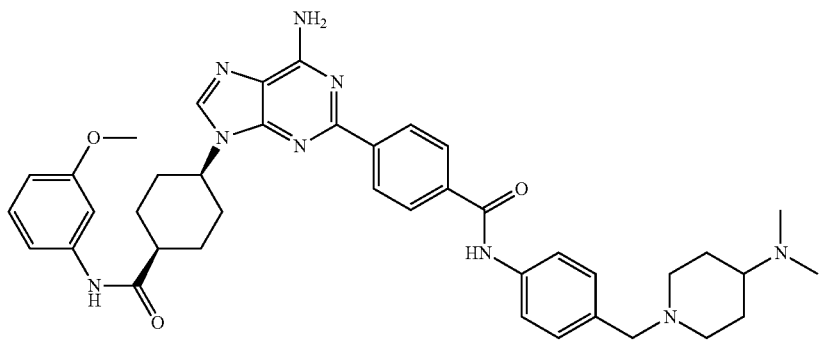 [SMILES: COc1cccc(NC(=O)[C@H]2CC[C@@H](n3cnc4c(N)nc(-c5ccc(C(=O)Nc6ccc(CN7CCC(N(C)C)CC7)cc6)cc5)nc43)CC2)c1]

¹H NMR (499.7 MHz, DMSO-d₆) δ ppm 1.30-1.42 (m, 2H), 1.66-1.72 (m, 2H), 1.75-1.85 (m, 2H), 1.86-1.97 (m, 4H), 1.97-2.06 (m, 1H), 2.08-2.20 (m, 8H), 2.56-2.64 (m, 2H), 2.72-2.77 (m, 1H), 2.80-2.85 (m, 2H), 3.41 (s, 2H), 3.71 (s, 3H), 4.49-4.58 (m, 1H), 6.58-6.64 (m, 1H), 7.19-7.23 (m, 1H), 7.24-7.29 (m, 3H), 7.32 (br. s., 2H), 7.41 (t, J=2.0 Hz, 1H), 7.74 (d, J=8.4 Hz, 2H), 8.01 (d, J=8.5 Hz, 2H), 8.22 (s, 1H), 8.53 (d, J=8.5 Hz, 2H), 9.84 (s, 1H), 10.30 (s, 1H).

HRMS (ESI+): calcd. for $C_{40}H_{48}N_9O_3$ [M+H]⁺ 702.3875; found 702.3856.

cis-4-[6-amino-2-(pyridin-4-yl)-9H-purin-9-yl]-N-(3,4-dimethoxyphenyl)cyclohexanecarboxamide (I), cpd 37

[X=N, R1=CONR4R5, R4=Substituted Aryl, R5=H, R3=Heteroaryl]

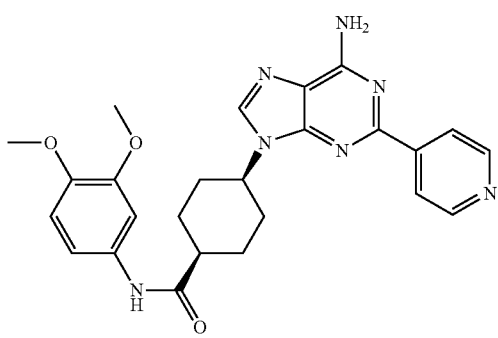 [SMILES: COc1ccc(NC(=O)[C@H]2CC[C@@H](n3cnc4c(N)nc(-c5ccncc5)nc43)CC2)cc1OC]

¹H NMR (499.7 MHz, DMSO-d₆) δ ppm 1.75-1.84 (m, 2H), 1.90-1.97 (m, 2H), 2.11-2.18 (m, 2H), 2.52-2.59 (m, 2H), 2.69-2.73 (m, 1H), 3.72 (s, 6H), 4.50-4.56 (m, 1H), 6.90 (d, J=8.8 Hz, 1H), 7.24 (dd, J=8.8, 2.3 Hz, 1H), 7.37 (d, J=2.3 Hz, 1H), 7.40 (br. s., 2H), 8.24 (d, J=5.9 Hz, 2H), 8.26 (s, 1H), 8.62 (d, J=5.80 Hz, 2H) 9.69 (s, 1H)

HRMS (ESI+): calcd. for $C_{25}H_{28}N_7O_3$ [M+H]⁺ 474.2248; found 474.2263.

cis-4-{6-amino-2-[3-(methylsulfonyl)phenyl]-9H-purin-9-yl}-N-(3-methoxyphenyl)cyclohexanecarboxamide (I), cpd 38

[X=N, R1=CONR4R5, R4=Substituted Aryl, R5=H, R3=Substituted Aryl]

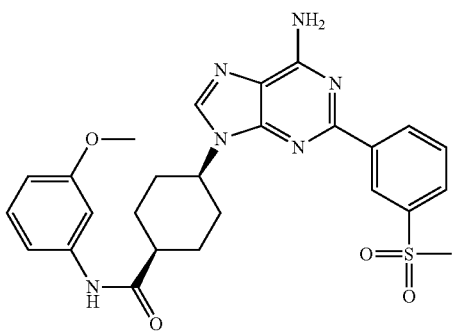 [SMILES: COc1cccc(NC(=O)[C@H]2CC[C@@H](n3cnc4c(N)nc(-c5cccc(S(C)(=O)=O)c5)nc43)CC2)c1]

¹H NMR (499.7 MHz, DMSO-d₆) δ ppm 1.76-1.86 (m, 2H), 1.89-1.98 (m, 1H), 2.10-2.17 (m, 2H), 2.51-2.59 (m, 2H), 2.70-2.78 (m, 1H), 3.26 (s, 3H), 3.74 (s, 3H), 4.50-4.60 (m, 1H), 6.61-6.66 (m, 1H), 7.19-7.25 (m, 2H), 7.39-7.41 (m, 1H), 7.42 (br. s., 2H), 7.71 (t, J=7.9 Hz, 1H), 8.00 (ddd, J=7.9, 1.8, 1.1 Hz, 1H), 8.24 (s, 1H), 8.76 (dt, J=7.9, 1.4 Hz, 1H), 8.86 (t, J=1.7 Hz, 1H), 9.84 (s, 1H).

HRMS (ESI+): calcd. for $C_{26}H_{29}N_6O_4S$ [M+H]⁺ 521.1966; found 521.1989.

cis-4-[6-amino-2-(3-cyanophenyl)-9H-purin-9-yl]-N-(3-methoxyphenyl)cyclohexanecarboxamide (I), cpd 39

[X=N, R1=CONR4R5, R4=Substituted Aryl, R5=H, R3=Substituted Aryl]

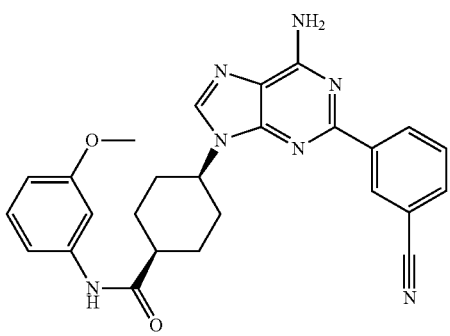 [SMILES: COc1cccc(NC(=O)[C@H]2CC[C@@H](n3cnc4c(N)nc(-c5cccc(C#N)c5)nc43)CC2)c1]

¹H NMR (499.7 MHz, DMSO-d₆) δ ppm 1.76-1.87 (m, 2H), 1.88-1.97 (m, 2H), 2.09-2.16 (m, 2H), 2.52-2.60 (m, 2H), 2.70-2.76 (m, 1H), 3.73 (s, 3H), 4.50-4.60 (m, 1H), 6.62 (dd, J=8.2, 1.7 Hz, 1H), 7.18-7.23 (m, 1H), 7.25-7.29

(m, 1H), 7.35-7.37 (m, 1H), 7.39 (br. s., 2H), 7.64-7.68 (m, 1H), 7.90-7.93 (m, 1H), 8.23 (s, 1H), 8.70-8.73 (m, 2H), 9.84 (s, 1H).

HRMS (ESI+): calcd. for $C_{26}H_{26}N_7O_2$ [M+H]$^+$ 468.2143; found 468.2151.

tert-butyl 4-(6-amino-9-{cis-4-[(3-methoxyphenyl)carbamoyl]cyclohexyl}-9H-purin-2-yl)-3,6-dihydropyridine-1(2H)-carboxylate (I), cpd 40

[X=N, R1=CONR4R5, R4=Substituted Aryl, R5=H, R3=Substituted Heterocyclyl]

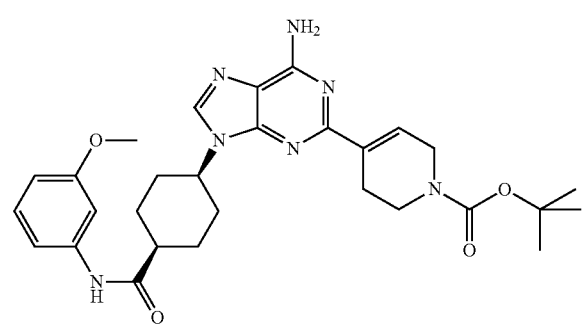 [SMILES: COc1cccc(NC(=O)[C@H]2CC[C@@H](n3cnc4c(N)nc(C5=CCN(C(=O)OC(C)(C)C)CC5)nc43)CC2)c1]

$^1$H NMR (499.7 MHz, DMSO-d$_6$) δ ppm 1.43 (s, 9H), 1.70-1.82 (m, 2H), 1.83-1.93 (m, 2H), 2.03-2.15 (m, 2H), 2.44-2.53 (m, 2H), 2.58-2.63 (m, 1H), 2.68-2.74 (m, 1H), 3.45-3.51 (m, 1H), 3.73 (s, 3H), 3.99-4.06 (m, 2H), 4.37-4.46 (m, 1H), 6.58-6.63 (m, 1H), 6.97 (br. s., 1H), 7.05 (br. s., 2H), 7.14-7.27 (m, 2H), 7.29-7.32 (m, 1H), 8.12 (s, 1H), 9.79 (s, 1H).

HRMS (ESI+): calcd. for $C_{29}H_{38}N_7O_4$ [M+H]$^+$ 548.2980; found 548.2974.

cis-4-[6-amino-2-(1H-indazol-6-yl)-9H-purin-9-yl]-N-(3-methoxyphenyl)cyclohexanecarboxamide (I), cpd 43

[X=N, R1=CONR4R5, R4=Substituted Aryl, R5=H, R3=Heteroaryl]

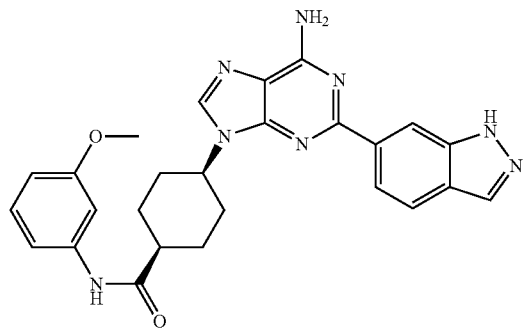 [SMILES: COc1cccc(NC(=O)[C@H]2CC[C@@H](n3cnc4c(N)nc(-c5ccc6cn[nH]c6c5)nc43)CC2)c1]

$^1$H NMR (499.7 MHz, DMSO-d$_6$) δ ppm 1.76-1.86 (m, 2H), 1.93-2.02 (m, 2H), 2.09-2.16 (m, 2H), 2.50-2.58 (m, 2H), 2.72-2.77 (m, 1H), 3.74 (s, 3H), 4.52-4.59 (m, 1H), 6.61-6.65 (m, 1H), 7.18-7.25 (m, 2H), 7.28 (br. s., 2H), 7.41-7.43 (m, 1H), 7.77 (d, J=8.6 Hz, 1H), 8.10 (s, 1H), 8.20 (s, 1H), 8.26 (dd, J=8.6, 1.1 Hz, 1H), 8.55 (s, 1H), 9.84 (s, 1H), 13.20 (s, 1H).

HRMS (ESI+): calcd. for $C_{26}H_{27}N_8O_2$ [M+H]$^+$ 483.2252; found 483.2247.

cis-4-[6-amino-2-(1H-indazol-5-yl)-9H-purin-9-yl]-N-(3-methoxyphenyl)cyclohexanecarboxamide (I), cpd 46

[X=N, R1=CONR4R5, R4=Substituted Aryl, R5=H, R3=Heteroaryl]

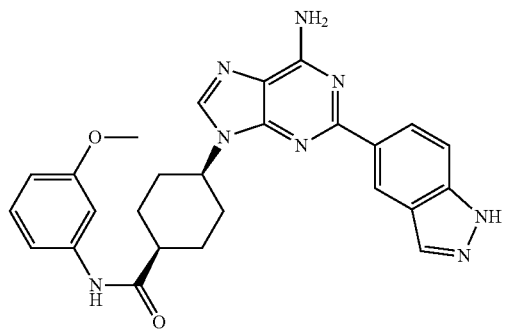 [SMILES: COc1cccc(NC(=O)[C@H]2CC[C@@H](n3cnc4c(N)nc(-c5ccc6[nH]ncc6c5)nc43)CC2)c1]

$^1$H NMR (400.5 MHz, DMSO-d$_6$) δ ppm 1.77-1.87 (m, 2H), 1.91-1.99 (m, 2H), 2.10-2.19 (m, 2H), 2.53-2.63 (m, 2H), 2.72-2.77 (m, 1H), 3.74 (s, 3H), 4.49-4.59 (m, 1H), 6.60-6.66 (m, 1H), 7.15 (br. s., 2H), 7.18-7.29 (m, 2H), 7.40 (t, J=2.1 Hz, 1H), 7.54 (d, J=8.8 Hz, 1H), 8.15 (s, 2H), 8.49 (dd, J=8.8, 1.5 Hz, 1H), 8.81 (s, 1H), 9.81 (s, 1H), 13.12 (br. s., 1H).

HRMS (ESI+): calcd. for $C_{26}H_{27}N_8O_2$ [M+H]$^+$ 483.2252; found 483.2261.

cis-4-[6-amino-2-(pyridin-4-yl)-9H-purin-9-yl]-N-(3-methoxybenzyl)cyclohexanecarboxamide (I), cpd 49

[X=N, R1=CONR4R5, R4=substituted aryl($C_1$-$C_6$)alkyl, R5=H, R3=Heteroaryl]

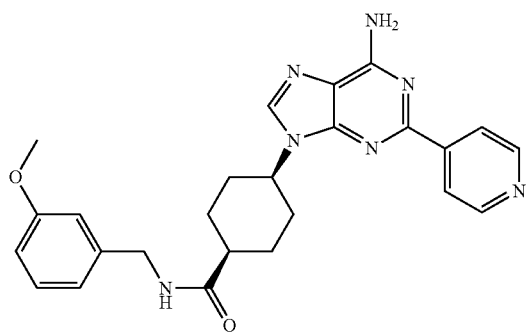 [SMILES: COc1cccc(CNC(=O)[C@H]2CC[C@@H](n3cnc4c(N)nc(-c5ccncc5)nc43)CC2)c1]

$^1$H NMR (499.7 MHz, DMSO-d$_6$) δ ppm 1.69-1.78 (m, 2H), 1.88-1.96 (m, 2H), 2.07-2.14 (m, 2H), 2.40-2.48 (m, 2H), 2.57-2.62 (m, 1H), 3.68 (s, 3H), 4.34 (d, J=5.9 Hz, 2H), 4.48-4.56 (m, 1H), 6.77 (dd, J=8.2, 2.2 Hz, 1H), 6.88 (s, 1H), 6.86 (d, J=7.8 Hz, 1H), 7.20 (t, J=7.8 Hz, 1H), 7.41 (br. s., 2H), 8.20 (s, 1H), 8.23 (d, J=5.9 Hz, 2H), 8.35 (t, J=5.9 Hz, 1H), 8.64 (d, J=5.9 Hz, 2H).

HRMS (ESI+): calcd. for $C_{25}H_{28}N_7O_2$ [M+H]$^+$ 458.2299; found 458.2303.

cis-4-[6-amino-2-(pyridin-4-yl)-9H-purin-9-yl]-N-(3-methylphenyl)cyclohexanecarboxamide (I), cpd 50

[X=N, R1=CONR4R5, R4=Substituted Aryl, R5=H, R3=Heteroaryl]

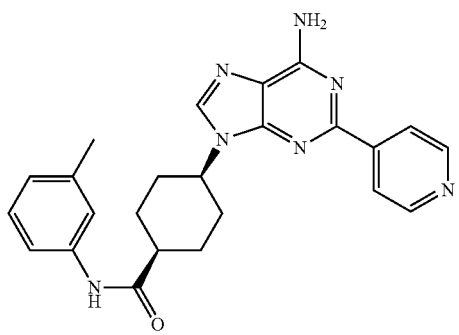 [SMILES: Cc1cccc(NC(=O)[C@H]2CC[C@@H](n3cnc4c(N)nc(-c5ccncc5)nc43)CC2)c1]

$^1$H NMR (499.7 MHz, DMSO-d$_6$) δ ppm 1.78-1.86 (m, 2H), 1.91-2.01 (m, 2H), 2.15-2.23 (m, 2H), 2.32 (s, 3H), 2.57-2.64 (m, 2H), 2.75-2.80 (m, 1H), 4.52-4.59 (m, 1H), 6.90 (d, J=7.3 Hz, 1H), 7.23 (t, J=7.8 Hz, 1H), 7.43 (br. s., 2H), 7.52 (d, J=7.8 Hz, 1H), 7.57 (s, 1H), 8.28 (s, 1H), 8.27-8.31 (m, 2H), 8.64-8.67 (m, 2H), 9.79 (br. s., 1H).

HRMS (ESI+): calcd. for C$_{24}$H$_{26}$N$_7$O [M+H]$^+$ 428.2194; found 428.2173.

cis-4-[6-amino-2-(2-fluoropyridin-3-yl)-9H-purin-9-yl]-N-(3-methoxyphenyl)cyclohexanecarboxamide (I), cpd 51

[X=N, R1=CONR4R5, R4=Substituted Aryl, R5=H, R3=Substituted Heteroaryl]

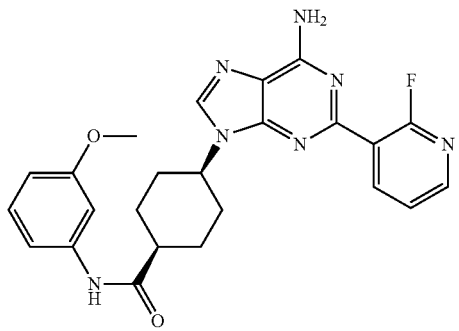 [SMILES: COc1cccc(NC(=O)[C@H]2CC[C@@H](n3cnc4c(N)nc(-c5cccnc5F)nc43)CC2)c1]

$^1$H NMR (499.7 MHz, DMSO-d$_6$) δ ppm 1.74-1.83 (m, 2H), 1.93-2.00 (m, 2H), 2.02-2.12 (m, 2H), 2.36-2.46 (m, 2H), 2.68-2.72 (m, 1H), 3.73 (s, 3H), 4.45-4.54 (m, 1H), 6.59-6.63 (m, 1H), 7.14-7.21 (m, 2H), 7.36 (s, 1H), 7.39 (br. s., 2H), 7.43-7.46 (m, 1H), 8.27 (s, 1H), 8.29 (d, J=4.3 Hz, 1H), 8.43-8.49 (m, 1H), 9.82 (s, 1H).

HRMS (ESI+): calcd. for C$_{24}$H$_{25}$FN$_7$O$_2$ [M+H]$^+$ 462.2049; found 462.2040.

cis-4-[6-amino-2-(3-fluoropyridin-4-yl)-9H-purin-9-yl]-N-(3-methoxyphenyl)cyclohexanecarboxamide (I), cpd 52

[X=N, R1=CONR4R5, R4=Substituted Aryl, R5=H, R3=Substituted Heteroaryl]

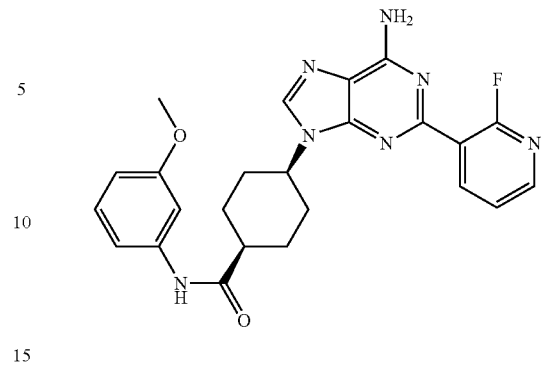

$^1$H NMR (400.5 MHz, DMSO-d$_6$) δ ppm 1.73-1.84 (m, 2H), 1.92-2.01 (m, 2H), 2.04-2.13 (m, 2H), 2.38-2.47 (m, 2H), 2.68-2.73 (m, 1H), 3.73 (s, 3H), 4.46-4.55 (m, 1H), 6.60-6.64 (m, 1H), 7.16-7.21 (m, 2H), 7.35-7.38 (m, 1H), 7.42 (br. s., 2H), 7.95 (dd, J=6.8, 4.9 Hz, 1H), 8.29 (s, 1H), 8.49 (dd, J=4.9, 0.8 Hz, 1H), 8.61 (d, J$_{HF}$=2.8 Hz, 1H), 9.79 (br. s., 1H).

HRMS (ESI+): calcd. for C$_{24}$H$_{25}$FN$_7$O$_2$ [M+H]$^+$ 462.2049; found 462.2047.

cis-4-[6-amino-2-(pyridin-4-yl)-9H-purin-9-yl]-N-(4-methyl-1,3-thiazol-2-yl)cyclohexanecarboxamide (I), cpd 81

[X=N, R1=CONR4R5, R4=Substituted Heteroaryl, R5=H, R3=Heteroaryl]

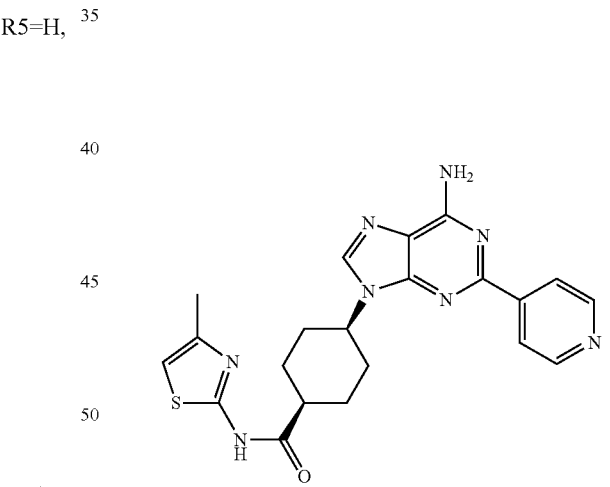

$^1$H NMR (499.7 MHz, DMSO-d$_6$) δ ppm 1.75-1.84 (m, 2H), 1.87-1.93 (m, 2H), 2.18-2.23 (m, 2H), 2.27 (s, 3H), 2.54-2.62 (m, 2H), 2.84-2.89 (m, 1H), 4.46-4.53 (m, 1H), 6.83 (s, 1H), 7.39 (br. s., 1H), 8.22 (s, 1H), 8.25 (d, J=5.8 Hz, 2H), 8.65 (d, J=5.8 Hz, 1H), 12.04 (s, 1H).

HRMS (ESI+): calcd. for C$_{21}$H$_{23}$N$_8$OS [M+H]$^+$ 435.1710; found 435.1709.

9-(cis-4-tert-butylcyclohexyl)-2-(pyridin-4-yl)-9H-purin-6-amine (I), cpd 82

[X=N, R1=(C$_1$-C$_6$)alkyl, R3=Heteroaryl]

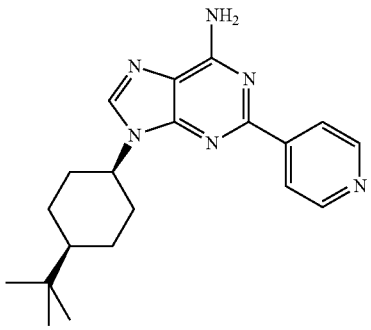 [SMILES: CC(C)(C)[C@H]1CC[C@@H](n2cnc3c(N)nc(-c4ccncc4)nc32)CC1]

$^1$H NMR (499.7 MHz, DMSO-d$_6$) δ ppm 0.84 (s, 9H), 1.15-1.25 (m, 3H), 1.63-1.70 (m, 2H), 1.86-1.96 (m, 2H), 2.62-2.69 (m, 2H), 4.71-4.75 (m, 1H), 7.41 (br. s., 2H), 8.17-8.21 (m, 2H), 8.34 (s, 1H), 8.66-8.70 (m, 2H).

HRMS (ESI+): calcd. for C$_{20}$H$_{27}$N$_6$[M+H]$^+$ 351.2292; found 351.2289.

3-(6-amino-9-{cis-4-[(4-methyl-1,3-thiazol-2-yl)carbamoyl]cyclohexyl}-9H-purin-2-yl)-N-(4-{[4-(dimethylamino)piperidin-1-yl]methyl}phenyl)benzamide bis-trifluoroacetate (I), cpd 85

[X=N, R1=CONR4R5, R4=Substituted Heteroaryl, R5=H, R3=Substituted Aryl]

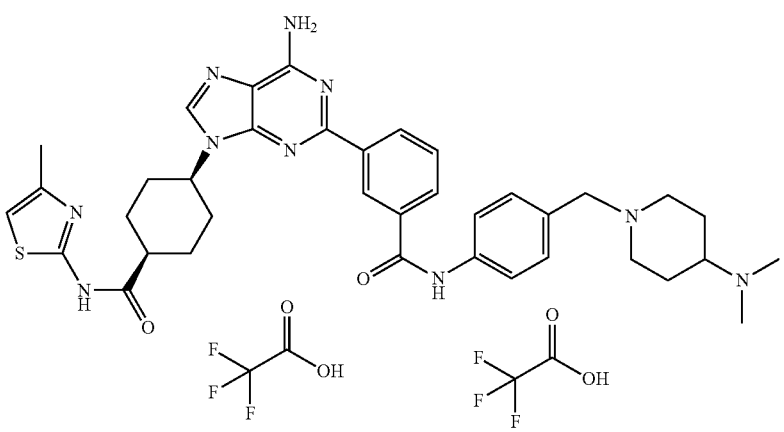

$^1$H NMR (499.7 MHz, DMSO-d$_6$) δ ppm 1.75-1.91 (m, 4H), 1.93-2.00 (m, 2H), 2.12-2.25 (m, 4H), 2.27 (d, J=0.9 Hz, 3H), 2.46-2.55 (m overlapped by water signal, 2H), 2.76 (2×s, 6H), 2.82-2.90 (m, 1H), 2.91-3.01 (m, 2H), 3.38-3.44 (m, 2H), 3.48-3.30 (m, overlapped by water signal, 1H), 4.30 (br. s., 2H), 4.47-4.57 (m, 1H), 6.76-6.79 (m, 1H), 7.37 (br. s., 2H), 7.49 (d, J=8.7 Hz, 2H), 7.60 (t, J=7.8 Hz, 1H), 7.91 (d, J=8.7 Hz, 2H), 7.98 (d, J=7.8 Hz, 1H), 8.24 (s, 1H), 8.62 (d, J=7.8 Hz, 1H), 8.87-8.91 (m, 1H), 9.86 (br. s., 1H), 10.05 (br. s., 1H), 10.60 (m, 1H), 12.04 (br. s., 1H).

HRMS (ESI+): calcd. for C$_{37}$H$_{45}$N$_{10}$O$_2$S [M+H]$^+$ 693.3442; found 693.3465.

cis-4-(6-amino-2-cyclopropyl-9H-purin-9-yl)-N-(3-methoxyphenyl)cyclohexanecarboxamide (I), cpd 87

[X=N, R1=CONR4R5, R4=Substituted Aryl, R5=H, R3=(C$_3$-C$_7$)cycloalkyl]

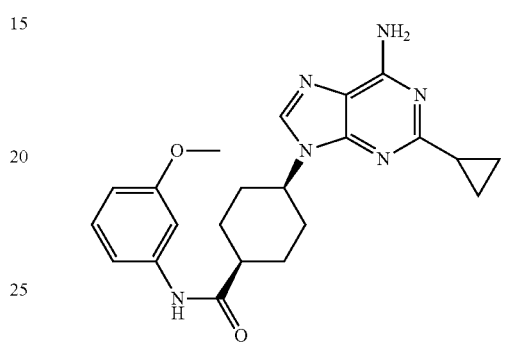

$^1$H NMR (499.7 MHz, DMSO-d$_6$) δ ppm 0.80-0.87 (m, 2H), 0.90-0.96 (m, 2H), 1.72-1.81 (m, 2H), 1.85-1.93 (m, 2H), 1.94-1.98 (m, 1H), 2.01-2.08 (m, 2H), 2.28-2.36 (m, 2H), 2.66-2.71 (m, 1H), 3.72 (s, 3H), 4.35-4.42 (m, 1H), 6.59-6.62 (m, 1H), 6.97 (s, 2H), 7.15-7.21 (m, 2H), 7.35-7.38 (m, 1H), 8.04 (s, 1H), 9.80 (s, 1H).

HRMS (ESI+): calcd. for C$_{22}$H$_{27}$N$_6$O$_2$ [M+H]$^+$ 407.2190; found 407.2190.

3-(6-amino-9-{cis-4-[(4-methyl-1,3-thiazol-2-yl)carbamoyl]cyclohexyl}-9H-purin-2-yl)benzamide (I), cpd 96

[X=N, R1=CONR4R5, R4=Substituted Heteroaryl, R5=H, R3=Substituted Aryl]

111

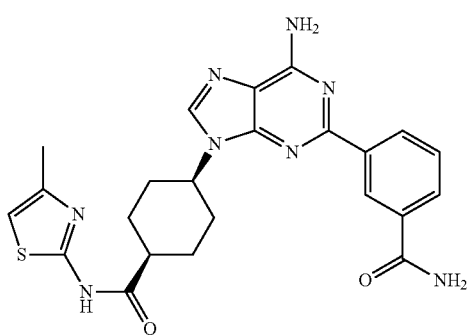 [SMILES: Cc1csc(NC(=O)[C@H]2CC[C@@H](n3cnc4c(N)nc(-c5cccc(C(N)=O)c5)nc43)CC2)n1]

¹H NMR (499.7 MHz, DMSO-d$_6$) δ ppm 1.78-1.87 (m, 2H), 1.92-2.00 (m, 2H), 2.09-2.20 (m, 2H), 2.27 (s, 3H), 2.40-2.47 (m, 2H), 2.82-2.89 (m, 1H), 4.46-4.56 (m, 1H), 6.78 (s, 1H), 7.29 (br. s., 2H), 7.40 (br. s., 1H), 7.45-7.52 (m, 1H), 7.89 (d, J=7.8 Hz, 1H), 8.04 (br. s., 1H), 8.19 (s, 1H), 8.53 (d, J=7.8 Hz, 1H), 8.85 (s, 1H), 12.03 (s, 1H).

HRMS (ESI+): calcd. for C$_{23}$H$_{25}$N$_8$O$_2$S [M+H]⁺ 477.1816; found 477.1817.

3-(6-amino-9-{trans-4-[(4-methyl-1,3-thiazol-2-yl)carbamoyl]cyclohexyl}-9H-purin-2-yl)benzamide (I), cpd 97

[X=N, R1=CONR4R5, R4=Substituted Heteroaryl, R5=H, R3=Substituted Aryl]

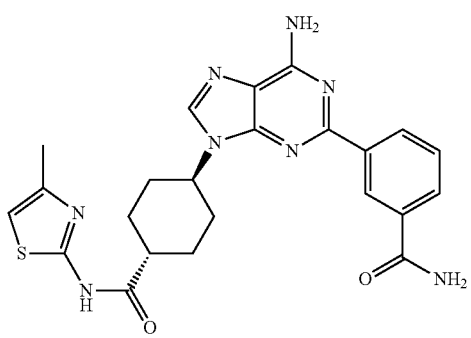 [SMILES: Cc1csc(NC(=O)[C@H]2CC[C@H](n3cnc4c(N)nc(-c5cccc(C(N)=O)c5)nc43)CC2)n1]

¹H NMR (499.7 MHz, DMSO-d$_6$) δ ppm 1.71-1.78 (m, 2H), 2.01-2.20 (m, 6H), 2.27 (s, 3H), 2.62-2.65 (m, 1H), 4.49-4.55 (m, 1H), 6.74-6.76 (m, 1H), 7.31 (br. s., 2H), 7.39-7.33 (m, 2H), 7.91 (d, J=7.8 Hz, 1H), 8.06 (br. s., 1H), 8.30 (s, 1H), 8.51 (d, J=7.8 Hz, 1H), 8.85-8.87 (m, 1H), 12.11 (br. s., 1H).

HRMS (ESI+): calcd. for C$_{23}$H$_{25}$N$_8$O$_2$S [M+H]⁺ 477.1816; found 477.1818.

112

3-[6-amino-9-(cis-4-tert-butylcyclohexyl)-9H-purin-2-yl]-N-(4-methyl-1,3-thiazol-2-yl)benzamide (I), cpd 99

[X=N, R1=(C$_1$-C$_6$)alkyl, R3=Substituted Aryl]

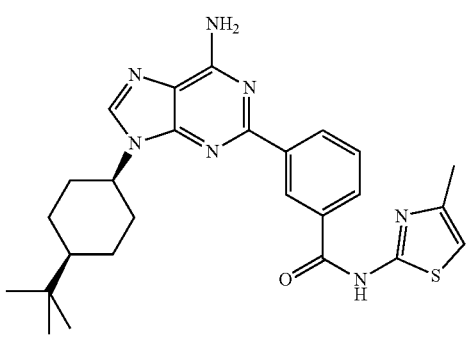 [SMILES: Cc1csc(NC(=O)c2cccc(-c3nc(N)c4ncn([C@H]5CC[C@@H](C(C)(C)C)CC5)c4n3)c2)n1]

¹H NMR (499.7 MHz, DMSO-d$_6$) δ ppm 0.84 (s, 9H), 1.17-1.28 (m, 5H), 1.66-1.73 (m, 2H), 1.88-1.97 (m, 2H), 2.32 (s, 3H), 2.62-2.65 (m, 1H), 4.74-4.78 (m, 1H), 6.84 (br. s., 1H), 7.34 (br. s., 2H), 7.60-7.64 (m, 1H), 8.15 (ddd, J=7.6, 1.7, 1.1 Hz, 1H), 8.29 (s, 1H), 8.56 (d, J=8.1 Hz, 1H), 8.99 (s, 1H), 12.67 (br. s., 1H).

HRMS (ESI+): calcd. for C$_{26}$H$_{32}$N$_7$OS [M+H]⁺ 490.2384; found 490.2379.

cis-4-{6-amino-2-[3-(benzyloxy)phenyl]-9H-purin-9-yl}-N-(4-methyl-1,3-thiazol-2-yl)cyclohexanecarboxamide (I), cpd 100

[X=N, R1=CONR4R5, R4=Substituted Heteroaryl, R5=H, R3=Substituted Aryl]

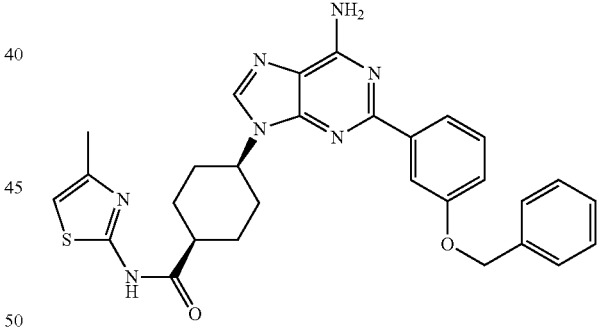

¹H NMR (499.7 MHz, DMSO-d$_6$) δ ppm 1.76-1.88 (m, 2H), 1.90-1.98 (m, 2H), 2.11-2.19 (m, 2H), 2.25 (d, J=0.9 Hz, 3H), 2.39-2.48 (m, 2H), 2.83-2.87 (m, 1H), 4.45-4.53 (m, 1H), 5.18 (s, 2H), 6.73-6.77 (m, 1H), 7.07 (ddd, J=8.2, 2.6, 0.8 Hz, 1H), 7.22 (br. s., 2H), 7.31-7.36 (m, 2H), 7.38-7.43 (m, 2H), 7.47-7.52 (m, 2H), 7.98-8.01 (m, 1H), 8.02 (dd, J=2.5, 1.4 Hz, 1H), 8.17 (s, 1H), 12.02 (s, 1H).

HRMS (ESI+): calcd. for C$_{29}$H$_{30}$N$_7$O$_2$S [M+H]⁺ 540.2176; found 540.2180.

trans-4-{6-amino-2-[3-(benzyloxy)phenyl]-9H-purin-9-yl}-N-(4-methyl-1,3-thiazol-2-yl)cyclohexanecarboxamide (I), cpd 101

[X=N, R1=CONR4R5, R4=Substituted Heteroaryl, R5=H, R3=Substituted Aryl]

113

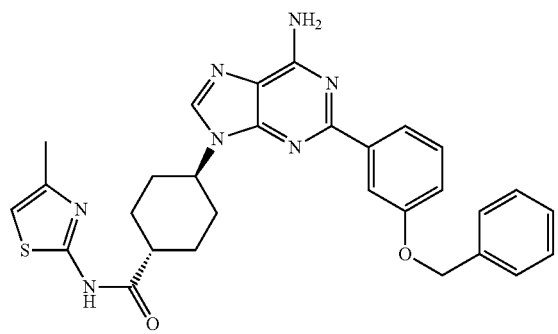 [SMILES: Cc1csc(NC(=O)[C@H]2CC[C@H](n3cnc4c(N)nc(-c5cccc(OCc6ccccc6)c5)nc43)CC2)n1]

¹H NMR (499.7 MHz, DMSO-d₆) δ ppm 1.70-1.80 (m, 2H), 1.92-2.17 (m, 6H), 2.26 (d, J=0.9 Hz, 3H), 2.61-2.69 (m, 1H), 4.44-2.52 (m, 1H), 5.20 (s, 2H), 6.75 (s, 1H), 7.09 (dd, J=7.8, 2.2 Hz, 1H), 7.23 (br. s., 2H), 7.31-7.35 (m, 1H), 7.36-7.39 (m, 1H), 7.39-7.44 (m, 2H), 7.49-7.52 (m, 2H), 7.99 (d, J=7.8 Hz, 1H), 8.01 (dd, J=2.6, 1.4 Hz, 1H), 8.26 (s, 1H), 12.11 (s, 1H).

HRMS (ESI+): calcd. for $C_{29}H_{30}N_7O_2S$ [M+H]⁺ 540.2176; found 540.2174.

cis-4-[6-amino-2-(1H-pyrazol-3-yl)-9H-purin-9-yl]-N-(3-methoxyphenyl)cyclohexanecarboxamide (I), cpd 107

[X=N, R1=CONR4R5, R4=Substituted Aryl, R5=H, R3=Heteroaryl]

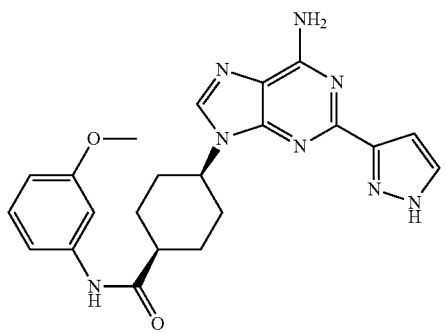 [SMILES: COc1cccc(NC(=O)[C@H]2CC[C@@H](n3cnc4c(N)nc(-c5cc[nH]n5)nc43)CC2)c1]

¹H NMR (499.7 MHz, DMSO-d₆) δ ppm 1.74-1.85 (m, 2H), 1.91-2.00 (m, 2H), 2.08-2.16 (m, 2H), 2.37-2.45 (m, 2H), 2.71-2.76 (m, 1H), 3.73 (s, 3H), 4.49-4.57 (m, 1H), 6.59-6.65 (m, 1H), 6.77 (br. s., 1H), 7.09-7.26 (m, 4H), 7.36-7.39 (m, 1H), 7.52 (br. s., 1H), 8.19 (br. s., 1H), 9.85 (br. s., 1H).

HRMS (ESI+): calcd. for $C_{22}H_{25}N_8O_2$ [M+H]⁺ 433.2095; found 433.2094.

cis-4-[6-amino-2-(1H-pyrazol-3-yl)-9H-purin-9-yl]-N-(4-methyl-1,3-thiazol-2-yl)cyclohexanecarboxamide (I), cpd 112

[X=N, R1=CONR4R5, R4=Substituted Heteroaryl, R5=H, R3=Heteroaryl]

114

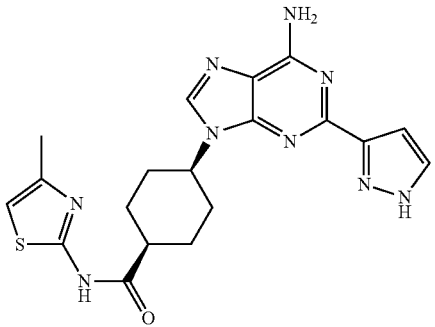 [SMILES: Cc1csc(NC(=O)[C@H]2CC[C@@H](n3cnc4c(N)nc(-c5cc[nH]n5)nc43)CC2)n1]

¹H NMR (499.7 MHz, DMSO-d₆) δ ppm 1.76-1.85 (m, 2H), 1.93-2.01 (m, 2H), 2.10-2.18 (m, 2H), 2.26 (d, J=0.9 Hz, 3H), 2.29-2.38 (m, 2H), 2.852-2.89 (m, 1H), 4.45-4.53 (m, 1H), 6.76 (q, J=0.9 Hz, 1H), 6.78 (br. s., 1H), 7.21 (br. s., 2H), 8.18 (br. s., 1H), 12.02 (br. s., 1H), 13.20 (br. s., 1H).

HRMS (ESI+): calcd. for $C_{19}H_{22}N_9OS$ [M+H]⁺ 424.1663; found 424.1667.

trans-4-[6-amino-2-(1H-pyrazol-3-yl)-9H-purin-9-yl]-N-(4-methyl-1,3-thiazol-2-yl)cyclohexanecarboxamide (I), cpd 113

[X=N, R1=CONR4R5, R4=Substituted Heteroaryl, R5=H, R3=Heteroaryl]

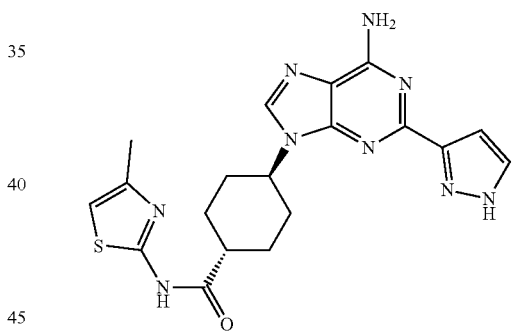

¹H NMR (499.7 MHz, DMSO-d₆) δ ppm 1.65-1.77 (m, 2H), 1.95-2.14 (m, 6H), 2.26 (s, 3H), 2.63-2.73 (m, 1H), 4.42-4.53 (m, 1H), 6.74 (br. s., 1H), 6.77 (br. s., 1H), -7.21 (br. s., 2H), 7.54 (br. s., 1H), 8.27 (s, 1H).

HRMS (ESI+): calcd. for $C_{19}H_{22}N_9OS$ [M+H]⁺ 424.1663; found 424.1656.

Example 5

Conv. 1 cis-4-[6-amino-2-(3-hydroxy-3-methylbut-1-yn-1-yl)-9H-purin-9-yl]-N-(3-methoxyphenyl)cyclohexanecarboxamide (I), cpd 54

[X=N, R1=CONR4R5, R4=Substituted Aryl, R5=H, R3=Substituted (C₂-C₆)alkynyl]

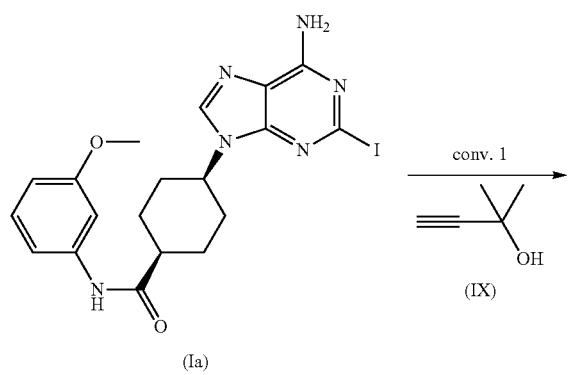

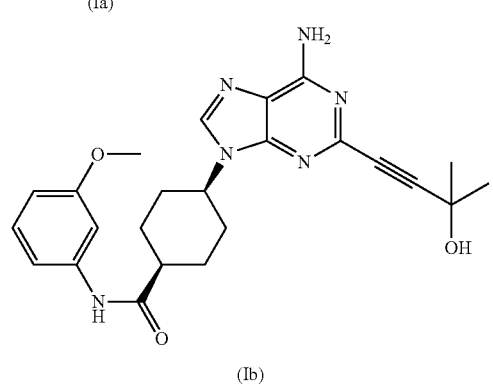

cis-4-(6-amino-2-iodo-9H-purin-9-yl)-N-(3-methoxyphenyl)cyclohexanecarboxamide (Ia) (20 mg, 0.041 mmol), CuI (0.4 mg, 0.002 mmol) and PdCl$_2$dppf (1.6 mg, 0.002 mmol) were charged in a Schlenk tube under argon, then a degassed solution of 2-methylbut-3-yn-2-ol (IX) (0.005 mL, 0.053 mmol) and TEA (0.011 mL, 0.081 mmol) in dry ACN (0.2 mL) was added and the mixture was heated at 80° C. for 2 h. The mixture was diluted with EtOAc (10 mL) and washed with aqueous ammonia, water and brine. The organic layer was dried over Na$_2$SO$_4$, filtered and the solvent removed under reduced pressure. The title compound was purified by column chromatography (eluant DCM: 7N NH$_3$ in MeOH=95:5, 90:10) and isolated as brownish solid (8.7 mg, 48%).

$^1$H NMR (400.5 MHz, DMSO-d$_6$) δ ppm 1.46 (s, 6H), 1.74-1.86 (m, 2H), 1.88-1.98 (m, 2H), 2.02-2.12 (m, 2H), 2.19-2.30 (m, 2H), 2.67-2.72 (m, 1H), 3.73 (s, 3H), 4.39-4.48 (m, 1H), 5.54 (s, 1H), 6.59-6.63 (m, 1H), 7.14-7.21 (m, 2H), 7.32 (br. s., 2H), 7.35 (m, 1H), 8.23 (s, 1H), 9.80 (s, 1H).

HRMS (ESI+): calcd. for C$_{24}$H$_{29}$N$_6$O$_3$ [M+H]$^+$ 449.2296; found 449.2287.

Operating in an analogous way, but employing suitably substituted starting materials (Ia) and (IX), the following compounds were obtained:

cis-4-{6-amino-2-[3-(1,1-dioxidothiomorpholin-4-yl)prop-1-yn-1-yl]-9H-purin-9-yl}-N-(3-methoxyphenyl)cyclohexanecarboxamide (I), cpd 55

[X=N, R1=CONR4R5, R4=Substituted Aryl, R5=H, R3=Substituted (C$_2$-C$_6$)alkynyl]

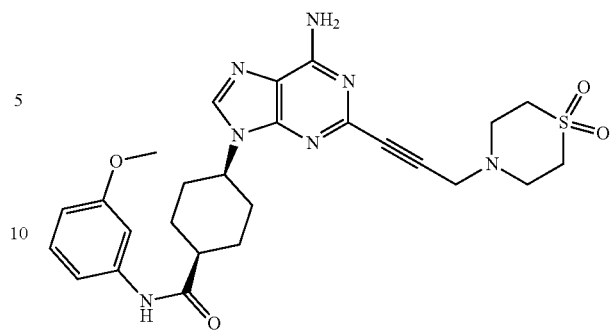

$^1$H NMR (400.5 MHz, DMSO-d$_6$) δ ppm 1.74-1.86 (m, 1H), 1.88-1.98 (m, 2H), 2.01-2.12 (m, 2H), 2.19-2.30 (m, 2H), 2.68-2.73 (m, 1H), 2.99-3.04 (m, 4H), 3.14-3.19 (m, 4H), 3.71 (s, 2H), 3.73 (s, 3H), 4.40-4.49 (m, 1H), 6.58-6.63 (m, 1H), 7.14-7.22 (m, 2H), 7.33-7.35 (m, 1H), 7.36 (br. s., 2H), 8.25 (s, 1H), 9.79 (br. s., 1H).

HRMS (ESI+): calcd. for C$_{26}$H$_{32}$N$_7$O$_4$S [M+H]$^+$ 538.2231; found 538.2240.

cis-4-[6-amino-2-(cyclohexylethynyl)-9H-purin-9-yl]-N-(3-methoxyphenyl)cyclohexanecarboxamide (I), cpd 56

[X=N, R1=CONR4R5, R4=Substituted Aryl, R5=H, R3=Substituted (C$_2$-C$_6$)alkynyl]

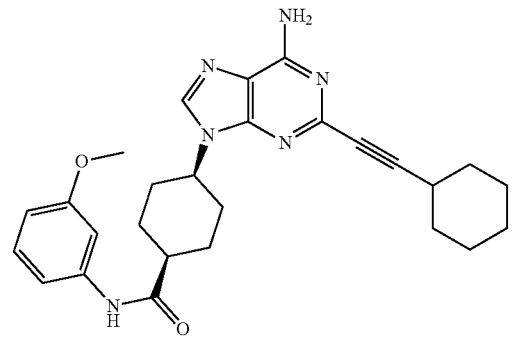 [SMILES: COc1cccc(NC(=O)[C@H]2CC[C@@H](n3cnc4c(N)nc(C#CC5CCCCC5)nc43)CC2)c1]

$^1$H NMR (400.5 MHz, DMSO-d$_6$) δ ppm 1.27-1.85 (m, 10H), 1.78-1.88 (m, 2H), 1.88-1.97 (m, 2H), 2.02-2.12 (m, 2H), 2.16-2.31 (m, 2H), 2.57-2.65 (m, 1H), 2.68-2.73 (m, 1H), 3.73 (s, 3H), 4.40-4.48 (m, 1H), 6.59-6.63 (m, 1H), 7.16-7.22 (m, 2H), 7.28 (s, 2H), 7.34-7.36 (m, 1H), 8.21 (s, 1H), 9.79 (br. s., 1H).

HRMS (ESI+): calcd. for C$_{27}$H$_{33}$N$_6$O$_2$ [M+H]$^+$ 473.2660; found 473.2647.

cis-4-[6-amino-2-(3,3-dimethylbut-1-yn-1-yl)-9H-purin-9-yl]-N-(3-methoxyphenyl)cyclohexanecarboxamide (I), cpd 57

[X=N, R1=CONR4R5, R4=Substituted Aryl, R5=H, R3=Substituted (C$_2$-C$_6$)alkynyl]

117

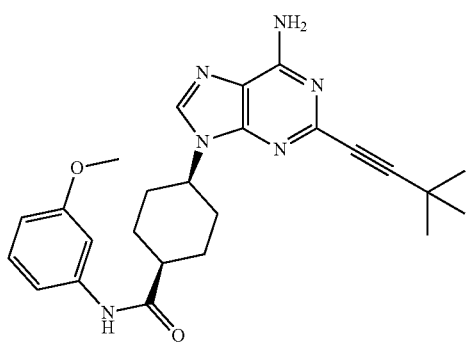 [SMILES: COc1cccc(NC(=O)[C@H]2CC[C@@H](n3cnc4c(N)nc(C#CC(C)(C)C)nc43)CC2)c1]

¹H NMR (400.5 MHz, DMSO-d$_6$) δ ppm 1.29 (s, 9H), 1.75-1.86 (m, 2H), 1.87-1.96 (m, 2H), 2.03-2.11 (m, 2H), 2.18-2.29 (m, 2H), 2.68-2.73 (m, 1H), 3.73 (s, 3H), 4.40-4.50 (m, 1H), 6.59-6.64 (m, 1H), 7.15-7.22 (m, 2H), 7.29 (br. s., 2H), 7.35 (dd, J=2.9, 1.8 Hz, 1H), 8.21 (s, 1H), 9.79 (s, 1H).

HRMS (ESI+): calcd. for C$_{25}$H$_{31}$N$_6$O$_2$ [M+H]$^+$ 447.2503; found 447.2494.

cis-4-[6-amino-2-(cyclopropylethynyl)-9H-purin-9-yl]-N-(3-methoxyphenyl)cyclohexanecarboxamide (I), cpd 58

[X=N, R1=CONR4R5, R4=Substituted Aryl, R5=H, R3=Substituted (C$_2$-C$_6$)alkynyl]

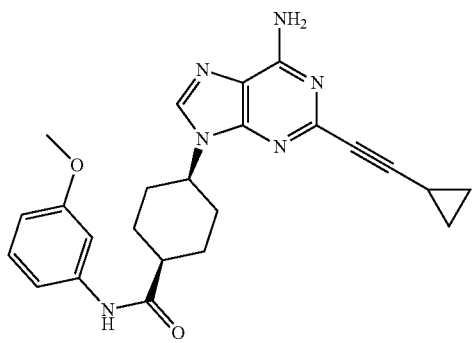 [SMILES: COc1cccc(NC(=O)[C@H]2CC[C@@H](n3cnc4c(N)nc(C#CC5CC5)nc43)CC2)c1]

¹H NMR (400.5 MHz, DMSO-d$_6$) δ ppm 0.71-0.78 (m, 2H), 0.88-0.93 (m, 2H), 1.50-1.57 (m, 1H), 1.73-1.84 (m, 2H), 1.86-1.98 (m, 2H), 2.02-2.11 (m, 2H), 2.18-2.29 (m, 2H), 2.68-2.72 (m, 1H), 3.73 (s, 3H), 4.37-4.45 (m, 1H), 6.59-6.62 (m, 1H), 7.15-7.21 (m, 2H), 7.25 (br. s., 2H), 7.34-7.36 (m, 1H), 8.21 (br. s., 1H), 9.79 (s, 1H).

HRMS (ESI+): calcd. for C$_{24}$H$_{27}$N$_6$O$_2$ [M+H]$^+$ 431.2190; found 431.2193.

cis-4-{6-amino-2-[3-(dimethylamino)prop-1-yn-1-yl]-9H-purin-9-yl}-N-(3-methoxyphenyl)cyclohexanecarboxamide (I), cpd 59

[X=N, R1=CONR4R5, R4=Substituted Aryl, R5=H, R3=Substituted (C$_2$-C$_6$)alkynyl]

118

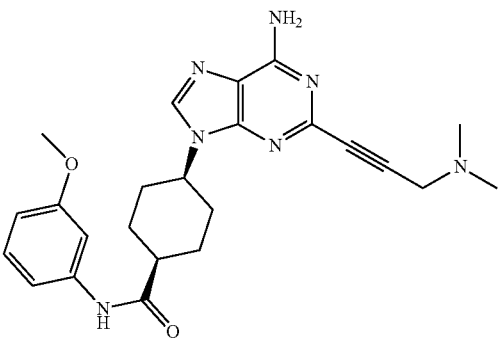 [SMILES: COc1cccc(NC(=O)[C@H]2CC[C@@H](n3cnc4c(N)nc(C#CCN(C)C)nc43)CC2)c1]

¹H NMR (400.5 MHz, DMSO-d$_6$) δ ppm 1.75-1.85 (m, 2H), 1.89-1.98 (m, 2H), 2.01-2.11 (m, 2H), 2.20-2.30 (m, 2H), 2.25 (s, 6H), 2.68-2.73 (m, 1H), 3.45 (s, 2H), 3.73 (s, 3H), 4.40-4.48 (m, 1H), 6.59-6.62 (m, 1H), 7.15-7.21 (m, 2H), 7.32 (br. s., 2H), 7.35 (dd, J=2.9, 1.6 Hz, 1H), 8.24 (s, 1H), 9.79 (s, 1H).

HRMS (ESI+): calcd. for C$_{24}$H$_{30}$N$_7$O$_2$ [M+H]$^+$ 448.2456; found 448.2439.

cis-4-[6-amino-2-(3-hydroxyprop-1-yn-1-yl)-9H-purin-9-yl]-N-(3-methoxyphenyl)cyclohexanecarboxamide (I), cpd 60 [X=N, R1=CONR4R5, R4=Substituted Aryl, R5=H, R3=Substituted (C$_2$-C$_6$)alkynyl]

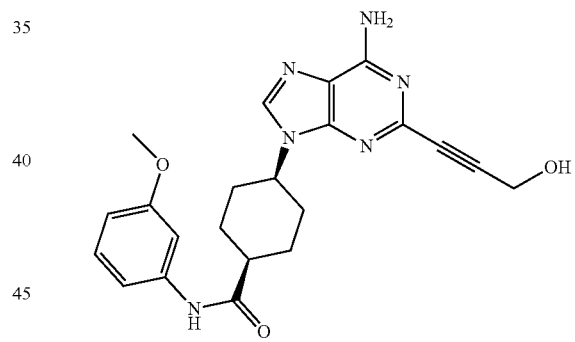

¹H NMR (400.5 MHz, DMSO-d$_6$) δ ppm 1.74-1.85 (m, 2H), 1.90-1.99 (m, 2H), 2.02-2.10 (m, 2H), 2.18-2.31 (m, 2H), 2.38-2.73 (m, 1H), 3.73 (s, 3H), 4.28 (d, J=6.1 Hz, 2H), 4.39-4.47 (m, 1H), 5.37 (d, J=6.1 Hz, 1H), 6.59-6.62 (m, 1H), 7.15-7.22 (m, 2H), 7.31 (br. s., 2H), 7.34-7.36 (m, 1H), 8.24 (s, 1H), 9.80 (s, 1H).

HRMS (ESI+): calcd. for C$_{22}$H$_{25}$N$_6$O$_3$ [M+H]$^+$ 421.1983; found 421.1970.

cis-4-[6-amino-2-(pyridin-4-ylethynyl)-9H-purin-9-yl]-N-(3-methoxyphenyl)cyclohexanecarboxamide (I), cpd 61

[X=N, R1=CONR4R5, R4=Substituted Aryl, R5=H, R3=Substituted (C$_2$-C$_6$)alkynyl]

119

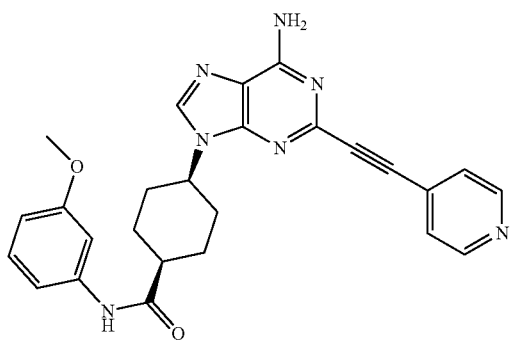 [SMILES: COc1cccc(NC(=O)[C@H]2CC[C@@H](n3cnc4c(N)nc(C#Cc5ccncc5)nc43)CC2)c1]

¹H NMR (400.5 MHz, DMSO-$d_6$) δ ppm 1.77-1.87 (m, 2H), 1.92-2.00 (m, 2H), 2.04-2.13 (m, 2H), 2.23-2.33 (m, 2H), 2.69-2.75 (m, 1H), 3.72 (s, 3H), 4.45-4.53 (m, 1H), 6.57-6.65 (m, 1H), 7.14-7.21 (m, 2H), 7.34-7.37 (m, 1H), 7.49 (br. s., 2H), 7.55-7.59 (m, 2H), 8.32 (s, 1H), 8.62-8.69 (m, 2H), 9.90 (s, 1H).

HRMS (ESI+): calcd. for $C_{26}H_{26}N_7O_2$ [M+H]⁺ 468.2143; found 468.2134.

cis-4-{6-amino-2-[(trimethylsilyl)ethynyl]-9H-purin-9-yl}-N-(4-methyl-1,3-thiazol-2-yl)cyclohexanecarboxamide (I), cpd 98

[X=N, R1=CONR4R5, R4=Substituted Heteroaryl, R5=H, R3=Substituted ($C_2$-$C_6$)alkynyl]

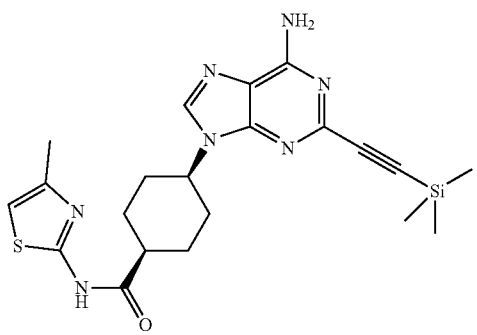 [SMILES: Cc1csc(NC(=O)[C@H]2CC[C@@H](n3cnc4c(N)nc(C#C[Si](C)(C)C)nc43)CC2)n1]

¹H NMR (499.7 MHz, DMSO-$d_6$) δ ppm 0.24 (s, 9H), 1.77-1.86 (m, 2H), 1.90-1.96 (m, 2H), 2.06-2.13 (m, 2H), 2.13-2.22 (m, 2H), 2.26 (d, J=0.9 Hz, 3H), 2.80-2.84 (m, 1H), 4.40-4.46 (m, 1H), 6.74 (s, 1H), 7.41 (s, 2H), 8.27 (s, 1H), 12.01 (br. s., 1H).

HRMS (ESI+): calcd. for $C_{21}H_{28}N_7OSSi$ [M+H]⁺ 454.1840; found 454.1844.

cis-4-[6-amino-2-(3-hydroxy-3-methylbut-1-yn-1-yl)-9H-purin-9-yl]-N-(4-methyl-1,3-thiazol-2-yl)cyclohexanecarboxamide (I), cpd 121

[X=N, R1=CONR4R5, R4=Substituted Heteroaryl, R5=H, R3=Substituted ($C_2$-$C_6$)alkynyl]

120

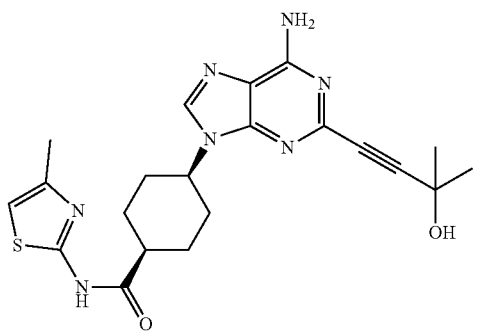 [SMILES: Cc1csc(NC(=O)[C@H]2CC[C@@H](n3cnc4c(N)nc(C#CC(C)(C)O)nc43)CC2)n1]

HRMS (ESI+): calcd. for $C_{21}H_{26}N_7O_2S$ [M+H]⁺ 440.1863; found 440.1860.

cis-4-{6-amino-2-[(trimethylsilyl)ethynyl]-9H-purin-9-yl}-N-(4-methoxy-1,3-benzothiazo-2-yl)cyclohexanecarboxamide (I), cpd 118

[X=N, R1=CONR4R5, R4=Substituted Heteroaryl, R5=H, R3=Substituted ($C_2$-$C_6$)alkynyl]

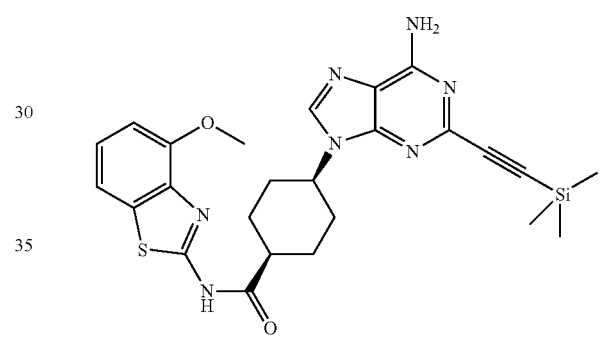

HRMS (ESI+): calcd. for $C_{25}H_{30}N_7O_2SSi$ [M+H]⁺ 520.1946; found 520.1938.

cis-4-{6-amino-2-[(trimethylsilyl)ethynyl]-9H-purin-9-yl}-N-(5-methyl-4,5,6,7-tetrahydro[1,3]thiazolo[5,4-c]pyridin-2-yl)cyclohexanecarboxamide (I), cpd 199

[X=N, R1=CONR4R5, R4=Substituted Heteroaryl, R5=H, R3=Substituted ($C_2$-$C_6$)alkynyl]

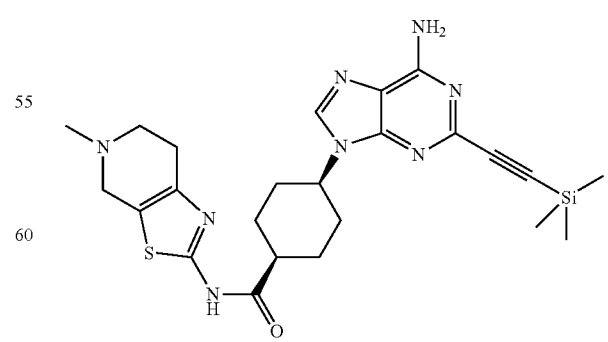

¹H NMR (500 MHz, DMSO-$d_6$) δ ppm 0.24 (s, 9H) 1.75-1.87 (m, 2H) 1.86-1.97 (m, 2H) 2.05-2.12 (m, 2H)

2.13-2.21 (m, 2H) 2.40 (br. s., 3H) 2.61-2.69 (m, 2H) 2.69-2.79 (m, 2H) 2.79-2.86 (m, 1H) 3.38-3.61 (m, 2H) 4.39-4.51 (m, 1H) 7.41 (br. s., 2H) 8.25 (s, 1H) 11.96 (br. s., 1H).

HRMS (ESI+): calcd. for $C_{24}H_{33}N_8OSSi$ $[M+H]^+$ 509.2262; found 509.2231.

Example 6

Deprotection cis-4-(6-amino-2-ethynyl-9H-purin-9-yl)-N-(4-methyl-1,3-thiazol-2-yl)cyclohexanecarboxamide (I), cpd 77

[X=N, R1=CONR4R5, R4=Substituted Heteroaryl, R5=H, R3=$(C_2-C_6)$alkynyl]

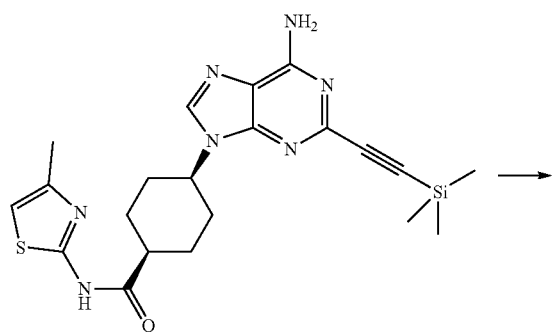

A solution of cis-4-{6-amino-2-[(trimethylsilyl)ethynyl]-9H-purin-9-yl}-N-(4-methyl-1,3-thiazol-2-yl)cyclohexane carboxamide (35 mg, 0.077 mmol) in MeOH (10 mL) was treated with TEA (2 mL) for 2 h at rt. After removal of the solvent under vacuo, the title compound was purified by column chromatography (eluant DCM:MeOH=95:5) and isolated as white solid (25 mg, 85%).

$^1$H NMR (499.7 MHz, DMSO-$d_6$) δ ppm 1.76-1.86 (m, 2H), 1.90-1.97 (m, 2H), 2.05-2.12 (m, 2H), 2.12-2.22 (m, 2H), 2.26 (d, J=0.9 Hz, 3H), 2.80-2.85 (m, 1H), 3.97 (s, 1H), 4.39-4.46 (m, 1H), 6.74 (s, 1H), 7.41 (br. s., 2H), 8.27 (s, 1H), 12.01 (br. s., 1H).

HRMS (ESI+): calcd. for $C_{18}H_{20}N_7OS$ $[M+H]^+$ 382.1445; found 382.1448.

Operating in an analogous way, but employing suitably substituted starting material, the following compound was obtained:

cis-4-(6-amino-2-ethynyl-9H-purin-9-yl)-N-(4-methoxy-1,3-benzothiazol-2-yl)cyclohexanecarboxamide (I), cpd 119

[X=N, R1=CONR4R5, R4=Substituted Heteroaryl, R5=H, R3=$(C_2-C_6)$alkynyl]

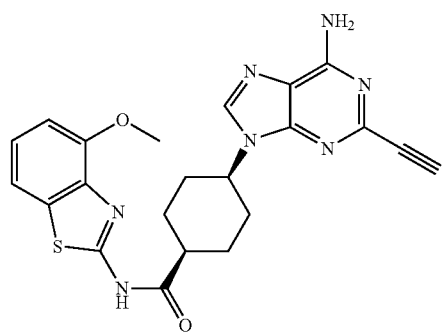 [SMILES: C#Cc1nc(N)c2ncn([C@H]3CC[C@@H](C(=O)Nc4nc5c(OC)cccc5s4)CC3)c2n1]

$^1$H NMR (499.7 MHz, DMSO-$d_6$) δ ppm 1.81-1.90 (m, 2H), 1.93-2.01 (m, 2H), 2.10-2.22 (m, 4H), 2.85-2.90 (m, 1H), 3.91 (s, 3H), 3.96 (s, 1H), 4.41-4.47 (m, 1H), 6.99 (d, J=8.1 Hz, 1H), 7.24 (t, J=7.9 Hz, 1H), 7.40 (s, 2H) 7.51 (d, J=7.8 Hz, 1H), 8.28 (s, 1H), 12.45 (br. s., 1H).

HRMS (ESI+): calcd. for $C_{22}H_{22}N_7O_2S$ $[M+H]^+$ 448.1550; found 448.1546.

cis-4-(6-amino-2-ethynyl-9H-purin-9-yl)-N-(5-methyl-4,5,6,7-tetrahydro[1,3]thiazolo[5,4-c]pyridin-2-yl)cyclohexanecarboxamide (I), cpd 201

[X=N, R1=CONR4R5, R4=Substituted Heteroaryl, R5=H, R3=$(C_2-C_6)$alkynyl]

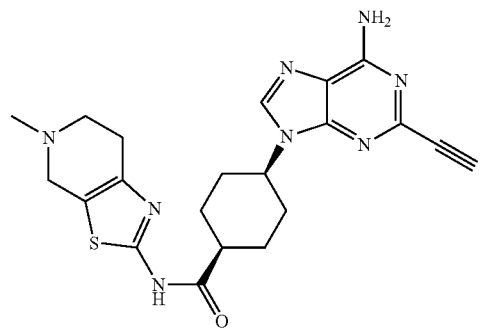 [SMILES: C#Cc1nc(N)c2ncn([C@H]3CC[C@@H](C(=O)Nc4nc5c(s4)CN(C)CC5)CC3)c2n1]

$^1$H NMR (500 MHz, DMSO-$d_6$) δ ppm 1.76-1.85 (m, 2H) 1.91-1.99 (m, 2H) 2.05-2.11 (m, 2H) 2.14-2.23 (m, 2H) 2.36 (s, 3H) 2.60-2.64 (m, 2H) 2.66-2.70 (m, 2H) 2.77-2.83 (m, 1H) 3.47 (br. s., 2H) 3.97 (s, 1H) 4.38-4.46 (m, 1H) 7.41 (br. s., 2H) 8.25 (s, 1H) 11.93 (br. s., 1H).

HRMS (ESI+): calcd. for $C_{21}H_{25}N_8OS$ $[M+H]^+$ 437.1867; found 437.1860.

Example 7 cis-4-{6-amino-2-[(Z)-2-(propan-2-yloxy)ethenyl]-9H-purin-9-yl}-N-(4-methyl-1,3-thiazol-2-yl)cyclohexanecarboxamide (I), cpd 78

[X=N, R1=CONR4R5, R4=Substituted Heteroaryl, R5=H, R3=Substituted $(C_2-C_6)$alkenyl]

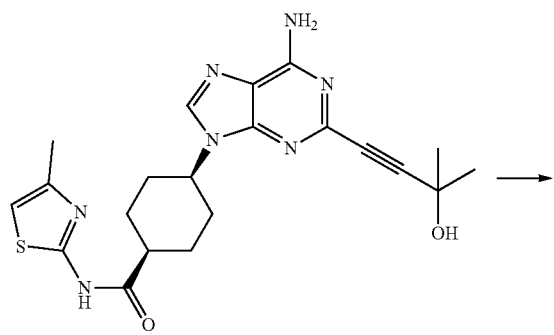

cpd 77

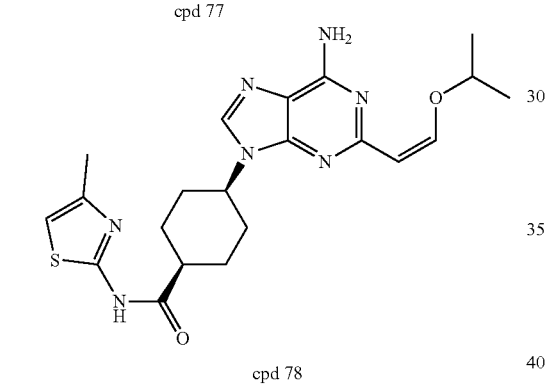

cpd 78

Cis-4-[6-amino-2-(3-hydroxy-3-methylbut-1-yn-1-yl)-9H-purin-9-yl]-N-(4-methyl-1,3-thiazol-2-yl)cyclohexanecarboxamide (8 mg, 0.018 mmol) was treated with a 0.03 M solution of KOH in i-propanol and heated at 80° C. for 2 h. The mixture was then neutralized with AcOH and diluted with DCM. The organic phase was washed with water, dried over $Na_2SO_4$ and filtered. Purification by column chromatography afforded the title compound as brownish solid (2 mg, 25%) and cpd 77 (3 mg, 44%).

$^1$H NMR (499.7 MHz, DMSO-$d_6$) δ ppm 1.25 (d, J=6.1 Hz, 6H), 1.72-1.81 (m, 2H), 2.00-2.09 (m, 4H), 2.25 (s, 3H), 2.24-2.34 (m, 2H), 2.78-2.83 (m, 1H), 4.11 (quin, J=6.1 Hz, 1H), 4.33-4.38 (m, 1H), 5.16 (d, J=7.3 Hz, 1H), 6.51 (d, J=7.3 Hz, 1H), 6.73 (s, 1H), 6.83 (br. s., 2H), 8.08 (s, 1H), 12.00 (br. s., 1H).

HRMS (ESI+): calcd. for $C_{21}H_{28}N_7O_2S$ [M+H]$^+$ 442.2020; found 442.2026.

Example 8 cis-4-[6-amino-2-(3-hydroxyphenyl)-9H-purin-9-yl]-N-(3-methoxyphenyl)cyclohexanecarboxamide (I), cpd 18

[X=N, R1=CONR4R5, R4=Substituted Aryl, R5=H, R3=Substituted Aryl]

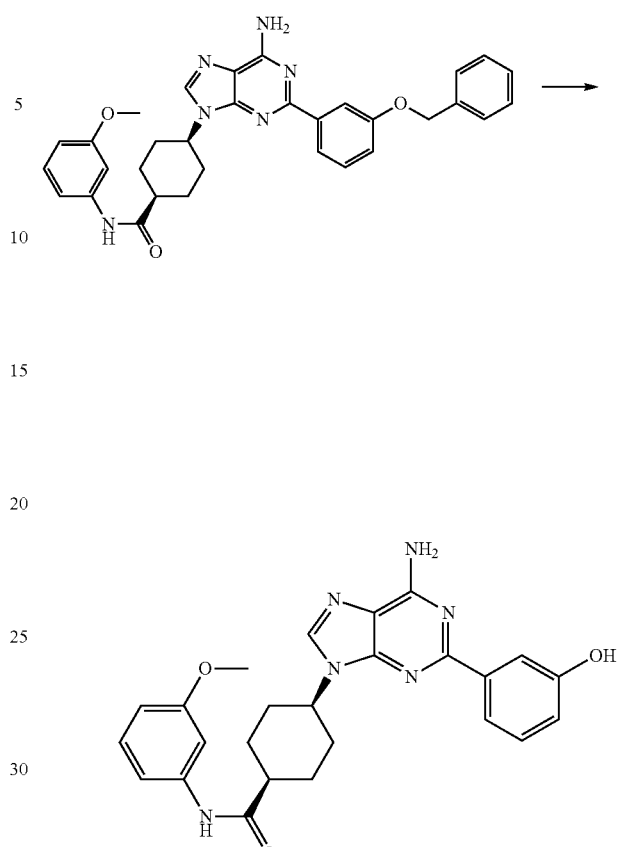

cis-4-{6-Amino-2-[3-(benzyloxy)phenyl]-9H-purin-9-yl}-N-(3-methoxyphenyl)cyclohexanecarboxamide (32 mg, 0.058 mmol), 1,4-cyclohexadiene (0.054 mL, 0.58 mmol) and 10% Pd/C (3 mg) were suspended in MeOH (1 mL) in a microwave tube and heated under microwave irradiation at 100° C. for 5 min. The mixture was then filtered over a pad of celite and taken to dryness under reduced pressure. The product was purified by column chromatography (eluant DCM:MeOH=95:5) and isolated as white solid (12 mg, 45%).

$^1$H NMR (400.5 MHz, DMSO-$d_6$) δ ppm 1.75-1.86 (m, 2H), 1.91-2.00 (m, 2H), 2.06-2.16 (m, 2H), 2.43-2.50 (m, 2H), 2.70-2.75 (m, 1H), 3.73 (s, 3H), 4.48-4.56 (m, 1H), 6.62 (dt, J=7.6, 2.1 Hz, 1H), 6.81 (ddd, J=8.0, 2.5, 1.0 Hz, 1H), 7.14 (br. s., 1H), 7.17-7.27 (m, 3H), 7.37 (t, J=2.0 Hz, 1H), 7.80 (t, J=1.5 Hz, 1H), 7.84 (dt, J=7.9, 1.1 Hz, 1H), 8.18 (s, 1H), 9.39 (s, 1H), 9.80 (s, 1H).

HRMS (ESI+): calcd. for $C_{25}H_{27}N_6O_3$ [M+H]$^+$ 459.2139; found 459.2141.

Operating in an analogous way, but employing suitably substituted starting material, the following compound was obtained:

cis-4-[6-amino-2-(4-hydroxyphenyl)-9H-purin-9-yl]-N-(3-methoxyphenyl)cyclohexanecarboxamide (I), cpd 17

[X=N, R1=CONR4R5, R4=Substituted Aryl, R5=H, R3=Substituted Aryl]

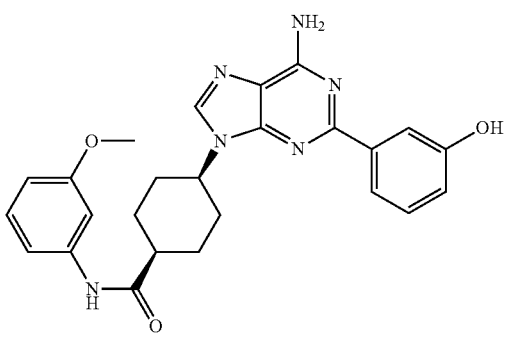 [SMILES: COc1cccc(NC(=O)[C@H]2CC[C@@H](n3cnc4c(N)nc(-c5cccc(O)c5)nc43)CC2)c1]

¹H NMR (400.5 MHz, DMSO-d₆) δ ppm 1.73-1.85 (m, 2H), 1.87-1.98 (m, 2H), 2.00-2.18 (m, 2H), 2.51-2.60 (m, 2H), 2.70-2.77 (m, 1H), 3.74 (s, 3H), 4.44-4.53 (m, 1H), 6.63 (ddd, J=8.1, 2.4, 1.0 Hz, 1H), 6.78-6.81 (m, 2H), 7.05 (br. s., 2H), 7.22 (dd, J=8.4, 8.1 Hz, 1H), 7.27 (dt, J=8.40, 1.6 Hz, 1H) 7.35 (t, J=2.1 Hz, 1H), 8.10 (s, 1H), 8.21-8.25 (m, 2H), 9.64 (s, 1H), 9.79 (br. s., 1H).

HRMS (ESI+): calcd. for $C_{25}H_{27}N_6O_3$ [M+H]⁺ 459.2139; found 459.2132.

Example 9 cis-4-[6-amino-2-(3-hydroxyphenyl)-9H-purin-9-yl]-N-(4-methyl-1,3-thiazol-2-yl)cyclohexanecarboxamide (I), cpd 103

[X=N, R1=CONR4R5, R4=Substituted Heteroaryl, R5=H, R3=Substituted Aryl]

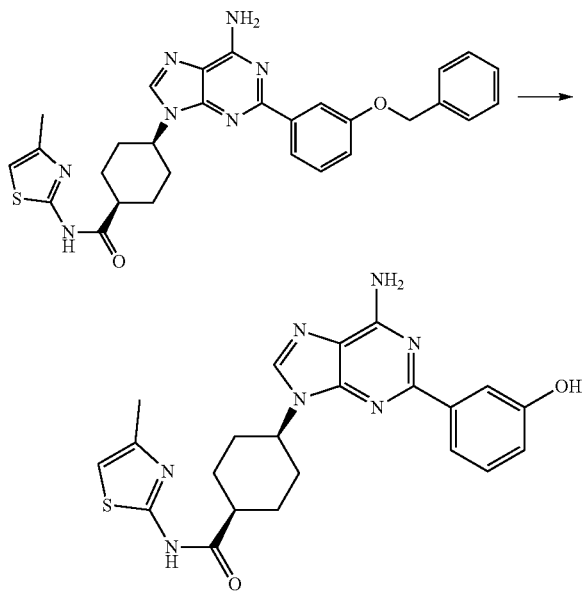

A solution of cis-4-{6-amino-2-[3-(benzyloxy)phenyl]-9H-purin-9-yl}-N-(4-methyl-1,3-thiazol-2-yl)cyclohexanecarboxamide (20 mg, 0.037 mmol) in dry DCM (5 mL) was treated with 1M BBr₃ in DCM (0.112 mL) at rt for 3 h. The reaction was quenched with methanol (5 mL) and let under stirring for 1 h. After addition of 33% aqueous ammonia (2 mL), the mixture was diluted with DCM. The organic phase was washed with water, dried over Na₂SO₄ and filtered. The product was purified by column chromatography (eluant DCM:MeOH=95:5, 90:10) and isolated as white solid (7 mg, 42%).

¹H NMR (499.7 MHz, DMSO-d₆) δ ppm 1.77-1.85 (m, 2H), 1.92-1.99 (m, 2H), 2.10-2.17 (m, 2H), 2.26 (d, J=0.9 Hz, 3H), 2.38-2.44 (m, 2H), 2.82-2.87 (m, 1H), 4.44-4.54 (m, 1H), 6.77 (q, J=0.9 Hz, 1H), 6.80 (ddd, J=8.0, 2.5, 0.9 Hz, 1H), 7.16 (br. s., 2H), 7.20 (t, J=7.9 Hz, 1H), 7.79 (dd, J=2.3, 1.7 Hz, 1H), 7.82-7.85 (m, 1H), 8.17 (s, 1H), 9.42 (s, 1H), 12.01 (br. s., 1H).

HRMS (ESI+): calcd. for $C_{22}H_{24}N_7O_2S$ [M+H]⁺ 450.1707; found 450.1709.

Example 10 cis-4-[6-amino-2-(1,2,3,6-tetrahydropyridin-4-yl)-9H-purin-9-yl]-N-(3-methoxyphenyl)cyclohexanecarboxamide (I), cpd 42

[X=N, R1=CONR4R5, R4=Substituted Aryl, R5=H, R3=Heterocyclyl]

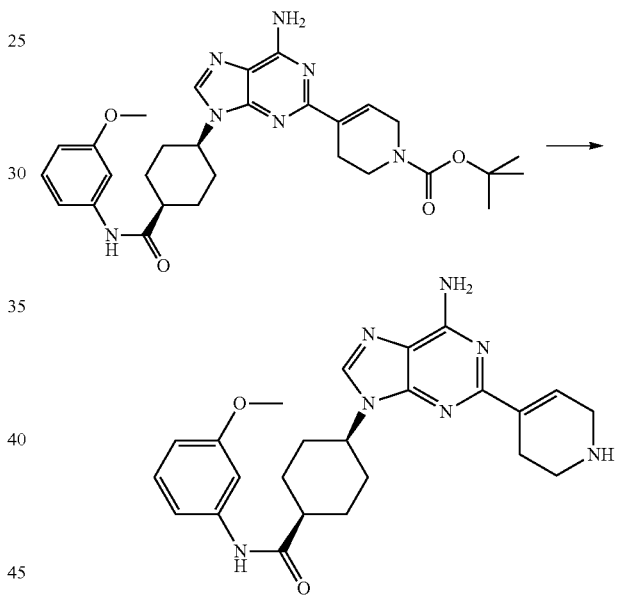

A solution of tert-butyl 4-(6-amino-9-{cis-4-[(3-methoxyphenyl)carbamoyl]cyclohexyl}-9H-purin-2-yl)-3,6-dihydropyridine-1(2H)-carboxylate (20 mg, 0.036 mmol) in DCM (3 mL) was treated with TFA (0.6 mL) for 2 h at rt. After neutralization with a saturated solution of NaHCO₃, the organic layer was washed with water and brine, dried over Na₂SO₄ and filtered. The solvent was removed under reduced pressure and the title compound was isolated as white solid (13 mg, 80%).

¹H NMR (499.7 MHz, DMSO-d₆) δ ppm 1.70-1.80 (m, 2H), 1.83-1.92 (m, 2H), 2.05-2.14 (m, 2H), 2.43-2.50 (m, 2H), 2.65-2.72 (m, 1H), 2.88-2.91 (m, 2H), 3.43 (br. s., 2H), 3.73 (s, 3H), 4.37-4.45 (m, 1H), 6.59-6.63 (m, 1H), 6.97-7.03 (m, 3H), 7.16-7.22 (m, 2H), 7.34-7.37 (m, 1H), 8.10 (s, 1H), 9.79 (s, 1H).

HRMS (ESI+): calcd. for $C_{24}H_{30}N_7O_2$ [M+H]⁺ 448.2456; found 448.2451.

Operating in an analogous way, but employing a 4 M solution of hydrochloric acid in dioxane, the following compound was obtained:

cis-4-(6-amino-2-chloro-9H-purin-9-yl)-N-(4,5,6,7-tetrahydro[1,3]thiazolo[5,4-c]pyridin-2-yl)cyclohexanecarboxamide hydrochloride (I), cpd 172

[X=N, R1=CONR4R5, R4=Substituted Hetroaryl, R5=H, n=0, R3=Cl]

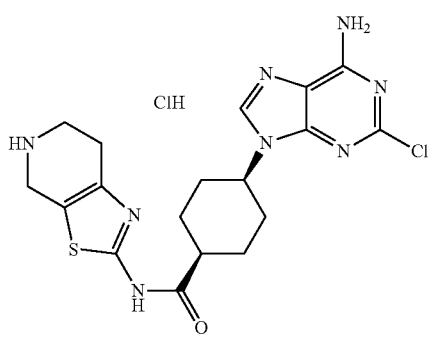 [SMILES: Nc1nc(Cl)nc2c1ncn2[C@H]1CC[C@@H](C(=O)Nc2nc3c(s2)CNCC3)CC1 ; Cl]

$^1$H NMR (500 MHz, DMSO-d$_6$) δ ppm 1.74-1.88 (m, 2H) 1.88-2.00 (m, 2H) 2.02-2.11 (m, 2H) 2.11-2.23 (m, 2H) 2.79-2.93 (m, 3H) 3.36-3.48 (m, 2H) 4.26-4.33 (m, 2H) 4.34-4.44 (m, 1H) 7.76 (br. s., 2H) 8.23 (s, 1H) 9.37 (br. s., 2H) 12.16 (s, 1H).

HRMS (ESI+): calcd. for $C_{18}H_{22}ClN_8OS$ [M+H]$^+$ 433.1321; found 433.1317.

cis-4-(6-amino-2-chloro-9H-purin-9-yl)-N-[(5S,8R)-5,6,7,8-tetrahydro-4H-5,8-epiminocyclohepta[d][1,3]thiazol-2-yl]cyclohexanecarboxamide hydrochloride (I), cpd 189

[X=N, R1=CONR4R5, R4=Substituted Hetroaryl, R5=H, n=0, R3=Cl]

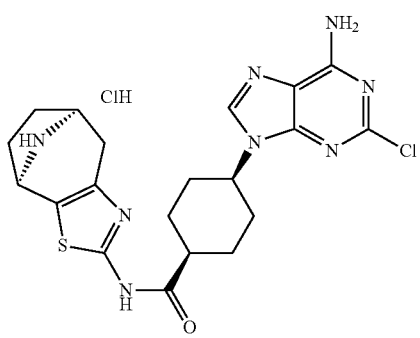 [SMILES: Nc1nc(Cl)nc2c1ncn2[C@H]1CC[C@@H](C(=O)Nc2nc3c(s2)[C@H]2CC[C@@H](C3)N2)CC1 ; Cl]

$^1$H NMR (500 MHz, DMSO-d$_6$) δ ppm 1.72-1.88 (m, 3H) 1.89-1.98 (m, 3H) 2.01-2.28 (m, 6H) 2.69-2.75 (m, 1H) 2.82-2.88 (m, 1H) 3.20 (dd, J=17.08, 4.42 Hz, 2H) 4.32-4.47 (m, 2H) 5.10 (br. s., 1H) 7.76 (br. s., 2H) 8.23 (s, 1H) 9.47 (br. s., 2H) 12.18 (s, 1H).

HRMS (ESI+): calcd. for $C_{20}H_{24}ClN_8OS$ [M+H]$^+$ 459.1477; found 459.1479.

Example 11

Conv. 2 cis-4-[6-amino-2-(4-methylpiperazin-1-yl)-9H-purin-9-yl]-N-(3-methoxyphenyl)cyclohexanecarboxamide (I), cpd 106

[X=N, R1=CONR4R5, R4=Substituted Aryl, R5=H, R3=NR4R5, R4 and R5=Taken Together Form a Substituted Heterocyclyl Group]

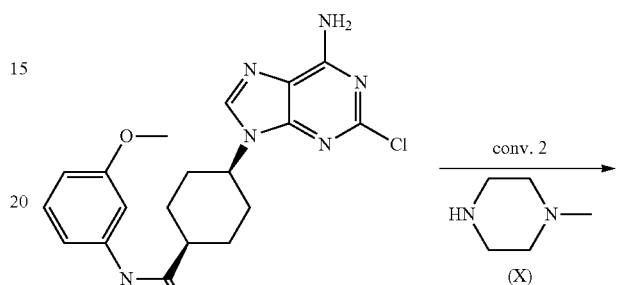

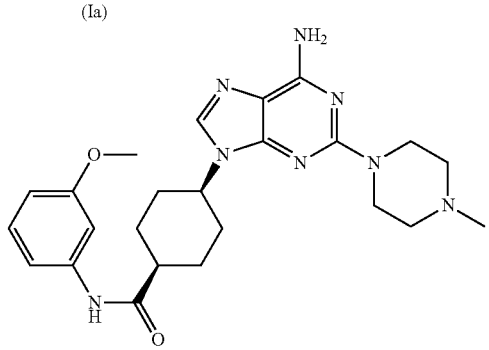

A solution of cis-4-(6-amino-2-chloro-9H-purin-9-yl)-N-(3-methoxyphenyl)cyclohexanecarboxamide (Ia) (14 mg, 0.035 mmol) and N-methylpiperazine (X) (0.041 mL, 0.35 mmol) in NMP (1.5 mL) was heated at 150° C. overnight. The mixture was then diluted with AcOEt and washed with water. The organic layer was dried over Na$_2$SO$_4$, filtered and evaporated under reduced pressure. The product was purified by column chromatography (eluant DCM:MeOH=95:5) and isolated as brown solid (6 mg, 37%).

$^1$H NMR (499.7 MHz, DMSO-d$_6$) δ ppm 1.67-1.75 (m, 2H), 1.75-1.83 (m, 2H), 2.04-2.13 (m, 2H), 2.17 (s, 3H), 2.26-2.29 (m, 4H), 2.40-2.48 (m, 2H), 2.65-2.69 (m, 1H), 3.69-3.65 (m, 2H), 3.72 (s, 3H), 4.22-4.29 (m, 1H), 6.59-6.63 (m, 1H), 6.72 (br. s., 2H), 7.13-7.20 (m, 2H), 7.36-7.39 (m, 1H), 7.76 (s, 1H), 9.76 (br. s., 1H).

HRMS (ESI+): calcd. for $C_{24}H_{33}N_8O_2$ [M+H]$^+$ 465.2721; found 465.2730.

Operating in an analogous way, but employing suitably substituted reagents (X), the following compounds were obtained:

cis-4-[6-amino-2-(dimethylamino)-9H-purin-9-yl]-N-(3-methoxyphenyl)cyclohexanecarboxamide (I), cpd 104

[X=N, R1=CONR4R5, R4=Substituted Aryl, R5=H, R3=NR4R5, R4=R5=(C$_1$-C$_6$)alkyl]

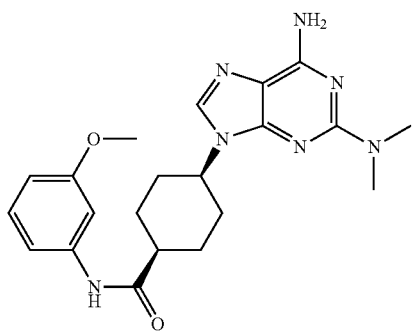 [SMILES: COc1cccc(NC(=O)[C@H]2CC[C@@H](n3cnc4c(N)nc(N(C)C)nc43)CC2)c1]

¹H NMR (499.7 MHz, DMSO-d₆) δ ppm 1.68-1.77 (m, 2H), 1.80-1.86 (m, 2H), 2.02-2.11 (m, 2H), 2.36-2.44 (m, 2H), 2.64-2.69 (m, 1H), 3.04 (s, 6H), 3.72 (s, 3H), 4.23-4.30 (m, 1H), 6.58-6.62 (m, 1H), 6.66 (br. s., 2H), 7.13-7.20 (m, 2H), 7.34-7.37 (m, 1H), 7.74 (s, 1H), 9.78 (s, 1H).

HRMS (ESI+): calcd. for $C_{21}H_{28}N_7O_2$ [M+H]⁺ 410.2299; found 410.2299.

cis-4-[6-amino-2-(methylamino)-9H-purin-9-yl]-N-(3-methoxyphenyl)cyclohexanecarboxamide (I), cpd 105

[X=N, R1=CONR4R5, R4=Substituted Aryl, R5=H, R3=NR4R5, R4=(C₁-C₆)alkyl, R5=H]

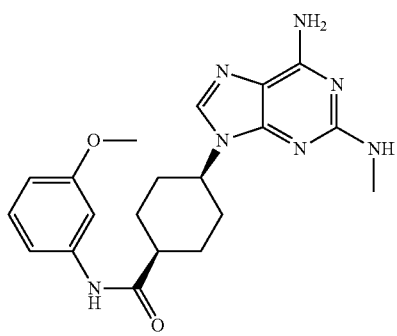 [SMILES: CNc1nc(N)c2ncn([C@H]3CC[C@@H](C(=O)Nc4cccc(OC)c4)CC3)c2n1]

¹H NMR (499.7 MHz, DMSO-d₆) δ ppm 1.69-1.78 (m, 2H), 1.83-1.89 (m, 2H), 2.01-2.08 (m, 2H), 2.25-2.34 (m, 2H), 2.64-2.69 (m, 1H), 2.74 (d, J=4.9 Hz, 3H), 3.72 (s, 3H), 4.23-4.30 (m, 1H), 6.11 (q, J=4.9 Hz, 1H), 6.57-6.63 (m, 3H), 7.14-7.20 (m, 2H), 7.35 (t, J=2.0 Hz, 1H), 7.73 (s, 1H), 9.80 (br. s., 1H).

HRMS (ESI+): calcd. for $C_{20}H_{26}N_7O_2$ [M+H]⁺ 396.2143; found 396.2144.

Example 12

Conv. 2 cis-4-[6-amino-2-(pyridin-3-ylamino)-9H-purin-9-yl]-N-(3-methoxyphenyl)cyclohexanecarboxamide (I), cpd 12

[X=N, R1=CONR4R5, R4=Substituted Aryl, R5=H, R3=NR4R5, R4=Heteroaryl, R5=H]

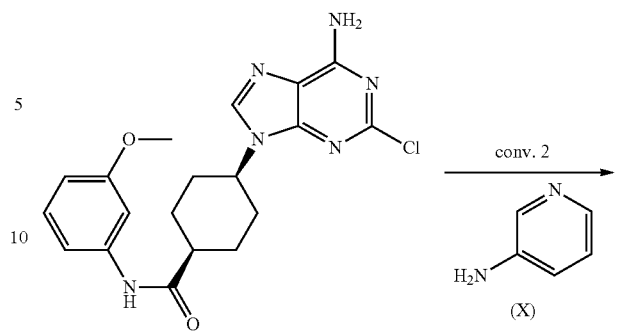

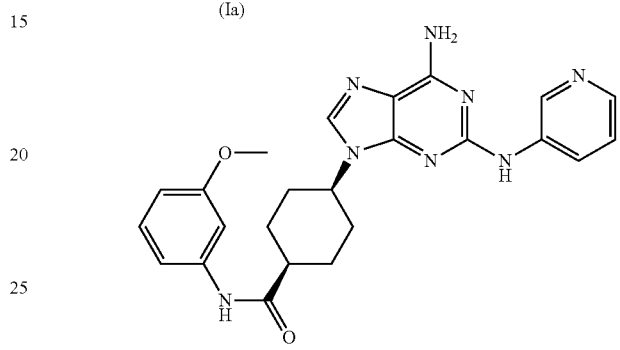

In a Schlenk tube, Pd(OAc)₂ (3 mg, 0.013 mmol) and rac-BINAP (10 mg, 0.016 mmol) were charged under argon, dissolved in DMA (5 mL) and let under stirring at rt for 20 min. Then cis-4-(6-amino-2-chloro-9H-purin-9-yl)-N-(3-methoxyphenyl)cyclohexanecarboxamide (Ia) (35 mg, 0.087 mmol), Cs₂CO₃ (34 mg, 0.105 mmol) and pyridin-3-amine (X) (9 mg, 0.096 mmol) were added and the mixture was heated at 100° C. for 6 h. The mixture was diluted with EtOAc and filtered over a pad of celite. The filtrate was then washed with water and brine, dried over Na₂SO₄, filtered and taken to dryness under reduced pressure. The title compound was purified by column chromatography (eluant EtOAc, EtOAc:MeOH=95:5) and isolated as brownish solid (11 mg, 27%).

¹H NMR (400.5 MHz, DMSO-d₆) δ ppm 1.71-1.84 (m, 2H), 1.91-2.00 (m, 2H), 2.03-2.13 (m, 2H), 2.23-2.38 (m, 2H), 2.67-2.76 (m, 1H), 3.72 (s, 3H), 4.31-4.39 (m, 1H), 6.60-6.63 (m, 1H), 6.99 (br. s., 2H), 7.13-7.26 (m, 3H), 7.36 (m, 1H), 7.93 (s, 1H), 8.02 (dd, J=4.6, 1.3 Hz, 1H), 8.38 (d, J=9.4 Hz, 1H), 8.92 (d, J=2.4 Hz, 1H), 9.07 (s, 1H), 9.81 (s, 1H).

HRMS (ESI+): calcd. for $C_{24}H_{27}N_8O_2$ [M+H]⁺ 401.1488; found 401.1488.

Example 13

Conv. 2 trans-4-(6-amino-2-methoxy-9H-purin-9-yl)-N-(3-methoxyphenyl)cyclohexanecarboxamide (I), cpd 34

[X=N, R1=CONR4R5, R4=Substituted Aryl, R5=H, R3=OR6, R6=(C₁-C₆)alkyl]

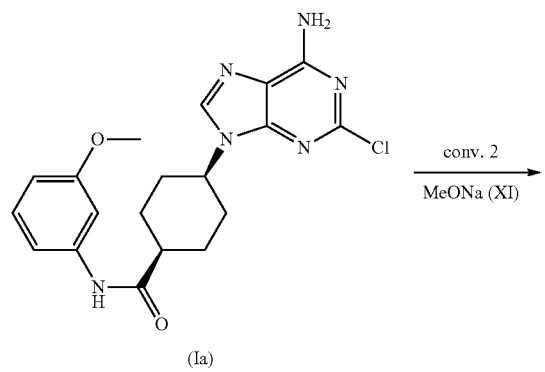

(Ia)

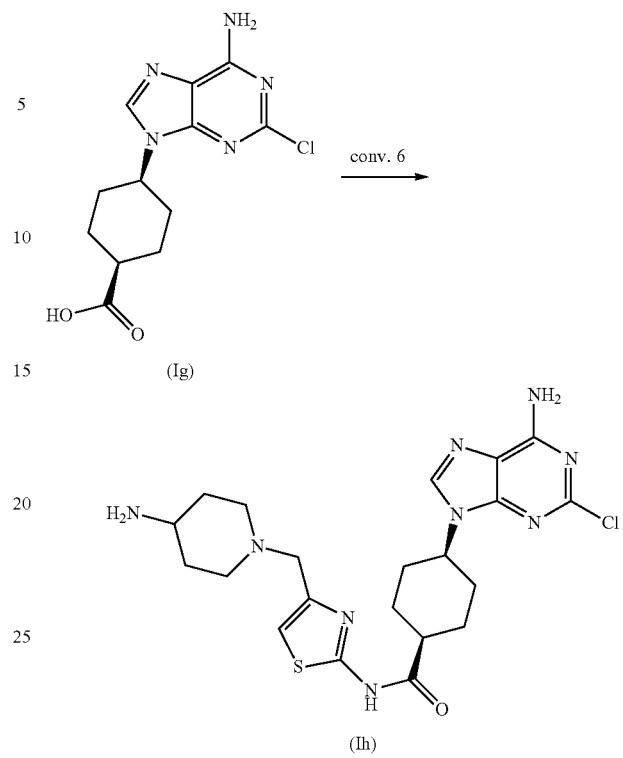

(Ih)

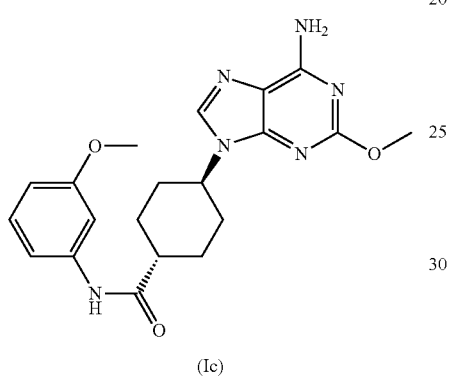

(Ic)

In a microwave vial cis-4-(6-amino-2-chloro-9H-purin-9-yl)-N-(3-methoxyphenyl)cyclohexanecarboxamide (Ia) (30 mg, 0.075 mmol) was suspended in MeOH (2.5 mL), treated with MeONa (XI) (16 mg, 0.3 mmol) and heated under microwave irradiation at 120° C. for 1 h. After solvent removal under reduced pressure, the residue was dissolved in DCM, washed with water and brine, dried over $Na_2SO_4$ and filtered. The product was purified by column chromatography (eluant EtOAc:MeOH=97:3) and isolated as white solid (13 mg, 44%).

$^1$H NMR (499.7 MHz, DMSO-$d_6$) δ ppm 1.57-1.73 (m, 2H), 1.96-2.09 (m, 6H), 2.42-2.45 (m, 1H), 3.72 (s, 3H), 3.82 (s, 3H), 4.22-4.32 (m, 1H), 6.59-6.64 (m, 1H), 7.13-7.16 (m, 1H), 7.17-7.20 (m, 1H), 7.20 (br. s., 2H), 7.35 (t, J=1.9 Hz, 1H), 8.03 (s, 1H), 9.93 (s, 1H).

HRMS (ESI+): calcd. for $C_{20}H_{25}N_6O_3$ [M+H]$^+$ 397.1983; found 397.1985.

Example 14

Conv. 6 cis-4-(6-amino-2-chloro-9H-purin-9-yl)-N-{4-[(4-aminopiperidin-1-yl)methyl]-1,3-thiazol-2-yl}cyclohexanecarboxamide (I), cpd 120

[X=N, R1=CONR4R5, R4=Substituted Heteroaryl, R5=H, n=0, R3=Cl]

A solution of cis-4-(6-amino-2-chloro-9H-purin-9-yl)cyclohexanecarboxylic acid (16 mg, 0.056 mmol), TBTU (22 mg, 0.068 mmol), DIPEA (0.029 mL, 0.17 mmol) and tert-butyl {1-[(2-amino-1,3-thiazol-4-yl)methyl]piperidin-4-yl}carbamate (18 mg, 0.056 mmol) in DMA (4 mL) was let under stirring at rt for four days. The mixture was then diluted with EtOAc, washed with a saturated solution of $NaHCO_3$, water and brine, dried over $Na_2SO_4$ and filtered. After solvent removal, the crude was then dissolved in THF (2 mL) and treated with a 1:1 solution of conc. HCl/water (3 mL) overnight at rt. After neutralization with a saturated solution of $NaHCO_3$, the product was extracted with DCM. The combined organic layers were then washed with water and brine, dried over $Na_2SO_4$, filtered and taken to dryness under vacuo. The title compound was purified by column chromatography (eluant DCM:7 N $NH_3$ in MeOH=9:1) and isolated as white solid (11 mg, 38%).

$^1$H NMR (499.7 MHz, DMSO-$d_6$) δ ppm 1.15-1.32 (m, 2H), 1.61-1.69 (m, 2H), 1.77-1.86 (m, 2H), 1.77-1.85 (m, 2H), 1.88-2.04 (m, 4H), 2.04-2.14 (m, 2H) 2.14-2.22 (m, 2H), 2.52-2.57 (m, 1H), 2.74-2.79 (m, 2H), 2.79-2.84 (m, 1H), 3.43 (s, 2H), 4.33-4.41 (m, 1H), 6.90 (s, 1H), 7.73 (br. s., 2H), 8.21 (s, 1H).

HRMS (ESI+): calcd. for $C_{21}H_{29}ClN_9OS$ [M+H]$^+$ 490.1899; found 490.1896.

Operating in an analogous way, but employing suitably substituted reagents, the following compounds were obtained:

cis-4-(6-amino-2-iodo-9H-purin-9-yl)-N-(4-methoxy-1,3-benzothiazol-2-yl)cyclohexanecarboxamide (I), cpd 116

[X=N, R1=CONR4R5, R4=Substituted Heteroaryl, R5=H, n=0, R3=I]

133

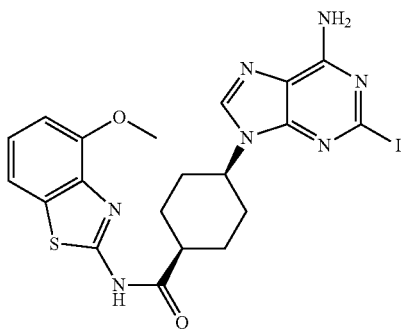 [SMILES: COc1cccc2sc(NC(=O)[C@H]3CC[C@@H](n4cnc5c(N)nc(I)nc54)CC3)nc12]

¹H NMR (499.7 MHz, DMSO-$d_6$) δ ppm 1.80-1.90 (m, 2H), 1.90-1.98 (m, 2H), 2.09-2.22 (m, 4H), 2.85-2.89 (m, 1H), 3.91 (s, 3H), 4.35-4.42 (m, 1H), 6.99 (d, J=7.6 Hz, 1H), 7.25 (t, J=7.9 Hz, 1H), 7.52 (dd, J=7.9, 0.8 Hz, 1H), 7.63 (br. s., 2H), 8.14 (s, 1H), 12.48 (br. s., 1H).

HRMS (ESI+): calcd. for $C_{20}H_{21}IN_7O_2S$ [M+H]⁺ 550.0517; found 550.0528.

cis-4-(6-amino-2-chloro-9H-purin-9-yl)-N-(4-hydroxy-1,3-benzothiazol-2-yl)cyclohexanecarboxamide (I), cpd 122

[X=N, R1=CONR4R5, R4=Substituted Heteroaryl, R5=H, n=0, R3=Cl]

134

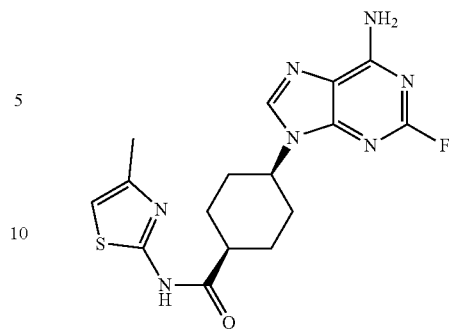

¹H NMR (499.7 MHz, DMSO-$d_6$) δ ppm 1.75-1.84 (m, 2H), 1.90-1.95 (m, 2H), 2.04-2.10 (m, 2H), 2.12-2.22 (m, 2H), 2.26 (d, J=0.9 Hz, 3H), 2.79-2.83 (m, 1H), 4.29-4.37 (m, 1H), 6.74 (q, J=0.9 Hz, 1H), 7.75 (br. s., 2H), 8.17 (s, 1H), 12.00 (br. s., 1H).

HRMS (ESI+): calcd. for $C_{16}H_{19}FN_7OS$ [M+H]⁺ 376.1351; found 376.1342.

cis-4-(6-amino-2-fluoro-9H-purin-9-yl)-N-(4-methoxy-1,3-benzothiazol-2-yl)cyclohexanecarboxamide (I)m cpd 126

[X=N, R1=CONR4R5, R4=Substituted Heteroaryl, R5=H, n=0, R3=F]

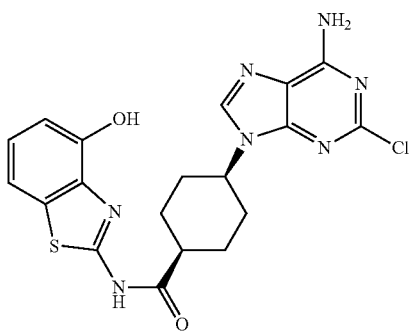 [SMILES: Nc1nc(Cl)nc2c1ncn2[C@H]1CC[C@@H](C(=O)Nc2nc3c(O)cccc3s2)CC1]

¹H NMR (499.7 MHz, DMSO-$d_6$) δ ppm 1.77-1.88 (m, 2H), 1.91-2.01 (m, 2H), 2.08-2.24 (m, 4H), 2.86-2.92 (m, 1H), 4.37-4.42 (m, 1H), 6.82 (d, J=7.9 Hz, 1H), 7.09 (t, J=7.9 Hz, 1H), 7.35 (d, J=7.8 Hz, 1H), 7.74 (br. s., 2H), 8.23 (s, 1H), 9.77 (br. s., 1H), 12.34 (br. s., 1H).

HRMS (ESI+): calcd. for $C_{19}H_{19}ClN_7O_2S$ [M+H]⁺ 444.1004; found 444.1008.

cis-4-(6-amino-2-fluoro-9H-purin-9-yl)-N-(4-methyl-1,3-thiazol-2-yl)cyclohexanecarboxamide (I), cpd 124

[X=N, R1=CONR4R5, R4=Substituted Heteroaryl, R5=H, n=0, R3=F]

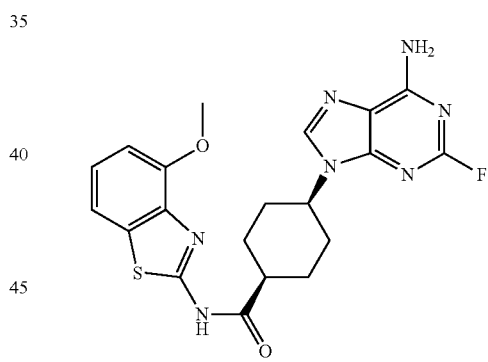

¹H NMR (500 MHz, DMSO-$d_6$) δ ppm 1.76-1.87 (m, 2H) 1.90-1.99 (m, 2H) 2.09-2.24 (m, 4H) 2.84-2.90 (m, 1H) 3.91 (s, 3H) 4.24-4.43 (m, 1H) 6.99 (d, J=8.01 Hz 1H) 7.25 (t, J=8.01 Hz, 1H) 7.52 (dd, J=8.01, 0.84 Hz, 1H) 7.76 (br. s., 2H) 8.18 (s, 1H) 12.48 (br. s., 1H).

HRMS (ESI+): calcd. for $C_{20}H_{21}FN_7O_2S$ [M+H]⁺ 442.1456; found 442.1450.

10 cis-4-(6-amino-2-fluoro-9H-purin-9-yl)-N-(4-hydroxy-1,3-benzothiazol-2-yl)cyclohexanecarboxamide (I), cpd 127

[X=N, R1=CONR4R5, R4=Substituted Heteroaryl, R5=H, n=0, R3=F]

135

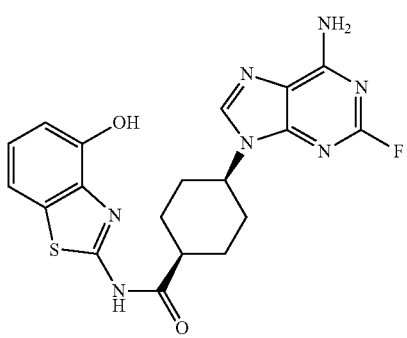 [SMILES: Nc1nc(F)nc2c1ncn2[C@H]1CC[C@@H](C(=O)Nc2nc3c(O)cccc3s2)CC1]

¹H NMR (500 MHz, DMSO-d₆) δ ppm 1.71-1.86 (m, 2H) 1.87-1.99 (m, 2H) 2.09-2.24 (m, 4H) 2.74-2.91 (m, 1H) 4.29-4.38 (m, 1H) 6.58-6.88 (m, 1H) 6.88-7.16 (m, 1H) 7.19-7.40 (m, 1H) 7.76 (br. s., 2H) 8.16 (s, 1H) 9.80 (br. s., 1H) 12.35 (br. s., 1H).

HRMS (ESI+): calcd. for $C_{19}H_{19}FN_7O_2S$ [M+H]⁺ 428.13; found 428.1304.

2-amino-1,3-benzothiazol-4-yl cis-4-(6-amino-2-fluoro-9H-purin-9-yl)cyclohexanecarboxylate (I), cpd 160

[X=N, R1=COOR4, R4=Substituted Heteroaryl, n=0, R3=F]

136

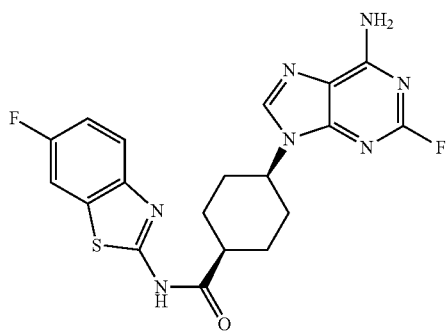

¹H NMR (500 MHz, DMSO-d₆) δ ppm 1.77-1.88 (m, 2H) 1.91-1.98 (m, 2H) 2.08-2.16 (m, 2H) 2.16-2.26 (m, 2H) 2.86-2.95 (m, 1H) 4.31-4.41 (m, 1H) 7.28 (td, J=9.07, 2.59 Hz, 1H) 7.74 (dd, J=8.77, 4.80 Hz, 1H) 7.90 (dd, J=8.77, 2.59 Hz, 1H) 8.18 (s, 1H) 12.39 (br. s., 1H).

HRMS (ESI+): calcd. for $C_{19}H_{18}F_2N_7OS$ [M+H]⁺ 430.1256; found 430.1256.

cis-4-[6-amino-2-(trifluoromethyl)-9H-purin-9-yl]-N-(4-methyl-1,3-thiazol-2-yl)cyclohexanecarboxamide (I), cpd 129

[X=N, R1=CONR4R5, R4=Substituted Heteroaryl, R5=H, n=0, R3=Polifluorinated Alkyl]

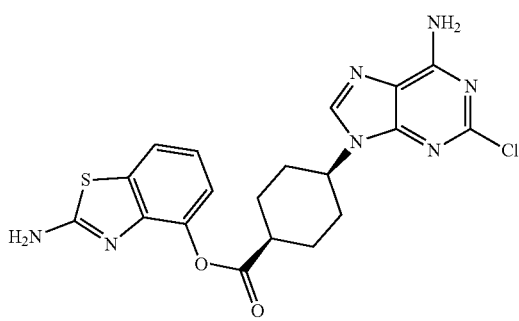 [SMILES: Nc1nc2c(OC(=O)[C@H]3CC[C@@H](n4cnc5c(N)nc(Cl)nc54)CC3)cccc2s1]

¹H NMR (500 MHz, DMSO-d₆) δ ppm 1.80-1.94 (m, 2H) 1.97-2.07 (m, 2H) 2.13-2.26 (m, 2H) 2.27-2.36 (m, 2H) 3.01-3.10 (m, 1H) 4.32-4.44 (m, 1H) 7.03 (t, J=7.93 Hz, 1H) 7.11 (dd, J=7.93, 1.22 Hz, 1H) 7.56 (dd, J=7.93, 1.22 Hz, 1H) 7.59 (br. s., 2H) 7.74 (br. s., 2H) 8.21 (s, 1H).

HRMS (ESI+): calcd. for $C_{19}H_{19}FN_7O_2S$ [M+H]⁺ 428.13; found 428.1298.

cis-4-(6-amino-2-fluoro-9H-purin-9-yl)-N-(6-fluoro-1,3-benzothiazol-2-yl)cyclohexanecarboxamide (I), cpd 128

[X=N, R1=CONR4R5, R4=Substituted Heteroaryl, R5=H, n=0, R3=F]

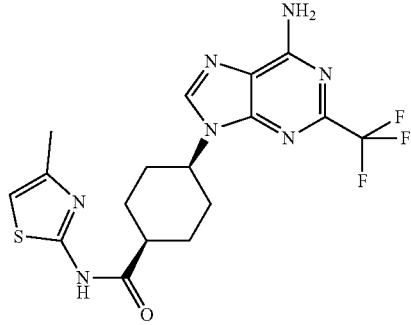 [SMILES: Cc1csc(NC(=O)[C@H]2CC[C@@H](n3cnc4c(N)nc(C(F)(F)F)nc43)CC2)n1]

¹H NMR (500 MHz, DMSO-d₆) δ ppm 1.76-1.87 (m, 2H) 1.92-2.01 (m, 2H) 2.05-2.13 (m, 2H) 2.17-2.25 (m, 2H) 2.26 (s, 3H) 2.79-2.85 (m, 1H) 4.43-4.53 (m, 1H) 6.74 (s, 1H) 7.85 (br. s., 2H) 8.40 (s, 1H) 12.01 (br. s., 1H).

HRMS (ESI+): calcd. for $C_{17}H_{19}F_3N_7OS$ [M+H]⁺ 426.1319; found 426.1321.

cis-4-[6-amino-2-(trifluoromethyl)-9H-purin-9-yl]-N-(6-fluoro-1,3-benzothiazol-2-yl)cyclohexanecarboxamide (I), cpd 132

[X=N, R1=CONR4R5, R4=Substituted Heteroaryl, R5=H, n=0, R3=Polifluorinated Alkyl]

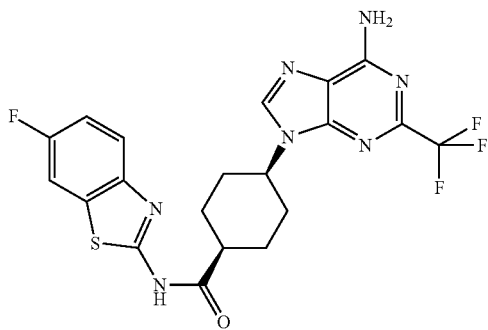 [SMILES: Nc1nc(C(F)(F)F)nc2c1ncn2[C@H]1CC[C@@H](C(=O)Nc2nc3ccc(F)cc3s2)CC1]

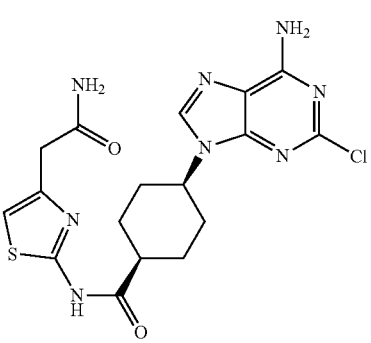 [SMILES: NC(=O)Cc1csc(NC(=O)[C@H]2CC[C@@H](n3cnc4c(N)nc(Cl)nc43)CC2)n1]

¹H NMR (500 MHz, DMSO-d₆) δ ppm 1.79-1.92 (m, 2H) 1.93-2.05 (m, 2H) 2.09-2.19 (m, 2H) 2.19-2.32 (m, 2H) 2.86-2.93 (m, 1H) 4.45-4.54 (m, 1H) 7.27 (td, J=9.07, 2.75 Hz, 1H) 7.73 (dd, J=8.85, 4.88 Hz, 1H) 7.85 (br. s., 2H) 7.88 (dd, J=8.69, 2.59 Hz, 1H) 8.41 (s, 1H) 12.37 (br. s., 1H).

HRMS (ESI+): calcd. for $C_{20}H_{18}F_4N_7OS$ [M+H]⁺ 480.1224; found 480.1220.

cis-4-(6-amino-2-chloro-9H-purin-9-yl)-N-(6-fluoro-1,3-benzothiazol-2-yl)cyclohexanecarboxamide (I), cpd 134

[X=N, R1=CONR4R5, R4=Substituted Heteroaryl, R5=H, n=0, R3=Cl]

¹H NMR (500 MHz, DMSO-d₆) δ ppm 1.72-1.87 (m, 2H) 1.88-1.97 (m, 2H) 2.03-2.11 (m, 2H) 2.11-2.24 (m, 2H) 2.78-2.85 (m, 1H) 3.42 (s, 2H) 4.32-4.43 (m, 1H) 6.88 (s, 1H) 6.94 (br. s., 1H) 7.34 (br. s., 1H) 7.74 (br. s., 2H) 8.22 (s, 1H) 12.10 (br. s., 1H).

HRMS (ESI+): calcd. for $C_{17}H_{20}ClN_8O_2S$ [M+H]⁺ 435.1113; found 435.1111.

cis-4-(6-amino-2-chloro-9H-purin-9-yl)-N-(6-hydroxy-1,3-benzothiazol-2-yl)cyclohexanecarboxamide (I), cpd 137

[X=N, R1=CONR4R5, R4=Substituted Heteroaryl, R5=H, n=0, R3=Cl]

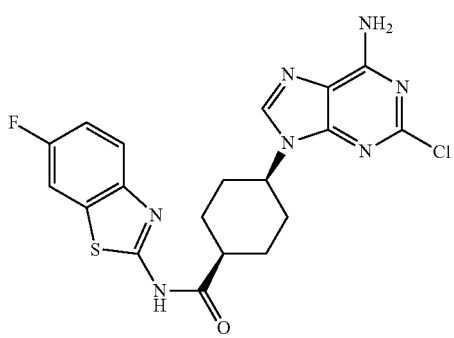

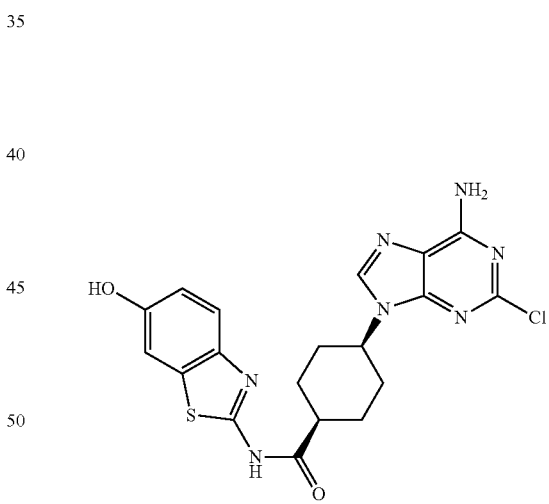

¹H NMR (500 MHz, DMSO-d₆) δ ppm 1.78-1.91 (m, 2H) 1.92-2.00 (m, 2H) 2.07-2.26 (m, 4H) 2.87-2.94 (m, 2H) 4.31-4.48 (m, 1H) 7.28 (td, J=9.07, 2.75 Hz, 1H) 7.74 (dd, J=8.85, 4.73 Hz, 3H) 7.89 (dd, J=8.69, 2.75 Hz, 1H) 8.23 (s, 1H) 12.39 (br. s., 1H).

HRMS (ESI+): calcd. for $C_{19}H_{18}ClFN_7OS$ [M+H]⁺ 446.0961; found 446.0958.

cis-4-(6-amino-2-chloro-9H-purin-9-yl)-N-[4-(2-amino-2-oxoethyl)-1,3-thiazol-2-yl]cyclohexanecarboxamide (I), cpd 135

[X=N, R1=CONR4R5, R4=Substituted Heteroaryl, R5=H, n=0, R3=Cl]

¹H NMR (500 MHz, DMSO-d₆) δ ppm 1.77-1.88 (m, 2H) 1.91-1.99 (m, 2H) 2.07-2.13 (m, 2H) 2.14-2.25 (m, 2H) 2.84-2.91 (m, 1H) 4.29-4.45 (m, 1H) 6.87 (dd, J=8.69, 2.44 Hz, 1H) 7.26 (d, J=2.44 Hz, 1H) 7.53 (d, J=8.69 Hz, 1H) 7.74 (br. s., 2H) 8.22 (s, 1H) 9.52 (s, 1H) 12.14 (br. s., 1H).

HRMS (ESI+): calcd. for $C_{19}H_{19}ClN_7O_2S$ [M+H]⁺ 444.1004; found 444.1003.

2-amino-1,3-benzothiazol-6-yl cis-4-(6-amino-2-chloro-9H-purin-9-yl)cyclohexanecarboxylate (I), cpd 159

[X=N, R1=COOR4, R4=Substituted Aryl, n=0, R3=Cl]

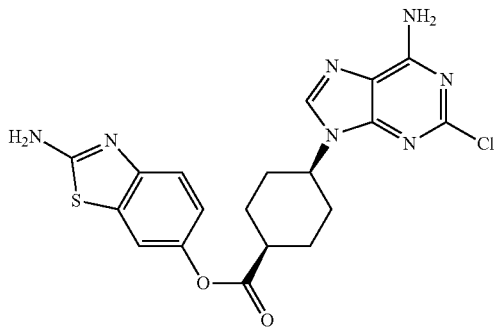 [SMILES: Nc1nc2ccc(OC(=O)[C@H]3CC[C@@H](n4cnc5c(N)nc(Cl)nc54)CC3)cc2s1]

$^1$H NMR (500 MHz, DMSO-d$_6$) δ ppm 1.76-1.89 (m, 2H) 1.93-2.03 (m, 2H) 2.07-2.20 (m, 2H) 2.27-2.35 (m, 2H) 3.03-3.12 (m, 1H) 4.35-4.46 (m, 1H) 7.07 (dd, J=8.54, 2.44 Hz, 1H) 7.35 (d, J=8.54 Hz, 1H) 7.59 (d, J=2.44 Hz, 1H) 7.64 (br. s., 2H) 7.75 (br. s., 2H) 8.27 (s, 1H).

HRMS (ESI+): calcd. for C$_{19}$H$_{19}$ClN$_7$O$_2$S [M+H]$^+$ 444.1004; found 444.0999.

cis-4-(6-amino-2-chloro-9H-purin-9-yl)-N-([1,3]thiazolo[5,4-c]pyridin-2-yl)cyclohexanecarboxamide hydrochloride (I), cpd 138

[X=N, R1=CONR4R5, R4=Substituted Heteroaryl, R5=H, n=0, R3=Cl]

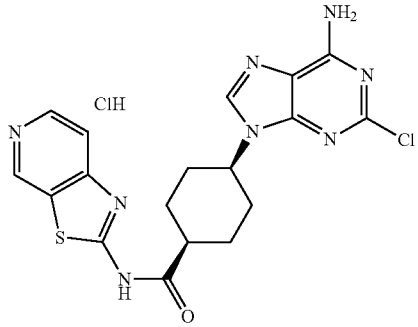 [SMILES: Nc1nc(Cl)nc2c1ncn2[C@H]1CC[C@@H](C(=O)Nc2nc3ccncc3s2)CC1 ; Cl]

$^1$H NMR (500 MHz, DMSO-d$_6$) δ ppm 1.85-2.02 (m, 4H) 2.09-2.27 (m, 4H) 2.99-3.09 (m, 1H) 4.34-4.47 (m, 1H) 7.75 (br. s., 2H) 8.16 (d, J=6.41 Hz, 1H) 8.24 (s, 1H) 8.75 (d, J=6.41 Hz, 1H) 9.55 (s, 1H) 13.37 (br. s., 1H).

HRMS (ESI+): calcd. for C$_{18}$H$_{18}$ClN$_8$OS [M+H]$^+$ 429.1008; found 429.1004.

2-({[cis-4-(6-amino-2-chloro-9H-purin-9-yl)cyclohexyl]carbonyl}amino)-1,3-benzothiazole-6-carboxamide (I), cpd 163 [X=N, R1=CONR4R5, R4=Substituted Heteroaryl, R5=H, n=0, R3=Cl]

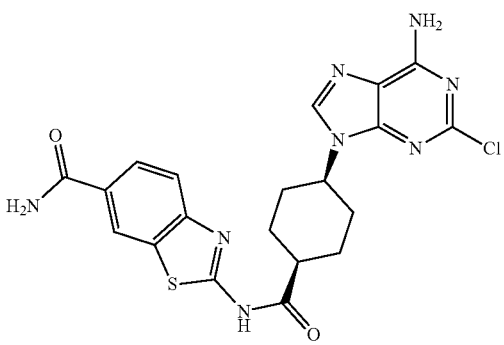 [SMILES: NC(=O)c1ccc2nc(NC(=O)[C@H]3CC[C@@H](n4cnc5c(N)nc(Cl)nc54)CC3)sc2c1]

$^1$H NMR (500 MHz, DMSO-d$_6$) δ ppm 1.78-1.90 (m, 2H) 1.91-2.02 (m, 2H) 2.10-2.25 (m, 4H) 2.88-2.97 (m, 1H) 4.24-4.45 (m, 1H) 7.37 (br. s., 1H) 7.74 (br. s., 2H) 7.76 (d, J=8.54 Hz, 1H) 7.95 (dd, J=8.54, 1.68 Hz, 1H) 8.02 (br. s., 1H) 8.24 (s, 1H) 8.50 (d, J=1.68 Hz, 1H) 12.53 (s, 1H).

HRMS (ESI+): calcd. for C$_{20}$H$_{20}$ClN$_8$O$_2$S [M+H]$^+$ 471.1113; found 471.1114.

cis-4-(6-amino-2-chloro-9H-purin-9-yl)-N-[4-(2-amino-2-oxoethyl)-1,3-thiazol-2-yl]-N-methylcyclohexanecarboxamide (I), cpd 164

[X=N, R1=CONR4R5, R4=Substituted Heteroaryl, R5=(C$_1$-C$_6$)alkyl, n=0, R3=Cl]

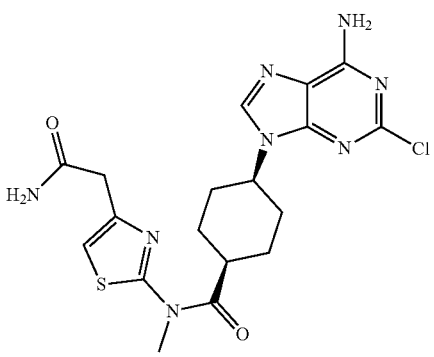 [SMILES: CN(c1nc(CC(N)=O)cs1)C(=O)[C@H]1CC[C@@H](n2cnc3c(N)nc(Cl)nc32)CC1]

$^1$H NMR (500 MHz, DMSO-d$_6$) δ ppm 1.77-1.91 (m, 2H) 1.91-2.05 (m, 4H) 2.22-2.35 (m, 2H) 3.45 (s, 2H) 3.69 (s, 3H) 4.38-4.49 (m, 1H) 6.95 (s, 2H) 7.34 (br. s., 1H) 7.75 (br. s., 2H) 8.23 (s, 1H).

HRMS (ESI+): calcd. for C$_{18}$H$_{22}$ClN$_8$O$_2$S [M+H]$^+$ 449.1270; found 449.1277.

cis-4-(6-amino-2-chloro-9H-purin-9-yl)-N-[6-(dimethylamino)-1,3-benzothiazol-2-yl]cyclohexanecarboxamide (I), cpd 165

[X=N, R1=CONR4R5, R4=Substituted Heteroaryl, R5=H, n=0, R3=Cl]

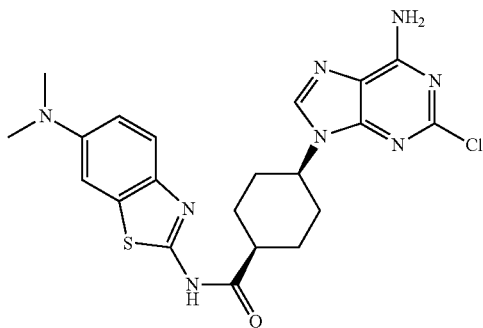 [SMILES: CN(C)c1ccc2nc(NC(=O)[C@H]3CC[C@@H](n4cnc5c(N)nc(Cl)nc54)CC3)sc2c1]

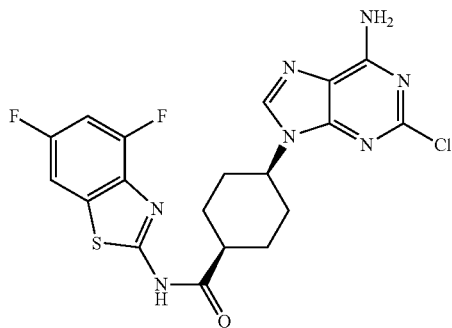

$^1$H NMR (500 MHz, DMSO-d$_6$) δ ppm 1.77-1.88 (m, 2H) 1.92-2.00 (m, 2H) 2.06-2.12 (m, 2H) 2.14-2.26 (m, 2H) 2.83-2.90 (m, 1H) 2.93 (s, 6H) 4.33-4.44 (m, 1H) 6.91 (dd, J=9.00, 2.44 Hz, 1H) 7.23 (d, J=2.44 Hz, 1H) 7.54 (d, J=9.00 Hz, 1H) 7.75 (br. s., 2H) 8.23 (s, 1H) 12.07 (br. s., 1H).

HRMS (ESI+): calcd. for C$_{21}$H$_{24}$ClN$_8$OS [M+H]$^+$ 471.1477; found 471.1483.

cis-4-(6-amino-2-chloro-9H-purin-9-yl)-N-[5-(2-amino-2-oxoethyl)-1,3-thiazol-2-yl]cyclohexanecarboxamide (I), cpd 166

[X=N, R1=CONR4R5, R4=Substituted Heteroaryl, R5=H, n=0, R3=Cl]

$^1$H NMR (500 MHz, DMSO-d$_6$) δ ppm 1.78-1.89 (m, 2H) 1.92-1.99 (m, 2H) 2.11-2.21 (m, 4H) 2.85-2.95 (m, 1H) 4.33-4.46 (m, 1H) 7.34-7.41 (m, 1H) 7.74 (br. s., 2H) 7.78-7.82 (m, 1H) 8.22 (s, 1H) 12.65 (br. s., 1H).

HRMS (ESI+): calcd. for C$_{19}$H$_{17}$ClF$_2$N$_7$OS [M+H]$^+$ 464.0867; found 464.0861.

cis-4-(6-amino-2-chloro-9H-purin-9-yl)-N-(5,6-difluoro-1,3-benzothiazol-2-yl)cyclohexanecarboxamide (I), cpd 168

[X=N, R1=CONR4R5, R4=Substituted Heteroaryl, R5=H, n=0, R3=Cl]

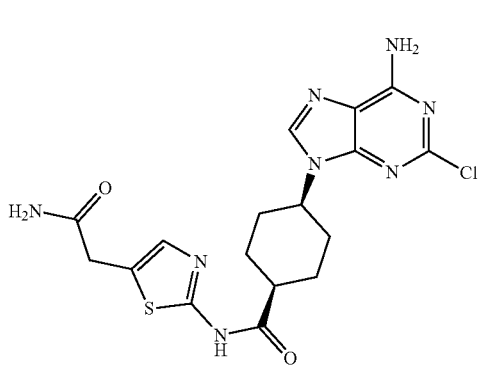 [SMILES: NC(=O)Cc1cnc(NC(=O)[C@H]2CC[C@@H](n3cnc4c(N)nc(Cl)nc43)CC2)s1]

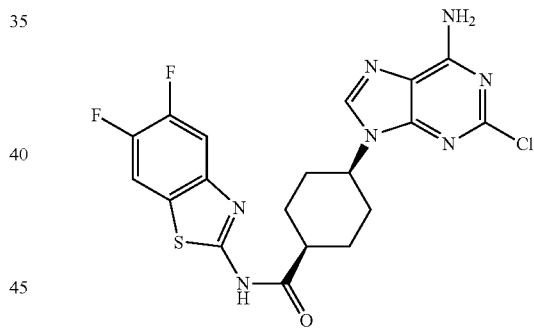

$^1$H NMR (500 MHz, DMSO-d$_6$) δ ppm 1.74-1.85 (m, 2H) 1.86-1.97 (m, 3H) 2.04-2.10 (m, 2H) 2.12-2.24 (m, 2H) 2.77-2.86 (m, 1H) 3.55 (s, 2H) 4.33-4.42 (m, 1H) 7.02 (br. s., 1H) 7.19 (s, 1H) 7.53 (br. s., 1H) 7.74 (br. s., 2H) 8.22 (s, 1H) 11.92 (br. s., 1H).

HRMS (ESI+): calcd. for C$_{17}$H$_{20}$ClN$_8$O$_2$S [M+H]$^+$ 435.1113; found 435.1114.

cis-4-(6-amino-2-chloro-9H-purin-9-yl)-N-(4,6-difluoro-1,3-benzothiazol-2-yl)cyclohexanecarboxamide (I), cpd 167

[X=N, R1=CONR4R5, R4=Substituted Heteroaryl, R5=H, n=0, R3=Cl]

$^1$H NMR (500 MHz, DMSO-d$_6$) δ ppm 1.78-1.90 (m, 2H) 1.91-2.03 (m, 2H) 2.07-2.22 (m, 4H) 2.85-2.94 (m, 1H) 4.34-4.47 (m, 1H) 7.74 (br. s., 2H) 7.82 (dd, J=11.29, 7.17 Hz, 1H) 8.14 (dd, J=10.29, 8.01 Hz, 1H) 8.22 (s, 1H) 12.49 (br. s., 1H).

HRMS (ESI+): calcd. for C$_{19}$H$_{17}$ClF$_2$N$_7$OS [M+H]$^+$ 464.0867; found 464.0858.

tert-butyl 2-({[cis-4-(6-amino-2-chloro-9H-purin-9-yl)cyclohexyl]carbonyl}amino)-6,7-dihydro[1,3]thiazolo[5,4-c]pyridine-5(4H)-carboxylate (I), cpd 169

[X=N, R1=CONR4R5, R4=Substituted Heteroaryl, R5=H, n=0, R3=Cl]

143

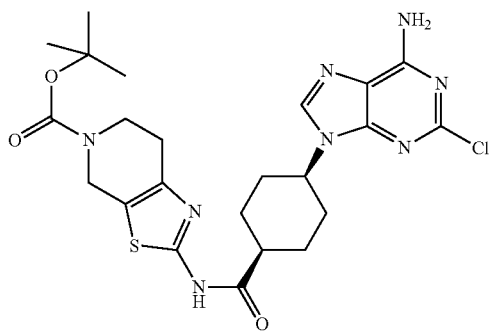 [SMILES: CC(C)(C)OC(=O)N1CCc2nc(NC(=O)[C@H]3CC[C@@H](n4cnc5c(N)nc(Cl)nc54)CC3)sc2C1]

¹H NMR (500 MHz, DMSO-d₆) δ ppm 1.42 (s, 9H) 1.75-1.87 (m, 2H) 1.90-1.97 (m, 2H) 2.02-2.21 (m, 4H) 2.60-2.67 (m, 2H) 2.79-2.85 (m, 1H) 3.63 (t, J=5.72 Hz, 2H) 4.33-4.42 (m, 1H) 4.49 (br. s., 2H) 7.74 (br. s., 2H) 8.20 (s, 1H) 11.99 (br. s., 1H).

HRMS (ESI+): calcd. for $C_{23}H_{30}ClN_8O_3S$ [M+H]⁺ 533.1845; found 533.1855.

cis-4-(6-amino-2-methoxy-9H-purin-9-yl)-N-(6-fluoro-1,3-benzothiazol-2-yl)cyclohexanecarboxamide (I), cpd 170

[X=N, R1=CONR4R5, R4=Substituted Heteroaryl, R5=H, n=0, R3=OR6, R6=(C₁-C₆)alkyl]

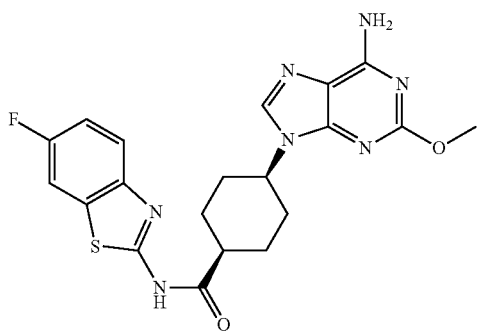 [SMILES: COc1nc(N)c2ncn([C@H]3CC[C@@H](C(=O)Nc4nc5ccc(F)cc5s4)CC3)c2n1]

¹H NMR (500 MHz, DMSO-d₆) δ ppm 1.73-1.85 (m, 2H) 1.85-1.96 (m, 2H) 2.10-2.22 (m, 2H) 2.27-2.38 (m, 2H) 2.83-2.95 (m, 1H) 3.79 (s, 3H) 4.26-4.39 (m, 1H) 7.18 (br. s., 2H) 7.27 (td, J=8.77, 2.75 Hz, 1H) 7.73 (dd, J=8.77, 4.80 Hz, 1H) 7.89 (dd, J=8.69, 2.75 Hz, 1H) 7.96 (s, 1H) 12.37 (br. s., 1H).

HRMS (ESI+): calcd. for $C_{20}H_{21}FN_7O_2S$ [M+H]⁺ 442.1456; found 442.1463.

cis-4-(6-amino-2-chloro-9H-purin-9-yl)-N-(5,6,7-trifluoro-1,3-benzothiazol-2-yl)cyclohexanecarboxamide (I), cpd 171

[X=N, R1=CONR4R5, R4=Substituted Heteroaryl, R5=H, n=0, R3=Cl]

144

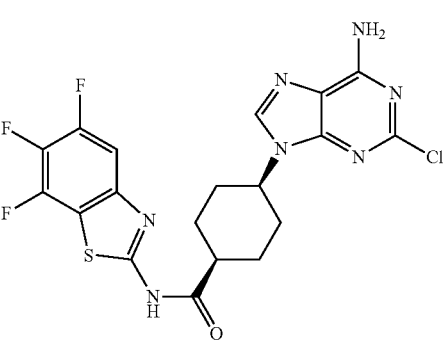 [SMILES: Nc1nc(Cl)nc2c1ncn2[C@H]1CC[C@@H](C(=O)Nc2nc3cc(F)c(F)c(F)c3s2)CC1]

¹H NMR (500 MHz, DMSO-d₆) δ ppm 1.73-2.01 (m, 4H) 2.09-2.22 (m, 4H) 2.86-2.94 (m, 1H) 4.34-4.43 (m, 1H) 7.18 (br. s., 3H) 8.22 (s, 1H) 12.79 (br. s., 1H).

HRMS (ESI+): calcd. for $C_{19}H_{16}ClF_3N_7OS$ [M+H]⁺ 482.0772; found 482.0772.

cis-4-(6-amino-2-chloro-9H-purin-9-yl)-N-(5-methyl-4,5,6,7-tetrahydro[1,3]thiazolo[5,4-c]pyridin-2-yl)cyclohexanecarboxamide (I), cpd 173

[X=N, R1=CONR4R5, R4=Substituted Heteroaryl, R5=H, n=0, R3=Cl]

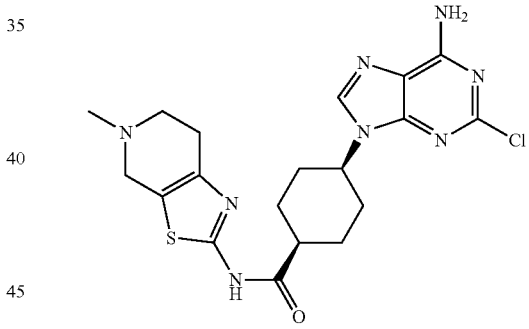

¹H NMR (500 MHz, DMSO-d₆) δ ppm 1.74-1.84 (m, 2H) 1.89-1.98 (m, 2H) 2.03-2.11 (m, 2H) 2.12-2.20 (m, 2H) 2.36 (s, 3H) 2.60-2.72 (m, 4H) 2.77-2.85 (m, 1H) 3.48 (br. s., 2H) 4.32-4.42 (m, 1H) 7.74 (br. s., 2H) 8.20 (s, 1H) 11.92 (br. s., 1H).

HRMS (ESI+): calcd. for $C_{19}H_{24}ClN_8OS$ [M+H]⁺ 447.1477; found 447.1466.

methyl [2-({[cis-4-(6-amino-2-chloro-9H-purin-9-yl)cyclohexyl]carbonyl}amino)-1,3-benzothiazol-6-yl]acetate (I), cpd 174

[X=N, R1=CONR4R5, R4=Substituted Heteroaryl, R5=H, n=0, R3=Cl]

145

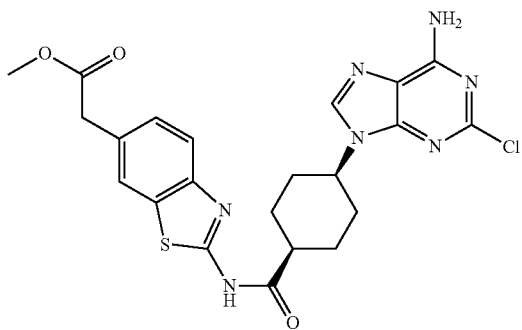 [SMILES: COC(=O)Cc1ccc2nc(NC(=O)[C@H]3CC[C@@H](n4cnc5c(N)nc(Cl)nc54)CC3)sc2c1]

¹H NMR (500 MHz, DMSO-d$_6$) δ ppm 1.77-1.89 (m, 2H) 1.92-2.00 (m, 2H) 2.07-2.26 (m, 4H) 2.87-2.94 (m, 1H) 3.62 (s, 3H) 3.79 (s, 2H) 4.32-4.46 (m, 1H) 7.33 (dd, J=8.39, 1.68 Hz, 1H) 7.68 (d, J=8.39 Hz, 1H) 7.75 (br. s., 2H) 7.86 (d, J=1.22 Hz, 1H) 8.23 (s, 1H) 12.35 (s, 1H).

HRMS (ESI+): calcd. for C$_{22}$H$_{23}$ClN$_7$O$_3$S [M+H]$^+$ 500.1266; found 500.1263.

cis-4-(6-amino-2-chloro-9H-purin-9-yl)-N-((6-bromo-1,3-benzothiazol-2-yl)cyclohexanecarboxamide (I), cpd 175

[X=N, R1=CONR4R5, R4=Substituted Heteroaryl, R5=H, n=0, R3=Cl]

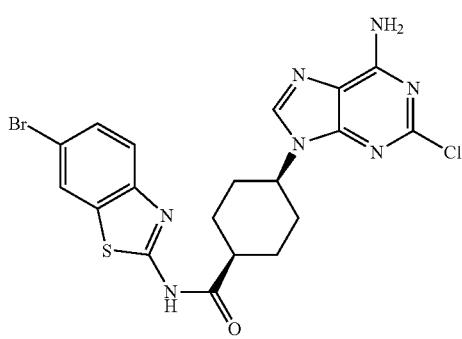

¹H NMR (500 MHz, DMSO-d$_6$) δ ppm 1.73-1.90 (m, 2H) 1.91-2.02 (m, 2H) 2.04-2.27 (m, 4H) 2.88-2.95 (m, 1H) 4.34-4.45 (m, 1H) 7.57 (dd, J=8.54, 1.98 Hz, 1H) 7.67 (d, J=8.54 Hz, 1H) 7.75 (br. s., 2H) 8.23 (s, 1H) 8.26 (d, J=1.98 Hz, 1H) 12.46 (br. s., 1H)

HRMS (ESI+): calcd. for C$_{19}$H$_{18}$BrClN$_7$OS [M+H]$^+$ 506.0160; found 506.0165.

cis-4-(6-amino-2-chloro-9H-purin-9-yl)-N-(4,4,6,6-tetramethyl-4,5,6,7-tetrahydro[1,3]thiazolo[5,4-c]pyridin-2-yl)cyclohexanecarboxamide (I), cpd 178

[X=N, R1=CONR4R5, R4=Substituted Heteroaryl, R5=H, n=0, R3=Cl]

146

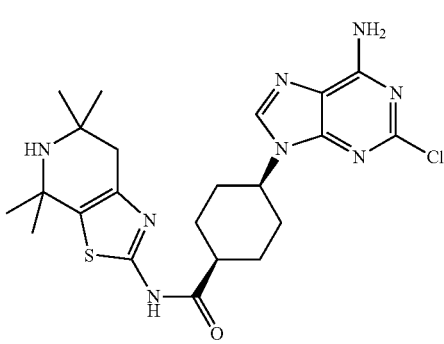 [SMILES: CC1(C)Cc2nc(NC(=O)[C@H]3CC[C@@H](n4cnc5c(N)nc(Cl)nc54)CC3)sc2C(C)(C)N1]

¹H NMR (500 MHz, DMSO-d$_6$) δ ppm 1.11 (s, 6H) 1.37 (s, 6H) 1.72-1.85 (m, 2H) 1.87-1.98 (m, 2H) 2.02-2.25 (m, 4H) 2.42 (s, 2H) 2.74-2.86 (m, 1H) 4.28-4.43 (m, 1H) 7.74 (br. s., 2H) 8.21 (s, 1H) 11.91 (br. s., 1H).

HRMS (ESI+): calcd. for C$_{22}$H$_{30}$ClN$_8$OS [M+H]$^+$ 489.1947; found 489.1938.

cis-4-(6-amino-2-fluoro-9H-purin-9-yl)-N-(5-methyl-4,5,6,7-tetrahydro[1,3]thiazolo[5,4-c]pyridin-2-yl)cyclohexanecarboxamide (I), cpd 179

[X=N, R1=CONR4R5, R4=Substituted Heteroaryl, R5=H, n=0, R3=F]

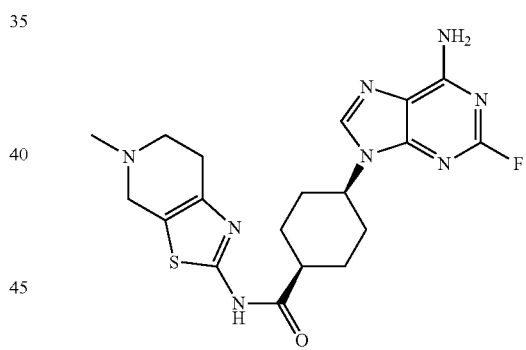

¹H NMR (500 MHz, DMSO-d$_6$) δ ppm 1.73-1.85 (m, 2H) 1.88-1.98 (m, 2H) 2.02-2.11 (m, 2H) 2.13-2.24 (m, 2H) 2.36 (s, 3H) 2.61-2.70 (m, 4H) 2.77-2.84 (m, 1H) 3.48 (s, 2H) 4.27-4.40 (m, 1H) 7.76 (br. s., 2H) 8.16 (s, 1H) 11.93 (s, 1H).

HRMS (ESI+): calcd. for C$_{19}$H$_{24}$FN$_8$OS [M+H]$^+$ 431.1773; found 431.1768.

cis-4-(6-amino-2-chloro-9H-purin-9-yl)-N-[6-(difluoromethoxy)-1,3-benzothiazol-2-yl]cyclohexanecarboxamide (I), cpd 180

[X=N, R1=CONR4R5, R4=Substituted Heteroaryl, R5=H, n=0, R3=Cl]

147

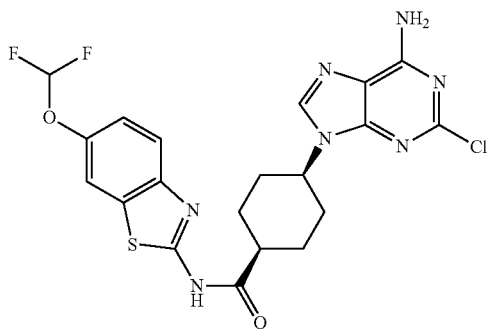 [SMILES: Nc1nc(Cl)nc2c1ncn2[C@H]1CC[C@@H](C(=O)Nc2nc3ccc(OC(F)F)cc3s2)CC1]

¹H NMR (500 MHz, DMSO-d₆) δ ppm 1.80-1.90 (m, 2H) 1.91-2.01 (m, 2H) 2.10-2.25 (m, 4H) 2.86-2.97 (m, 1H) 4.30-4.45 (m, 1H) 7.23 (t, J=74.12 Hz, 1H) 7.25 (dd, J=8.69, 2.59 Hz, 1H) 7.75 (br. s, 2H) 7.76 (d, J=8.69 Hz, 3H) 7.88 (d, J=2.59 Hz, 1H) 8.23 (s, 1H) 12.41 (br. s., 1H).

HRMS (ESI+): calcd. for $C_{20}H_{19}ClF_2N_7O_2S$ [M+H]⁺ 494.0972; found 494.0965.

cis-4-(6-amino-2-chloro-9H-purin-9-yl)-N-[6-(trifluoromethoxy)-1,3-benzothiazol-2-yl]cyclohexanecarboxamide (I), cpd 181

[X=N, R1=CONR4R5, R4=Substituted Heteroaryl, R5=H, n=0, R3=Cl]

148

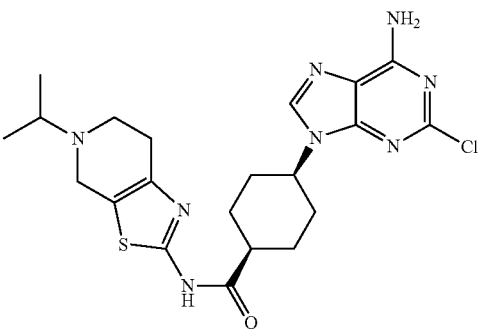

¹H NMR (500 MHz, DMSO-d₆) δ ppm 1.05 (d, J=6.56 Hz, 6H) 1.76-1.86 (m, 2H) 1.89-1.97 (m, 2H) 2.02-2.11 (m, 2H) 2.11-2.21 (m, 2H) 2.57-2.62 (m, 2H) 2.72-2.78 (m, 2H) 2.79-2.85 (m, 1H) 2.86-2.95 (m, 1H) 3.60 (s, 2H) 4.32-4.43 (m, 1H) 7.74 (br. s., 2H) 8.21 (s, 1H) 11.90 (br. s., 1H).

HRMS (ESI+): calcd. for $C_{21}H_{28}ClN_8OS$ [M+H]⁺ 475.1790; found 475.1783; cis-N-[6-(acetylamino)-1,3-benzothiazol-2-yl]-4-(6-amino-2-chloro-9H-purin-9-yl)cyclohexanecarboxamide (I), cpd 183

[X=N, R1=CONR4R5, R4=Substituted Heteroaryl, R5=H, n=0, R3=Cl]

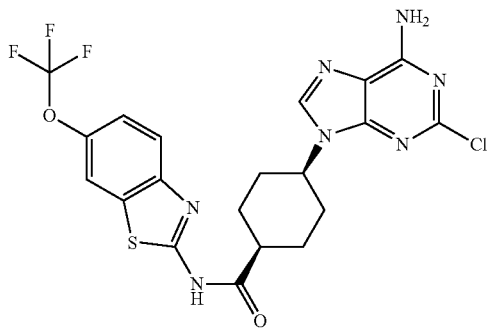 [SMILES: Nc1nc(Cl)nc2c1ncn2[C@H]1CC[C@@H](C(=O)Nc2nc3ccc(OC(F)(F)F)cc3s2)CC1]

¹H NMR (500 MHz, DMSO-d₆) δ ppm 1.79-1.92 (m, 2H) 1.93-2.02 (m, 2H) 2.10-2.25 (m, 4H) 2.85-2.94 (m, 1H) 4.30-4.46 (m, 1H) 7.41 (dd, J=8.62, 1.60 Hz, 1H) 7.75 (br. s., 2H) 7.81 (d, J=8.62 Hz, 1H) 8.12 (s, 1H) 8.23 (s, 1H) 12.50 (br. s., 1H)

HRMS (ESI+): calcd. for $C_{20}H_{18}ClF_3N_7O_2S$ [M+H]⁺ 512.0878; found 512.0878.

cis-4-(6-amino-2-chloro-9H-purin-9-yl)-N-[5-(propan-2-yl)-4,5,6,7-tetrahydro[1,3]thiazolo[5,4-c]pyridin-2-yl]cyclohexanecarboxamide (I), cpd 182

[X=N, R1=CONR4R5, R4=Substituted Heteroaryl, R5=H, n=0, R3=Cl]

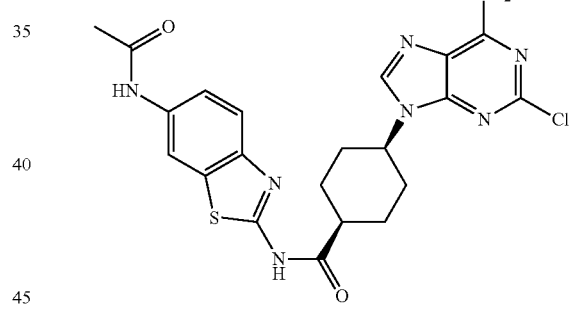

¹H NMR (500 MHz, DMSO-d₆) δ ppm 1.78-1.91 (m, 2H) 1.93-1.99 (m, 2H) 2.06 (s, 3H) 2.08-2.25 (m, 4H) 2.85-2.93 (m, 1H) 4.34-4.45 (m, 1H) 7.47 (dd, J=8.69, 1.98 Hz, 1H) 7.65 (d, J=8.69 Hz, 1H) 7.74 (br. s., 2H) 8.23 (s, 1H) 8.31 (d, J=1.98 Hz, 1H) 10.08 (br. s., 1H) 12.29 (br. s., 1H).

HRMS (ESI+): calcd. for $C_{21}H_{22}ClN_8O_2S$ [M+H]⁺ 485.1270; found 485.1268.

cis-4-(6-amino-2-chloro-9H-purin-9-yl)-N-(5-cyclopropyl-4,5,6,7-tetrahydro[1,3]thiazolo[5,4-c]pyridin-2-yl)cyclohexanecarboxamide (I), cpd 184

[X=N, R1=CONR4R5, R4=Substituted Heteroaryl, R5=H, n=0, R3=Cl]

149

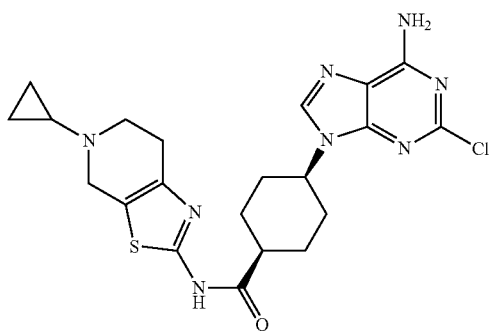 [SMILES: Nc1nc(Cl)nc2c1ncn2[C@H]1CC[C@@H](C(=O)Nc2nc3c(s2)CN(C2CC2)CC3)CC1]

¹H NMR (500 MHz, DMSO-d₆) δ ppm 0.36-0.43 (m, 2H) 0.45-0.53 (m, 2H) 1.74-1.84 (m, 2H) 1.88-1.96 (m, 2H) 2.03-2.09 (m, 2H) 2.10-2.21 (m, 2H) 2.58-2.65 (m, 2H) 2.77-2.84 (m, 1H) 2.88-2.95 (m, 2H) 3.69 (s, 2H) 4.33-4.42 (m, 1H) 7.74 (br. s., 2H) 8.20 (s, 1H) 11.92 (br. s., 1H).

HRMS (ESI+): calcd. for $C_{21}H_{26}ClN_8OS$ [M+H]⁺ 473.1634; found 473.1628.

cis-4-(6-amino-2-chloro-9H-purin-9-yl)-N-(6,7-dihydro-4H-pyrano[4,3-d][1,3]thiazol-2-yl)cyclohexanecarboxamide (I), cpd 185

[X=N, R1=CONR4R5, R4=Substituted Heteroaryl, R5=H, n=0, R3=Cl]

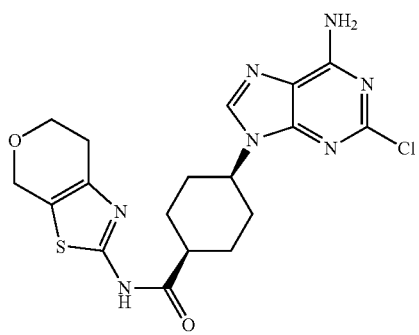 [SMILES: Nc1nc(Cl)nc2c1ncn2[C@H]1CC[C@@H](C(=O)Nc2nc3c(s2)COCC3)CC1]

¹H NMR (500 MHz, DMSO-d₆) δ ppm 1.74-1.86 (m, 2H) 1.89-2.00 (m, 2H) 2.03-2.10 (m, 2H) 2.11-2.21 (m, 2H) 2.60-2.70 (m, 2H) 2.78-2.86 (m, 1H) 3.91 (t, J=5.57 Hz, 2H) 4.33-4.44 (m, 1H) 4.68 (s, 2H) 7.74 (br. s., 2H) 8.21 (s, 1H) 12.00 (br. s., 1H).

HRMS (ESI+): calcd. for $C_{18}H_{21}ClN_7O_2S$ [M+H]⁺ 434.1161; found 434.1161.

cis-4-(6-amino-2-chloro-9H-purin-9-yl)-N-([1,3]dioxolo[4,5-f][1,3]benzothiazol-6-yl)cyclohexanecarboxamide (I), cpd 186

[X=N, R1=CONR4R5, R4=Substituted Heteroaryl, R5=H, n=0, R3=Cl]

150

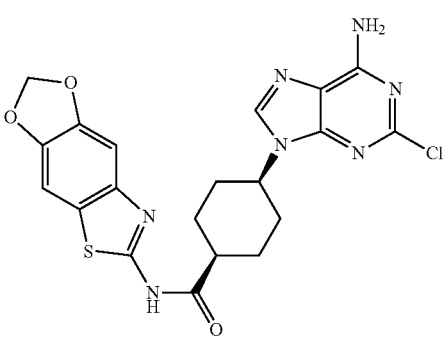 [SMILES: Nc1nc(Cl)nc2c1ncn2[C@H]1CC[C@@H](C(=O)Nc2nc3cc4c(cc3s2)OCO4)CC1]

¹H NMR (500 MHz, DMSO-d₆) δ ppm 1.69-1.88 (m, 2H) 1.90-1.99 (m, 2H) 2.06-2.13 (m, 2H) 2.16-2.24 (m, 2H) 2.81-2.95 (m, 1H) 4.35-4.44 (m, 1H) 6.07 (s, 2H) 7.27 (s, 1H) 7.52 (s, 1H) 7.75 (br. s., 2H) 8.22 (s, 1H) 12.22 (br. s., 1H).

HRMS (ESI+): calcd. for $C_{20}H_{19}ClN_7O_3S$ [M+H]⁺ 472.0953; found 472.0949.

tert-butyl (5S,8R)-2-({[cis-4-(6-amino-2-chloro-9H-purin-9-yl)cyclohexyl]carbonyl}amino)-5,6,7,8-tetrahydro-4H-5,8-epiminocyclohepta[d][1,3]thiazole-9-carboxylate (I), cpd 187

[X=N, R1=CONR4R5, R4=Substituted Heteroaryl, R5=H, n=0, R3=Cl]

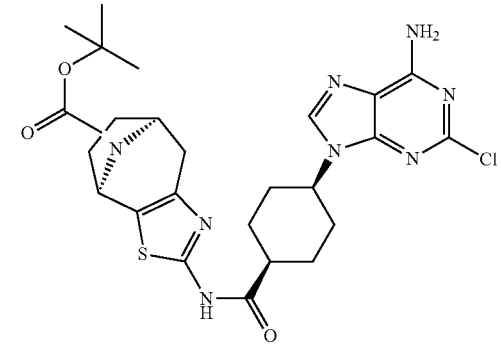

¹H NMR (500 MHz, DMSO-d₆) δ ppm 1.31 (s, 9H) 1.54-1.67 (m, 1H) (br. s., 1H) 1.71-1.85 (m, 4H) 1.86-1.99 (m, 2H) 1.99-2.31 (m, 6H) 2.40-2.47 (m, 1H) 2.79-2.83 (m, 1H) 3.05-3.16 (m, 1H) 4.27-4.48 (m, 2H) 4.93-5.01 (m, 1H) 7.74 (br. s., 2H) 8.21 (s, 1H) 11.96 (br. s., 1H).

HRMS (ESI+): calcd. for $C_{25}H_{32}ClN_8O_3S$ [M+H]⁺ 472.0953; found 472.0949.

cis-4-(6-amino-2-chloro-9H-purin-9-yl)-N-(6,6-difluoro-4,5,6,7-tetrahydro-1,3-benzothiazol-2-yl)cyclohexanecarboxamide (I), cpd 188

[X=N, R1=CONR4R5, R4=Substituted Heteroaryl, R5=H, n=0, R3=Cl]

151

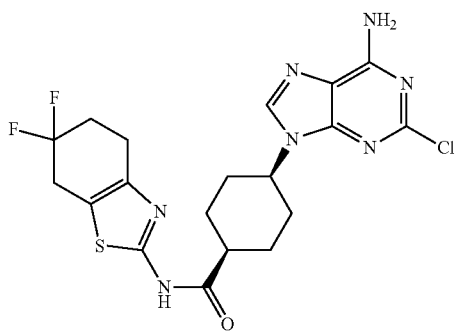 [SMILES: Nc1nc(Cl)nc2c1ncn2[C@H]1CC[C@@H](C(=O)Nc2nc3c(s2)CC(F)(F)CC3)CC1]

¹H NMR (500 MHz, DMSO-d$_6$) δ ppm 1.72-1.84 (m, 2H) 1.88-1.99 (m, 2H) 2.03-2.20 (m, 4H) 2.23-2.36 (m, 2H) 2.78 (t, J=6.63 Hz, 2H) 2.79-2.85 (m, 1H) 3.27 (t, J=13.50 Hz, 2H) 4.31-4.47 (m, 1H) 7.74 (br. s., 2H) 8.20 (s, 1H) 12.02 (br. s., 1H).

HRMS (ESI+): calcd. for C$_{19}$H$_{21}$ClF$_2$N$_7$OS [M+H]$^+$ 468.1180; found 468.1173.

cis-4-(6-amino-2-fluoro-9H-purin-9-yl)-N-(4,4,6,6-tetramethyl-4,5,6,7-tetrahydro[1,3]thiazolo[5,4-c]pyridin-2-yl)cyclohexanecarboxamide (I), cpd 190

[X=N, R1=CONR4R5, R4=Substituted Heteroaryl, R5=H, n=0, R3=F]

152

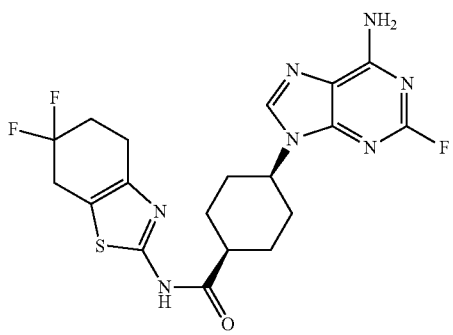

¹H NMR (500 MHz, DMSO-d$_6$) δ ppm 1.73-1.85 (m, 2H) 1.87-1.98 (m, 2H) 2.04-2.10 (m, 2H) 2.14-2.21 (m, 2H) 2.23-2.35 (m, 2H) 2.78 (t, J=6.71 Hz, 2H) 2.80-2.85 (m, 1H) 3.27 (t, J=13.73 Hz, 2H) 4.25-4.38 (m, 1H) 7.74 (br. s., 2H) 8.15 (s, 1H) 12.02 (br. s., 1H).

HRMS (ESI+): calcd. for C$_{19}$H$_{21}$F$_3$N$_7$OS [M+H]$^+$ 452.1475; found 452.1468.

cis-4-(6-amino-2-chloro-9H-purin-9-yl)-N-(5,5-dioxido-6,7-dihydro-4H-thiopyrano[4,3-d][1,3]thiazol-2-yl)cyclohexanecarboxamide (I), cpd 194

[X=N, R1=CONR4R5, R4=Substituted Heteroaryl, R5=H, n=0, R3=Cl]

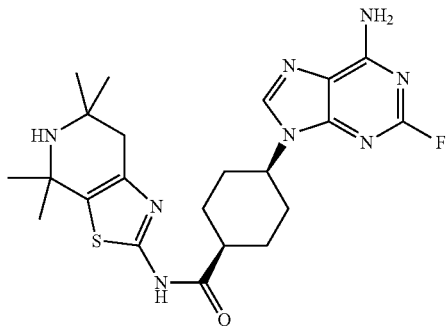 [SMILES: CC1(C)Cc2nc(NC(=O)[C@H]3CC[C@@H](n4cnc5c(N)nc(F)nc54)CC3)sc2C(C)(C)N1]

¹H NMR (500 MHz, DMSO-d$_6$) δ ppm 1.11 (s, 6H) 1.36 (s, 6H) 1.70-1.81 (m, 2H) 1.82-1.87 (br. s., 1H) 1.89-1.96 (m, 2H) 2.01-2.11 (m, 2H) 2.13-2.23 (m, 2H) 2.41 (s, 2H) 2.77-2.83 (m, 1H) 4.25-4.38 (m, 1H) 7.75 (br. s., 2H) 8.16 (s, 1H) 11.91 (br. s., 1H).

HRMS (ESI+): calcd. for C$_{22}$H$_{30}$FN$_8$OS [M+H]$^+$ 473.2242; found 473.2235.

cis-4-(6-amino-2-fluoro-9H-purin-9-yl)-N-(6,6-difluoro-4,5,6,7-tetrahydro-1,3-benzothiazol-2-yl)cyclohexanecarboxamide (I), cpd 191

[X=N, R1=CONR4R5, R4=Substituted Heteroaryl, R5=H, n=0, R3=F]

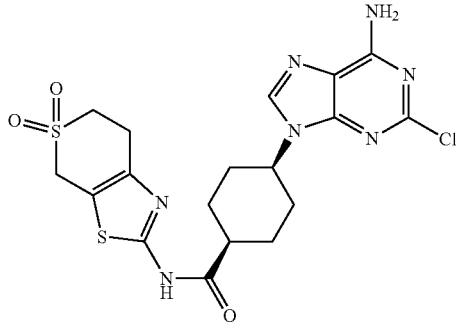 [SMILES: Nc1nc(Cl)nc2c1ncn2[C@H]1CC[C@@H](C(=O)Nc2nc3c(s2)CS(=O)(=O)CC3)CC1]

¹H NMR (500 MHz, DMSO-d$_6$) δ ppm 1.74-1.85 (m, 2H) 1.87-1.99 (m, 2H) 2.04-2.22 (m, 4H) 2.79-2.87 (m, 1H) 3.13 (t, J=6.41 Hz, 2H) 3.48 (t, J=6.10 Hz, 2H) 4.32-4.42 (m, 1H) 4.49 (s, 2H) 7.74 (br. s., 2H) 8.20 (s, 1H) 12.15 (br. s., 1H).

HRMS (ESI+): calcd. for C$_{18}$H$_{21}$ClN$_7$O$_3$S$_2$ [M+H]$^+$ 482.0831; found 482.0831.

cis-4-(6-amino-2-chloro-9H-purin-9-yl)-N-(6,6-dimethyl-6,7-dihydro-4H-pyrano[4,3-d][1,3]thiazol-2-yl)cyclohexanecarboxamide (I), cpd 195

[X=N, R1=CONR4R5, R4=Substituted Heteroaryl, R5=H, n=0, R3=Cl]

153

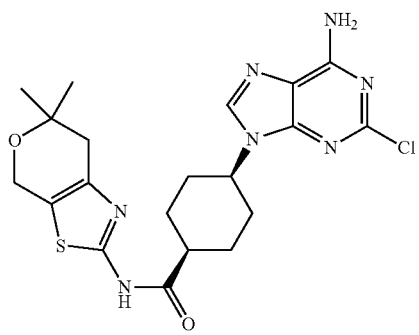 [SMILES: CC1(C)Cc2nc(NC(=O)[C@H]3CC[C@@H](n4cnc5c(N)nc(Cl)nc54)CC3)sc2CO1]

¹H NMR (500 MHz, DMSO-d₆) δ ppm 1.23 (s, 6H) 1.72-1.88 (m, 2H) 1.87-2.00 (m, 2H) 2.02-2.23 (m, 4H) 2.55 (br. s., 2H) 2.79-2.85 (m, 1H) 4.31-4.43 (m, 1H) 4.65 (br. s., 2H) 7.74 (br. s., 2H) 8.21 (s, 1H) 12.00 (br. s., 1H).

HRMS (ESI+): calcd. for $C_{20}H_{25}ClN_7O_3S_2$ [M+H]⁺ 462.1474; found 462.1466.

cis-4-(6-amino-2-chloro-9H-purin-9-yl)-N-[5-(2-amino-2-oxoethyl)-4,5,6,7-tetrahydro[1,3]thiazolo[5,4-c]pyridin-2-yl]cyclohexanecarboxamide (I), cpd 196

[X=N, R1=CONR4R5, R4=Substituted Heteroaryl, R5=H, n=0, R3=Cl]

154

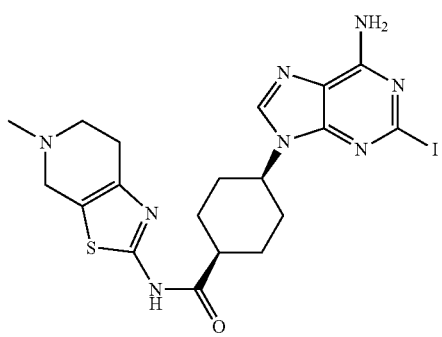

¹H NMR (500 MHz, DMSO-d₆) δ ppm 1.74-1.85 (m, 2H) 1.87-1.98 (m, 2H) 2.01-2.09 (m, 2H) 2.10-2.20 (m, 2H) 2.39 (s, 3H) 2.60-2.67 (m, 2H) 2.68-2.76 (m, 2H) 2.76-2.84 (m, 1H) 3.52 (br. s., 2H) 4.29-4.43 (m, 1H) 7.63 (br. s., 2H) 8.12 (s, 1H) 11.94 (br. s., 1H).

HRMS (ESI+): calcd. for $C_{19}H_{24}IN_8OS$ [M+H]⁺ 539.0833; found 539.0842.

cis-4-(6-amino-2-fluoro-9H-purin-9-yl)-N-(6,7-dihydro-4H-pyrano[4,3-d][1,3]thiazol-2-yl)cyclohexanecarboxamide (I), cpd 200

[X=N, R1=CONR4R5, R4=Substituted Heteroaryl, R5=H, n=0, R3=F]

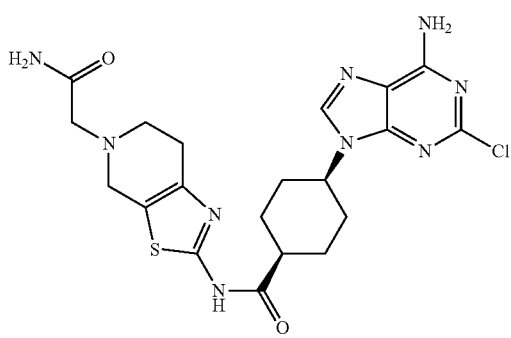 [SMILES: NC(=O)CN1CCc2nc(NC(=O)[C@H]3CC[C@@H](n4cnc5c(N)nc(Cl)nc54)CC3)sc2C1]

¹H NMR (500 MHz, DMSO-d₆) δ ppm 1.75-1.86 (m, 2H) 1.90-1.99 (m, 2H) 2.03-2.10 (m, 2H) 2.11-2.21 (m, 2H) 2.65-2.71 (m, 2H) 2.77-2.86 (m, 3H) 3.08 (s, 2H) 3.65 (s, 2H) 4.34-4.42 (m, 1H) 7.14 (br. s., 1H) 7.27 (br. s., 1H) 7.74 (br. s., 2H) 8.20 (s, 1H) 11.95 (s, 1H).

HRMS (ESI+): calcd. for $C_{20}H_{25}ClN_9O_2S$ [M+H]⁺ 490.1535; found 490.1535.

cis-4-(6-amino-2-iodo-9H-purin-9-yl)-N-(5-methyl-4,5,6,7-tetrahydro[1,3]thiazolo[5,4-c]pyridin-2-yl) cyclohexanecarboxamide (I), cpd 198

[X=N, R1=CONR4R5, R4=Substituted Heteroaryl, R5=H, n=0, R3=I]

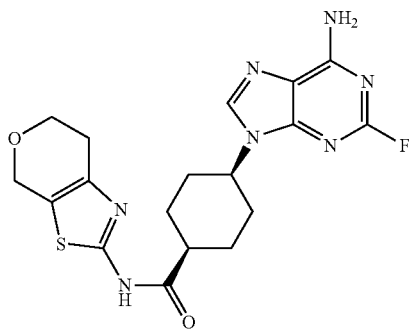 [SMILES: Nc1nc(F)nc2c1ncn2[C@H]1CC[C@@H](C(=O)Nc2nc3c(s2)COCC3)CC1]

¹H NMR (500 MHz, DMSO-d₆) δ ppm 1.72-1.86 (m, 2H) 1.88-1.98 (m, 2H) 2.03-2.11 (m, 2H) 2.13-2.23 (m, 2H) 2.61-2.70 (m, 2H) 2.78-2.85 (m, 1H) 3.91 (t, J=5.57 Hz, 2H) 4.29-4.40 (m, 1H) 4.68 (br. s., 2H) 7.74 (br. s., 2H) 8.16 (s, 1H) 12.00 (s, 1H).

HRMS (ESI+): calcd. for $C_{18}H_{21}FN_7O_2S$ [M+H]⁺ 418.1456; found 418.1457.

cis-4-(4-amino-1H-imidazo[4,5-c]pyridin-1-yl)-N-(4-methyl-1,3-thiazol-2-yl)cyclohexanecarboxamide (I), cpd 204

[X=CH, R1=CONR4R5, R4=Substituted Heteroaryl, R5=H, n=0, R3=H]

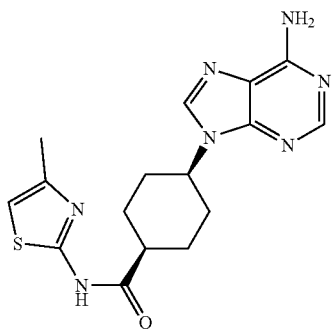 [SMILES: Cc1csc(NC(=O)[C@H]2CC[C@@H](n3cnc4c(N)ncnc43)CC2)n1]

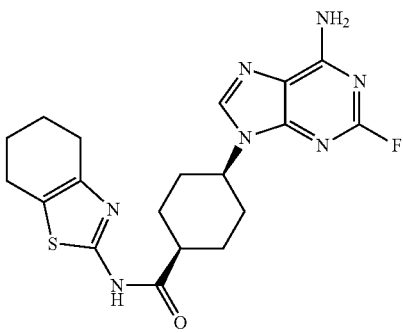

¹H NMR (500 MHz, DMSO-d₆) δ ppm 1.77-1.85 (m, 2H) 1.87-1.94 (m, 2H) 2.07-2.14 (m, 2H) 2.16-2.22 (m, 2H) 2.26 (s, 3H) 2.80-2.90 (m, 1H) 4.29-4.39 (m, 1H) 6.11 (s, 2H) 6.75 (s, 1H) 6.82 (d, J=5.80 Hz, 1H) 7.64 (d, J=5.80 Hz, 1H) 8.09 (s, 1H) 12.04 (br. s., 1H).

HRMS (ESI+): calcd. for $C_{17}H_{21}N_6OS$ [M+H]⁺ 357.1492; found 357.1496.

cis-4-(6-amino-2-chloro-9H-purin-9-yl)-N-(4,5,6,7-tetrahydro-1,3-benzothiazol-2-yl)cyclohexanecarboxamide (I), cpd 205

[X=N, R1=CONR4R5, R4=Substituted Heteroaryl, R5=H, n=0, R3=Cl]

¹H NMR (500 MHz, DMSO-d₆) δ ppm 1.71-1.84 (m, 6H) 1.88-1.97 (m, 2H) 2.02-2.11 (m, 2H) 2.11-2.23 (m, 2H) 2.54-2.56 (m, 2H) 2.61-2.66 (m, 2H) 2.76-2.82 (m, 1H) 4.28-4.37 (m, 1H) 7.74 (br. s., 2H) 8.15 (s, 1H) 11.85 (br. s., 1H).

HRMS (ESI+): calcd. for $C_{19}H_{23}FN_7OS$ [M+H]⁺ 416.1664; found 416.1666.

Example 15 cis-4-(6-amino-2-cyano-9H-purin-9-yl)-N-(4-methyl-1,3-thiazol-2-yl)cyclohexanecarboxamide (I), cpd 102

[X=N, R1=CONR4R5, R4=Substituted Heteroaryl, R5=H, n=0, R3=cyano]

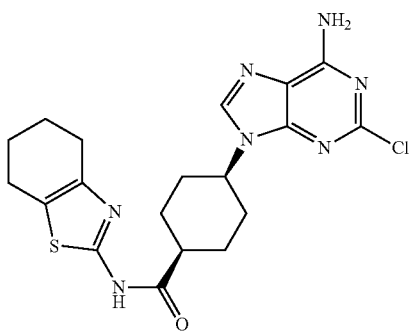 [SMILES: Nc1nc(Cl)nc2c1ncn2[C@H]1CC[C@@H](C(=O)Nc2nc3c(s2)CCCC3)CC1]

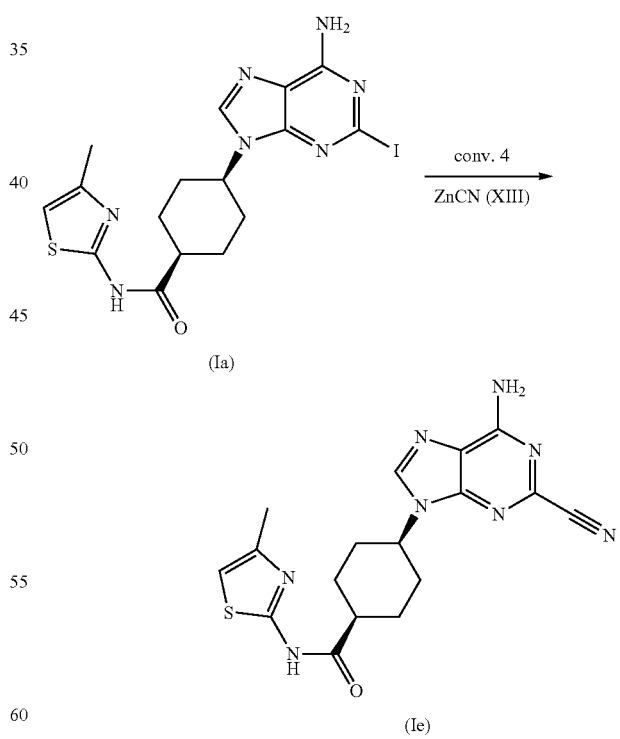

¹H NMR (500 MHz, DMSO-d₆) δ ppm 1.66-1.86 (m, 4H) 1.88-1.97 (m, 2H) 2.01-2.09 (m, 2H) 2.09-2.21 (m, 2H) 2.53-2.58 (m, 2H) 2.59-2.69 (m, 2H) 2.76-2.84 (m, 1H) 4.28-4.44 (m, 1H) 7.74 (br. s., 2H) 8.20 (s, 1H) 11.85 (s, 1H).

HRMS (ESI+): calcd. for $C_{19}H_{23}ClN_7OS$ [M+H]⁺ 432.1368; found 432.1373.

cis-4-(6-amino-2-fluoro-9H-purin-9-yl)-N-(4,5,6,7-tetrahydro-1,3-benzothiazol-2-yl)cyclohexanecarboxamide (I), cpd 206

[X=N, R1=CONR4R5, R4=Substituted Heteroaryl, R5=H, n=0, R3=F]

cis-4-(6-amino-2-iodo-9H-purin-9-yl)-N-(4-methyl-1,3-thiazol-2-yl)cyclohexanecarboxamide (Ia) (28 mg, 0.058 mmol), ZnCN (XIII) (17 mg, 0.145 mmol) and Pd(PPh₃)₄ (13 mg, 0.012 mmol) were charged in a microwave vial and dissolved in dry DMF (2 mL). The mixture was heated under microwave irradiation at 120° C. for 1 h. The same microwave irradiation cycle was repeated for another time. The mixture was diluted with EtOAc, washed with water and brine, dried over Na$_2$SO$_4$ and filtered. After solvent removal under reduced pressure, the title compound was purified by preparative HPLC and isolated as white solid (2 mg, 10%).

$^1$H NMR (499.7 MHz, DMSO-d$_6$) δ ppm 1.77-1.87 (m, 2H), 1.92-1.99 (m, 2H), 2.06-2.14 (m, 2H), 2.14-2.24 (m, 2H), 2.25 (d, J=0.9 Hz, 3H), 2.79-2.84 (m, 1H), 4.43-4.50 (m, 1H), 6.73 (s, 1H), 7.91 (br. s., 2H), 8.46 (s, 1H), 12.01 (br. s., 1H).

HRMS (ESI+): calcd. for C$_{17}$H$_{19}$N$_8$OS [M+H]$^+$ 383.1397; found 383.14.

Example 16

N-[cis-4-(6-amino-2-chloro-9H-purin-9-yl)cyclohexyl]-4-methyl-1,3-thiazole-2-carboxamide (I), cpd 139

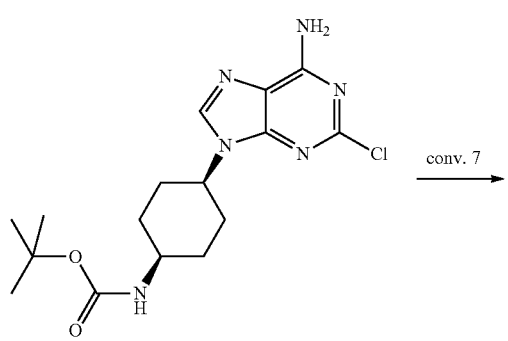

Conv. 7

9-(cis-4-aminocyclohexyl)-2-chloro-9H-purin-6-amine dihydrochloride (I), cpd 193

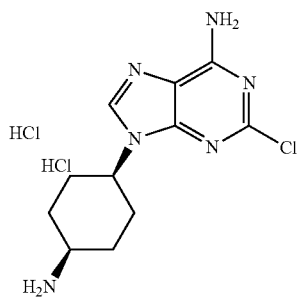 [SMILES: Cl ; Cl ; Nc1nc(Cl)nc2c1ncn2[C@H]1CC[C@@H](N)CC1]

Tert-butyl [cis-4-(6-amino-2-chloro-9H-purin-9-yl)cyclohexyl]carbamate (72 mg, 0.196 mmol) was treated with a 4 M solution of HCl in dioxane (4 mL) for 3 h at room temperature. The solvent was then removed under reduced pressure and the product was dried under vacuo (65 mg, quantitative yield).

$^1$H NMR (500 MHz, DMSO-d$_6$) δ ppm 1.88 (m, 6H) 2.19-2.34 (m, 2H) 3.64-3.74 (m, 1H) 4.37-4.49 (m, 1H) 4.38-4.48 (m, 1H) 7.78 (br. s., 2H) 8.11 (br. s., 3H) 8.40 (s, 1H).

HRMS (ESI+): calcd. for C$_{11}$H$_{16}$ClN$_6$ [M+H]$^+$ 267.1120; found 267.1120.

Conv. 9

N-[cis-4-(6-amino-2-chloro-9H-purin-9-yl)cyclohexyl]-4-methyl-1,3-thiazole-2-carboxamide (I), cpd 139

[X=N, R1=NR4COR5, R4=H, R5=Substituted Heteroaryl, n=0, R3=Cl]

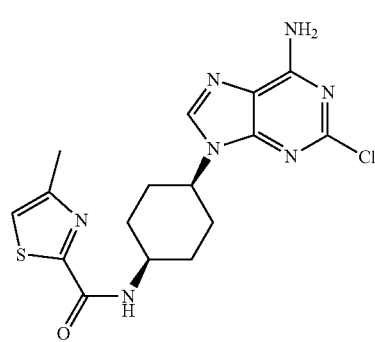 [SMILES: Cc1csc(C(=O)N[C@H]2CC[C@@H](n3cnc4c(N)nc(Cl)nc43)CC2)n1]

To a solution of 9-(cis-4-aminocyclohexyl)-2-chloro-9H-purin-6-amine dihydrochloride (20 mg, 0.059 mmol) in DMA (4 mL), TBTU (28 mg, 0.088 mmol), DIPEA (0.03 mL, 0.177 mmol) and 4-methyl-1,3-thiazole-2-carboxylic acid (XVII) (10 mg, 0.071 mmol) were added. The mixture was let under stirring overnight. After dilution with AcOEt, the organic layer was washed with a saturated solution of NaHCO$_3$, water and brine. The organic layer was dried over Na$_2$SO$_4$, filtered and taken to dryness under reduced pressure. The title product was purified on by column chromatography (eluant AcOEt, AcOEt:MeOH=95:5) and recovered as yellowish solid (7.5 mg, 32%).

$^1$H NMR (500 MHz, DMSO-d$_6$) δ ppm 1.76-1.84 (m, 2H) 1.86-1.96 (m, 4H) 2.21-2.34 (m, 2H) 4.13-4.21 (m, 1H) 4.39-4.49 (m, 1H) 7.61 (s, 1H) 7.75 (br. s., 2H) 8.40 (s, 1H) 8.53 (d, J=8.08 Hz, 1H).

HRMS (ESI+): calcd. for C$_{16}$H$_{19}$ClN$_7$OS [M+H]$^+$ 392.1055; found 392.1052.

Operating in an analogous way, but employing suitably substituted compounds, the following compounds were obtained:

N-[cis-4-(6-amino-2-chloro-9H-purin-9-yl)cyclohexyl]-1,3-benzothiazole-2-carboxamide (I), cpd 140

[X=N, R1=NR4COR5, R4=H, R5=Substituted Heteroaryl, n=0, R3=Cl]

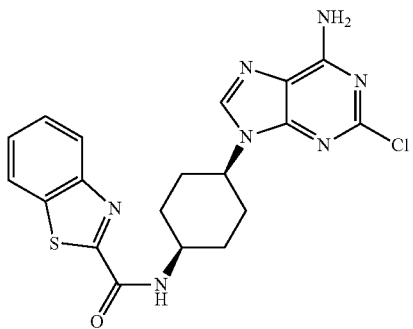 [SMILES: Nc1nc(Cl)nc2c1ncn2[C@H]1CC[C@@H](NC(=O)c2nc3ccccc3s2)CC1]

$^1$H NMR (500 MHz, DMSO-d$_6$) δ ppm 1.78-2.02 (m, 6H) 2.28-2.35 (m, 2H) 4.19-4.30 (m, 1H) 4.41-4.50 (m, 1H) 7.59 (dt, J=8.1, 1 Hz, 1H) 7.64 (dt, J=8.1, 1 Hz, 2H) 7.76 (br. s., 2H) 8.18 (d, J=8.1 Hz, 1H) 8.25 (d, J=8.1 Hz, 1H) 8.42 (s, 1H) 8.97 (d, J=7.93 Hz, 1H).

HRMS (ESI+): calcd. for C$_{19}$H$_{19}$ClN$_7$OS [M+H]$^+$ 428.1055; found 428.1057.

N-[cis-4-(6-amino-2-chloro-9H-purin-9-yl)cyclohexyl]-3-methoxybenzamide (I), cpd 144

[X=N, R1=NR4COR5, R4=H, R5=Substituted Aryl, n=0, R3=Cl]

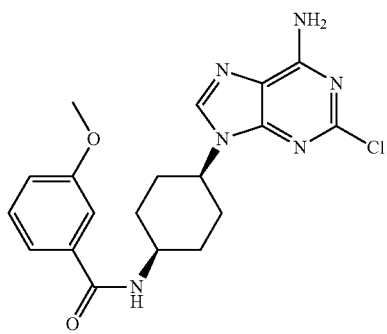 [SMILES: COc1cccc(C(=O)N[C@H]2CC[C@@H](n3cnc4c(N)nc(Cl)nc43)CC2)c1]

$^1$H NMR (500 MHz, DMSO-d$_6$) δ ppm 1.73-1.82 (m, 2H) 1.84-1.97 (m, 4H) 2.22-2.34 (m, 2H) 3.81 (s, 3H) 4.12-4.18 (m, 1H) 4.36-4.44 (m, 1H) 7.11 (ddd, J=8.12, 2.71, 0.91 Hz, 1H) 7.35-7.38 (m, 1H) 7.39 (t, J=8.12 Hz, 1H) 7.44-7.47 (m, 1H) 7.75 (br. s., 2H) 8.11 (d, J=7.02 Hz, 1H) 8.30 (s, 1H).

HRMS (ESI+): calcd. for C$_{19}$H$_{22}$ClN$_6$O$_2$ [M+H]$^+$ 401.1488; found 401.1483.

Example 17

1-[cis-4-(6-amino-2-chloro-9H-purin-9-yl)cyclohexyl]-3-(3-methoxyphenyl)urea (I), cpd 197

[X=N, R1=NR4CONR4R5, R4=H, R5=Substituted Aryl, n=0, R3=Cl]

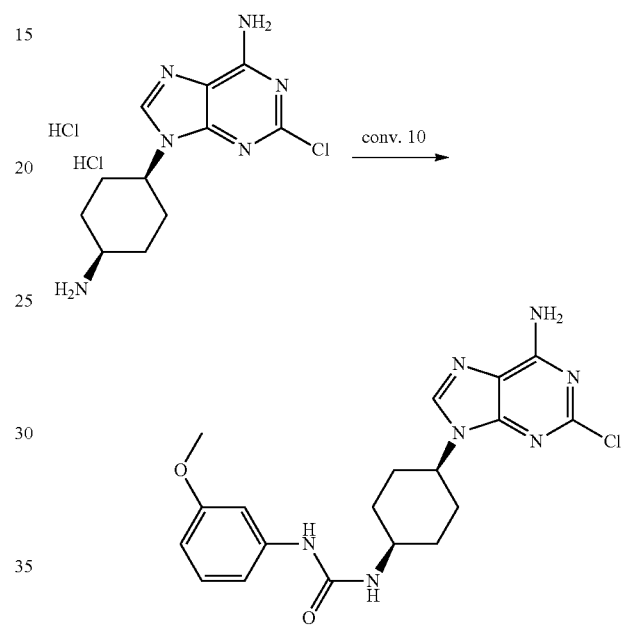

9-(Cis-4-aminocyclohexyl)-2-chloro-9H-purin-6-amine dihydrochloride (25 mg, 0.074 mmol) in DCM (4 mL) was treated with DIPEA (0.05 mL, 0.296 mmol) and 3-methoxyphenylisocyanate (XVIII) (0.015 mL, 0.111 mmol). The mixture was let under stirring at rt for 3 h, then the reaction was quanched with water. The mixture was extracted with DCM and the organic layer washed with water and brine. After treatment with Na$_2$SO$_4$ and filtration, the solvent was removed under reduced pressure. The title compound was purified by flash chromatography (eluant DCM, DCM:MeOH=98:2) and isolated as white solid (9.5 mg, 31%).

$^1$H NMR (500 MHz, DMSO-d$_6$) δ ppm 1.69-1.87 (m, 4H) 1.90-2.07 (m, 4H) 3.71 (s, 3H) 3.84-3.93 (m, 1H) 4.29-4.41 (m, 1H) 6.41-6.51 (m, 2H) 6.85 (dd, J=8.08, 1.22 Hz, 1H) 7.12 (t, J=8.08 Hz, 1H) 7.15 (t, J=2.14 Hz, 1H) 7.76 (br. s., 2H) 8.23 (s, 1H) 8.32 (s, 1H).

HRMS (ESI+): calcd. for C$_{19}$H$_{23}$ClN$_7$O$_2$ [M+H]$^+$ 416.1597; found 416.1596.

Example 18

N-[cis-4-(6-amino-2-chloro-9H-purin-9-yl)cyclohexyl]-3-methoxybenzenesulfonamide (I), cpd 141

[X=N, R1=NR4SO$_2$R6, R4=H, R6=Substituted Aryl, n=0, R3=Cl]

161

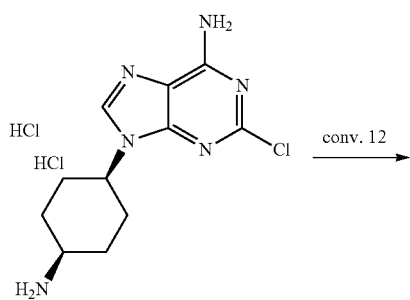

conv. 12 →

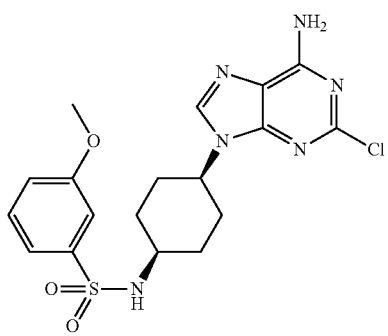

9-(Cis-4-aminocyclohexyl)-2-chloro-9H-purin-6-amine dihydrochloride (20 mg, 0.059 mmol) in DCM (4 mL) was treated with DIPEA (0.04 mL, 0.236 mmol) and 3-methoxyphenylsulfonyl chloride (XX) (0.01 mL, 0.065 mmol). The mixture was let under stirring at rt for 3 h, then the reaction was quanched with water. The mixture was extracted with DCM and the organic layer washed with water and brine. After treatment with Na$_2$SO$_4$ and filtration, the solvent was removed under reduced pressure. The title compound was purified by flash chromatography (eluant AcOEt, AcOEt:MeOH=95:5) and isolated as white solid (15 mg, 56%).

$^1$H NMR (500 MHz, DMSO-d$_6$) δ ppm 1.50-1.68 (m, 4H) 1.59-1.71 (m, 2H) 2.01-2.17 (m, 2H) 3.36-3.42 (m, 1H) 3.82 (s, 3H) 4.19-4.30 (m, 1H) 7.20 (ddd, J=8.24, 2.59, 0.92 Hz, 1H) 7.36-7.40 (m, 1H) 7.41-7.46 (m, 1H) 7.52 (t, J=8.24 Hz, 1H) 7.75 (br. s., 2H) 7.86 (d, J=7.32 Hz, 1H) 8.24 (s, 1H).

HRMS (ESI+): calcd. for C$_{18}$H$_{22}$ClN$_6$O$_3$S [M+H]$^+$ 437.1157; found 437.1163.

Example 19 cis-4-(6-amino-2-chloro-9H-purin-9-yl)-N-[6-(2-amino-2-oxoethyl)-1,3-benzothiazol-2-yl]cyclohexanecarboxamide (I), cpd 177

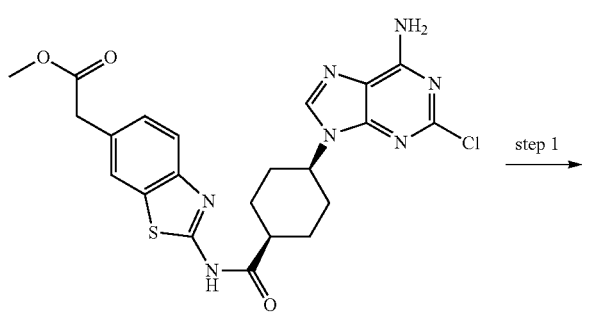

step 1 →

162

-continued

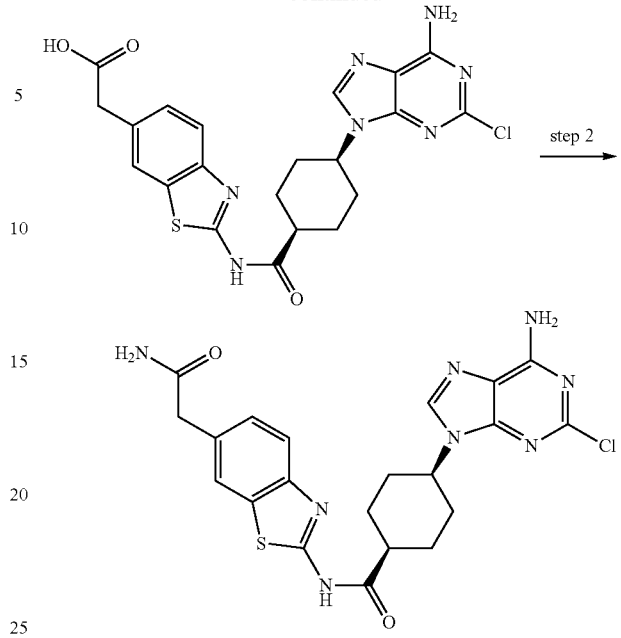

Step 1

[2-({[cis-4-(6-amino-2-chloro-9H-purin-9-yl)cyclohexyl]carbonyl}amino)-1,3-benzothiazol-6-yl]acetic acid (I), cpd 176

[X=N, R1=CONR4R5, R4=Substituted Heteroaryl, R5=H, n=0, R3=Cl]

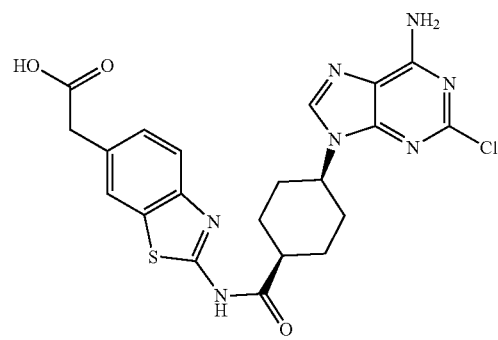 [SMILES: Nc1nc(Cl)nc2c1ncn2[C@H]1CC[C@@H](C(=O)Nc2nc3ccc(CC(=O)O)cc3s2)CC1]

A suspension of methyl [2-({[cis-4-(6-amino-2-chloro-9H-purin-9-yl)cyclohexyl]carbonyl}amino)-1,3-benzothiazol-6-yl]acetate (33 mg, 0.066 mmol) in THF (1.4 mL) and water (2.8 mL) was treated with 2 N NaOH (0.1 mL, 0.198 mmol) for 2 h at rt. After quenching with 2 N HCl (0.1 mL), the precipitate was filtered and the title compound was isolated as white solid (22 mg, 67%).

$^1$H NMR (500 MHz, DMSO-d$_6$) δ ppm 1.78-1.91 (m, 2H) 1.91-2.03 (m, 2H) 2.08-2.26 (m, 4H) 2.87-2.95 (m, 1H) 3.67 (s, 2H) 4.34-4.45 (m, 1H) 7.32 (dd, J=8.39, 1.22 Hz, 1H) 7.67 (d, J=8.39 Hz, 1H) 7.75 (br. s., 2H) 7.84 (d, J=1.22 Hz, 1H) 8.24 (s, 1H) 12.34 (br. s., 2H).

HRMS (ESI+): calcd. for C$_{21}$H$_{21}$ClN$_7$O$_3$S [M+H]$^+$ 486.1110; found 486.1111.

Step 2 cis-4-(6-amino-2-chloro-9H-purin-9-yl)-N-[6-(2-amino-2-oxoethyl)-1,3-benzothiazol-2-yl]cyclohexanecarboxamide (I), cpd 177

[X=N, R1=CONR4R5, R4=Substituted Heteroaryl, R5=H, n=0, R3=Cl]

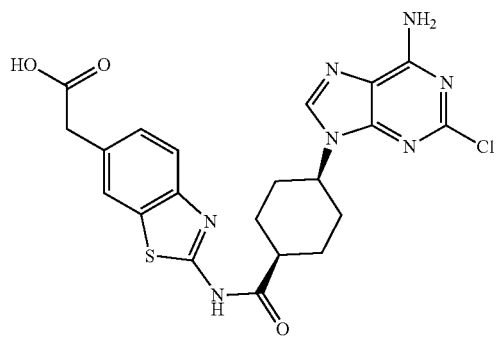 [SMILES: Nc1nc(Cl)nc2c1ncn2[C@H]1CC[C@@H](C(=O)Nc2nc3ccc(CC(=O)O)cc3s2)CC1]

A solution of [2-({[cis-4-(6-amino-2-chloro-9H-purin-9-yl)cyclohexyl]carbonyl}amino)-1,3-benzothiazol-6-yl]acetic acid (17 mg, 0.035 mmol), TBTU (17 mg, 0.052 mmol), DIPEA (0.018 mL, 0.139 mmol) and NH$_4$Cl (4 mg, 0.069 mmol) in DMA (3 mL) was let under stirring at rt overnight. After dilution with EtOAc, the mixture was washed with a saturated solution of NaHCO$_3$, water and brine, dried over Na$_2$SO$_4$ and filtered. The title compound was isolated as white solid (10 mg, 65%).

$^1$H NMR (500 MHz, DMSO-d$_6$) δ ppm 1.78-1.91 (m, 2H) 1.91-2.02 (m, 2H) 2.09-2.25 (m, 4H) 2.84-2.96 (m, 1H) 3.47 (s, 2H) 4.30-4.48 (m, 1H) 6.91 (br. s., 1H) 7.32 (dd, J=8.31, 1.45 Hz, 1H) 7.46-7.52 (m, 2H) 7.66 (d, J=8.24 Hz, 1H) 7.75 (br. s., 2H) 7.82 (s, 1H) 8.24 (s, 1H) 12.33 (br. s., 1H).

HRMS (ESI+): calcd. for C$_{21}$H$_{22}$ClN$_8$O$_2$S [M+H]$^+$ 485.1270; found 485.1266.

Example 20

6-amino-9-{cis-4-[(4-methyl-1,3-thiazol-2-yl)carbamoyl]cyclohexyl}-9H-purine-2-carboxamide (I), cpd 146

[X=N, R1=CONR4R5, R4=Substituted Heteroaryl, R5=H, n=0, R3=CONR4R5, R4=R5=H]

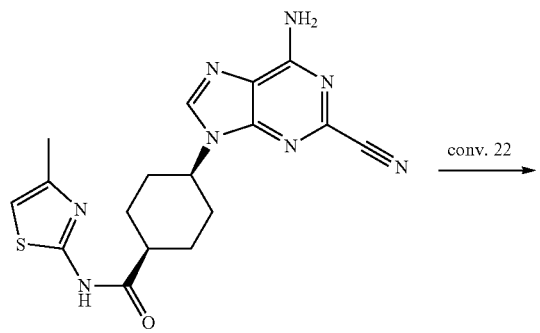

conv. 22

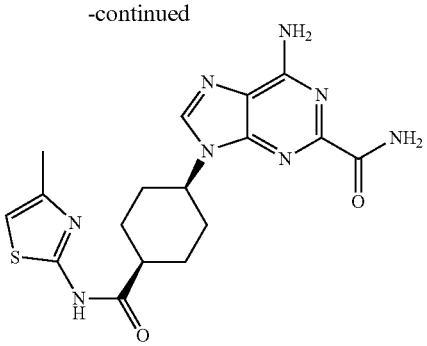

Conv. 22

A solution of cis-4-(6-amino-2-cyano-9H-purin-9-yl)-N-(4-methyl-1,3-thiazol-2-yl)cyclohexanecarboxamide (98 mg, 0.256 mmol) in 1,2-dichlorobenzene (12 mL) was treated with InCl$_3$ (6 mg, 0.026 mmol) and acetaldoxime (0.31 mL, 5.12 mmol) and heated at 120° C. for 3 h. The mixture was let to reach rt, diluted with DCM and washed with water. The aqueous layer was extracted with n-butanol for 3 times and the organic layer was evaporated to dryness under reduced pressure. After column chromatography (eluant DCM, DCM:MeOH=95:5 to 85:15), the title compound was isolated was light yellow solid (26 mg, 25%).

$^1$H NMR (500 MHz, DMSO-d$_6$) δ ppm 1.75-1.83 (m, 2H) 1.86-1.96 (m, 2H) 2.06-2.15 (m, 2H) 2.26 (s, 3H) 2.32-2.45 (m, 2H) 2.79-2.88 (m, 1H) 4.44-4.55 (m, 1H) 6.73 (s, 1H) 7.43 (br. s., 2H) 7.57 (br. s., 1H) 7.92 (br. s., 1H) 8.29 (s, 1H) 12.03 (br. s., 1H).

HRMS (ESI+): calcd. for C$_{17}$H$_{21}$N$_8$O$_2$S [M+H]$^+$ 485.1270; found 485.1266.

Preparations

Preparation 1

2-Methoxy-9H-purin-6-amine (VII)

[X=N, R3=OR6, R6=(C$_1$-C$_6$)alkyl]

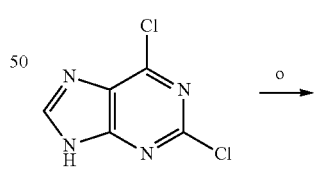

(VI)

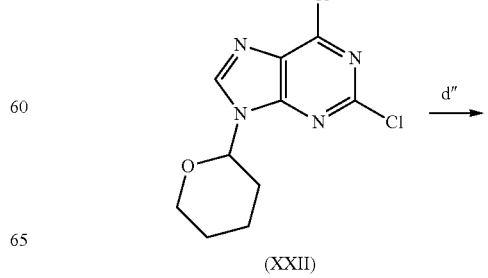

(XXII)

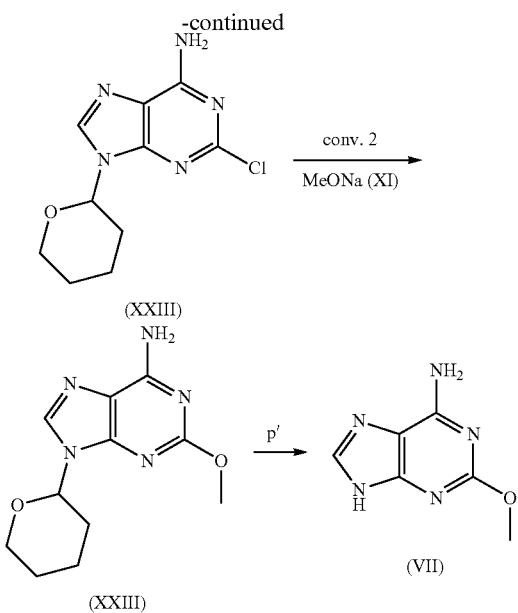

Step o 2,6-Dichloro-9-(tetrahydro-2H-pyran-2-yl)-9H-purine (XXII)

[X=N, R3=Cl, PG'=tetrahydropyranyl]

2,6-Dichloropurine (VI) (1 g, 5.29 mmol), 3,4-dihydro-2H-pyran (DHP) (0.525 mL, 9 mmol) and p-toluensulfonic acid mono hydrate (10 mg, 0.053 mmol) were added to EtOAc (20 mL) heated at 50° C. The solution was kept at 60° C. for 2 h. After cooling to rt and quenching with 33% aqueous ammonia (1 mL), the mixture was diluted with EtOAc and washed with water and brine. The organic layer was dried over $Na_2SO_4$, filtered and evaporated to dryness in vacuo. The title compound was obtained as a white solid (840 mg, 60%) after column chromatography (eluant hex:EtOAc=9:1).

$^1$H NMR (500 MHz, DMSO-$d_6$) δ ppm 1.52-1.67 (m, 2H) 1.69-1.82 (m, 1H) 1.92-2.04 (m, 2H) 2.19-2.32 (m, 1H) 3.68-3.79 (m, 1H) 3.96-4.08 (m, 1H) 5.74 (dd, J=10.90, 2.21 Hz, 1H) 8.96 (s, 1H).

HRMS (ESI+): calcd. for $C_{10}H_{10}Cl_2N_4NaO$ [M+Na]$^+$ 295.0124; found 295.0129.

Step d''

2-Chloro-9-(tetrahydro-2H-pyran-2-yl)-9H-purin-6-amine (XXIII)

[X=N, R3=Cl, PG'=tetrahydropyranyl]

2,6-Dichloro-9-(tetrahydro-2H-pyran-2-yl)-9H-purine (XXII) (834 mg, 3.06 mmol) was treated with a 7 N methanolic ammonia solution (10 mL) in a sealed tube at 100° C. for 3 h. While cooling to rt, a white precipitate formed. Water (5 mL) was added and the suspension was let under stirring for 1.5 h. The white solid was filtered, washed with water and dried affording 600 mg (77%) of the title compound.

$^1$H NMR (500 MHz, DMSO-$d_6$) δ ppm 1.43-1.63 (m, 2H) 1.65-1.83 (m, 1H) 1.88-2.04 (m, 2H) 2.13-2.28 (m, 1H) 3.63-3.73 (m, 1H) 3.96-4.02 (m, 1H) 5.55 (dd, J=10.98, 1.98 Hz, 1H) 7.81 (br. s., 2H) 8.36 (s, 1H) HRMS (ESI+): calcd. for $C_{10}H_{13}ClN_5O$ [M+H]$^+$ 254.0803; found 254.0807.

Conv. 2

2-methoxy-9-(tetrahydro-2H-pyran-2-yl)-9H-purin-6-amine (XXIII)

[X=N, R3=OR6, R6=($C_1$-$C_6$)alkyl, PG'=tetrahydropyranyl]

A solution of 2-chloro-9-(tetrahydro-2H-pyran-2-yl)-9H-purin-6-amine (XXIII) (530 mg, 2.08 mmol) and MeONa (XI) (451 mg, 8.34 mmol) in dry MeOH (10 mL) was heated under microwave irradiation at 120° C. for 1 h. After evaporation under reduced pressure, the residue was dissolved in DCM and the solution was washed with water and brine. The organic layer was dried over $Na_2SO_4$, filtered and evaporated to dryness in vacuo affording the title compound as white solid (450 mg, 86%).

$^1$H NMR (500 MHz, DMSO-$d_6$) δ ppm 1.50-1.62 (m, 2H) 1.64-1.77 (m, 1H) 1.84-2.01 (m, 2H) 2.15-2.31 (m, 1H) 3.54-3.71 (m, 1H) 3.81 (s, 3H) 3.96-4.02 (m, 1H) 5.49 (dd, J=11.06, 2.21 Hz, 1H) 7.27 (br. s., 2H) 8.12 (s, 1H).

HRMS (ESI+): calcd. for $C_{11}H_{16}N_5O_2$ [M+H]$^+$ 250.1299; found 250.1303.

Step p'

2-Methoxy-9H-purin-6-amine (VII)

[X=N, R3=OR6, R6=($C_1$-$C_6$)alkyl]

A mixture of 2-methoxy-9-(tetrahydro-2H-pyran-2-yl)-9H-purin-6-amine (XXIII) (350 mg, 1.4 mmol) and $CuCl_2$ (190 mg, 1.4 mmol) in EtOH/$H_2O$ 95:5 (5 mL) was heated at 85° C. for 2 h. After removal of the solvent under reduced pressure, the residue was dissolved in EtOAc, washed with 33% aqueous ammonia, water and brine, dried over $Na_2SO_4$, filtered and evaporated to dryness in vacuo. The product was purified by column chromatography (eluant EtOAc:hex=6:4 to 8:2) and isolated as white solid (192 mg, 83%).

$^1$H NMR (500 MHz, DMSO-$d_6$) δ ppm 3.78 (s, 3H) 7.11 (br. s., 2H) 7.87 (s, 1H) 12.60 (br. s., 1H).

HRMS (ESI+): calcd. for $C_6H_8N_5O$ [M+H]$^+$ 166.0724; found 166.0715.

Preparation 2

N-{4-[(4-methylpiperazin-1-yl)methyl]phenyl}-4-(4,4,5,5-tetramethyl-1,3,2-dioxaborolan-2-yl)benzamide

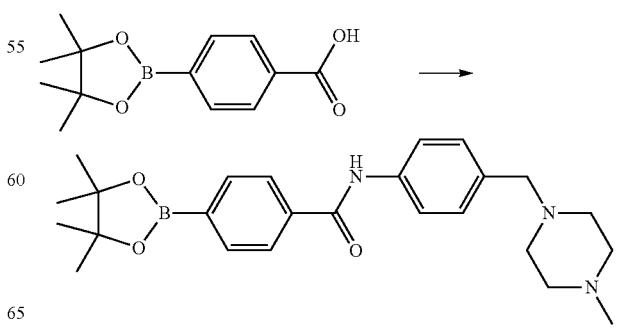

A solution of 4-(4,4,5,5-tetramethyl-1,3,2-dioxaborolan-2-yl)benzoic acid (154 mg, 0.605 mmol), TBTU (232 mg, 0.725 mmol), 4-[(4-methylpiperazin-1-yl)methyl]aniline (150 mg, 0.725 mmol) and DIPEA (0.155 mL, 0.907 mmol) in DMA (7 mL) was let under stirring at rt overnight. The mixture was diluted with EtOAc, washed with a saturated solution of NaHCO$_3$, water and brine, dried over Na$_2$SO$_4$, filtered and taken to dryness under reduced pressure. After treatment with Et$_2$O, the solid was filtered and used without any further purification.

HRMS (ESI+): calcd. for C$_{25}$H$_{35}$BN$_3$O$_3$ [M+H]$^+$ 436.2766; found 436.2762.

Operating in an analogous way, but employing suitably substituted reagents, the following compounds were obtained:

N-(4-{[4-(dimethylamino)piperidin-1-yl]methyl}phenyl)-4-(4,4,5,5-tetramethyl-1,3,2-dioxaborolan-2-yl)benzamide HRMS (ESI+): calcd. for C$_{27}$H$_{39}$BN$_3$O$_3$ [M+H]$^+$ 464.3079; found 464.3084.

N-(4-{[4-(dimethylamino)piperidin-1-yl]methyl}phenyl)-3-(4,4,5,5-tetramethyl-1,3,2-dioxaborolan-2-yl)benzamide HRMS (ESI+): calcd. for C$_{27}$H$_{39}$BN$_3$O$_3$ [M+H]$^+$ 464.3079; found 464.3071.

N-{4-[(4-methylpiperazin-1-yl)methyl]phenyl}-3-(4,4,5,5-tetramethyl-1,3,2-dioxaborolan-2-yl)benzamide HRMS (ESI+): calcd. for C$_{25}$H$_{35}$BN$_3$O$_3$ [M+H]$^+$ 436.2766; found 436.2769.

{3-[(4-methyl-1,3-thiazol-2-yl)carbamoyl]phenyl}boronic acid $^1$H NMR (500 MHz, DMSO-d$_6$) δ ppm 2.31 (s, 3H) 6.82 (s, 1H) 7.49 (t, J=7.60 Hz, 1H) 7.99 (d, J=7.32 Hz, 1H) 8.06-8.12 (m, 1H) 8.23 (br. s., 2H) 8.45 (s, 1H) 12.47 (br. s., 1H).

HRMS (ESI+): calcd. for C$_{11}$H$_{12}$BN$_2$O$_3$S [M+H]$^+$ 262.0693; found 262.0695.

Preparation 3

2-(2-amino-1,3-thiazol-4-yl)-1-(1,4'-bipiperidin-1'-yl)ethanone dihydrochloride

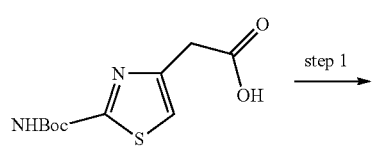

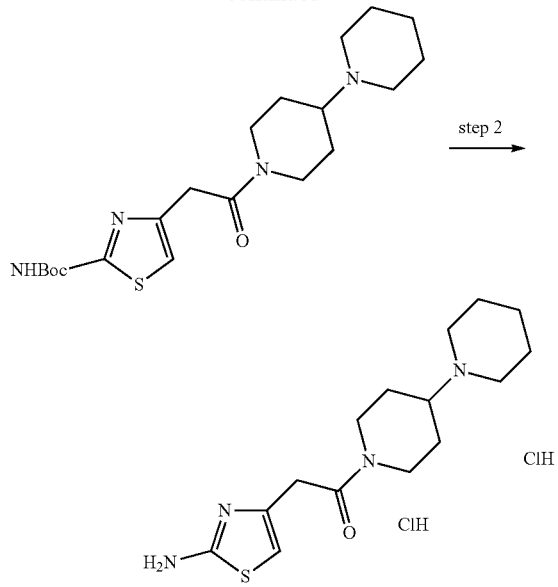

Step 1 tert-butyl {4-[2-(1,4'-bipiperidin-1'-yl)-2-oxoethyl]-1,3-thiazol-2-yl}carbamate A solution of {2-[(tert-butoxycarbonyl)amino]-1,3-thiazol-4-yl}acetic acid (250 mg, 0.968 mmol), TBTU (326 mg, 1.016 mmol), 1,4'-bipiperidine (257 mg, 1.452 mmol) and DIPEA (0.331 mL, 1.936 mmol) in DMA (8 mL) was let under stirring at rt overnight. The mixture was diluted with EtOAc, washed with a saturated solution of NaHCO$_3$, water and brine, dried over Na$_2$SO$_4$ and filtered. The title compound was purified by column chromatography (eluant DCM:7N NH$_3$ in MeOH=95:5) and isolated as white solid (356 mg, 96%).

$^1$H NMR (500 MHz, DMSO-d$_6$) δ ppm 1.12-1.28 (m, 2H) 1.30-1.39 (m, 2H) 1.41-1.49 (m, 4H) 1.47 (s, 9H) 1.56-1.76 (m, 2H) 2.27-2.44 (m, 5H) 2.46-2.54 (m, 1H) 2.86-2.97 (m, 1H) 3.64 (d, J=3.5 Hz, 2H) 3.93 (d, J=13.42 Hz, 1H) 4.37 (d, J=12.81 Hz, 1H) 6.80 (s, 1H) 11.39 (br. s., 1H).

HRMS (ESI+): calcd. for C$_{20}$H$_{33}$N$_4$O$_3$S [M+H]$^+$ 409.2268; found 409.2275.

Operating in an analogous way, but employing suitably substituted reagents, the following compounds were obtained:

tert-butyl {4-[2-({4-[(4-methylpiperazin-1-yl)methyl]-3-(trifluoromethyl)phenyl}amino)-2-oxoethyl]phenyl}carbamate HRMS (ESI+): calcd. for C$_{26}$H$_{34}$F$_3$N$_4$O$_3$ [M+H]$^+$ 507.2578; found 507.2571.

tert-butyl {4-[2-({4-[(4-methylpiperazin-1-yl)methyl]phenyl}amino)-2-oxoethyl]phenyl}carbamate HRMS (ESI+): calcd. for C$_{25}$H$_{35}$N$_4$O$_3$ [M+H]$^+$ 439.2704; found 439.2705.

4-amino-N-cyclohexylbenzamide $^1$H NMR (401 MHz, DMSO-$d_6$) δ ppm 1.02-1.18 (m, 1H) 1.20-1.40 (m, 4H) 1.55-1.65 (m, 1H) 1.66-1.82 (m, 4H) 3.60-3.78 (m, 1H) 5.52 (s, 2H) 6.50 (d, J=8.8 Hz, 2H) 7.55 (d, J=8.8 Hz, 2H) 7.64 (d, J=8.18 Hz, 1H).

HRMS (ESI+): calcd. for $C_{13}H_{19}N_2O$ [M+H]$^+$ 219.1492; found 219.1499.

Step 2

2-(2-amino-1,3-thiazol-4-yl)-1-(1,4'-bipiperidin-1'-yl)ethanone dihydrochloride Tert-butyl {4-[2-(1,4'-bipiperidin-1'-yl)-2-oxoethyl]-1,3-thiazol-2-yl}carbamate (350 mg, 0.856 mmol) was treated with 4M HCl in dioxane (5 mL) at rt overnight. The solvent was removed under vacuo. The solid was taken up with Et$_2$O, stirred and evaporated to dryness (257 mg, 78%).

$^1$H NMR (500 MHz, DMSO-$d_6$) δ ppm 1.31-1.89 (m, 10H) 2.03-2.21 (m, 2H) 2.55-2.65 (m, 1H) 2.82-2.95 (m, 2H) 3.00-3.11 (m, 1H) 3.63-3.85 (m, 3H) 4.00-4.09 (m, 1H) 4.45-4.55 (m, 1H) 6.57 (s, 1H) 8.89 (br. s., 2H).

HRMS (ESI+): calcd. for $C_{15}H_{25}N_4OS$ [M+H]$^+$ 309.1744; found 309.1742.

Alternatively:

2-(4-aminophenyl)-N-{4-[(4-methylpiperazin-1-yl)methyl]-3-(trifluoromethyl)phenyl}acetamide Tert-butyl {4-[2-({4-[(4-methyl piperazin-1-yl)methyl]-3-(trifluoromethyl)phenyl}amino)-2-oxoethyl]phenyl}carbamate (200 mg, 0.395 mmol) was treated with TFA (2 mL) in DCM (10 mL) for 3 h at rt. The mixture was neutralized with a saturated solution of NaHCO$_3$, washed with water and brine, dried over Na$_2$SO$_4$ and filtered. After solvent removal under reduced pressure, the product was purified by column chromatography (eluant EtOAc: MeOH=9:1+0.5% 7N NH$_3$ in MeOH) and isolated as white solid (118 mg, 74%).

$^1$H NMR (500 MHz, DMSO-$d_6$) δ ppm 2.13 (s, 3H) 2.18-2.44 (m, 6H) 3.32-3.48 (m, 2H) 3.51 (s, 2H) 4.94 (s, 2H) 6.50 (d, J=8.39 Hz, 2H) 6.96 (d, J=8.39 Hz, 2H) 7.62 (d, J=8.54 Hz, 1H) 7.70-7.77 (m, 1H) 8.03 (d, J=1.83 Hz, 1H) 10.31 (br. s., 1H).

HRMS (ESI+): calcd. for $C_{21}H_{26}F_3N_4O$ [M+H]$^+$ 407.2053; found 407.2044.

Operating in an analogous way, but employing suitably substituted reagents, the following compound was obtained:

2-(4-aminophenyl)-N-{4-[(4-methylpiperazin-1-yl)methyl]phenyl}acetamide

HRMS (ESI+): calcd. for $C_{20}H_{27}N_4O$ [M+H]$^+$ 339.2179; found 339.2184.

Preparation 4 tert-butyl {1-[(2-amino-1,3-thiazol-4-yl)methyl]piperidin-4-yl}carbamate

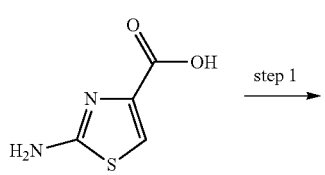

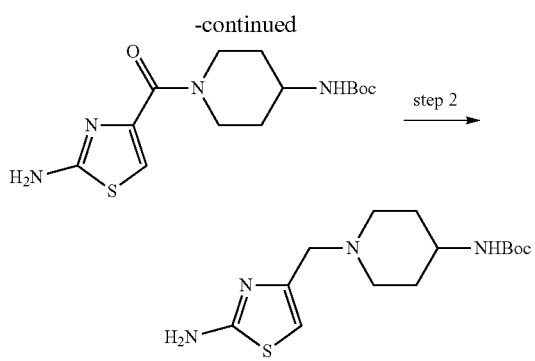

Step 1 tert-butyl {1-[(2-amino-1,3-thiazol-4-yl)carbonyl]piperidin-4-yl}carbamate

A solution of 2-amino-1,3-thiazole-4-carboxylic acid (85 mg, 0.59 mmol), TBTU (227 mg, 0.708 mmol), tert-butyl piperidin-4-ylcarbamate (236 mg, 1.18 mmol) and DIPEA (0.403 mL, 2.36 mmol) in dry DMF (5 mL) was let under stirring at rt overnight. The mixture was then diluted with EtOAc, washed with a saturated solution of NaHCO$_3$, water and brine, dried over Na$_2$SO$_4$ and filtered. The title compound was purified by column chromatography (eluant DCM:MeOH=98:2) and isolated as light yellow solid (147 mg, 77%).

$^1$H NMR (500 MHz, DMSO-$d_6$) δ ppm 1.21-1.32 (m, 2H) 1.38 (s, 9H) 1.65-1.81 (m, 2H) 2.71-2.90 (m, 1H) 2.96-3.15 (m, 1H) 3.44-3.57 (m, 1H) 4.21-4.32 (m, 2H) 6.88 (d, J=7.93 Hz, 1H) 6.92 (s, 1H) 7.10 (s, 2H).

HRMS (ESI+): calcd. for $C_{14}H_{23}N_4O_3S$ [M+H]$^+$ 327.1486; found 327.1473.

Step 2

Tert-butyl {1-[(2-amino-1,3-thiazol-4-yl)methyl]piperidin-4-yl}carbamate

To a solution of tert-butyl {1-[(2-amino-1,3-thiazol-4-yl)carbonyl]piperidin-4-yl}carbamate (110 mg, 0.337 mmol) in dry THF (8 mL), 2 M BH$_3$.SMe$_2$ in THF (0.843 mL, 1.685 mmol) was added dropwise at 0° C. The mixture was allowed to reach rt and was let under stirring for 4 h. The reaction was quenched by careful addition of MeOH until no more effervescence was produced then the solvent was removed under vacuo. The residue was dissolved in MeOH and heated at 60° C. for 1 h to remove borane complexes. The title compound was purified by column chromatography (eluant DCM:MeOH=95:5) and isolated as white solid (60 mg, 57%).

$^1$H NMR (500 MHz, DMSO-$d_6$) δ ppm 1.27-1.42 (m, 2H) 1.37 (s, 9H) 1.59-1.69 (m, 2H) 1.87-2.01 (m, 2H) 2.72-2.84 (m, 2H) 3.12-3.21 (m, 1H) 3.22 (br. s., 2H) 6.25 (s, 1H) 6.74 (d, J=7.47 Hz, 1H) 6.80 (s, 2H).

HRMS (ESI+): calcd. for $C_{14}H_{23}N_4O_3S$ [M+H]$^+$ 313.1693; found 313.1687.

Preparation 5

5-cyclopropyl-4,5,6,7-tetrahydro[1,3]thiazolo[5,4-c]pyridin-2-amine

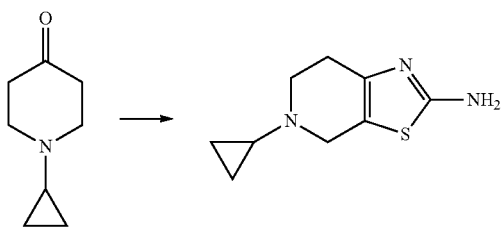 [SMILES: O=C1CCN(C2CC2)CC1 ; Nc1nc2c(s1)CN(C1CC1)CC2]

To a suspension of thiourea (328 mg, 4.31 mmol) in dioxane (5 mL) kept at 60° C., iodine (546 mg, 2.155 mmol) was added portionwise. After addition of 1-cyclopropylpiperidin-4-one hydrochloride (377 mg, 2.155 mmol), the mixture was heated at 100° C. for 5 h. After cooling to room temperature, the reaction was taken to a basic pH with NH$_4$OH and the extracted with EtOAc. The organic layer was washed with water and brine, dried over Na$_2$SO$_4$, filtered and taken to dryness under vacuum. The title compound was isolated by column chromatography (eluant EtOAc:MeOH=97:3) as light yellow solid (129 mg, 30%).

$^1$H NMR (500 MHz, DMSO-d$_6$) δ ppm 0.33-0.39 (m, 2H) 0.42-0.49 (m, 2H) 1.81-1.90 (m, 1H) 2.42 (t, J=5.72 Hz, 2H) 2.83 (t, J=5.72 Hz, 2H) 3.51 (br. s., 2H) 6.67 (br. s., 2H).

HRMS (ESI+): calcd. for C$_9$H$_{14}$N$_3$S [M+H]$^+$ 196.0903; found 196.0899.

Operating in an analogous way, but employing suitably substituted reagents, the following intermediate was obtained:

(5S,8R)-5,6,7,8-tetrahydro-4H-5,8-epiminocyclohepta[d][1,3]thiazol-2-amine

HRMS (ESI+): calcd. for C$_8$H$_{12}$N$_3$S [M+H]$^+$ 182.0746; found 182.0755.

Preparation 6

2-(2-amino-6,7-dihydro[1,3]thiazolo[5,4-c]pyridin-5(4H)-yl)acetamide

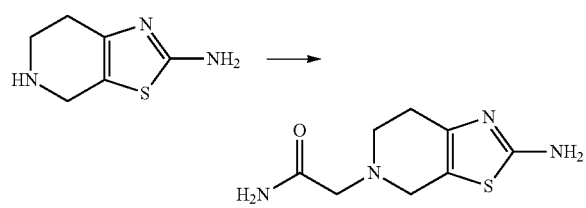

To a mixture of 4,5,6,7-tetrahydro[1,3]thiazolo[5,4-c]pyridin-2-amine (50 mg, 0.322 mmol) and DIPEA (0.072 mL, 0.418 mmol) in THF (3 mL), 2-iodoacetamide (65 mg, 0.354 mmol) was added and the reaction let under stirring at rt overnight. After solvent removal under reduced pressure, the title compound was isolated by column chromatography (eluant DCM:MeOH=90:10) as white solid (37 mg, 54%).

$^1$H NMR (500 MHz, DMSO-d$_6$) δ ppm 2.73 (t, J=5.72 Hz, 2H) 3.03 (s, 2H) 3.46 (s, 2H) 6.70 (br. s., 2H) 7.12 (br. s., 1H) 7.23 (br. s., 1H).

HRMS (ESI+): calcd. for C$_8$H$_{13}$N$_4$OS [M+H]$^+$ 213.0805; found 213.0799.

Preparation 7

2-[2-(methylamino)-1,3-thiazol-4-yl]acetamide trifluoroacetate

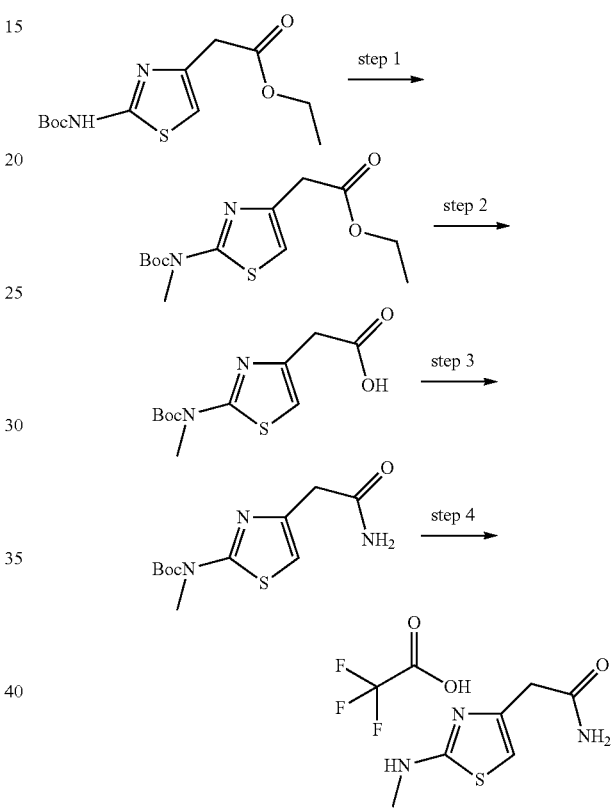

Step 1

Ethyl {2-[(tert-butoxycarbonyl)(methyl)amino]-1,3-thiazol-4-yl}acetate

The mixture of ethyl {2-[(tert-butoxycarbonyl)amino]-1,3-thiazol-4-yl}acetate (200 mg, 0.698 mmol), Cs$_2$CO$_3$ (245 mg, 0.751 mmol) and MeI (0.053 mL, 0.851 mmol) in dry DMF (10 mL) was let under stirring at rt overnight. After dilution with EtOAc, the organic layer was washed with water and brine, dried over Na$_2$SO$_4$, filtered and evaporated under reduced pressure. The title compound was purified by flash chromatography (eluant DCM, DCM:MeOH=95:5) and isolated as white solid (132 mg, 63%).

$^1$H NMR (500 MHz, DMSO-d$_6$) δ ppm 1.18 (t, J=7.09 Hz, 3H) 1.52 (s, 9H) 3.42 (s, 3H) 3.67 (s, 2H) 4.08 (q, J=7.07 Hz, 2H) 6.99 (s, 1H).

HRMS (ESI+): calcd. for C$_{13}$H$_{21}$N$_2$O$_4$S [M+H]$^+$ 301.1217; found 301.1230.

Step 2

{2-[(tert-butoxycarbonyl)(methyl)amino]-1,3-thiazol-4-yl}acetic acid

Ethyl {2-[(tert-butoxycarbonyl)(methyl)amino]-1,3-thiazol-4-yl}acetate (130 mg, 0.433 mmol) was dissolved in MeOH (2 mL) and treated with 1M NaOH (0.52 mL, 0.52 mmol) for 6 h at rt. After quenching with 2N HCl (0.26 mL), the mixture was extracted with DCM. The organic layer was washed with water and brine, dried over $Na_2SO_4$, filtered, evaporated under reduced pressure yielding the title compound as yellow oil (102 mg, 86%).

$^1$H NMR (500 MHz, DMSO-$d_6$) δ ppm 1.52 (s, 9H) 3.42 (s, 3H) 3.58 (s, 2H) 6.97 (s, 1H) 12.34 (br. s., 1H).

HRMS (ESI+): calcd. for $C_{11}H_{17}N_2O_4S$ [M+H]$^+$ 273.0904; found 273.0898.

Step 3 tert-butyl [4-(2-amino-2-oxoethyl)-1,3-thiazol-2-yl]methylcarbamate

The mixture of {2-[(tert-butoxycarbonyl)(methyl)amino]-1,3-thiazol-4-yl}acetic acid (60 mg, 0.22 mmol), TBTU (85 mg, 0.264 mmol), DIPEA (0.15 mL, 0.881 mmol) and $NH_4Cl$ (24 mg, 0.44 mmol) in DMA (5 mL) was let under stirring at rt overnight. After dilution with EtOAc, the organic layer was washed with water and brine, dried over $Na_2SO_4$, filtered and evaporated under reduced pressure. The title compound was purified by flash chromatography (eluant EtOAc) and isolated as white solid (44 mg, 74%).

$^1$H NMR (500 MHz, DMSO-$d_6$) δ ppm 1.52 (s, 9H) 3.41 (s, 2H) 3.43 (s, 3H) 6.91 (s, 1H) 6.94 (br. s., 1H) 7.32 (br. s., 1H).

HRMS (ESI+): calcd. for $C_1H_{18}N_3O_3S$ [M+H]$^+$ 272.1064; found 272.1068.

Step 4

2-[2-(methylamino)-1,3-thiazol-4-yl]acetamide trifluoroacetate

Tert-butyl [4-(2-amino-2-oxoethyl)-1,3-thiazol-2-yl]methylcarbamate (40 mg, 0.147 mmol) was dissolved in DCM (5 mL) and treated with TFA (1 mL) for 3 h at rt. The solvent was then evaporated under vacuum. The crude was taken up with $Et_2O$ and evaporated yielding the product as sticky oil.

$^1$H NMR (500 MHz, DMSO-$d_6$) δ ppm 2.90 (s, 1H) 3.37 (s, overlapped by water signal 2H) 6.55 (s, 1H) 7.08 (br. s., 1H) 7.45 (br. s., 1H).

HRMS (ESI+): calcd. for $C_6H_{10}N_3OS$ [M+H]$^+$ 172.0539; found 172.0536.

Preparation 8 tert-butyl (5S,8R)-2-amino-5,6,7,8-tetrahydro-4H-5,8-epiminocyclohepta[d][1,3]thiazole-9-carboxylate

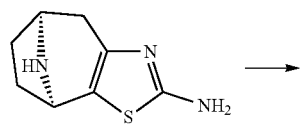

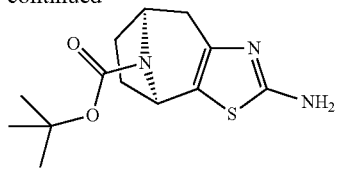

(5S,8R)-5,6,7,8-Tetrahydro-4H-5,8-epiminocyclohepta[d][1,3]thiazol-2-amine (83 mg, 0.458 mmol) was suspended in DCM (5 mL) and treated with DMAP (5 mg, 0.046 mmol) and $Boc_2O$ (100 mg, 0.458 mmol) portionwise. The mixture was let under stirring at rt for 3 h. After quenching with a 10% citric acid solution, the mixture was extracted with DCM and the organic layer washed with water and brine, dried over $Na_2SO_4$, filtered and taken to dryness under reduced pressure. The title compound was purified by column chromatography (eluant AcOEt: hexane=6:4 to 9:1) and isolated as white solid (66 mg, 51%).

$^1$H NMR (500 MHz, DMSO-$d_6$) δ ppm 1.37 (s, 9H) 1.50-1.64 (m, 1H) 1.79-1.90 (m, 1H) 1.9-2.05 (m, 1H) 2.10-2.32 (m, 2H) 2.84-3.08 (m, 1H) 4.25-4.35 (m, 1H) 4.68-4.78 (m, 1H) 6.73 (br. s., 2H).

HRMS (ESI+): calcd. for $C_{13}H_{20}N_3O_2S$ [M+H]$^+$ 282.1271; found 282.1269.

The invention claimed is:

1. A compound of formula (I):

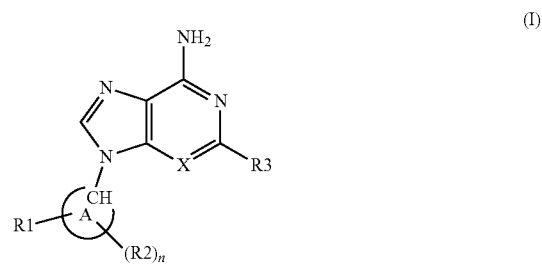

wherein:

X is CH or nitrogen;

A is a 6- or 7-membered cycloalkyl or a 6- or 7-membered nitrogen-containing heterocyclyl, or A is a 7- to 9-membered carbon bicyclic system, in which one ring carbon is optionally replaced by nitrogen;

R1 is linked:

either 1) to any A ring carbon, in which case R1 is fluorine, an optionally substituted ($C_3$-$C_7$)cycloalkyl, —COR6, —COOR4, —CONR4R5, —NR4COOR6, —NR4COR5, —NR4R5, —NR4CONR4R5, —NR4CSNR4R5, or —NR4SO$_2$R6;

or 2) to the A ring nitrogen, if present, in which case R1 is an optionally substituted ($C_1$-$C_6$)alkyl or ($C_3$-$C_7$)cycloalkyl, —COR5, —COOR6, —CONR4R5, —CSNR4R5, or —SO$_2$R6;

wherein:

R4 and R5 are independently hydrogen or an optionally substituted group selected from ($C_1$-$C_6$)alkyl, ($C_3$-$C_7$)cycloalkyl, heterocyclyl, aryl, aryl($C_1$-$C_6$)alkyl, heteroaryl and heteroaryl($C_1$-$C_6$)alkyl; or R4 and R5, taken together with the nitrogen atom to which they are bonded, may form an optionally substituted 5- or 6-membered heterocyclyl group optionally containing one additional heteroatom selected from N, O and S;
R6 is an optionally substituted group selected from ($C_1$-$C_6$)alkyl, ($C_3$-$C_7$)cycloalkyl, heterocyclyl, aryl, aryl($C_1$-$C_6$)alkyl, heteroaryl and heteroaryl($C_1$-$C_6$)alkyl;
n is 0, 1 or 2;
R2 is linked to any A ring atom and is selected from the group consisting of fluorine, an optionally substituted ($C_1$-$C_6$)alkyl or ($C_3$-$C_7$)cycloalkyl, and NR4R5;
provided that
when R2 is fluorine or NR4R5, then R2 is linked to a ring carbon;
when n is 2, then the R2 groups are not necessarily the same;
wherein the R1 and R2 groups can be linked to the same ring carbon;
R3 is hydrogen, halogen, cyano or an optionally substituted group selected from ($C_1$-$C_6$)alkyl, polyfluorinated ($C_1$-$C_6$)alkyl, ($C_2$-$C_6$)alkenyl, ($C_2$-$C_6$)alkynyl, ($C_3$-$C_7$)cycloalkyl, heterocyclyl, aryl, heteroaryl, —OR6, —SR6, —$SO_2$R6, —NR4R5 or —CONR4R5, wherein R4, R5 and R6 are as defined above;
provided that
when X is nitrogen, then R3 is not hydrogen and not NR4R5, wherein R4 is an optionally substituted aryl and R5 hydrogen; and that and also provided that
when X is nitrogen, then R1 and R2 may be optionally substituted by one or more groups but not hydroxy and hydroxy($C_1$-$C_6$)alkyl groups;
or a pharmaceutically acceptable salt thereof.

2. A compound or pharmaceutically acceptable salt according to claim 1, wherein:
X is CH or nitrogen;
A is a 6- or 7-membered cycloalkyl or a 6- or 7-membered nitrogen-containing heterocyclyl, or A is a 7- to 9-membered carbon bicyclic system, in which one ring carbon is optionally replaced by a nitrogen;
R1 is linked:
either
1) to any A ring carbon, in which case R1 is fluorine, —COOR4, —CONR4R5, —NR4COOR6, —NR4COR5, —NR4R5, —NR4CONR4R5, —NR4CSNR4R5, or —NR4$SO_2$R6;
or
2) to the A ring nitrogen, if present, in which case R1 is —COR5, —COOR6, —CONR4R5, —CSNR4R5, or —$SO_2$R6;
wherein:
R4 and R5 are independently hydrogen or an optionally substituted group selected from ($C_1$-$C_6$)alkyl, ($C_3$-$C_7$)cycloalkyl, heterocyclyl, aryl, aryl($C_1$-$C_6$)alkyl, heteroaryl and heteroaryl($C_1$-$C_6$)alkyl; or R4 and R5, taken together with the nitrogen atom to which they are bonded, may form an optionally substituted 5- or 6-membered heterocyclyl group optionally containing one additional heteroatom selected from N, O and S;
R6 is an optionally substituted group selected from ($C_1$-$C_6$)alkyl, ($C_3$-$C_7$)cycloalkyl, heterocyclyl, aryl, aryl($C_1$-$C_6$)alkyl, heteroaryl and heteroaryl($C_1$-$C_6$)alkyl;
n is 0, 1 or 2;
R2 is linked to any A ring atom and is selected from the group consisting of fluorine, an optionally substituted ($C_1$-$C_6$)alkyl and NR4R5;
provided that
when R2 is fluorine or NR4R5, then R2 is linked to a ring carbon;
when n is 2, then the R2 groups are not necessarily the same;
wherein the R1 and R2 groups can be linked to the same ring carbon;
R3 is hydrogen, halogen, cyano or an optionally substituted group selected from polyfluorinated ($C_1$-$C_6$)alkyl, ($C_3$-$C_7$)cycloalkyl, ($C_2$-$C_6$)alkynyl, heterocyclyl, aryl, heteroaryl, —OR6 or —CONR4R5, wherein R4, R5 and R6 are as defined above;
when X is nitrogen, then R3 is not hydrogen.

3. A compound or pharmaceutically acceptable salt according to claim 2, wherein:
X is CH or nitrogen;
A is a 6-membered cycloalkyl or a 6-membered nitrogen-containing heterocyclyl;
R1 is linked:
either
1) to any A ring carbon, in which case R1 is —CONR4R5, —NR4COR5, —NR4CONR4R5, —NR4CSNR4R5, or —NR4$SO_2$R6,
or
2) to the A ring nitrogen, in which case R1 is —COR5, —CONR4R5, —CSNR4R5 or —$SO_2$R6;
wherein:
R4 and R5 are independently hydrogen or an optionally substituted group selected from ($C_1$-$C_6$)alkyl, aryl and heteroaryl, and;
R6 is an optionally substituted group selected from ($C_1$-$C_6$)alkyl, aryl and heteroaryl;
n is 0, 1 or 2;
R2 is an optionally substituted ($C_1$-$C_6$)alkyl;
provided that
when n is 2 the R2 groups are not necessarily the same;
wherein the R1 and R2 groups can be linked to the same ring carbon;
R3 is halogen, cyano or an optionally substituted group selected from polyfluorinated($C_1$-$C_6$)alkyl, ($C_2$-$C_6$)alkynyl, aryl, heteroaryl, —OR6 and —CONR4R5, wherein R4, R5 and R6 are as defined above.

4. A compound or pharmaceutically acceptable salt according to claim 3, represented by formula (I)' below:

(I)' wherein:
X is nitrogen;
A is a 6-membered cycloalkyl, wherein A has a cis-1,4-disubstituted configuration;
R1 is linked:
to an A ring carbon, and is —CONR4R5, —NR4COR5, —NR4CONR4R5;

wherein R4 and R5 are independently hydrogen or an optionally substituted group selected from aryl and heteroaryl;

n is 0;

R3 is halogen, cyano or an optionally substituted group selected from (C$_2$-C$_6$)alkynyl, aryl, heteroaryl and —OR6, wherein R6 is an optionally substituted (C$_1$-C$_6$)alkyl.

5. A compound (cpd), or pharmaceutically acceptable salt according to claim 1, selected from the group consisting of:

cis-4-(6-amino-2-chloro-9H-purin-9-yl)-N-(3-methoxyphenyl)cyclohexanecarboxamide (cpd 3), cis-4-[6-amino-2-(pyridin-3-yl)-9H-purin-9-yl]-N-(3-methoxyphenyl)cyclohexanecarboxamide (cpd 4), cis-4-[6-amino-2-(pyridin-4-yl)-9H-purin-9-yl]-N-(3-methoxyphenyl)cyclohexanecarboxamide (cpd 9), cis-4-[6-amino-2-(2-fluoropyridin-4-yl)-9H-purin-9-yl]-N-(3-methoxyphenyl)cyclohexanecarboxamide (cpd 15), cis-4-[6-amino-2-(4-hydroxyphenyl)-9H-purin-9-yl]-N-(3-methoxyphenyl)cyclohexanecarboxamide (cpd 17), cis-4-[6-amino-2-(3-hydroxyphenyl)-9H-purin-9-yl]-N-(3-methoxyphenyl)cyclohexanecarboxamide (cpd 18), cis-4-[6-amino-2-(6-fluoropyridin-3-yl)-9H-purin-9-yl]-N-(3-methoxyphenyl)cyclohexanecarboxamide (cpd 19), cis-4-[6-amino-2-(2-methoxypyridin-4-yl)-9H-purin-9-yl]-N-(3-methoxyphenyl)cyclohexanecarboxamide (cpd 21), 3-(6-amino-9-{cis-4-[(3-methoxyphenyl)carbamoyl]cyclohexyl}-9H-purin-2-yl)benzamide (cpd 26), cis-4-(6-amino-2-chloro-9H-purin-9-yl)-N-{4-[(trifluoromethyl)sulfonyl]phenyl}cyclohexanecarboxamide (cpd 27), 4-(6-amino-9-{cis-4-[(3-methoxyphenyl)carbamoyl]cyclohexyl}-9H-purin-2-yl)-N-{4-[(4-methylpiperazin-1-yl)methyl]phenyl}benzamide (cpd 29), 3-(6-amino-9-{cis-4-[(3-methoxyphenyl)carbamoyl]cyclohexyl}-9H-purin-2-yl)-N-{4-[(4-methylpiperazin-1-yl)methyl]phenyl}benzamide (cpd 30), 3-(6-amino-9-{cis-4-[(3-methoxyphenyl)carbamoyl]cyclohexyl}-9H-purin-2-yl)-N-(4-{[4-(dimethylamino)piperidin-1-yl]methyl}phenyl)benzamide (cpd 31), cis-4-(6-amino-2-chloro-9H-purin-9-yl)-N-(3,4-dimethoxyphenyl)cyclohexanecarboxamide (cpd 32), 4-(6-amino-9-{cis-4-[(3-methoxyphenyl)carbamoyl]cyclohexyl}-9H-purin-2-yl)-N-(4-{[4-(dimethylamino)piperidin-1-yl]methyl}phenyl)benzamide (cpd 33), cis-4-(6-amino-2-chloro-9H-purin-9-yl)-N-{4-[2-({4-[(4-methylpiperazin-1-yl)methyl]-3-(trifluoromethyl)phenyl}amino)-2-oxoethyl]phenyl}cyclohexanecarboxamide (cpd 35), cis-4-(6-amino-2-chloro-9H-purin-9-yl)-N-{4-[2-({4-[(4-methylpiperazin-1-yl)methyl]phenyl}amino)-2-oxoethyl]phenyl}cyclohexanecarboxamide (cpd 36), cis-4-[6-amino-2-(pyridin-4-yl)-9H-purin-9-yl]-N-(3,4-dimethoxyphenyl)cyclohexanecarboxamide (cpd 37), cis-4-(6-amino-2-iodo-9H-purin-9-yl)-N-(3-methoxyphenyl)cyclohexanecarboxamide (cpd 41), cis-4-(6-amino-2-ethynyl-9H-purin-9-yl)-N-(3-methoxyphenyl)cyclohexanecarboxamide (cpd 45), cis-4-(6-amino-2-chloro-9H-purin-9-yl)-N-(3-methylphenyl)cyclohexanecarboxamide (cpd 48), cis-4-[6-amino-2-(pyridin-4-yl)-9H-purin-9-yl]-N-(3-methylphenyl)cyclohexanecarboxamide (cpd 50), cis-4-(6-amino-2-chloro-9H-purin-9-yl)cyclohexanecarboxamide (cpd 53), cis-4-[6-amino-2-(3-hydroxyprop-1-yn-1-yl)-9H-purin-9-yl]-N-(3-methoxyphenyl)cyclohexanecarboxamide (cpd 60), cis-4-(6-amino-2-chloro-9H-purin-9-yl)-N-[5-(trifluoromethyl)-1,3,4-thiadiazol-2-yl]cyclohexanecarboxamide (cpd 64), cis-4-(6-amino-2-chloro-9H-purin-9-yl)-N-(4-methyl-1,3-thiazol-2-yl)cyclohexanecarboxamide (cpd 65), cis-4-(6-amino-2-chloro-9H-purin-9-yl)-N-(1,3-benzothiazol-6-yl)cyclohexanecarboxamide (cpd 69), cis-4-(6-amino-2-iodo-9H-purin-9-yl)-N-(4-methyl-1,3-thiazol-2-yl)cyclohexanecarboxamide (cpd 70), 4-({[cis-4-(6-amino-2-chloro-9H-purin-9-yl)cyclohexyl]carbonyl}amino)-N-cyclohexylbenzamide (cpd 71), cis-4-(6-amino-2-chloro-9H-purin-9-yl)-N-(1,3-thiazol-2-yl)cyclohexanecarboxamide (cpd 72), cis-4-(6-amino-2-chloro-9H-purin-9-yl)-N-(5-methyl-1,3-thiazol-2-yl)cyclohexanecarboxamide (cpd 73), cis-4-(6-amino-2-chloro-9H-purin-9-yl)-N-(4-phenyl-1,3-thiazol-2-yl)cyclohexanecarboxamide (cpd 74), cis-4-(6-amino-2-chloro-9H-purin-9-yl)-N-(1,3-benzothiazol-2-yl)cyclohexanecarboxamide (cpd 75), cis-4-(6-amino-2-chloro-9H-purin-9-yl)-N-(pyridin-2-yl)cyclohexanecarboxamide (cpd 76), cis-4-(6-amino-2-ethynyl-9H-purin-9-yl)-N-(4-methyl-1,3-thiazol-2-yl)cyclohexanecarboxamide (cpd 77), cis-4-(6-amino-2-chloro-9H-purin-9-yl)-N-(1H-imidazol-2-yl)cyclohexanecarboxamide (cpd 79), cis-4-[6-amino-2-(pyridin-4-yl)-9H-purin-9-yl]-N-(4-methyl-1,3-thiazol-2-yl)cyclohexanecarboxamide (cpd 81), cis-4-(6-amino-2-methoxy-9H-purin-9-yl)-N-(3-methoxyphenyl)cyclohexanecarboxamide (cpd 83), cis-4-(6-amino-2-methoxy-9H-purin-9-yl)-N-(4-methyl-1,3-thiazol-2-yl)cyclohexanecarboxamide (cpd 84), 3-(6-amino-9-{cis-4-[(4-methyl-1,3-thiazol-2-yl)carbamoyl]cyclohexyl}-9H-purin-2-yl)-N-(4-{[4-(dimethylamino)piperidin-1-yl]methyl}phenyl)benzamide bis-trifluoroacetate (cpd 85), cis-4-(6-amino-2-chloro-9H-purin-9-yl)-N-{4-[2-(1,4'-bipiperidin-1'-yl)-2-oxoethyl]-1,3-thiazol-2-yl}cyclohexanecarboxamide (cpd 86), cis-4-(6-amino-2-cyclopropyl-9H-purin-9-yl)-N-(3-methoxyphenyl)cyclohexanecarboxamide (cpd 87), methyl cis-4-(6-amino-2-chloro-9H-purin-9-yl)cyclohexanecarboxylate (cpd 88), cis-4-(6-amino-2-chloro-9H-purin-9-yl)-N-[6-(methylsulfonyl)-1,3-benzothiazol-2-yl]cyclohexanecarboxamide (cpd 89), cis-4-(6-amino-2-chloro-9H-purin-9-yl)-N-(6-chloro-1,3-benzothiazol-2-yl)cyclohexanecarboxamide (cpd 90), cis-4-(6-amino-2-chloro-9H-purin-9-yl)-N-(4-methoxy-1,3-benzothiazol-2-yl)cyclohexanecarboxamide (cpd 91), cis-4-(6-amino-2-chloro-9H-purin-9-yl)-N-(6-methoxy-1,3-benzothiazol-2-yl)cyclohexanecarboxamide (cpd 92), cis-4-(6-amino-2-chloro-9H-purin-9-yl)-N-(5,6-dimethyl-1,3-benzothiazol-2-yl)cyclohexanecarboxamide (cpd 93), cis-4-(6-amino-2-chloro-9H-purin-9-yl)-N-(5-chloro-1,3-benzoxazol-2-yl)cyclohexanecarboxamide (cpd 94), cis-4-(6-amino-2-chloro-9H-purin-9-yl)-N-(1-methyl-1H-benzimidazol-2-yl)cyclohexanecarboxamide (cpd 95), 3-(6-amino-9-{cis-4-[(4-methyl-1,3-thiazol-2-yl)carbamoyl]cyclohexyl}-9H-purin-2-yl)benzamide (cpd 96), 3-(6-amino-9-{trans-4-[(4-methyl-1,3-thiazol-2-yl)carbamoyl]cyclohexyl}-9H-purin-2-yl)benzamide (cpd 97),
cis-4-{6-amino-2-[(trimethylsilyl)ethynyl]-9H-purin-9-yl}-N-(4-methyl-1,3-thiazol-2-yl)cyclohexanecarboxamide (cpd 98),
cis-4-{6-amino-2-[3-(benzyloxy)phenyl]-9H-purin-9-yl}-N-(4-methyl-1,3-thiazol-2-yl)cyclohexanecarboxamide (cpd 100),
cis-4-(6-amino-2-cyano-9H-purin-9-yl)-N-(4-methyl-1,3-thiazol-2-yl)cyclohexanecarboxamide (cpd 102),
cis-4-[6-amino-2-(3-hydroxyphenyl)-9H-purin-9-yl]-N-(4-methyl-1,3-thiazol-2-yl)cyclohexanecarboxamide (cpd 103),
cis-4-[6-amino-2-(1H-pyrazol-3-yl)-9H-purin-9-yl]-N-(3-methoxyphenyl)cyclohexanecarboxamide (cpd 107),
cis-4-(6-amino-2-chloro-9H-purin-9-yl)-N-(5-methyl-1,3,4-thiadiazol-2-yl)cyclohexanecarboxamide (cpd 108),
cis-4-(6-amino-2-chloro-9H-purin-9-yl)-N-(1,5-dimethyl-1H-pyrazol-3-yl)cyclohexanecarboxamide (cpd 109),
cis-4-[6-amino-2-(1H-pyrazol-3-yl)-9H-purin-9-yl]-N-(4-methyl-1,3-thiazol-2-yl)cyclohexanecarboxamide (cpd 112),
trans-4-[6-amino-2-(1H-pyrazol-3-yl)-9H-purin-9-yl]-N-(4-methyl-1,3-thiazol-2-yl)cyclohexanecarboxamide (cpd 113),
cis-4-(6-amino-2-chloro-9H-purin-9-yl)-N-(5-choro-1,3-thiazol-2-yl)cyclohexanecarboxamide (cpd 114),
cis-4-(6-amino-2-chloro-9H-purin-9-yl)-N-[4-(trifluoromethyl)-1,3-thiazol-2-yl]cyclohexanecarboxamide (cpd 115),
cis-4-(6-amino-2-iodo-9H-purin-9-yl)-N-(4-methoxy-1,3-benzothiazol-2-yl)cyclohexanecarboxamide (cpd 116),
cis-4-(6-amino-2-ethynyl-9H-purin-9-yl)-N-(4-methoxy-1,3-benzothiazol-2-yl)cyclohexanecarboxamide (cpd 119),
cis-4-(6-amino-2-chloro-9H-purin-9-yl)-N-{4-[(4-aminopiperidin-1-yl)methyl]-1,3-thiazol-2-yl}cyclohexanecarboxamide (cpd 120),
cis-4-(6-amino-2-chloro-9H-purin-9-yl)-N-(4-hydroxy-1,3-benzothiazol-2-yl)cyclohexanecarboxamide (cpd 122),
cis-4-(6-amino-2-fluoro-9H-purin-9-yl)-N-(4-methyl-1,3-thiazol-2-yl)cyclohexanecarboxamide (cpd 124),
cis-4-(6-amino-2-fluoro-9H-purin-9-yl)-N-(4-methoxy-1,3-benzothiazol-2-yl)cyclohexanecarboxamide (cpd 126),
cis-4-(6-amino-2-fluoro-9H-purin-9-yl)-N-(4-hydroxy-1,3-benzothiazol-2-yl)cyclohexanecarboxamide (cpd 127),
cis-4-(6-amino-2-fluoro-9H-purin-9-yl)-N-(6-fluoro-1,3-benzothiazol-2-yl)cyclohexanecarboxamide (cpd 128),
cis-4-[6-amino-2-(trifluoromethyl)-9H-purin-9-yl]-N-(4-methyl-1,3-thiazol-2-yl)cyclohexanecarboxamide (cpd 129),
cis-4-[6-amino-2-(trifluoromethyl)-9H-purin-9-yl]-N-(6-fluoro-1,3-benzothiazol-2-yl)cyclohexanecarboxamide (cpd 132),
cis-4-(6-amino-2-chloro-9H-purin-9-yl)-N-(6-fluoro-1,3-benzothiazol-2-yl)cyclohexanecarboxamide (cpd 134),
cis-4-(6-amino-2-chloro-9H-purin-9-yl)-N-[4-(2-amino-2-oxoethyl)-1,3-thiazol-2-yl]cyclohexanecarboxamide (cpd 135),
cis-4-(6-amino-2-chloro-9H-purin-9-yl)-N-(6-hydroxy-1,3-benzothiazol-2-yl)cyclohexanecarboxamide (cpd 137),
cis-4-(6-amino-2-chloro-9H-purin-9-yl)-N-([1,3]thiazolo[5,4-c]pyridin-2-yl)cyclohexanecarboxamide (cpd 138),
N-[cis-4-(6-amino-2-chloro-9H-purin-9-yl)cyclohexyl]-4-methyl-1,3-thiazole-2-carboxamide (cpd 139),
N-[cis-4-(6-amino-2-chloro-9H-purin-9-yl)cyclohexyl]-1,3-benzothiazole-2-carboxamide (cpd 140),
N-[cis-4-(6-amino-2-chloro-9H-purin-9-yl)cyclohexyl]-3-methoxybenzenesulfonamide (cpd 141),
N-[cis-4-(6-amino-2-chloro-9H-purin-9-yl)cyclohexyl]-3-methoxybenzamide (cpd 144),
6-amino-9-{cis-4-[(4-methyl-1,3-thiazol-2-yl)carbamoyl]cyclohexyl}-9H-purine-2-carboxamide (cpd 146),
2-amino-1,3-benzothiazol-6-yl cis-4-(6-amino-2-chloro-9H-purin-9-yl)cyclohexanecarboxylate (cpd 159,
2-amino-1,3-benzothiazol-4-yl cis-4-(6-amino-2-fluoro-9H-purin-9-yl)cyclohexanecarboxylate (cpd 160),
2-({[cis-4-(6-amino-2-chloro-9H-purin-9-yl)cyclohexyl]carbonyl}amino)-1,3-benzothiazole-6-carboxamide (cpd 163),
cis-4-(6-amino-2-chloro-9H-purin-9-yl)-N-[4-(2-amino-2-oxoethyl)-1,3-thiazol-2-yl]-N-methylcyclohexanecarboxamide (cpd 164),
cis-4-(6-amino-2-chloro-9H-purin-9-yl)-N-[6-(dimethylamino)-1,3-benzothiazol-2-yl]cyclohexanecarboxamide (cpd 165),
cis-4-(6-amino-2-chloro-9H-purin-9-yl)-N-[5-(2-amino-2-oxoethyl)-1,3-thiazol-2-yl]cyclohexanecarboxamide (cpd 166),
cis-4-(6-amino-2-chloro-9H-purin-9-yl)-N-(4,6-difluoro-1,3-benzothiazol-2-yl)cyclohexanecarboxamide (cpd 167),
cis-4-(6-amino-2-chloro-9H-purin-9-yl)-N-(5,6-difluoro-1,3-benzothiazol-2-yl)cyclohexanecarboxamide (cpd 168),
tert-butyl 2-({[cis-4-(6-amino-2-chloro-9H-purin-9-yl)cyclohexyl]carbonyl}amino)-6,7-dihydro[1,3]thiazolo[5,4-c]pyridine-5(4H)-carboxylate (cpd 169),
cis-4-(6-amino-2-methoxy-9H-purin-9-yl)-N-(6-fluoro-1,3-benzothiazol-2-yl)cyclohexanecarboxamide (cpd 170),
cis-4-(6-amino-2-chloro-9H-purin-9-yl)-N-(5,6,7-trifluoro-1,3-benzothiazol-2-yl)cyclohexanecarboxamide (cpd 171),
cis-4-(6-amino-2-chloro-9H-purin-9-yl)-N-(4,5,6,7-tetrahydro[1,3]thiazolo[5,4-c]pyridin-2-yl)cyclohexanecarboxamide hydrochloride (cpd 172),
cis-4-(6-amino-2-chloro-9H-purin-9-yl)-N-(5-methyl-4,5,6,7-tetrahydro[1,3]thiazolo[5,4-c]pyridin-2-yl)cyclohexanecarboxamide (cpd 173),
methyl [2-({[cis-4-(6-amino-2-chloro-9H-purin-9-yl)cyclohexyl]carbonyl}amino)-1,3-benzothiazol-6-yl]acetate (cpd 174),
cis-4-(6-amino-2-chloro-9H-purin-9-yl)-N-(6-bromo-1,3-benzothiazol-2-yl)cyclohexanecarboxamide (cpd 175),
[2-({[cis-4-(6-amino-2-chloro-9H-purin-9-yl)cyclohexyl]carbonyl}amino)-1,3-benzothiazol-6-yl]acetic acid (cpd 176),
cis-4-(6-amino-2-chloro-9H-purin-9-yl)-N-[6-(2-amino-2-oxoethyl)-1,3-benzothiazol-2-yl]cyclohexanecarboxamide (cpd 177), cis-4-(6-amino-2-chloro-9H-purin-9-yl)-N-(4,4,6,6-tetramethyl-4,5,6,7-tetrahydro[1,3]thiazolo[5,4-c]pyridin-2-yl)cyclohexanecarboxamide (cpd 178),
cis-4-(6-amino-2-fluoro-9H-purin-9-yl)-N-(5-methyl-4,5,6,7-tetrahydro[1,3]thiazolo[5,4-c]pyridin-2-yl)cyclohexanecarboxamide (cpd 179),
cis-4-(6-amino-2-chloro-9H-purin-9-yl)-N-[6-(difluoromethoxy)-1,3-benzothiazol-2-yl]cyclohexanecarboxamide (cpd 180),
cis-4-(6-amino-2-chloro-9H-purin-9-yl)-N-[6-(trifluoromethoxy)-1,3-benzothiazol-2-yl]cyclohexanecarboxamide (cpd 181),
cis-4-(6-amino-2-chloro-9H-purin-9-yl)-N-[5-(propan-2-yl)-4,5,6,7-tetrahydro[1,3]thiazolo[5,4-c]pyridin-2-yl]cyclohexanecarboxamide (cpd 182),
cis-N-[6-(acetylamino)-1,3-benzothiazol-2-yl]-4-(6-amino-2-chloro-9H-purin-9-yl)cyclohexanecarboxamide (cpd 183),
cis-4-(6-amino-2-chloro-9H-purin-9-yl)-N-(5-cyclopropyl-4,5,6,7-tetrahydro[1,3]thiazolo[5,4-c]pyridin-2-yl)cyclohexanecarboxamide (cpd 184),
cis-4-(6-amino-2-chloro-9H-purin-9-yl)-N-(6,7-dihydro-4H-pyrano[4,3-d][1,3]thiazol-2-yl)cyclohexanecarboxamide (cpd 185),
cis-4-(6-amino-2-chloro-9H-purin-9-yl)-N-([1,3]dioxolo[4,5-f][1,3]benzothiazol-6-yl)cyclohexanecarboxamide (cpd 186),
tert-butyl (5S,8R)-2-({[cis-4-(6-amino-2-chloro-9H-purin-9-yl)cyclohexyl]carbonyl}amino)-5,6,7,8-tetrahydro-4H-5,8-epiminocyclohepta[d][1,3]thiazole-9-carboxylate (cpd 187),
cis-4-(6-amino-2-chloro-9H-purin-9-yl)-N-(6,6-difluoro-4,5,6,7-tetrahydro-1,3-benzothiazol-2-yl)cyclohexanecarboxamide (cpd 188),
cis-4-(6-amino-2-chloro-9H-purin-9-yl)-N-[(5S,8R)-5,6,7,8-tetrahydro-4H-5,8-epiminocyclohepta[d][1,3]thiazol-2-yl]cyclohexanecarboxamide hydrochlorid (cpd 189),
cis-4-(6-amino-2-fluoro-9H-purin-9-yl)-N-(4,4,6,6-tetramethyl-4,5,6,7-tetrahydro[1,3]thiazolo[5,4-c]pyridin-2-yl)cyclohexanecarboxamide (cpd 190),
cis-4-(6-amino-2-fluoro-9H-purin-9-yl)-N-(6,6-difluoro-4,5,6,7-tetrahydro-1,3-benzothiazol-2-yl)cyclohexanecarboxamide (cpd 191),
cis-4-(6-amino-2-chloro-9H-purin-9-yl)-N-(5,5-dioxido-6,7-dihydro-4H-thiopyrano[4,3-d][1,3]thiazol-2-yl)cyclohexanecarboxamide (cpd 194),
cis-4-(6-amino-2-chloro-9H-purin-9-yl)-N-(6,6-dimethyl-6,7-dihydro-4H-pyrano[4,3-d][1,3]thiazol-2-yl)cyclohexanecarboxamide (cpd 195),
cis-4-(6-amino-2-chloro-9H-purin-9-yl)-N-[5-(2-amino-2-oxoethyl)-4,5,6,7-tetrahydro[1,3]thiazolo[5,4-c]pyridin-2-yl]cyclohexanecarboxamide (cpd 196),
1-[cis-4-(6-amino-2-chloro-9H-purin-9-yl)cyclohexyl]-3-(3-methoxyphenyl)urea (cpd1 197),
cis-4-(6-amino-2-iodo-9H-purin-9-yl)-N-(5-methyl-4,5,6,7-tetrahydro[1,3]thiazolo [5,4-c]pyridin-2-yl)cyclohexanecarboxamide (cpd 198),
cis-4-{6-amino-2-[(trimethylsilyl)ethynyl]-9H-purin-9-yl}-N-(5-methyl-4,5,6,7-tetrahydro[1,3]thiazolo[5,4-c]pyridin-2-yl)cyclohexanecarboxamide (cpd 199),
cis-4-(6-amino-2-fluoro-9H-purin-9-yl)-N-(6,7-dihydro-4H-pyrano[4,3-d][1,3]thiazol-2-yl)cyclohexanecarboxamide (cpd 200),
cis-4-(6-amino-2-ethynyl-9H-purin-9-yl)-N-(5-methyl-4,5,6,7-tetrahydro[,3]thiazolo[5,4-c]pyridin-2-yl)cyclohexanecarboxamide (cpd 201), cis-4-(4-amino-1H-imidazo [4,5-c]pyridin-1-yl)-N-(4-methyl-1,3-thiazol-2-yl)cyclohexanecarboxamide (cpd 204),
cis-4-(6-amino-2-chloro-9H-purin-9-yl)-N-(4,5,6,7-tetrahydro-1,3-benzothiazol-2-yl)cyclohexanecarboxamide (cpd 205),
-4-(6-amino-2-fluoro-9H-purin-9-yl)-N-(4,5,6,7-tetrahydro-1,3-benzothiazol-2-yl)cyclohexanecarboxamide (cpd 206).

6. A process for preparing a compound or a pharmaceutically acceptable salt according to claim 1, which comprises one of the following sequences of steps:

either

SEQUENCE A:

Step a) alkylating an intermediate compound of formula (VI):

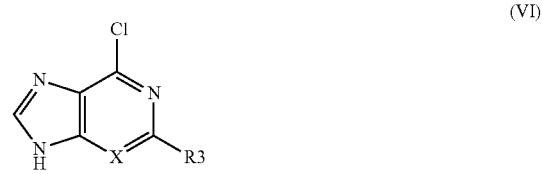

wherein X and R3 are as defined in claim 1, with an intermediate compound of formula (V):

wherein A, R1, R2 and n are as defined in claim 1 and J is selected from the group consisting of bromine, iodine, hydroxy, methansulfonyl (-OMs) and p-toluensulfonyl (-OTs);

Step b) substituting the chlorine of the resultant intermediate compound of formula (III)

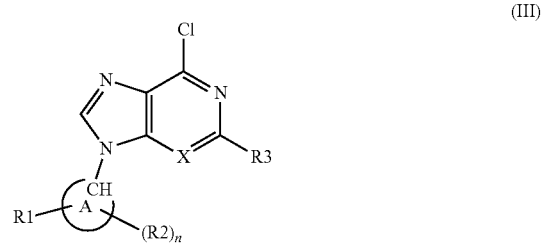

wherein X, A, R1, R2, R3 and n are as defined in claim 1, with a protected nitrogen source compound $NH(PG)_2$ (IV), wherein PG is independently hydrogen or a protecting group —COOR7, wherein R7 is a $(C_1-C_6)$alkyl, or an aryl$(C_1-C_6)$alkyl, with the proviso that such PGs are not simultaneously hydrogen; and Step c) removing the protecting group(s) PG of the resultant intermediate compound of formula (II)

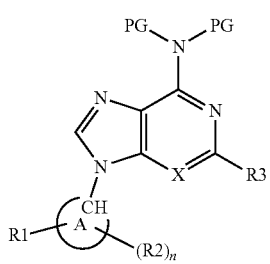

(II)

wherein X, A, R1, R2, R3, PG and n are as defined above, to yield a compound of formula (I), as defined in claim 1;

or

Step d) substituting the chlorine of the intermediate compound of formula (III), resulting from step a), with a nitrogen source, to yield a compound of formula (I), as defined in claim 1;

or

SEQUENCE B

Step b') substituting the chlorine of an intermediate compound of formula (VI):

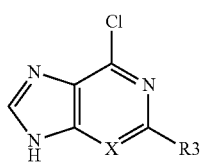

(VI)

as defined in step a, with a protected nitrogen source compound NH(PG)$_2$ (IV), as described for step b, to yield an intermediate compound of formula (VIII):

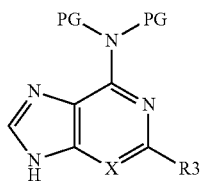

(VIII)

wherein X, R3 and PG are as defined above;

or

Step d') substituting the chlorine of an intermediate compound of formula (VI), as defined above, with a nitrogen source, as described for step d); and Step e) protecting the NH$_2$ group of the resultant intermediate compound of formula (VII)

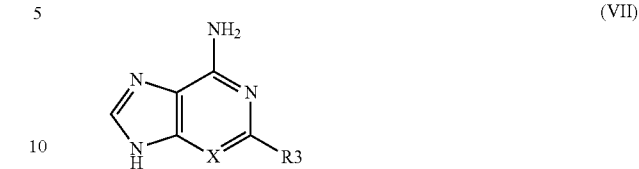

(VII)

wherein X and R3 are as defined in claim 1, with a reagent of formula (PG)$_2$O or PGCl to yield an intermediate compound of formula (VIII), as defined in step b');

then

Step a') alkylating the protected intermediate compound of formula (VIII), resulting from either step b' or step e, with an intermediate compound of formula (V), as defined in step a and in the conditions described therein;

Step c) removing the protecting group(s) PG of the resultant intermediate compound of formula (II) as defined in step c of Sequence A, to yield a compound of formula (I), as defined in claim 1; or

SEQUENCE C

Step d') substituting the chlorine of an intermediate compound of formula (VI) according to Sequence B;

Step a'') alkylating the resulting intermediate compound of formula (VII), as defined in Sequence B, with an intermediate of formula (V), as defined in step a, according to the conditions described therein;

optionally converting said compound of formula (I) into another compound of formula (I), converting said compound of formula (I) into a pharmaceutically acceptable salt thereof, or converting said salt into a free compound (I).

7. A pharmaceutical composition comprising a therapeutically effective amount of a compound of formula (I), or a pharmaceutically acceptable salt thereof, as defined in claim 1, and at least one pharmaceutically acceptable excipient, carrier or diluent.

8. A pharmaceutical composition according to claim 7, further comprising one or more chemotherapeutic agents.

9. A method for treating a disease by and/or associated with altered choline metabolism, wherein the disease is breast cancer, the method comprising:

administering to a mammal in need thereof an effective amount of a compound or pharmaceutically acceptable salt according to claim 1.

10. A compound, or pharmaceutically acceptable salt according to claim 1, wherein when R1 is linked to any A ring carbon, R1 is —CONR4R5.

* * * * *